(12) United States Patent
Wong et al.

(10) Patent No.: US 11,938,195 B2
(45) Date of Patent: Mar. 26, 2024

(54) UPCONVERSION NANOPARTICLE PEPTIDE CONJUGATES

(71) Applicant: BP InnoMed Limited, Hong Kong (CN)

(72) Inventors: Ka-Leung Wong, Hong Kong (CN); Hong Lok Lung, Hong Kong (CN); Shuai Zha, Hong Kong (CN); Ho-Fai Chau, Hong Kong (CN)

(73) Assignee: BP InnoMed Limited, Hong Kong (CN)

( * ) Notice: Subject to any disclaimer, the term of this patent is extended or adjusted under 35 U.S.C. 154(b) by 182 days.

(21) Appl. No.: 17/303,981

(22) Filed: Jun. 11, 2021

(65) Prior Publication Data

US 2022/0401578 A1 Dec. 22, 2022

(51) Int. Cl.
*A61K 47/69* (2017.01)
*A61K 51/12* (2006.01)

(52) U.S. Cl.
CPC ...... *A61K 47/6935* (2017.08); *A61K 47/6923* (2017.08); *A61K 51/1244* (2013.01)

(58) Field of Classification Search
CPC ............ A61K 47/6935; A61K 47/6923; A61K 51/1244
See application file for complete search history.

(56) References Cited

U.S. PATENT DOCUMENTS 10,137,115 B2   11/2018   Wong et al.
2017/0304284 A1*  10/2017  Wong ................... A61K 51/088

OTHER PUBLICATIONS

Yasui, et al. "Latent infection membrane protein transmembrane FWLY is critical for intermolecular interaction, raft localization, and signaling," PNAS, Jan. 6, 2004, vol. 101, No. 1, 278-283. (Year: 2004).*
Zha, S., et al., Dual-Targeting Peptide-Guided Approach for Precision Delivery and Cancer Monitoring by Using a Safe Upconversion Nanoplatform. Adv. Sci. 2021, 8, 2002919: p. 1-15.
Chau, H., et al., Lanthanide-Based Peptide-Directed Visible/Near-Infrared Imaging and Inhibition of LMP1. JACS Au 2021, 1: p. 1034-1043.
Zha, S., et al., Responsive upconversion nanoprobe for monitoring and inhibition of EBV-associated cancers via targeting EBNA1. Royal Society of Chemistry/Nanoscale, DOI: 10.1039/c8nr05015e.
Jiang, L., et al., Reactivation of Epstein-Barr virus by a dual-responsive fluorescent EBNA1-targeting agent with Zn2+-chelating function. PNAS, Dec. 26, 2019, vol. 116, No. 56: p. 26614-266624.
Jiang, L., et al., EBNA1-targeted probe for the imaging and growth inhibition of tumours associated with the Epstein-Barr virus. Nature Biomedical Engineering 1, 0042 (2017), DOI: 10.1038/s41551-017-0042: p. 1-10.

* cited by examiner

*Primary Examiner* — Michael P Cohen
(74) *Attorney, Agent, or Firm* — S&F/WEHRW

(57) ABSTRACT

The present disclosure provides EBNA1 and LMP1 dual-targeting peptides and upconversion nanoparticles conjugates comprising the same useful as therapeutic and theranostic agents capable of targeting EBNA1 and LMP1 proteins present in Epstein-Barr virus infected cells, such as cancer.

23 Claims, 114 Drawing Sheets
Specification includes a Sequence Listing.

A  Cytosolic fraction

Nuclear fraction

C

D

B                   Ligand RMSD

EBNA1 RMSD
without loop

C  Ligand RMSD

EBNA1 RMSD
without loop

A

B

A

B

C

D

E

F

A

B

UPCONVERSION NANOPARTICLE PEPTIDE CONJUGATES

TECHNICAL FIELD

The present disclosure relates to EBNA1 and LMP1 dual-targeting peptides and dual-targeting peptide upconversion nanoparticles (UCNP) conjugates comprising the same useful therapeutic and/or diagnostic agents capable of targeting EBNA1 and LMP1 proteins present in Epstein-Barr virus (EBV) infected cells, such as cancer.

BACKGROUND

In recent years, nanomaterials have been researched and investigated as promising agents for tumor bioimaging and cancer treatment in vivo due in part to their enhanced permeability and retention (EPR) effects. Lanthanide-based upconversion (UC) nanomaterials have emerged as exceptional candidates, superior to molecular compounds, because of their low toxicity, high photochemical stability, narrow and sharp emission bands, minimal auto-fluorescence, deep light penetration and uniform size distribution. Surface-functionalized UCNP of uniform quality, morphology and synthetic reproducibility have emerged as an excellent choice in recent studies of nano-biosafety. Although there are numerous laudable examples of UC nanomaterials that have been applied to biological uses, the biomedical application of pH-responsive peptide-functionalized stable nanoprobes with responsive UC emission for the inhibition and monitoring of a specific cancer type over normal cells is still rare.

There are approximately 200,000 new EBV-related cancer cases in the world reported annually. Notably, EBV is involved in a wide variety of lymphoid and epithelial cancers. Additionally, EBV causes lifelong latent infection in the host. The Epstein-Barr nuclear antigen 1 (EBNA1), normally in the form of a dimer, plays a significant role in the maintenance, replication and transcription of the EBV genome and is the only viral latent protein expressed in all EBV-associated cancers. All EBV-infected cells are EBNA1-positive.

The EBV-encoded latent infection membrane protein 1 (LMP1) is regarded as one of the primary oncogenes of EBV. LMP1 plays an important role in B cell transformation, proliferation and survival induced by EBV, induction of epithelial-mesenchymal transition and acquisition of cancer stem cell-like properties, which are subsequently involved in development and progression of EBV-associated tumors. In some EBV associated cancers (for example, EBV lymphomas in immunosuppressed patients), all the tumor cells express LMP1, but only about 40% of nasopharyngeal carcinoma (NPC) patients have LMP1-positive EBV-associated tumors. The reason why only a portion of NPC tumors have LMP1, is that the somatic nuclear factor kappa-light-chain-enhancer of activated B cells (NF-κB) signaling pathway aberrations have replaced the role of LMP1 in activating the NF-κB pathway for tumor growth in those NPC tumors and this absence of LMP1 expression provides an advantage to tumor cells that assists in escape from immune cell recognition.

LMP1 is a cell membrane protein, unlike EBNA1 which is a nuclear protein. Consequently, LMP1 is more likely to be an accessible drug target, allowing selective drug to LMP1 positive tumor cells. A cell surface or cytoplasmic membrane molecule represents a favorable opportunity for cancer cell tracking and may also reduce off-target effects, as up-take of a drug into the cell nucleus is not necessary. Hence in theory, the incorporation of tailor-made peptides could provide selective cytotoxicity to tumor cells with fewer side effects on normal tissues. LMP1 is therefore considered as a new potential target protein to improve treatment selectivity.

There is thus a need to develop improved theranostic nanoparticles capable of selectively targeting cells that express LMP1 and/or EBNA1 peptides.

SUMMARY

The present disclosure provides dual targeting polypeptides and upconversion nanoparticle conjugates comprising the same.

In a first aspect provided herein is a polypeptide comprising three peptide sequences or a pharmaceutically acceptable salt or zwitterion thereof, wherein the three peptide sequences are SEQ ID NO: 1, SEQ ID NO: 2, and SEQ ID NO: 3.

In certain embodiments, the polypeptide further comprises two linkers, wherein the each of the two linkers is covalently bonded between two of the three peptide sequences.

In certain embodiments, each of the two linkers is independently a polypeptide linker consisting of 1-4 amino acid residues.

In certain embodiments, the polypeptide consists of 15-21 amino acid residues and an optional linker covalently bonded to the N-terminal of the polypeptide.

In certain embodiments, the polypeptide comprises the structure: $L^1$-A-$L^2$-B-$L^3$-C, wherein each of A, B, and C are independently selected from the group consisting of SEQ ID NO: 1, SEQ ID NO: 2, and SEQ ID NO: 3; $L^1$ is a linker having the formula: $NH_2(CH_2)_m(C=O)-$, wherein m is a whole number selected from 1-10; and each of $L^2$ and $L^3$ is independently a polypeptide linker consisting of 1-4 amino acid residues.

In certain embodiments, the wherein each of the polypeptide linkers independently consists of 1-3 amino acid residues selected from the group consisting of alanine, asparagine, glycine, serine, and combinations thereof.

In certain embodiments, the each of $L^2$ and $L^3$ is independently a polypeptide linker consisting of 1-3 glycine residues.

In certain embodiments, the A is SEQ ID NO:2; B is SEQ ID NO:3; and C is SEQ ID NO:1; A is SEQ ID NO:3; B is SEQ ID NO:2; and C is SEQ ID NO:1; or A is SEQ ID NO:1; B is SEQ ID NO:3; and C is SEQ ID NO:2.

In certain embodiments, the polypeptide comprises the structure: $L^1$-A-$L^2$-B-$L^3$-C, wherein A is SEQ ID NO:2; B is SEQ ID NO:3; and C is SEQ ID NO:1; A is SEQ ID NO:3; B is SEQ ID NO:2; and C is SEQ ID NO:1; or A is SEQ ID NO:1; B is SEQ ID NO:3; and C is SEQ ID NO:2; $L^1$ is a linker having the formula: $NH_2(CH_2)_m(C=O)-$, wherein m is a whole number selected from 2-8; and each of $L^2$ and $L^3$ is independently a polypeptide linker consisting of 1-3 glycine residues.

In certain embodiments, the polypeptide comprises a peptide sequence selected from the group consisting of SEQ ID NO:5; SEQ ID NO:6; and SEQ ID NO:7.

In a second aspect, provided herein is an upconversion nanoparticle (UCNP) conjugate comprising a plurality of the polypeptides described herein conjugated to a surface of an UCNP via an optional linker.

In certain embodiments, the UCNP is a lanthanide-doped nanoparticle.

In certain embodiments, the UCNP comprises NaGdF$_4$:Yb$^{3+}$, Er$^{3+}$@NaGdF$_4$.

In certain embodiments, each of the plurality of polypeptides comprise the structure: L$^4$-A-L$^2$-B-L$^3$-C, wherein each of A, B, and C are independently selected from the group consisting of SEQ ID NO: 1, SEQ ID NO: 2, and SEQ ID NO: 3; L$^4$ is a linker having the formula: *—S-A(CH=N)(CH$_2$)$_m$(C=O)—, wherein m is a whole number selected from 1-10; A is polyethylene glycol; and * represents the site of conjugation to the UCNP; and each of L$^2$ and L$^3$ is independently a polypeptide linker consisting of 1-4 amino acid residues.

In certain embodiments, A is SEQ ID NO:2; B is SEQ ID NO:3; and C is SEQ ID NO:1; A is SEQ ID NO:3; B is SEQ ID NO:2; and C is SEQ ID NO:1; or A is SEQ ID NO:1; B is SEQ ID NO:3; and C is SEQ ID NO:2; and each of L$^2$ and L$^3$ is independently a polypeptide linker consisting of 1-3 glycine residues.

In certain embodiments, each of the plurality of polypeptides comprise the structure: L$^4$-A-L$^2$-B-L$^3$-C, wherein A is SEQ ID NO:2; B is SEQ ID NO:3; and C is SEQ ID NO:1; A is SEQ ID NO:3; B is SEQ ID NO:2; and C is SEQ ID NO:1; or A is SEQ ID NO:1; B is SEQ ID NO:3; and C is SEQ ID NO:2; L$^4$ is *—S-A(CH=N)(CH$_2$)$_m$(C=O)—, wherein m is a whole number selected from 2-8; A is polyethylene glycol; and * represents the site of conjugation to the UCNP; and each of L$^2$ and L$^3$ is a polypeptide linker consisting of 2 glycine residues.

In certain embodiments, the UCNP comprises NaGdF$_4$:Yb$^{3+}$, Er$^{3+}$@NaGdF$_4$.

In certain embodiments, A is SEQ ID NO:2; B is SEQ ID NO:3; and C is SEQ ID NO:1.

In a third aspect, provided herein is a pharmaceutical composition comprising a polypeptide described herein and at least one pharmaceutically acceptable excipient or carrier.

In a fourth aspect, provided herein is a pharmaceutical composition comprising an UCNP conjugate described herein and at least one pharmaceutically acceptable excipient or carrier.

In a fifth aspect, provided herein is a method of imaging an Epstein-Barr virus (EBV)-infected cell, the method comprising: contacting EBV-infected cell with an UCNP conjugate described herein; irradiating the EBV-infected cell with light; and detecting the luminescence of the conjugate.

In a sixth aspect, provided herein is a method of treating cancer in a subject in need thereof, the method comprising: administering a therapeutically effective amount of a polypeptide described herein to the subject, wherein the cancer is EBV-positive.

In a seventh aspect, provided herein is a method of treating cancer in a subject in need thereof, the method comprising: administering a therapeutically effective amount of an UCNP conjugate described herein to the subject, wherein the cancer is EBV-positive.

The FWLY (SEQ ID NO:1) motif is critical for the mediation of intermolecular interactions within the transmembrane domains of LMP1. The dual-EBNA1/LMP1-targeting protein-specific peptides [n=5, 6 and 7 (SEQ ID NO: 5, 6, 7)] were designed incorporating this motif. The EBNA1-targeting peptide sequence P$_4$ [YFMVF-GG-RrRK (SEQ ID NO:4); YFMVF (SEQ ID NO:2), EBNA1 binding motif, RrRK (SEQ ID NO:3), nucleus permeable motif] was combined with the FWLY (SEQ ID NO:1) motif for targeting the membrane LMP1; then the FWLY (SEQ ID NO:1) motif was engineered and placed at different sites: the C-terminal side [P$_5$: -Ahx-YFMVFGGRrRKGGFWLY (SEQ ID NO:5)], [P$_6$: -Ahx-RrRKGGYFMVFGGFWLY (SEQ ID NO:6)], or the N-terminal site [P$_7$: -Ahx-FWLYG-GRrRKGGYFMVF (SEQ ID NO:7)] to evaluate the effect on killing EBV-infected cancer cells. Dual-targeting peptide UCNP conjugates comprising imine linkers with pH-sensitive behaviors were introduced between NaGdF$_4$:Yb$^{3+}$, Er$^{3+}$@NaGdF$_4$ (UCNP) and the dual-targeting peptides allowing the intracellular release of the dual-targeting peptides in EBV-infected cancer cells. This peptide-guided dual-targeting nano-system was engineered to specifically traffic and deliver the peptides in EBV-associated cancer cells with responsive upconversion emission properties. Targeting the tumor cell surface protein plus the differential release of the anti-EBV peptides P$_n$ [n=5, 6 and 7 (SEQ ID NO: 5, 6, 7)] in the acidic tumor microenvironment helped to minimize undesirable and unintended damage to normal cells.

To assess this strategy for delivering precision monitoring and cancer treatment, the new dual-targeting peptides were tested with various EBV- or LMP1-positive and -negative cancer cell models. It was found that the presence of FWLY motif located at the C-terminus (P$_5$) of the EBV-targeting peptide, seemed to better facilitate the entrance of the dual-targeting peptides into EBV-infected cells and demonstrated stronger affinity towards the nuclear proteins for subsequent therapeutic applications. FIG. 56 illustrates an exemplary in vivo scenario of how the dual-targeting peptide conjugates described herein can be delivered from the tumor microenvironment, enter an EBV-positive cell via the cell surface LMP1 protein, penetrate into the cell nucleus and target EBNA1. In theory, the whole process could be monitored via responsive UC emission, and the EBV-positive cell would be killed by disruption of EBNA1 dimerization. Here, we have characterized the newly constructed nanoprobes UCNP-P$_n$ [n=5, 6 and 7 (SEQ ID NO: 5, 6, 7)] to show that UCNP-P$_5$ is the most potent pH-responsive anti-EBV nanoplatform with responsive upconversion emission, promising in vitro and in vivo anti-tumor activities and enhanced cellular and tumor uptake. This can provide a blueprint for such dual-target agents to be translated into therapies for EBV-associated cancer patients as well as other cancer patients.

Using EBV-induced cancer cells and HeLa cells as a comparative study model, a novel and safe dual-EBV-oncoproteins-targeting pH-responsive peptide engineering, coating and guiding approach to achieve precision targeting and treatment strategy against EBV-associated cancers is introduced. Individual functional peptide sequences that specifically bind to two overexpressed EBV-specific oncoproteins, EBNA1 (a latent cellular protein) and LMP1 (a transmembrane protein), are engineered in three different ways and incorporated with a pH-sensitive tumor microenvironment (TME)-cleavable linker onto the upconversion nanoparticles (UCNP) NaGdF$_4$:Yb$^{3+}$, Er$^{3+}$@NaGdF$_4$ [UCNP-P$_n$, n=5, 6 and 7 (SEQ ID NO: 5, 6, 7)]. A synergistic combination of the transmembrane LMP1 targeting ability and the pH responsiveness of UCNP-P$_n$ was found to give specific cancer differentiation with higher cellular uptake and accumulation in EBV-infected cells, thus a lower dose is needed and the side effects and health risks from treatment would be greatly reduced. It also gives responsive UC signal enhancement upon targeted dual-protein binding and shows efficacious EBV cancer inhibition in vitro and in vivo. This is the first example of simultaneous imaging and inhibition of two EBV latent proteins, and serves as a blueprint for next-generation peptide-guided precision delivery nanosystem for the safe monitoring and treatment against one specific cancer.

BRIEF DESCRIPTION OF THE FIGURES

The above and other objects and features of the present disclosure will become apparent from the following description of the disclosure, when taken in conjunction with the accompanying drawings.

DETAILED DESCRIPTION

Definitions

Figure 1:
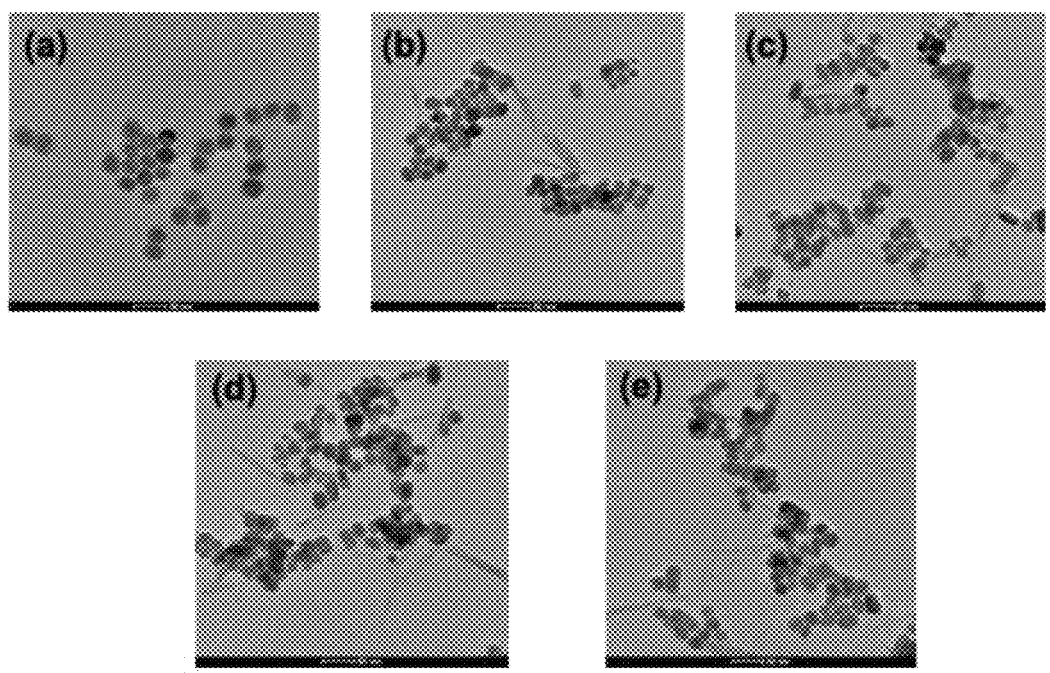
FIG. 1 depicts transmission electron microscope (TEM) images of UCNP-P$_5$ at (A) pH 7.0 (B) pH 6.5 (C) pH 6.0 (D) pH 5.5 (E) pH 5.0 PBS buffer.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

It should be understood that the order of steps or order for performing certain actions is immaterial so long as the present teachings remain operable. Moreover, two or more steps or actions may be conducted simultaneously.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

The term "attach" or "attached" as used herein, refers to connecting or uniting by a bond or non-bonding interaction in order to keep two or more compounds together, which encompasses either direct or indirect attachment such that for example where a first polypeptide is directly bound to a second polypeptide or other molecule, and the embodiments wherein one or more intermediate compounds (e.g., a linker), such as a polypeptide, is disposed between the first polypeptide and the second polypeptide or other molecule.

The term "protein" or "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein, the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

As used herein, the term "unnatural amino acid" refers to any amino acid, modified amino acid, and/or amino acid analogue that is not one of the 20 common naturally occurring amino acids, seleno cysteine or pyrrolysine.

Amino acid substitutions of the described polypeptides can be conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The terms "percentage homology" and "percentage sequence identity", when used in reference to a polypeptide or polynucleotide sequence, are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al. 1996, Methods Enzymol. 266:383-402; Altschul et al., 1990, J. Mol. Biol. 215(3):403-410; Altschul et al., 1993, Nature Genetics 3:266-272). In certain embodiments, protein and nucleic acid sequence homologies are evaluated using the Basic Local Alignment Search Tool ("BLAST") which is well-known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

As used herein, the terms "treat", "treating", "treatment", and the like refer to reducing or ameliorating a disorder and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

The present disclosure provides dual-targeting polypeptides capable of selectively targeting EBNA1 and LMP1 proteins. In certain embodiments, the polypeptide comprises three peptide sequences or a pharmaceutically acceptable salt or zwitterion thereof, wherein the three peptide sequences are SEQ ID NO: 1, which is capable of targeting LMP1; SEQ ID NO: 2, which is an EBNA1 binding motif, and SEQ ID NO: 3 which can improve cell nucleus permeability of the polypeptide.

Figure 30:
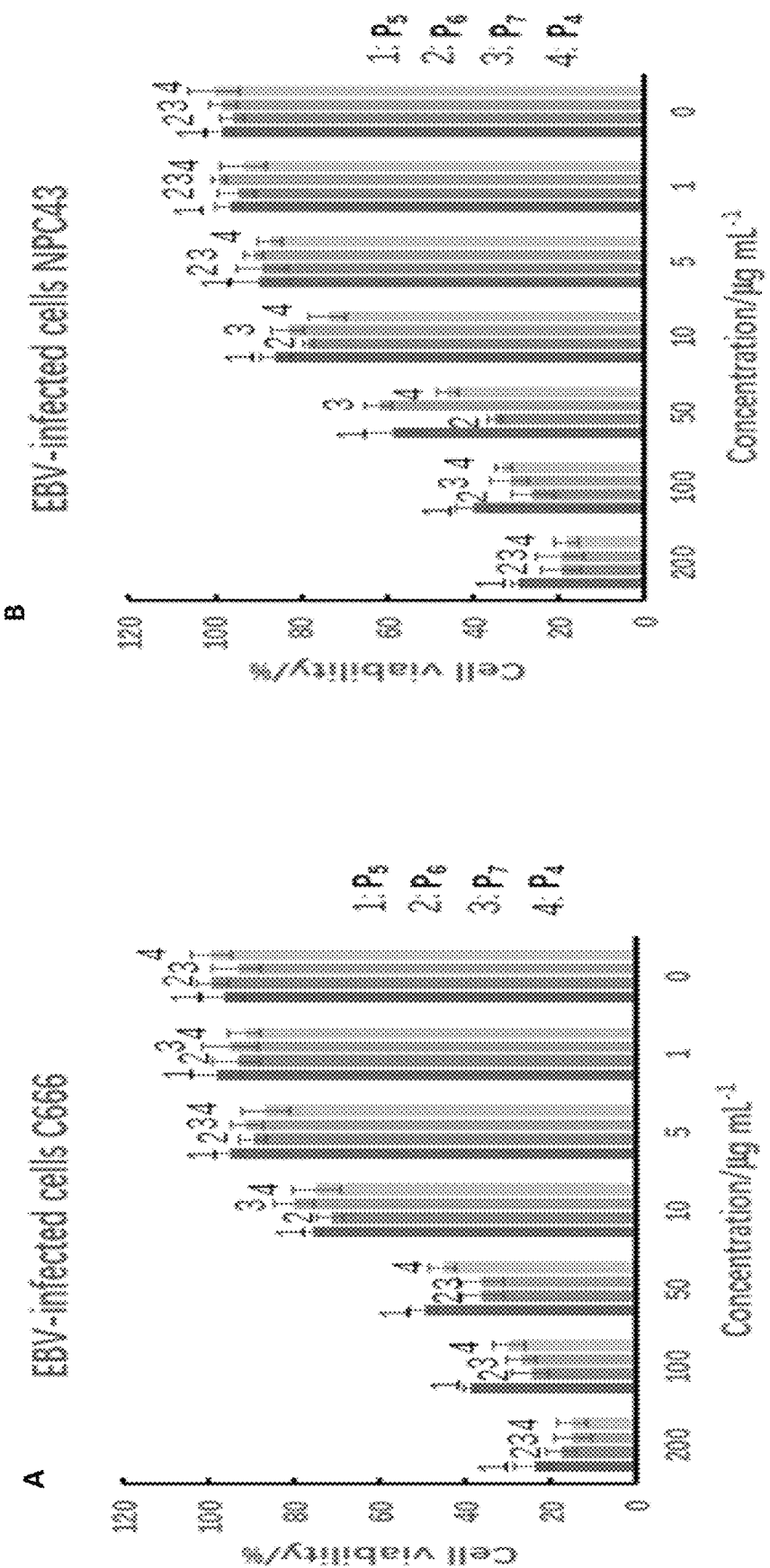
FIG. 30 depicts cytotoxicity assay of $P_5$, $P_6$, $P_7$ and $P_4$ on (A) EBV-positive nasopharyngeal carcinoma C666, (B) EBV-positive nasopharyngeal carcinoma NPC43, (C) LMP1 positive LCL3 cells and (D) LMP1 positive Raji cells were assayed (incubation time: 24 hours). $P_4$: -AhxYFMVFGGRrRK (SEQ ID NO:4).
Figure 30:
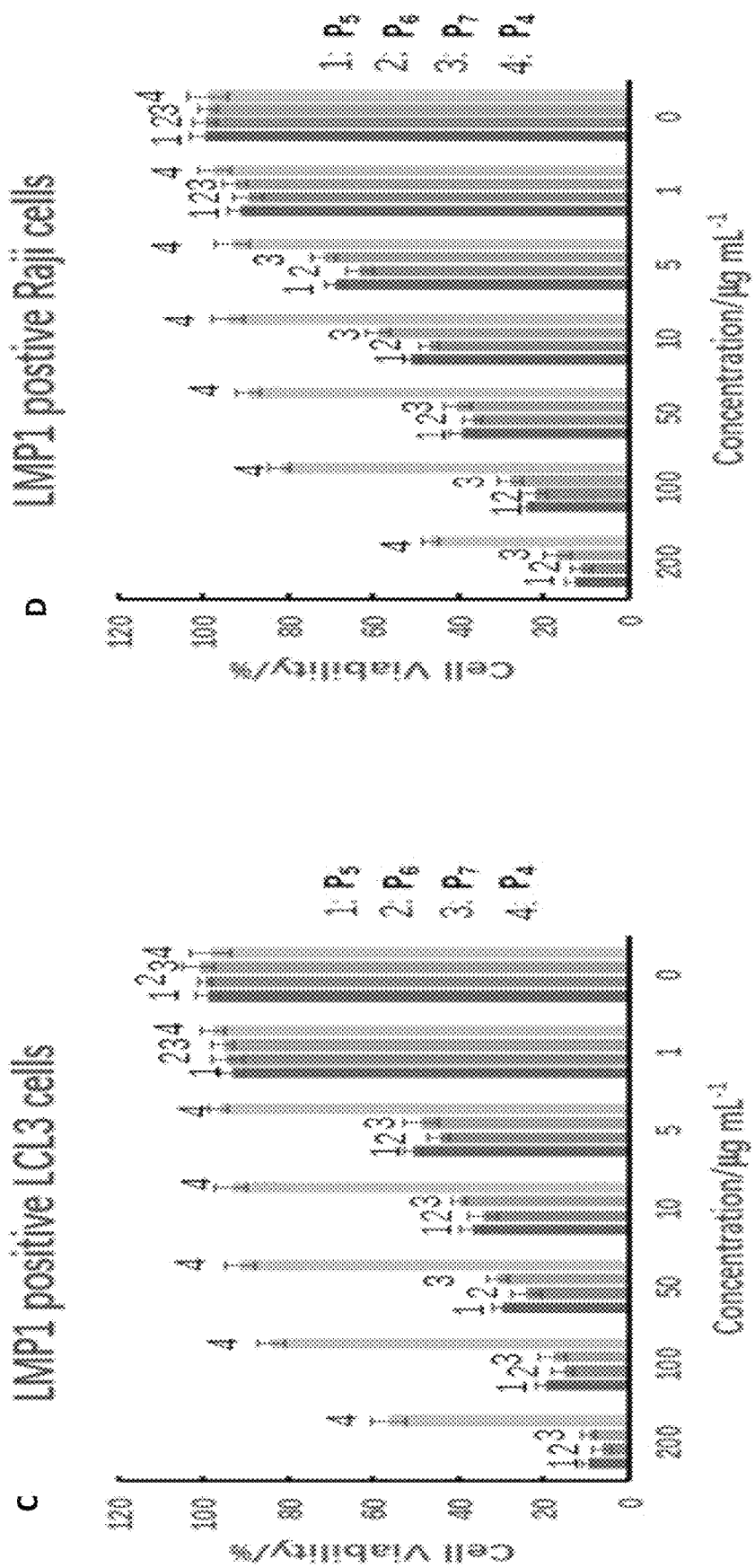
Figure 31:
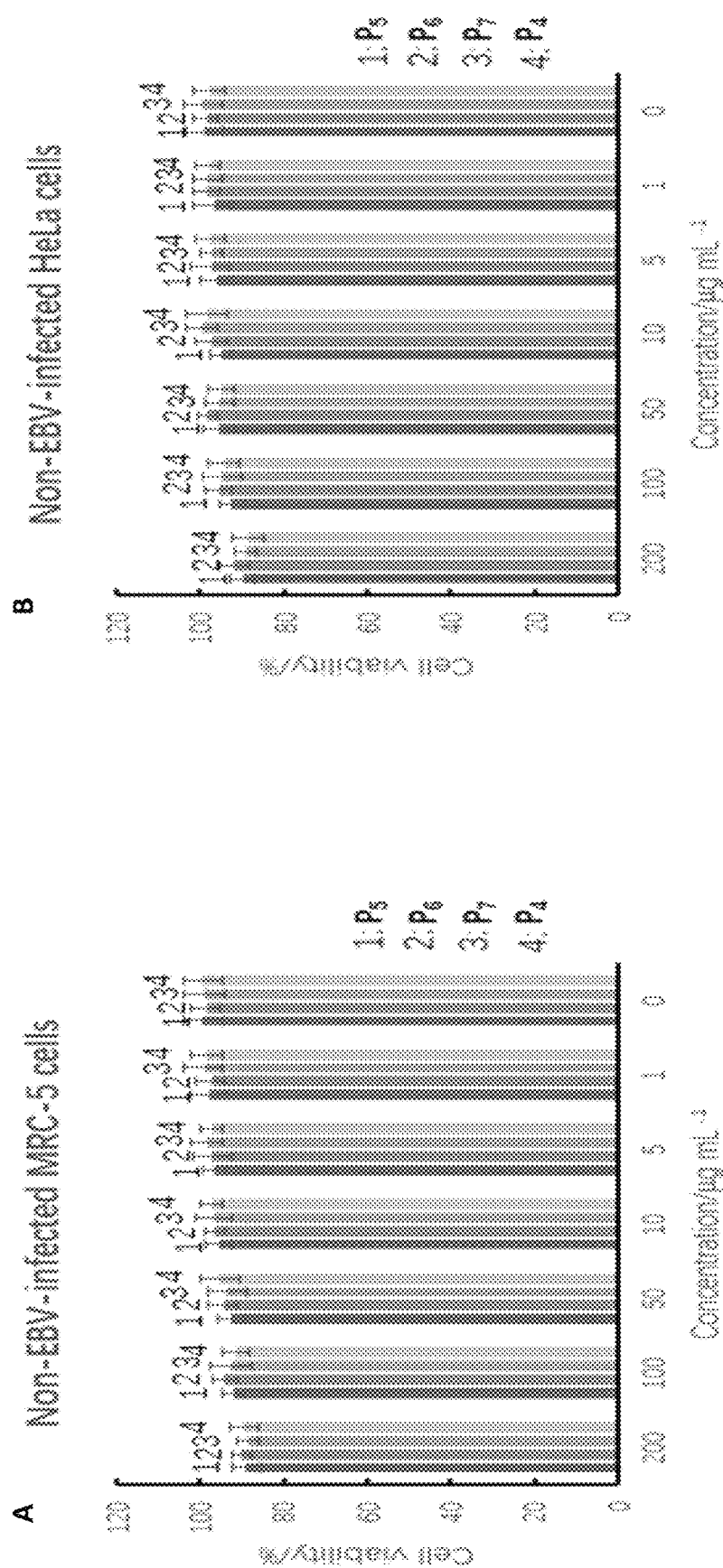
FIG. 31 depicts cytotoxicity assay of $P_5$, $P_6$, $P_7$ and $P_4$ on (A) EBV-negative human lung fibroblast normal MRC-5 cells, (B) EBV-negative human cervical carcinoma HeLa, (C) LMP1 negative HK1 cells and (D) LMP1 positive HK1-LMP1 cells were assayed (incubation time: 24 hours). $P_4$: -AhxYFMVFGGRrRK (SEQ ID NO:4).
Figure 31:
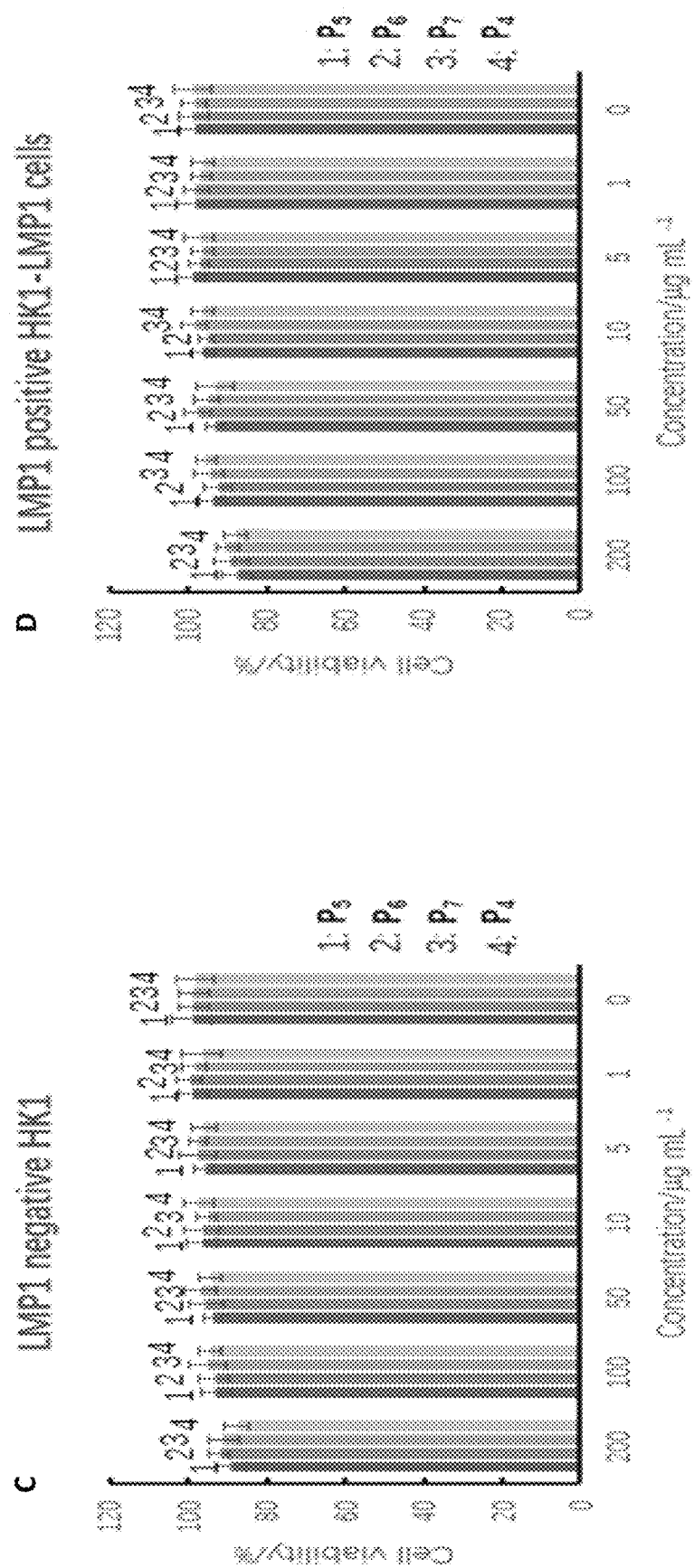

As demonstrated by the results presented in FIGS. 30 and 31, P5, P6, and P7 (SEQ ID NO:5, SEQ ID NO:6, and SEQ ID NO:7) are all capable of selectively targeting and killing EBV-infected cells and LMP1 positive cells, which demonstrates that the order in which SEQ ID NO:1, SEQ ID NO:2, and SEQ ID NO:3 are present in the polypeptide does not have a significant impact on their efficacy. Advantageously, the incorporation of SEQ ID NO:2, does not effect the activity of the polypeptides against EBV-infected cells, but has a marked improvement in the activity of the polypeptides against LMP1 positive cells relative to P4 (SEQ ID NO:4).

Thus, SEQ ID NO:1, SEQ ID NO:2, and SEQ ID NO:3 may be present in the polypeptide in any order. For example, the polypeptide may comprise SEQ ID NO:1, SEQ ID NO:2, and SEQ ID NO:3 in the following orders from the N-terminus to the C-terminus: SEQ ID NO:1, SEQ ID NO:2, and SEQ ID NO:3; SEQ ID NO:1, SEQ ID NO:3, and SEQ ID NO:2; SEQ ID NO:2, SEQ ID NO:1, and SEQ ID NO: 3; SEQ ID NO:3, SEQ ID NO:1, and SEQ ID NO:2; SEQ ID NO:3, SEQ ID NO:2, and SEQ ID NO: 1; SEQ ID NO:2, SEQ ID NO:3, and SEQ ID NO:1.

Each of peptides SEQ ID NO:1, SEQ ID NO:2, and SEQ ID NO:3 can independently be covalently bonded directly or via a linker to one and other. In certain embodiments, SEQ ID NO:1, SEQ ID NO:2, and SEQ ID NO:3 are covalently bonded to each other by two linkers. In certain embodiments, the linker is a peptide linker.

The peptide linker can be a polypeptide typically ranging from about 1, 2, 3, 4, 5, 6, 7, 8, 9, 10, 11, 12, 13, 14, 15, 16, 17, 18, 19, 20 or more amino acids in length, which is designed to facilitate the functional connection of SEQ ID NO:1, SEQ ID NO:2, and SEQ ID NO:3. The term functional connection denotes a connection that facilitates proper folding of the polypeptides into a three dimensional structure that allows the linked peptides to exhibit at least some or all of the functional aspects or biological activities of the peptides from which its polypeptide constituents are derived. The polypeptide linker can be disposed between the N-terminal of a first peptide and the C-terminal of a second peptide. The polypeptide can comprise up to two polypeptide linkers disposed in between SEQ ID NO:1, SEQ ID NO:2, and SEQ ID NO:3.

The peptide linker can comprise naturally occurring amino acids, unnatural amino acids, and combinations thereof.

In certain embodiments, the peptide linker can comprise alanine, glycine, serine, asparagine, or a combination thereof. Exemplary peptide linkers include example a linker containing poly-glycine (e.g., $(Gly)_n$), $(Gly-Ser)_n$, $(Gly-Gly-Ser)_n$, wherein n is 1-5, 1-4, 1-3, 1-2, or 1, and the like. In certain embodiments, the peptide linker is selected from $(Gly)_n$, wherein n is 1-6, 1-5, 1-4, 1-3, and 1-2. In certain embodiments, the peptide linker is Gly-Gly.

The polypeptide can include any number of amino acid residues. In certain embodiments, the polypeptide consists of between 11-100, 11-90, 11-80, 11-70, 11-60, 11-50, 11-40, 11-30, 11-20, 11-19, 11-18, 11-17, 11-16, 11-15, or 12-16 amino acid residues and an optional linker covalently bonded to the N-terminal of the polypeptide. In certain embodiments, the polypeptide consists of 15 amino acid residues and an optional linker covalently bonded to the N-terminal of the polypeptide.

In certain embodiments, the polypeptide comprises the structure: $L^1$-A-$L^2$-B-$L^3$-C, wherein each of A, B, and C are independently selected from the group consisting of SEQ ID NO: 1, SEQ ID NO: 2, and SEQ ID NO: 3; $L^1$ is a linker or is absent; and each of $L^2$ and $L^3$ is independently a polypeptide linker consisting of 1-4 amino acid residues.

In certain embodiments, the linker has the formula: $R^1(CH_2)_mX(C=O)-$, wherein m is a whole number selected from 1-10, 1-9, 1-8, 1-6, 1-6, 2-6, 3-6, or 4-6; X is a bond, $-O-$, or $-NH-$, and $R^1$ is a reactive functional group selected from the group consisting of $CO_2H$, $NH_2$, OH, SH, I, Br, C≡CH, N-maleimide, and $N_3$, ester, hydrazone, imine and acetal. In certain embodiments, the linker has the formula: $NH_2(CH_2)_m(C=O)-$, wherein m is a whole number selected from 1-10, 1-9, 1-8, 1-6, 1-6, 2-6, 3-6, or 4-6. In certain embodiments, the linker has the formula: $NH_2(CH_2)_5(C=O)-$.

In certain embodiments, A is SEQ ID NO:2; B is SEQ ID NO:3; and C is SEQ ID NO:1; A is SEQ ID NO:3; B is SEQ ID NO:2; and C is SEQ ID NO:1; A is SEQ ID NO:1; B is SEQ ID NO:3; and C is SEQ ID NO:2; A is SEQ ID NO:1; B is SEQ ID NO:2; and C is SEQ ID NO:3; A is SEQ ID NO:2; B is SEQ ID NO:1; and C is SEQ ID NO:3; or A is SEQ ID NO:3; B is SEQ ID NO:1; and C is SEQ ID NO:2. In certain embodiments, A is SEQ ID NO:2; B is SEQ ID NO:3; and C is SEQ ID NO:1.

In certain embodiments, each of $L^2$ and $L^3$ is independently a polypeptide linker consisting of 1-4 amino acid residues, wherein the amino acid residues are independently selected from alanine, asparagine, glycine, serine, and combinations thereof. In certain embodiments, each of $L^2$ and $L^3$ is independently a polypeptide linker represented by the formula $(Gly)_n$, wherein n is 1-4, 1-3, and 1-2. In certain embodiments, each of $L^2$ and $L^3$ is a peptide linker having the formula Gly-Gly.

In certain embodiments, the polypeptide comprises the structure: $L^1$-A-$L^2$-B-$L^3$-C, wherein A is SEQ ID NO:2; B is SEQ ID NO:3; and C is SEQ ID NO:1; A is SEQ ID NO:3; B is SEQ ID NO:2; and C is SEQ ID NO:1; or A is SEQ ID NO:1; B is SEQ ID NO:3; and C is SEQ ID NO:2; $L^1$ is a linker having the formula: $NH_2(CH_2)_m(C=O)-$, wherein m is a whole number selected from 2-8; and each of $L^2$ and $L^3$ is independently a polypeptide linker consisting of 1-3 glycine residues.

In certain embodiments, the polypeptide is selected from the group consisting of SEQ ID NO:5; SEQ ID NO:6; and SEQ ID NO:7.

The present disclosure also provides an upconversion nanoparticle (UCNP) conjugate comprising a plurality of the polypeptides described herein conjugated to a surface of an UCNP via an optional linker.

The UCNP can be a lanthanide-doped nanoparticle. The lanthanide-doped nanoparticle core can comprise a dielectric material doped with one or more lanthanide ions. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Suitable dielectric core materials include non-lanthanide elements, such as yttrium (Y) and scandium (Sc). Exemplary dielectric core materials include, but are not limited to, $Y_2O_3$, $LaPO_4$, $Y_2O_3$, $Y_2O_2S$, $NaYF_4$, $NaYbF_4$, Na doped $YbF_3$, YAG, YAP, $Nd_2O_3$, $LaF_3$, $NaGdF_4$, $LaCl_3$, $La_2O_3$, $TiO_2$, $LuPO_4$, $YVO_4$, $YbF_3$, $YF_3$, $BaGdF_5$, $BaYF_5$, $CaF_2$, $Er_2O_3$, $YbPO_4$, $GdVO_4$ or $SiO_2$. In one embodiment, the dielectric nanoparticle core is $NaYF_4$. These dielectric cores can be doped with one or more Er, Eu, Yb, Tm, Nd, Tb, Ce, Y, U, Pr, La, Gd and other rare-earth species or a combination thereof. In certain embodiments, the dielectric core material is doped with Gb, Yb, Er, or combinations thereof. In certain embodiments, the lanthanide-doped nanoparticle comprises $NaYF_4$:Yb/X/Gd, wherein X is Er, Tm, or Er/Tm. In certain embodiments, the lanthanide-doped nanoparticle is NaGdF$_4$:Yb/X/Gd, wherein X is Er, Tm, or Er/Tm. In certain embodiments, the UCNP comprises NaGdF$_4$:Yb$^{3+}$, Er$^{3+}$@NaGdF$_4$.

Each of the plurality of polypeptides can comprise the structure: L$^4$-A-L$^2$-B-L$^3$-C, wherein each of A, B, and C are independently selected from the group consisting of SEQ ID NO: 1, SEQ ID NO: 2, and SEQ ID NO: 3; L$^4$ is a linker having the formula: *—S-A(CH=N)(CH$_2$)$_m$(C=O)—, wherein m is a whole number selected from 1-10, 1-9, 1-8, 1-6, 1-6, 2-6, 3-6, or 4-6; A is polyethylene glycol (PEG); and * represents the site of conjugation to the UCNP; and each of L$^2$ and L$^3$ is independently a polypeptide linker consisting of 1-4 amino acid residues.

The PEG group can have an average molecular weight of about 500 to about 20,000 amu, about 500 to about 15,000 amu, about 500 to about 10,000 amu, about 500 to about 5,000 amu, about 500 to about 3,000 amu, about 500 to about 3,000 amu, about 1,000 to about 3,000 amu, about 1,000 to about 5.00 amu or about 1,500 to about 2,500 amu.

In certain embodiments, each of the plurality of polypeptides comprises the structure: L$^4$-A-L$^2$-B-L$^3$-C, wherein A is SEQ ID NO:2; B is SEQ ID NO:3; and C is SEQ ID NO:1; A is SEQ ID NO:3; B is SEQ ID NO:2; and C is SEQ ID NO:1; or A is SEQ ID NO:1; B is SEQ ID NO:3; and C is SEQ ID NO:2; L$^1$ is a linker having the formula: *—S-A(CH=N)(CH$_2$)$_m$(C=O)—, wherein m is a whole number selected from 4-6; each of L$^2$ and L$^3$ is independently a polypeptide linker consisting of 1-3 glycine residues; A is a PEG with an average molecular weight between about 500 to about 10,000 amu; and * represents the site of conjugation to the UCNP.

In certain embodiments, each of the plurality of polypeptides comprises the structure: L$^4$-A-L$^2$-B-L$^3$-C, wherein A is SEQ ID NO:2; B is SEQ ID NO:3; and C is SEQ ID NO:1; A is SEQ ID NO:3; B is SEQ ID NO:2; and C is SEQ ID NO:1; or A is SEQ ID NO:1; B is SEQ ID NO:3; and C is SEQ ID NO:2; L$^1$ is a linker having the formula: *—S-A(CH=N)(CH$_2$)$_m$(C=O)—, wherein m is 5; each of L$^2$ and L$^3$ is independently a polypeptide linker consisting of 2 glycine residues; A is a PEG with an average molecular weight between about 1,000 to about 3,000 amu; and * represents the site of conjugation to the UCNP.

In certain embodiments, UCNP conjugate is selected from the group consisting of UCNP-P$_5$, wherein the UCNP is NaGdF$_4$:Yb$^{3+}$, Er$^{3+}$@NaGdF$_4$ and plurality of polypeptides is Ahx-YFMVFGGRrRKGGFWLY (SEQ ID NO: 5); UCNP-P$_6$, wherein the UCNP is is NaGdF$_4$:Yb$^{3+}$, Er$^{3+}$@NaGdF$_4$ and the plurality of polypeptides is Ahx-RrRKG-GYFMVFGGFWLY (SEQ ID NO: 6); and UCNP-P$_7$, wherein the UCNP is NaGdF$_4$:Yb$^{3+}$, Er$^{3+}$@NaGdF$_4$ and the plurality of polypeptides is Ahx-FWLYGGRrRKG-GYFMVF (SEQ ID NO: 7).

The present disclosure also provides a pharmaceutical composition comprising a polypeptide or an UCNP conjugate described herein and at least one pharmaceutically acceptable excipient and/or pharmaceutically acceptable carrier.

The polypeptide or UCNP conjugate described herein and their pharmaceutically acceptable salts can be administered to a subject either alone or in combination with pharmaceutically acceptable carriers or diluents in a pharmaceutical composition according to standard pharmaceutical practice. The polypeptide or UCNP conjugate can be administered parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of the polypeptide or UCNP conjugate described herein, formulated together with one or more pharmaceutically acceptable carriers (additives) and/or diluents. The pharmaceutical compositions of the present disclosure may be specially formulated for administration in liquid form, including those adapted for the following: (1) parenteral administration, for example, by intravenous as, for example, a sterile solution or suspension.

As set out herein, certain embodiments of the polypeptide or UCNP conjugate described herein may contain a basic functional group, such as amino, and are, thus, capable of forming pharmaceutically-acceptable salts with pharmaceutically-acceptable acids. The term "pharmaceutically-acceptable salts" in this respect, refers to the relatively nontoxic, inorganic and organic acid addition salts of polypeptide or UCNP conjugate of the present disclosure. These salts can be prepared in situ in the administration vehicle or the dosage form manufacturing process, or by separately reacting a purified polypeptide or UCNP conjugate of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the polypeptide or UCNP conjugate of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the polypeptide or UCNP conjugate described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of the polypeptide or UCNP conjugate of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the polypeptide or UCNP conjugate include the step of bringing into association a polypeptide or an UCNP conjugate described herein with the carrier and, optionally, one or more accessory ingredients. In general, the formulations are prepared by uniformly and intimately bringing into association a polypeptide or an UCNP conjugate described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more polypeptide or UCNP conjugate described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars (such as sucrose), alcohols, non-ionic surfactants (such as Tween 20), antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The polypeptides and UCNP conjugates described herein are useful in the treatment and imaging of EBV associated diseases, such as cancer and infectious mononucleosis. Thus, the polypeptides or UCNP conjugates described herein can be used in a method of treating an EBV associated disease in a subject in need thereof, the method comprising: administering a therapeutically effective amount of a polypeptide or a UCNP described herein to the subject.

The present disclosure also provides a method of treating cancer in a subject in need thereof, the method comprising: administering a therapeutically effective amount of a polypeptide or an UCNP conjugate described herein to the subject, wherein the cancer is EBV-positive.

EBV-positive cancers refers to those cancers and cancer cells which express, e.g., in a latent form, EBV. Examples of such cancers include, but are not limited to, nasopharyngeal carcinoma, Burkitt's lymphoma, Hodgkin's Disease, T-cell lymphoma, B-cell lymphoma, transplant-associated lymphoproliferative disorders, gastric carcinoma, parotid carcinoma, breast carcinoma, leiomyosarcoma. In certain embodiments EBV-positive cancers are cancers wherein greater than about 30%, greater than about 40%, greater than about 50%, greater than about 60%, greater than about 70%, or greater than about 80% contain the EBV virus. In certain embodiments, the cancer and/or cancer cell for treatment with the method of the present disclosure is nasopharyngeal carcinoma (NPC).

In certain embodiments, the EBV-positive cancer is selected from the group consisting of nasopharyngeal carcinoma, Burkitt's lymphoma, Hodgkin's Disease, T-cell lymphoma/leukaemia, B-cell lymphoma, B lymphoproliferative disease, NK cell lymphoma/leukaemia, T/NK lymphoproliferative diseases, transplant-associated lymphoproliferative disorders, gastric carcinoma, parotid carcinoma, breast carcinoma, and leiomyosarcoma. In certain embodiments, the EBV-positive cancer is B cell-derived lymphomas, T-cell lymphomas, Hodgkin lymphoma, nasopharyngeal cancer, gastric carcinoma, Burkitt lymphoma, or diffuse large B-cell lymphoma.

Also provided herein is a method of imaging an EBV-infected cell, the method comprising: contacting EBV-infected cell with a UCNP conjugate described herein; irradiating the EBV-infected cell with light; and detecting the luminescence of the UCNP conjugate.

The UCNP conjugate upon excitation by light (e.g., near infrared or infrared light from about 700 nm to about 1,100 nm or about 900 nm to about 1,000 nm), can emit light of a wavelength from about 330 nm to about 700 nm or about 500 nm to 700 nm. In certain embodiments, the excitation wavelength of UCNP and UCNP-$P_n$ (n=5, 6 and 7) is 980 nm, and the emission bands are 520 nm, 540 nm and 654 nm.

The method of imaging an EBV-infected cell may also comprise treating the EBV-infected cell. In such instances, a therapeutically effective amount of the UCNP conjugate is brought into contact with the EBV-infected cell. In certain embodiments, the EBV-infected cell is an EBV-positive cancer cell.

The present disclosure also provides a method of treating cancer in a subject in need thereof, the method comprising: administering a therapeutically effective amount of a polypeptide or an UCNP conjugate described herein to the subject, wherein the cancer expresses LMP1.

Also provided herein is a method of imaging a cell that expressing LMP1, the method comprising: contacting the cell with a UCNP conjugate described herein; irradiating the cell with light; and detecting the luminescence of the UCNP conjugate.

The method of imaging a cell expressing LMP1 may also comprise treating the cell expressing LMP1. In such instances, a therapeutically effective amount of the UCNP conjugate is brought into contact with the cell.

Figure 2:
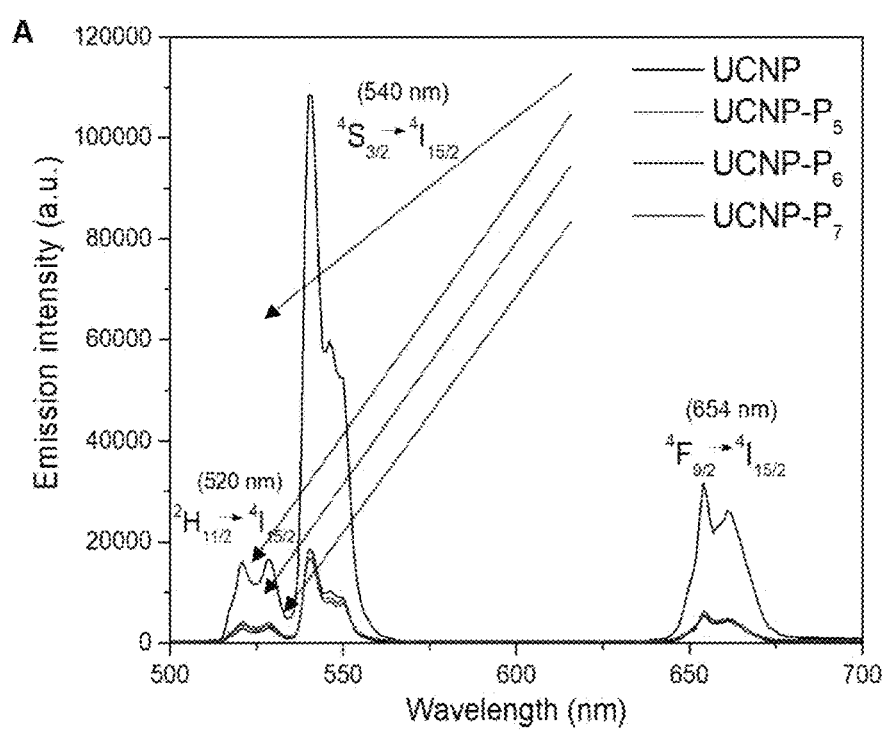
FIG. 2 depicts (A) the upconversion visible emission spectra of UCNP and UCNP-P$_n$[n=5, 6 and 7, (SEQ ID NO: 5, 6, 7)] (B) pH-responsive upconversion visible emission spectrum of UCNP-P$_5$; (C) Luminescence titration of UCNP-P$_5$ (conc.: 0.5 mg/mL; excitation at 980 nm) towards EBNA1; (D) change in emission intensity of UCNP-P$_5$ on addition of EBNA1, BSA, HSA, Avidin and NPM; (E) EBNA1 dimerization inhibition assay on 1: PBS, 2: UCNP, 3: UCNP-P$_4$, 4: UCNP-P$_5$, 5: UCNP-P$_6$ and 6: UCNP-P$_7$.
Figure 2:
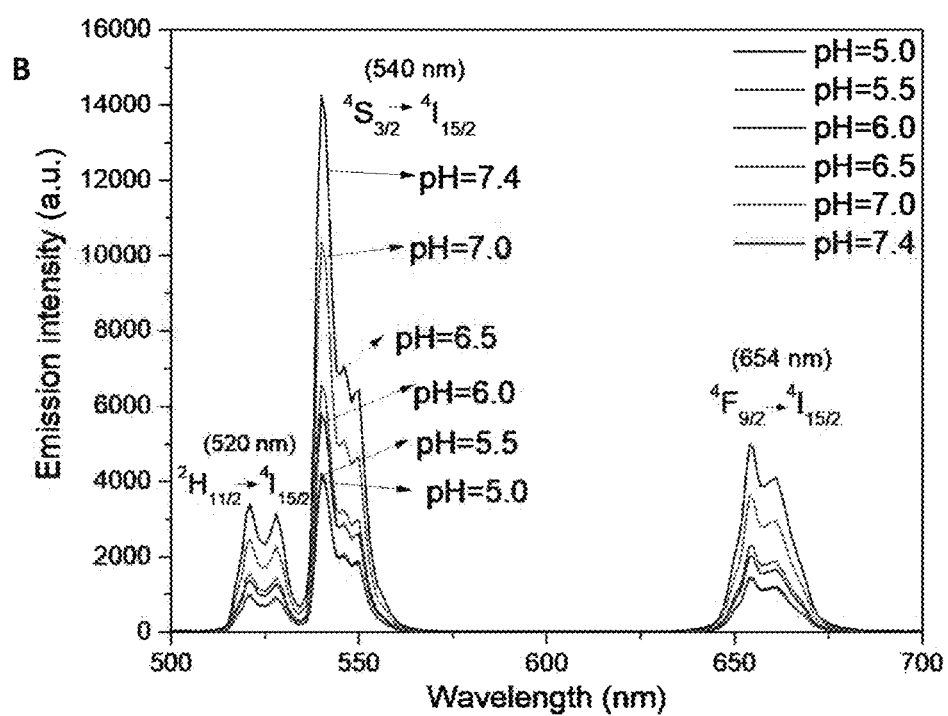
Figure 2:
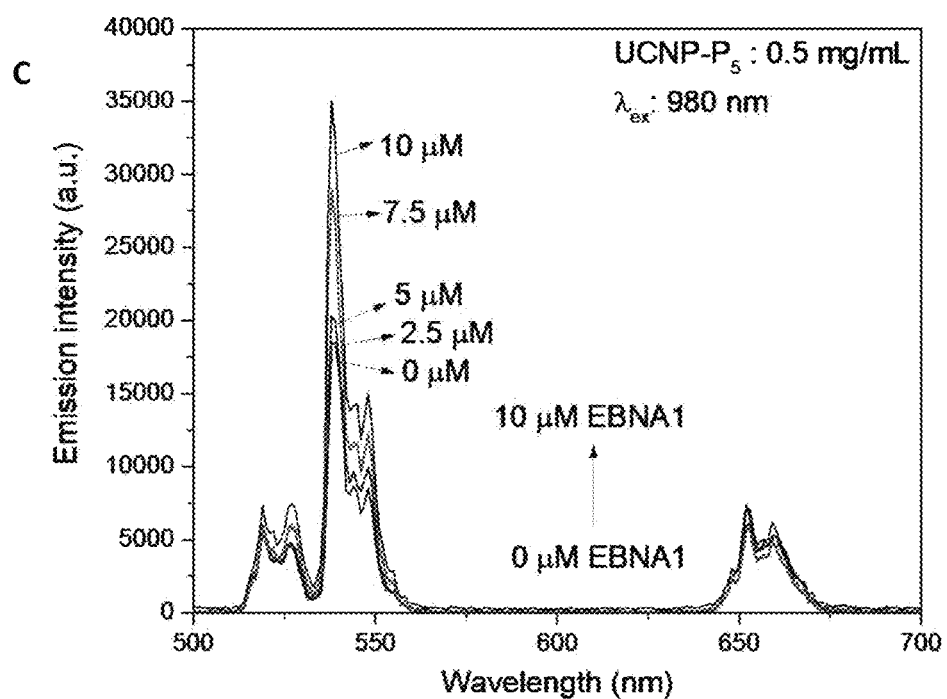
Figure 2:
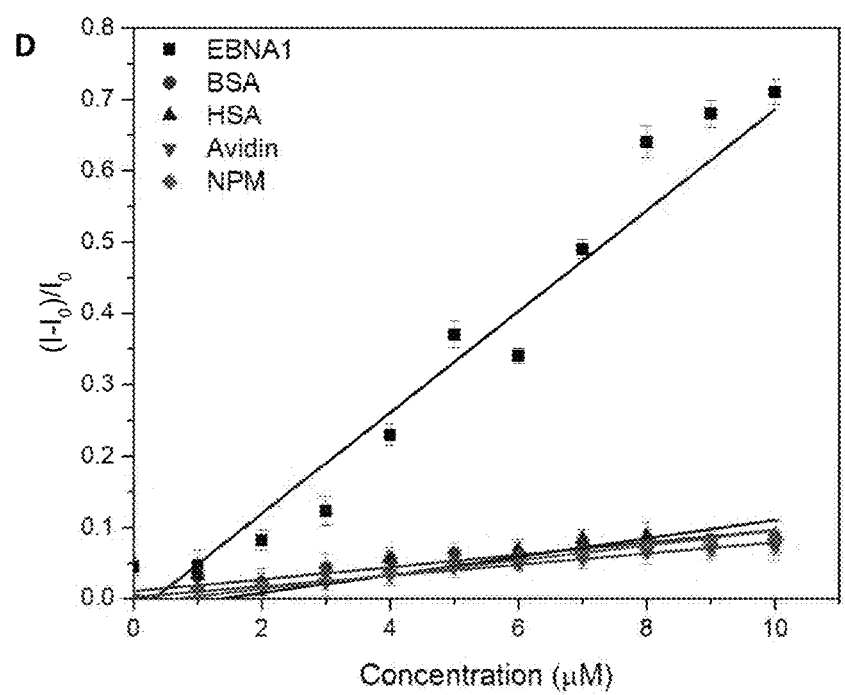
Figure 2:
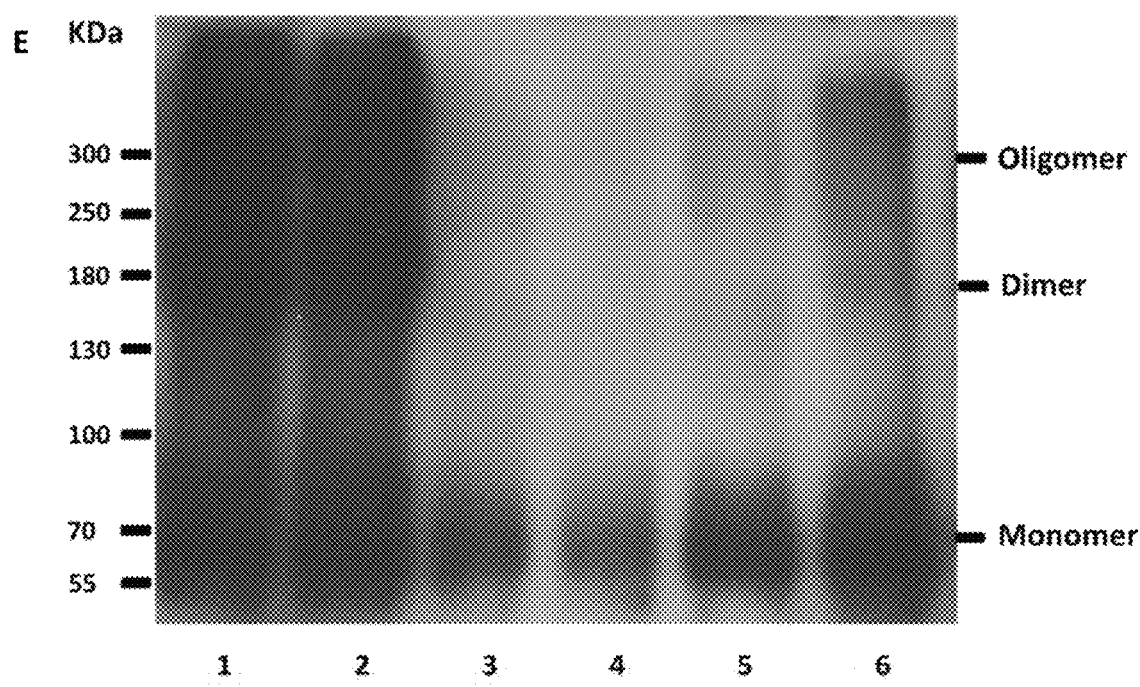

The upconversion luminescence properties of the UCNP and UCNP-$P_n$ [n=5, 6 and 7 (SEQ ID NO: 5, 6, 7)] were evaluated in DI-water at the same concentration of 0.5 mg/mL under continuous-wave 980 nm near-infrared laser excitation. All of the as-prepared samples exhibited three characteristic upconversion emission bands centered at the wavelength of 520, 540, and 654 nm, which correspond to the $^2H_{11/2}$, $^4S_{3/2} \rightarrow {}^4I_{15/2}$ and $^4F_{9/2} \rightarrow {}^4I_{15/2}$ transitions respectively. These represent efficient energy transfer from trivalent ytterbium ion ($Yb^{3+}$) to trivalent erbium ion ($Er^{3+}$), as shown in FIG. 2A. The upconversion emission intensity of UCNP is ~6-fold higher than that of UCNP-$P_n$ [n=5, 6 and 7 (SEQ ID NO: 5, 6, 7)], this is attributed to the quenching effect from the peptide coating.

Figure 25:
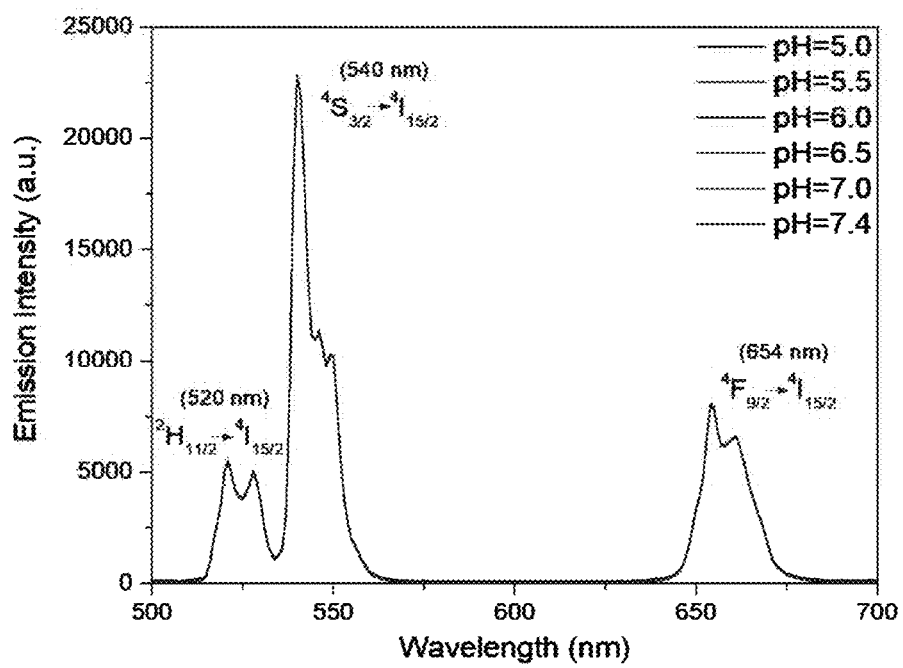
FIG. 25 depicts pH-responsive upconversion visible emission spectrum of (A) UCNP (B) UCNP-$P_5$ (C) UCNP-$P_7$ (D) UCNP-$P_4$.
Figure 25:
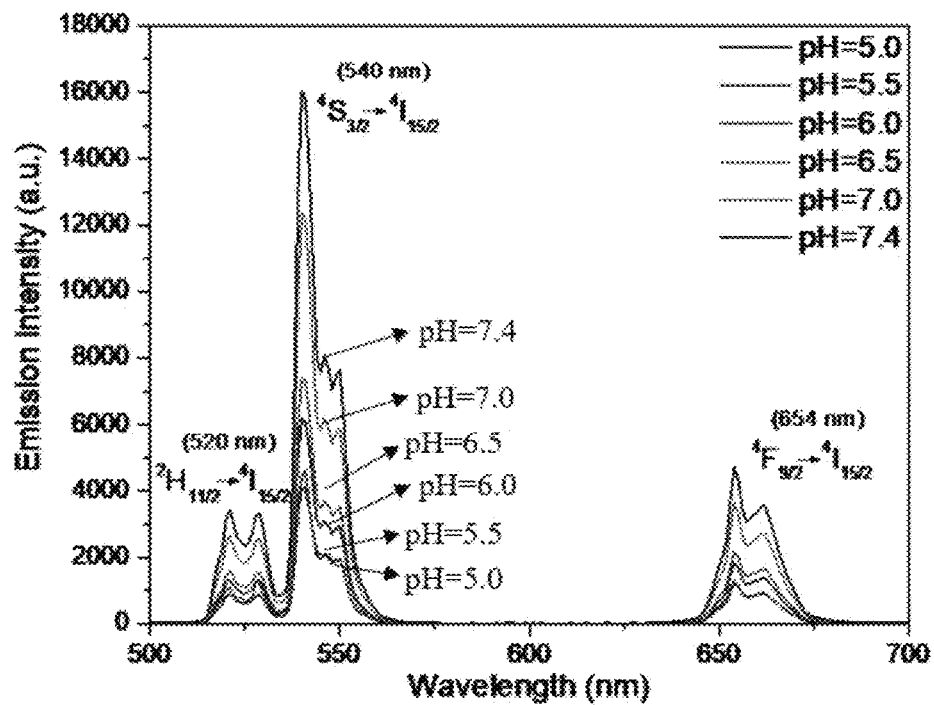
Figure 25:
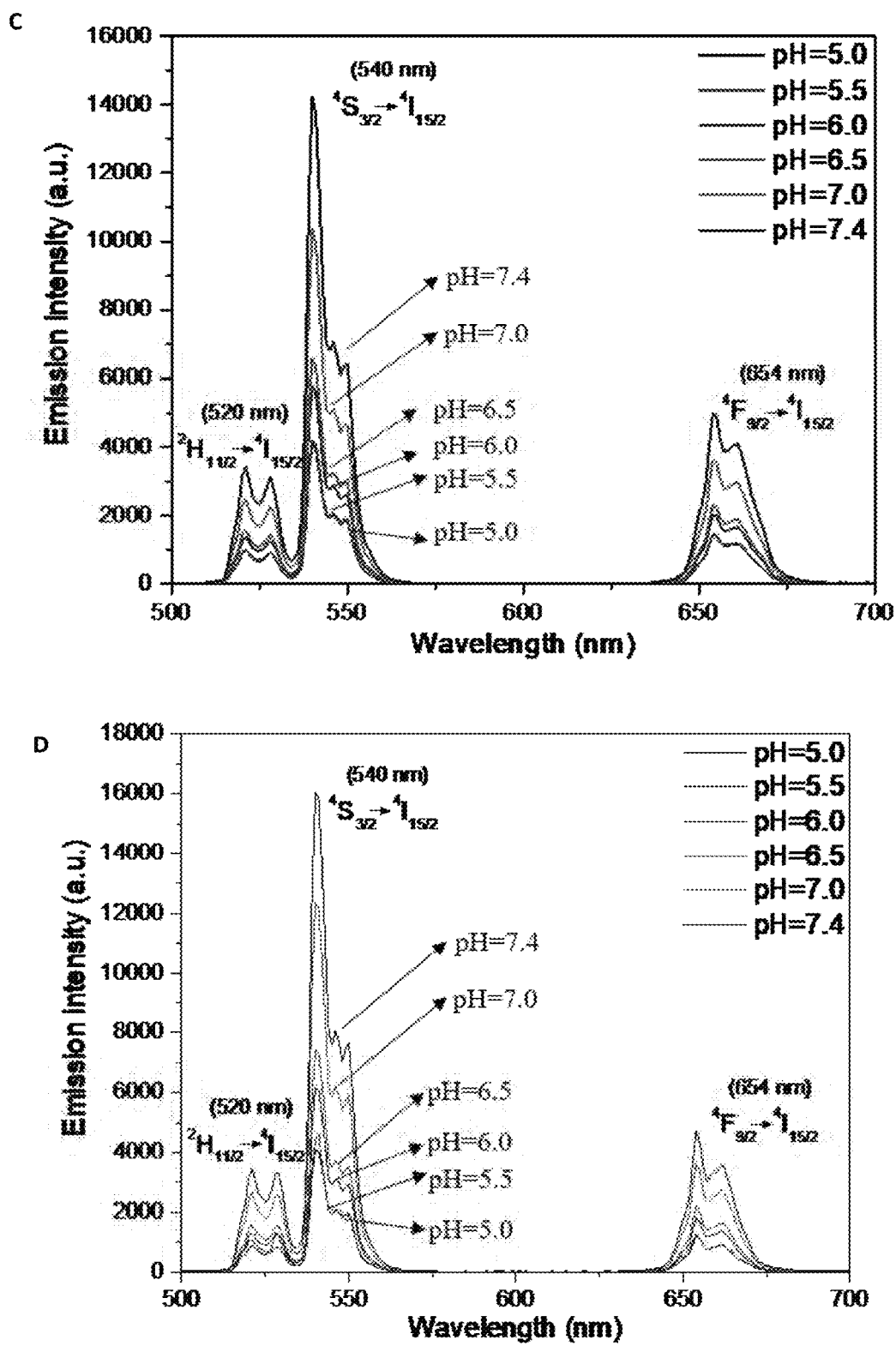

To further verify the association between the pH-responsive property of the nanoprobes in aqueous solution and their optical properties, the upconversion visible spectra of UCNP-P$_4$, UCNP and UCNP-P$_n$ [n=5, 6 and 7 (SEQ ID NO: 5, 6, 7)] were systematically investigated, as shown in FIG. 2B and FIG. 25 respectively. It is noted that UCNP-P$_4$ and UCNP-P$_n$ [n=5, 6 and 7 (SEQ ID NO: 5, 6, 7)] showed responsive upconversion emission and a 2-fold enhancement was observed when the environment was adjusted from pH 7.4 to pH 5.0. For comparison, UCNP showed negligible difference in its upconversion emission intensities in different pH buffers. The reduction of the quenching effect facilitates the emission intensity recovery of peptide capped nanoprobes. This implies that the cleavage ability of the pH linker in acidic environment of the nanoprobes is highly sensitive. The outstanding pH-responsiveness demonstrated in fluorescent studies is consistent with the results of TEM images of nanoprobes at different pH buffers.

Figure 23:
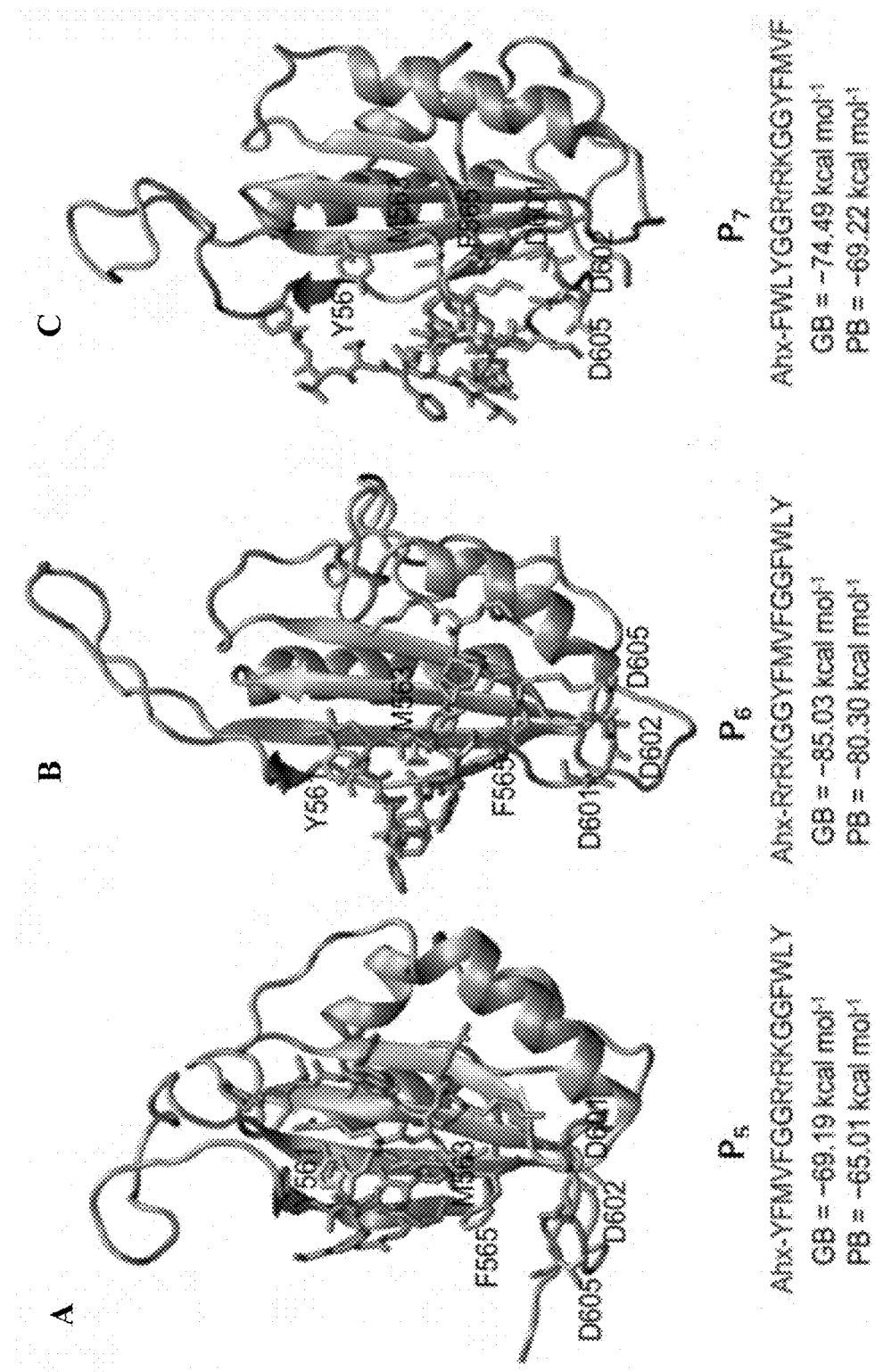
FIG. 23 depicts representative conformations of (A) P$_5$ [-Ahx-YFMVFGGRrRKGGFWLY (SEQ ID NO:5)], (B) P$_6$ [-Ahx-RrRKGGYFMVFGGFWLY (SEQ ID NO:6)] and (C) P$_7$ [-Ahx-FWLYGGRrRKGGYFMVF (SEQ ID NO:7)], with EBNA1 in the MD simulation. All binding energies calculated generalized Born (GB) and Poisson-Boltzmann (PB) values were shown for each designed peptide.
Figure 24:
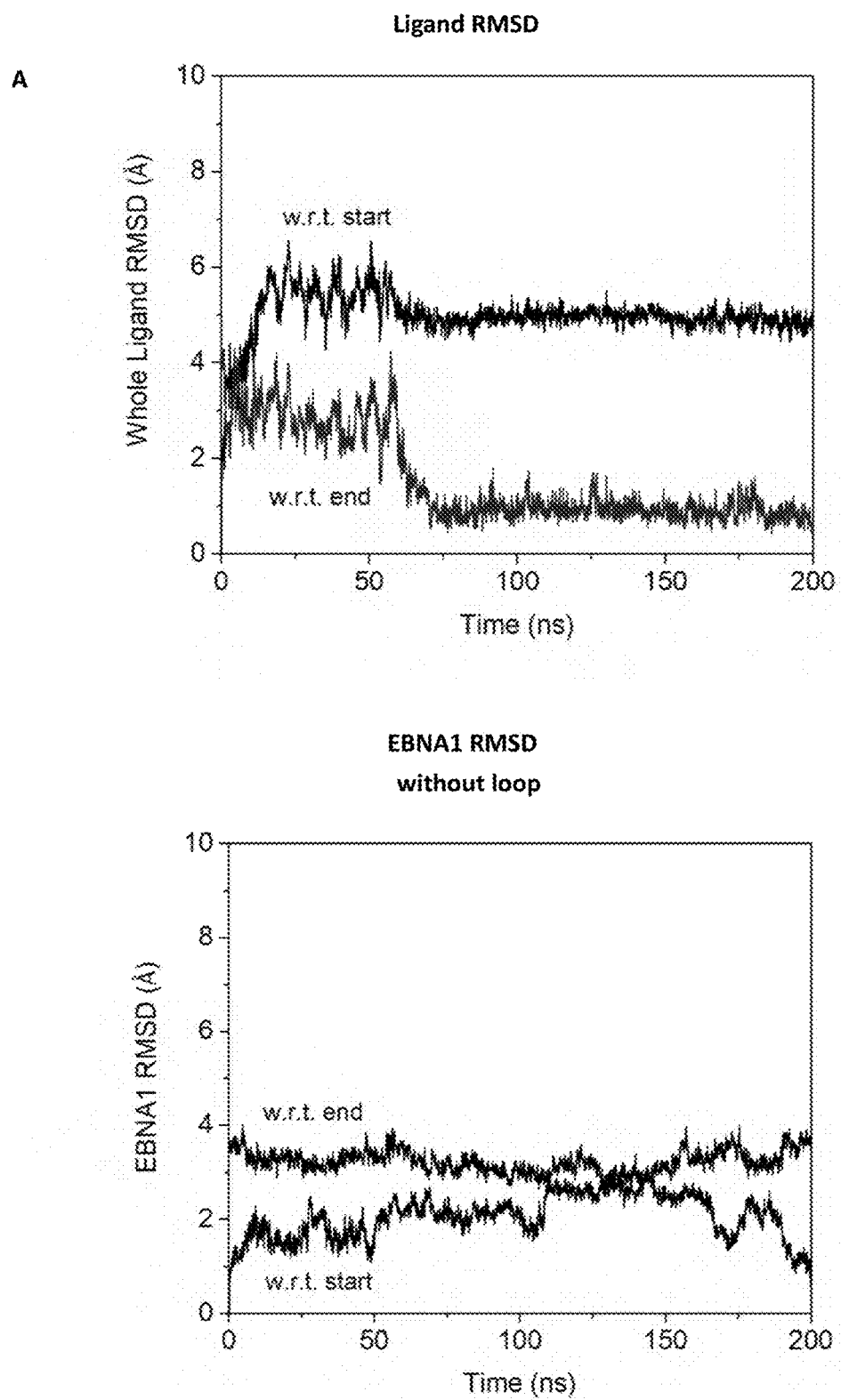
FIG. 24 depicts root-mean-square deviation (RMSD) of atomic positions of protein EBNA1 and designed peptides. The RMSD values of peptides (A) $P_5$, (B) $P_6$ and (C) $P_7$ with EBNA1 in the MD simulation. Black and red line represent the start and end of conformation respectively.
Figure 24:
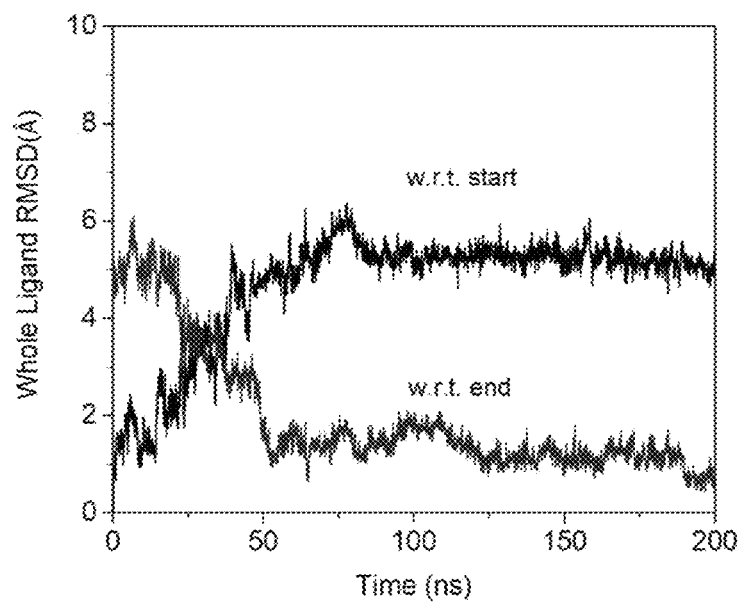
Figure 24:
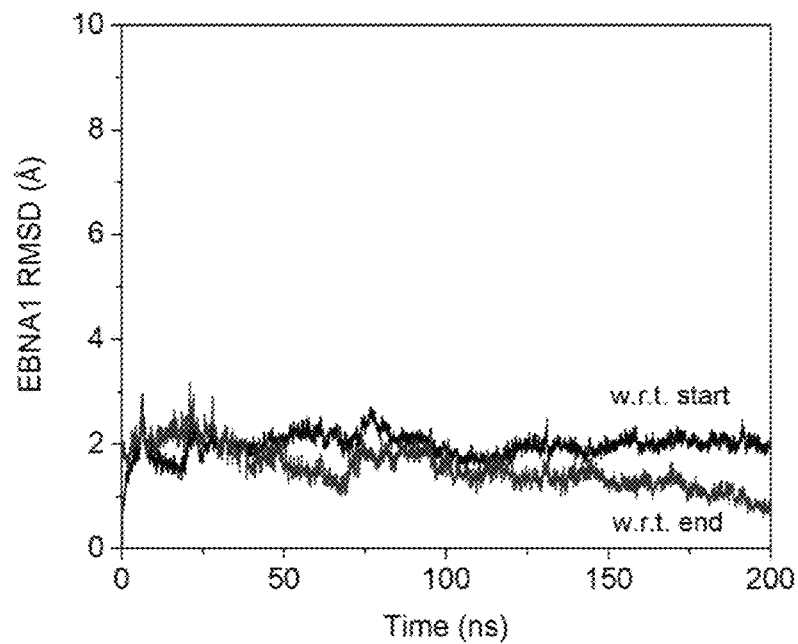
Figure 24:
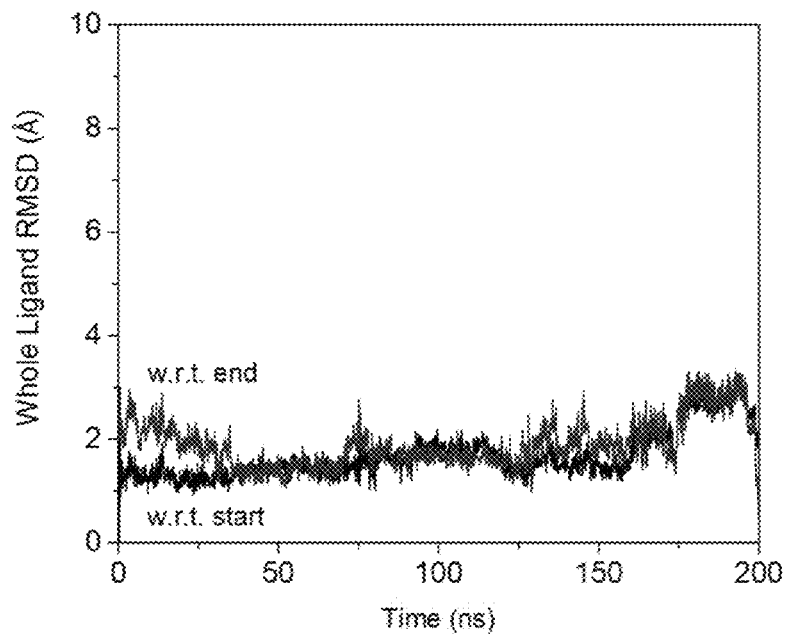
Figure 24:
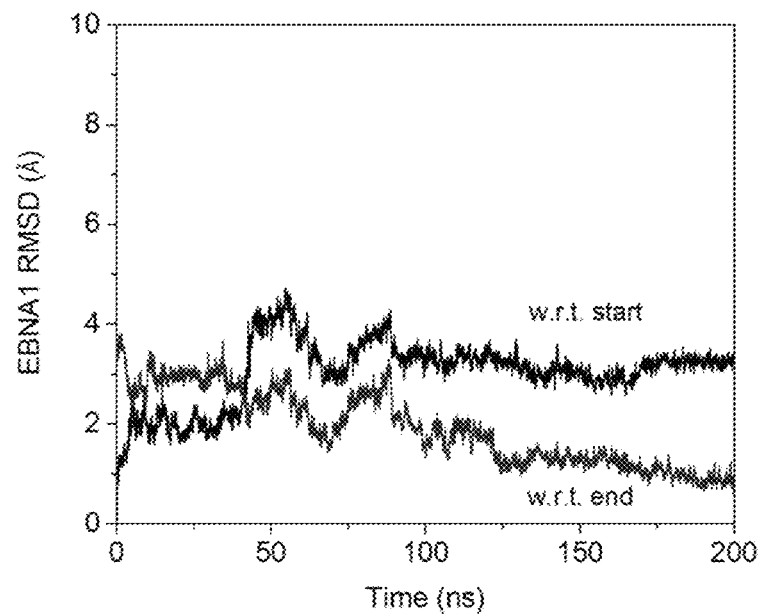
Figure 26:
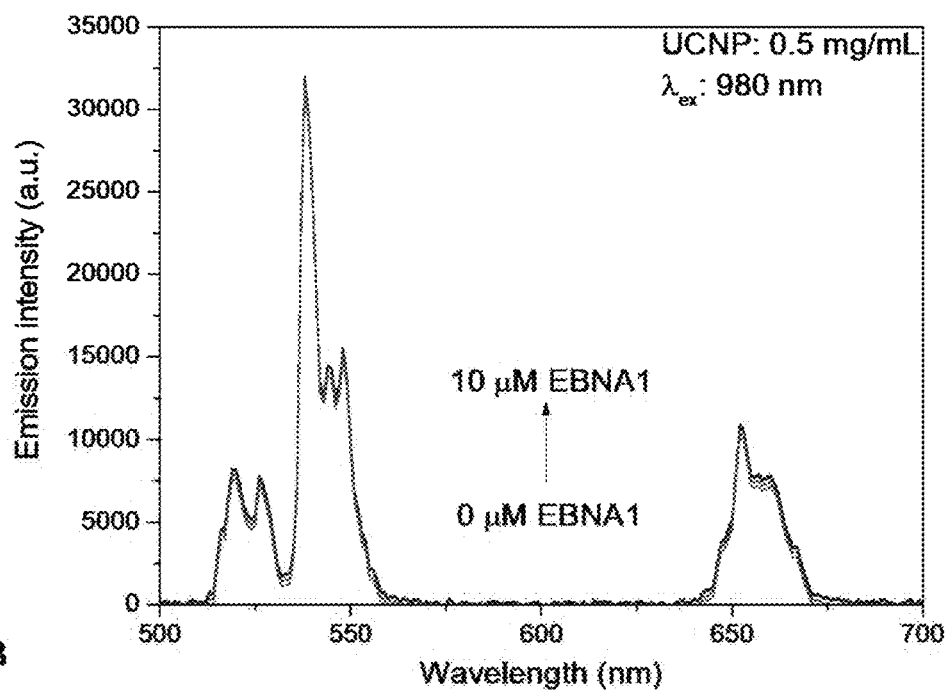
FIG. 26 depicts luminescence titration of UCNP (conc.: 0.5 mg/mL; excitation at 980 nm) towards (A) EBNA1, (B) HSA, (C) BSA, (D) Avidin, (E) NPM and (F) change in emission intensity of UCNP on addition of NPM, HSA, Avidin, BSA and EBNA1.
Figure 26:
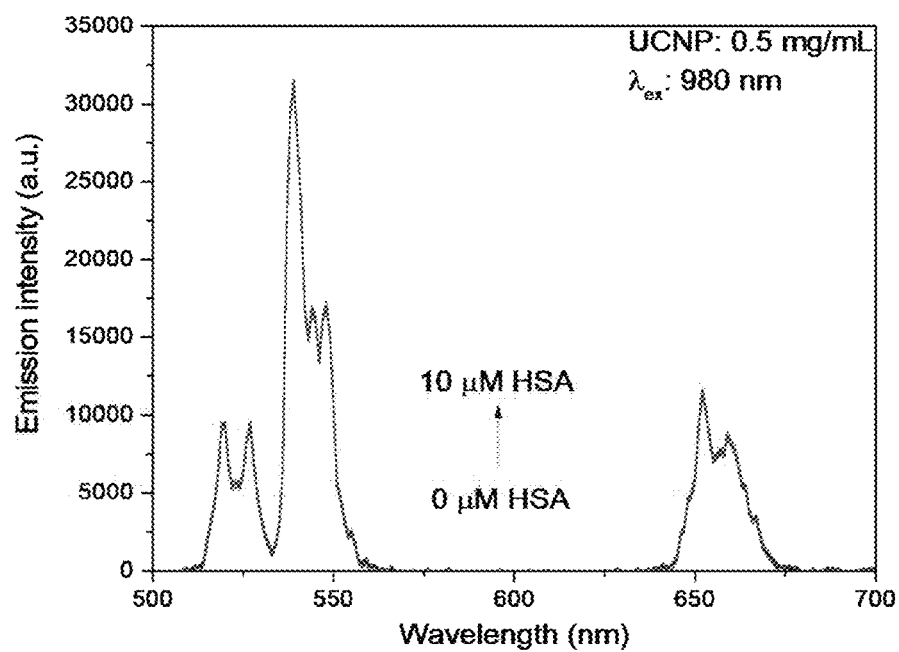
Figure 26:
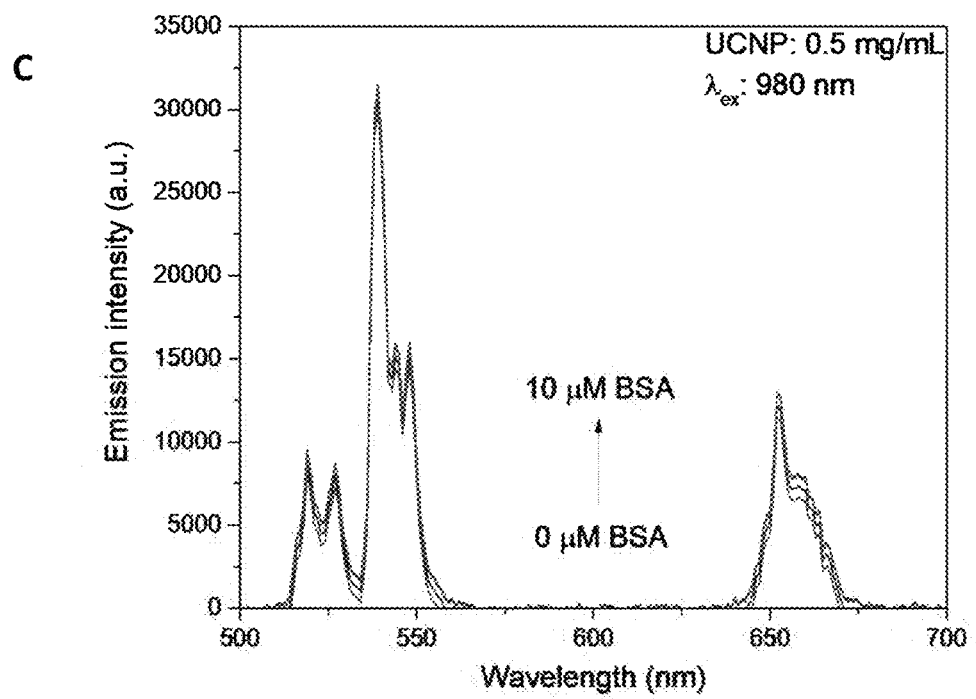
Figure 26:
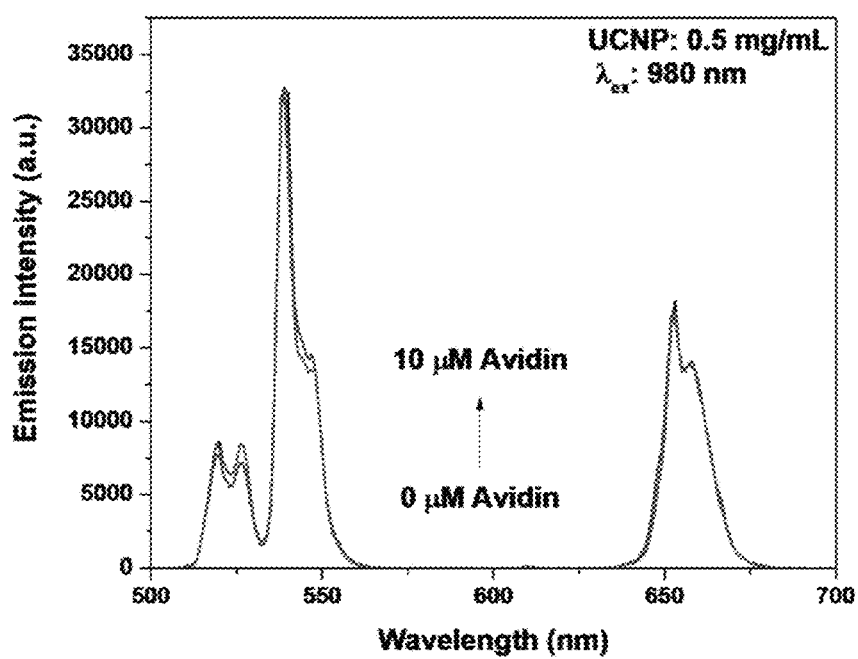
Figure 26:
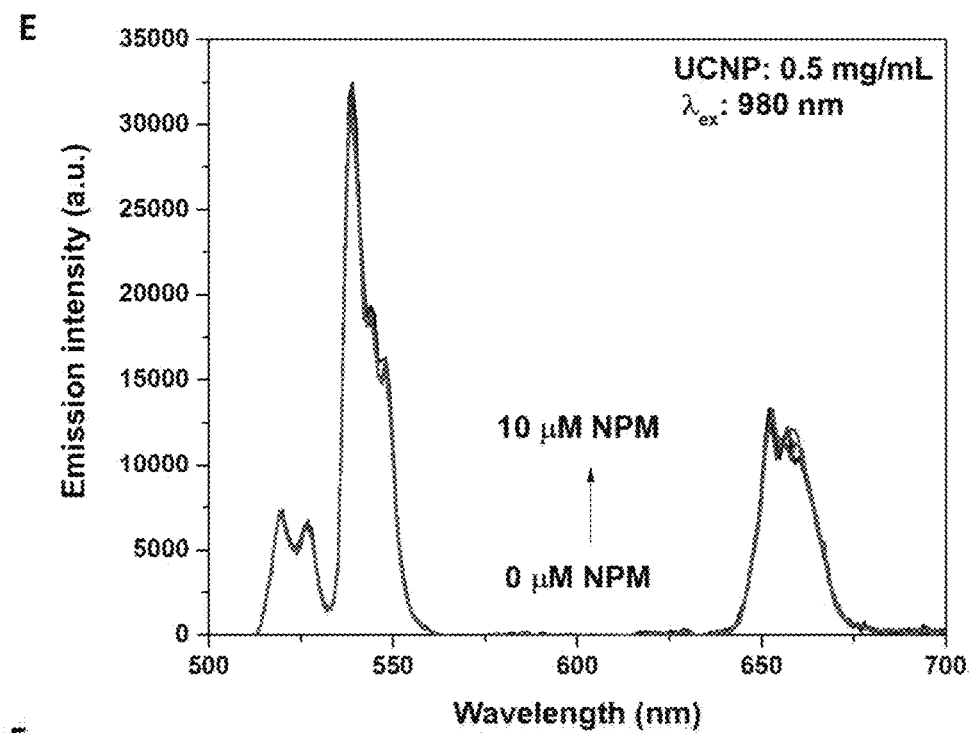
Figure 26:
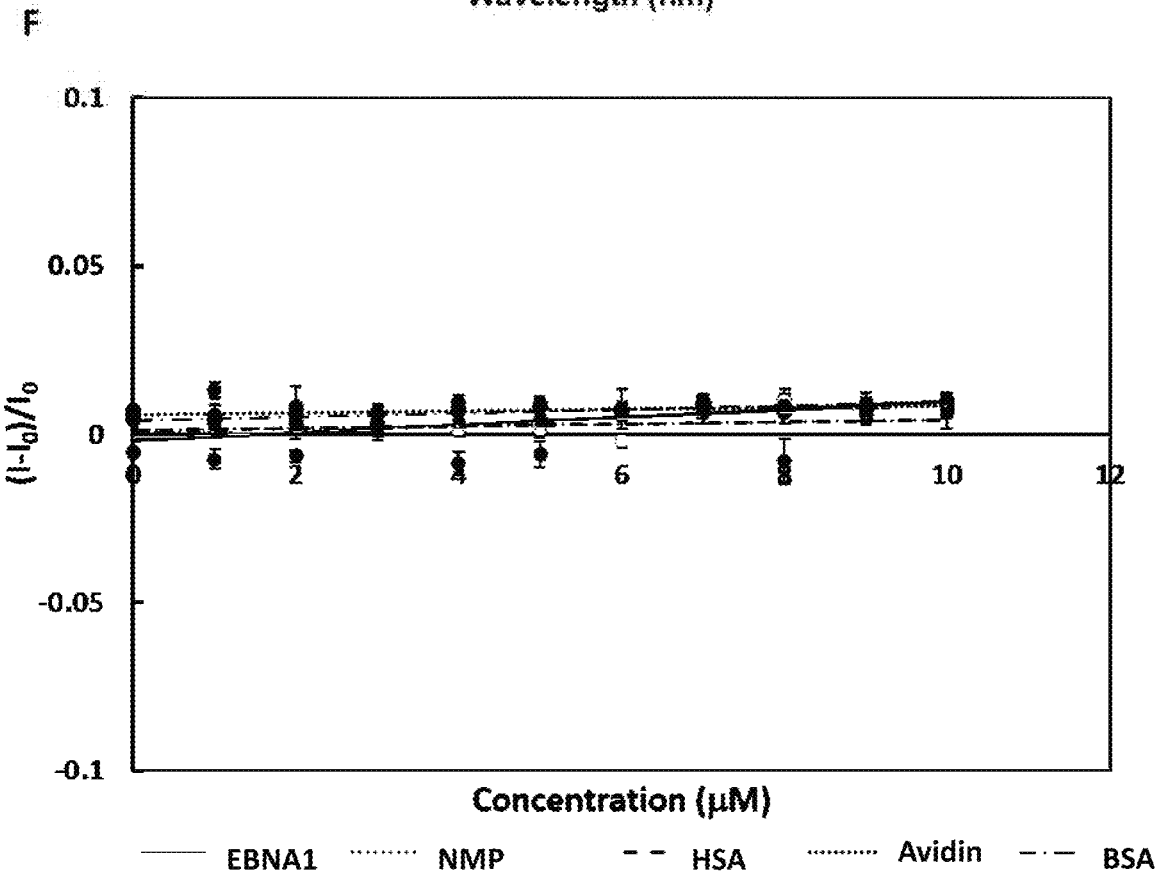
Figure 27:
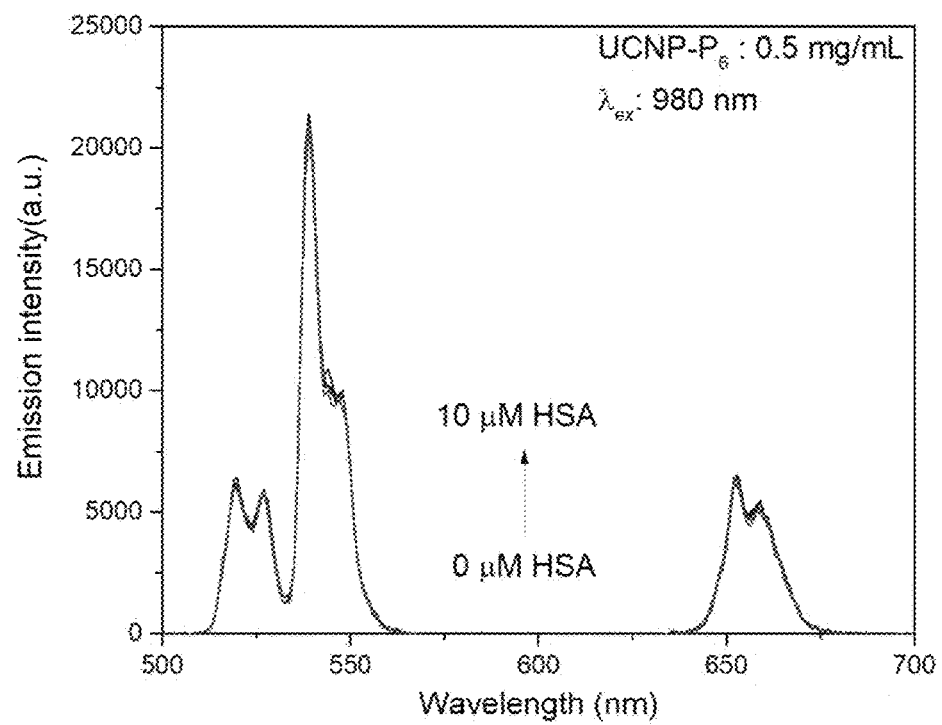
FIG. 27 depicts luminescence titration of UCNP-$P_6$ (conc.: 0.5 mg/mL; excitation at 980 nm) towards (A) HSA, (B) BSA, (C) EBNA1, (D) Avidin, (E) NPM and (F) change in emission intensity of UCNP-$P_6$ on addition of NPM, HSA, Avidin, BSA and EBNA1.
Figure 27:
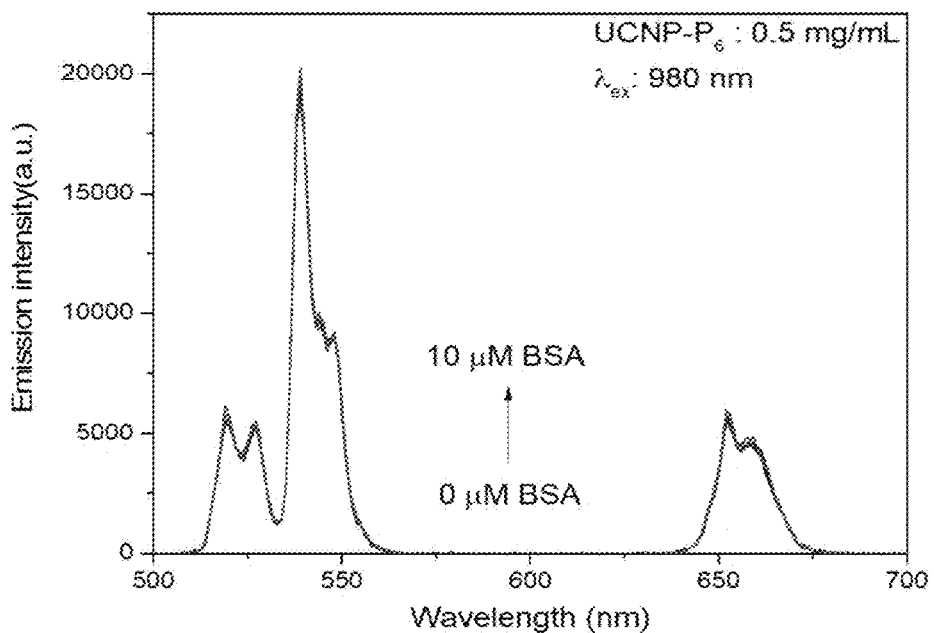
Figure 27:
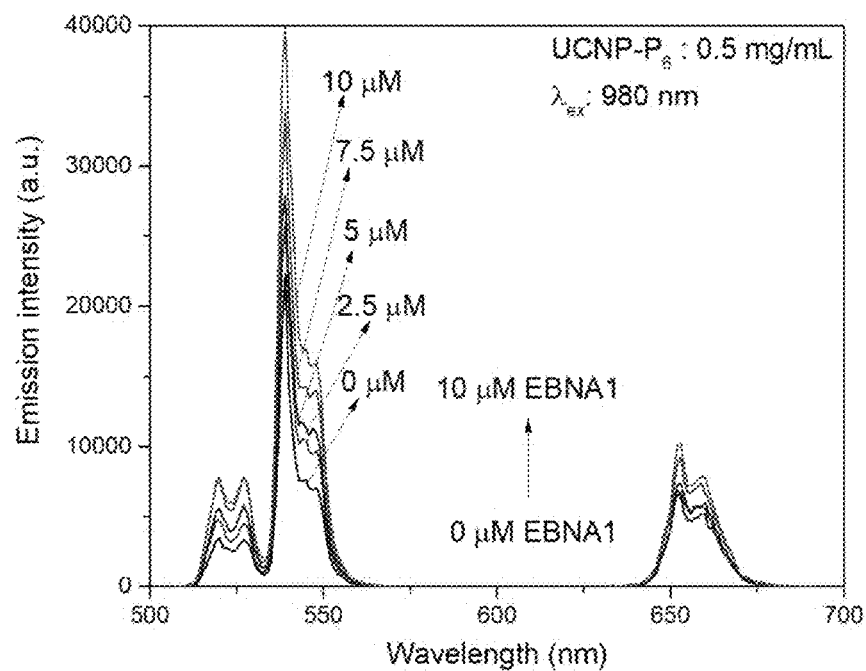
Figure 27:
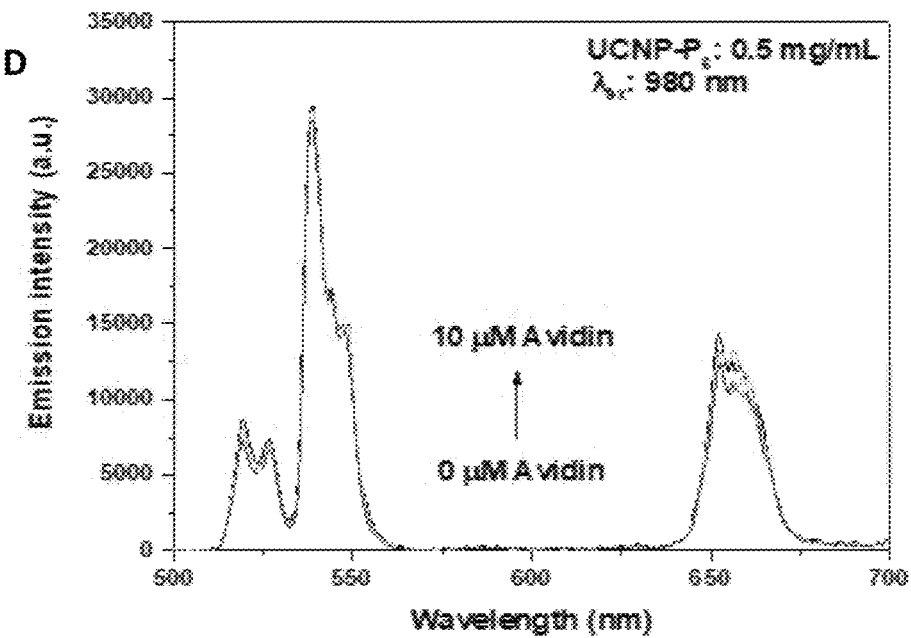
Figure 27:
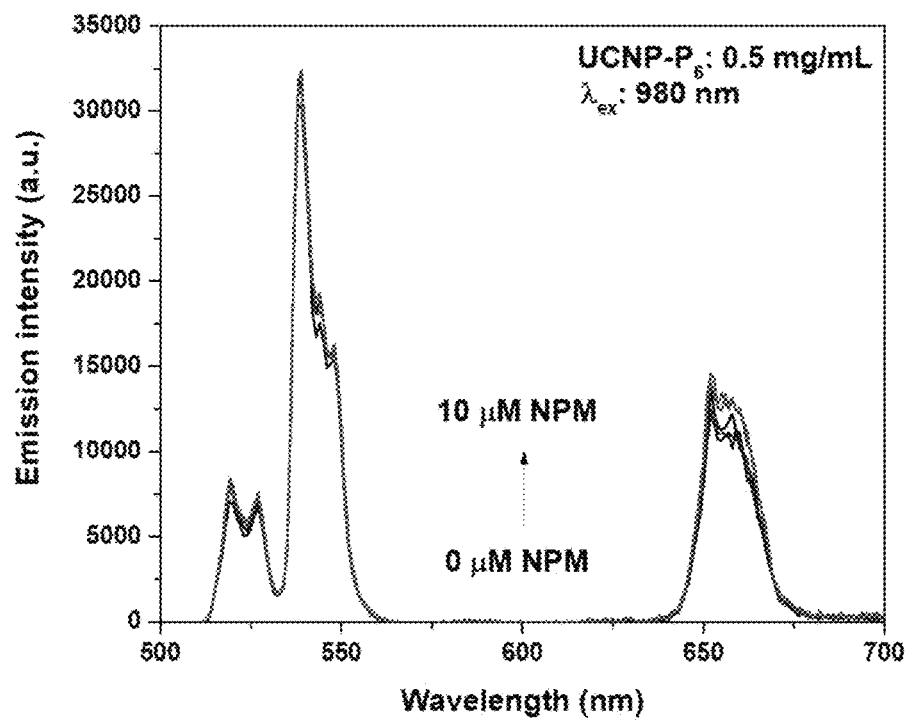
Figure 27:
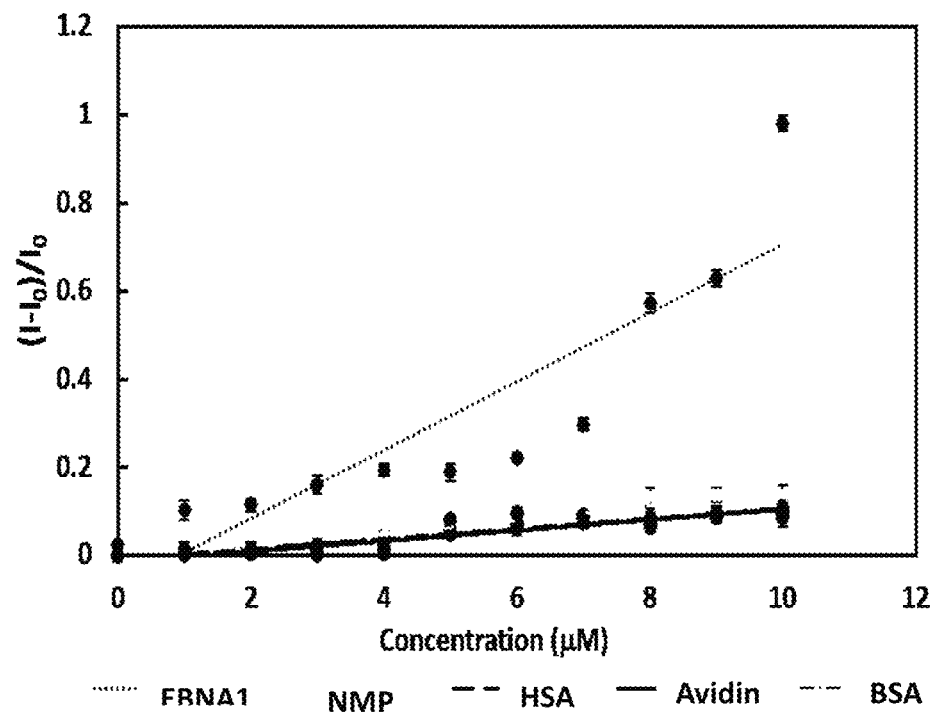
Figure 28:
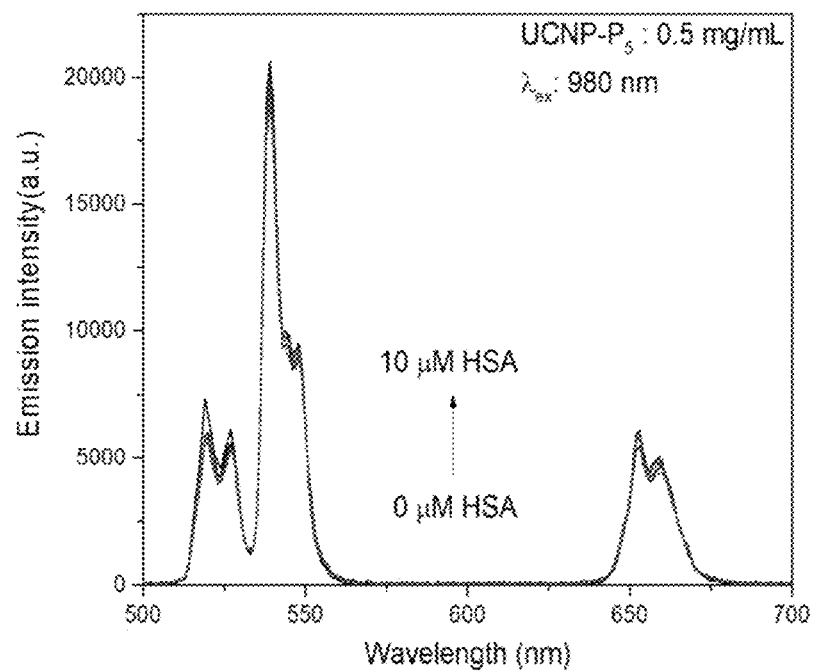
FIG. 28 depicts luminescence titration of UCNP-$P_5$ (conc.: 0.5 mg/mL; excitation at 980 nm) towards (A) HSA, (B) BSA, (C) Avidin and (D) NPM.
Figure 28:
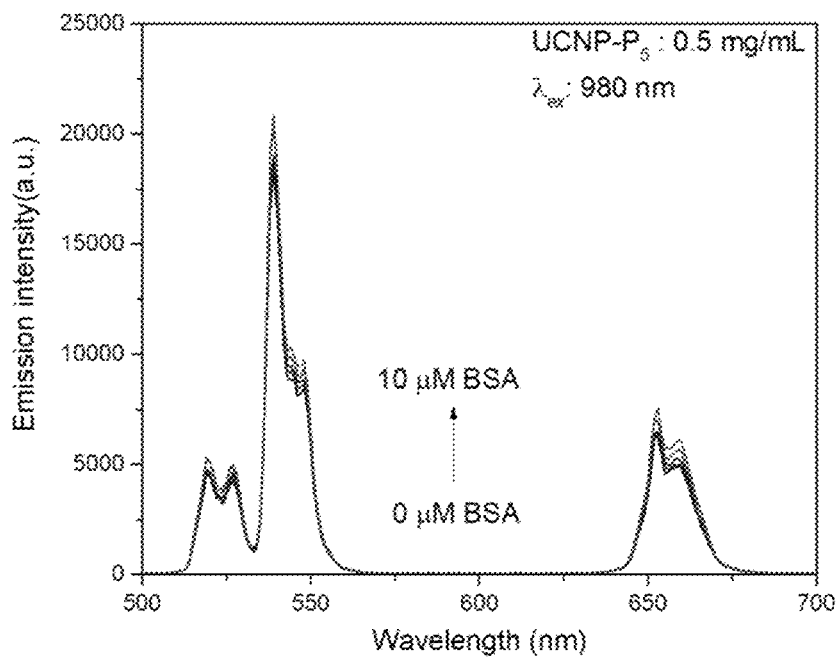
Figure 28:
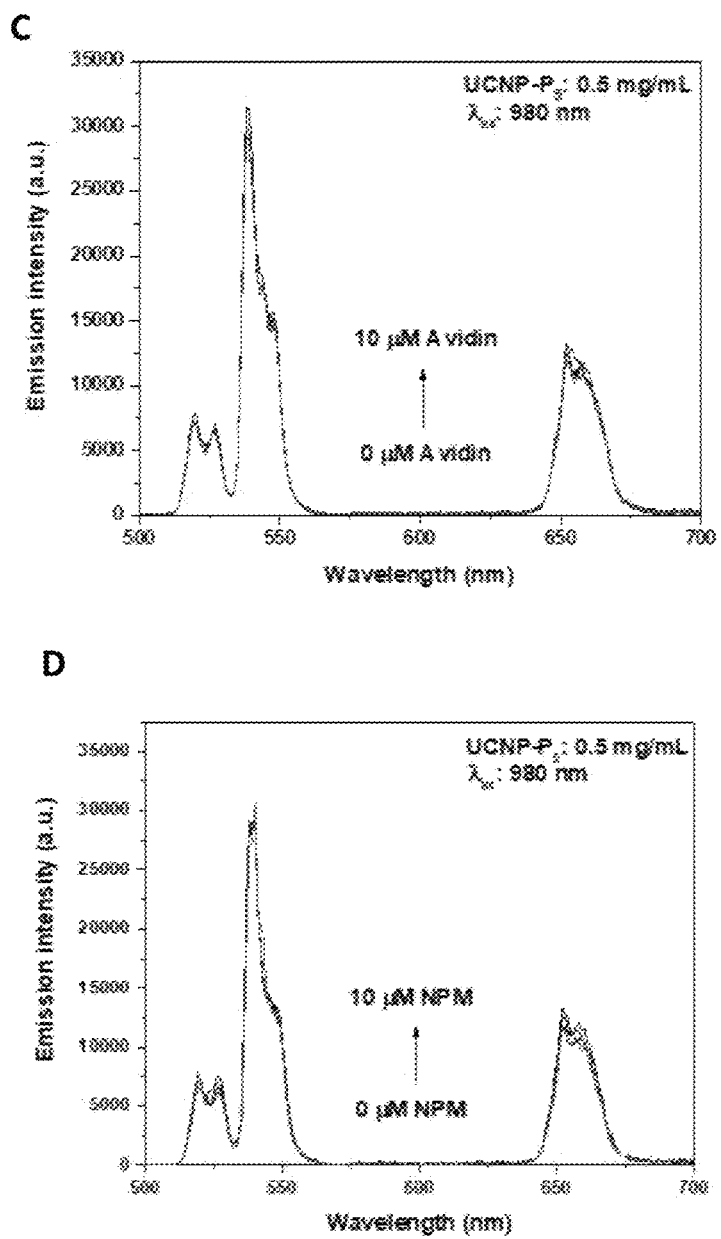
Figure 29:
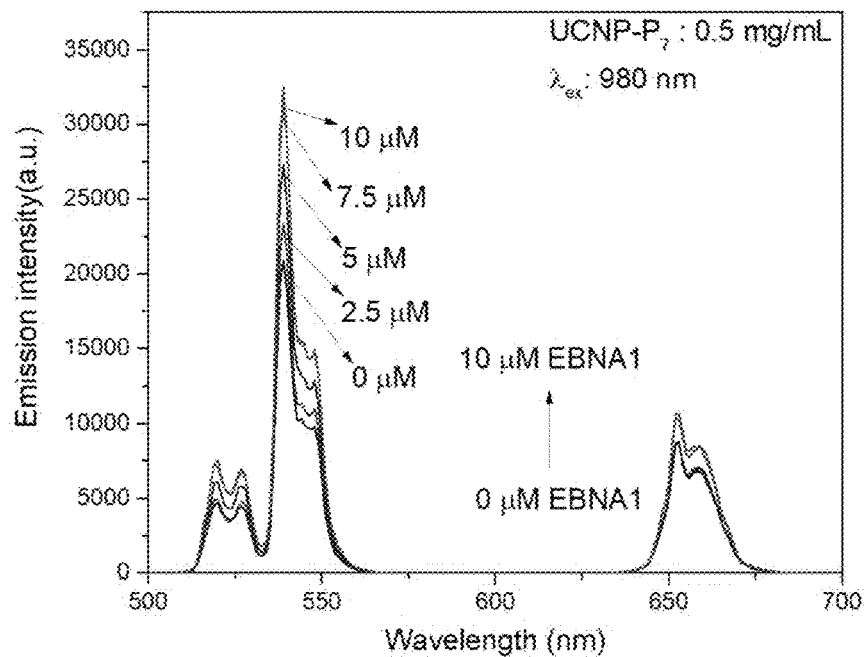
FIG. 29 depicts luminescence titration of UCNP-$P_7$ (conc.: 0.5 mg/mL; excitation at 980 nm) towards (A) EBNA1, (B) HSA, (C) BSA, (D) Avidin, (E) NPM and (F) change in emission intensity of UCNP on addition of NPM, HSA, Avidin, BSA and EBNA1.
Figure 29:
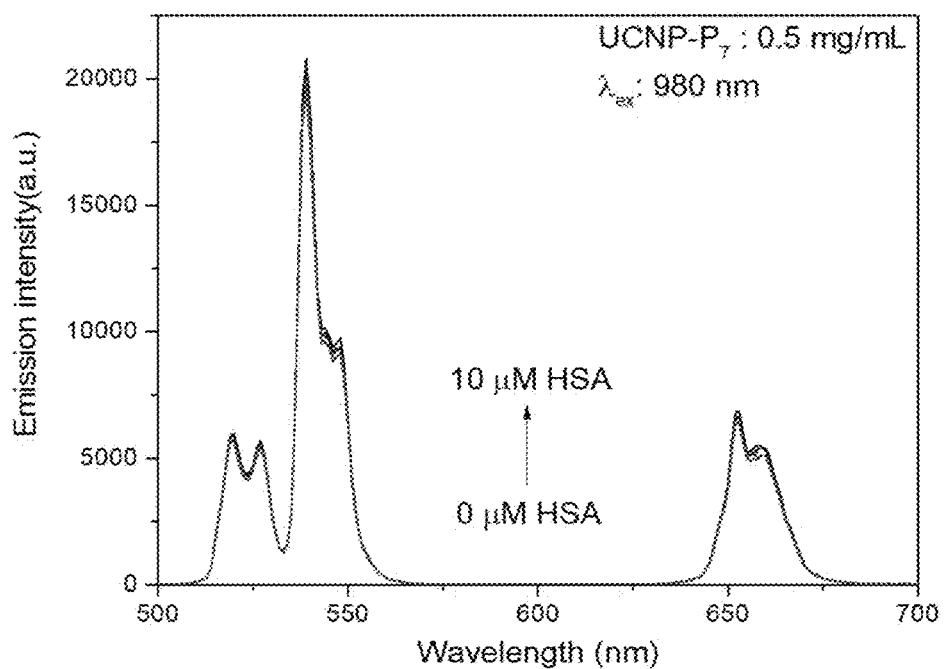
Figure 29:
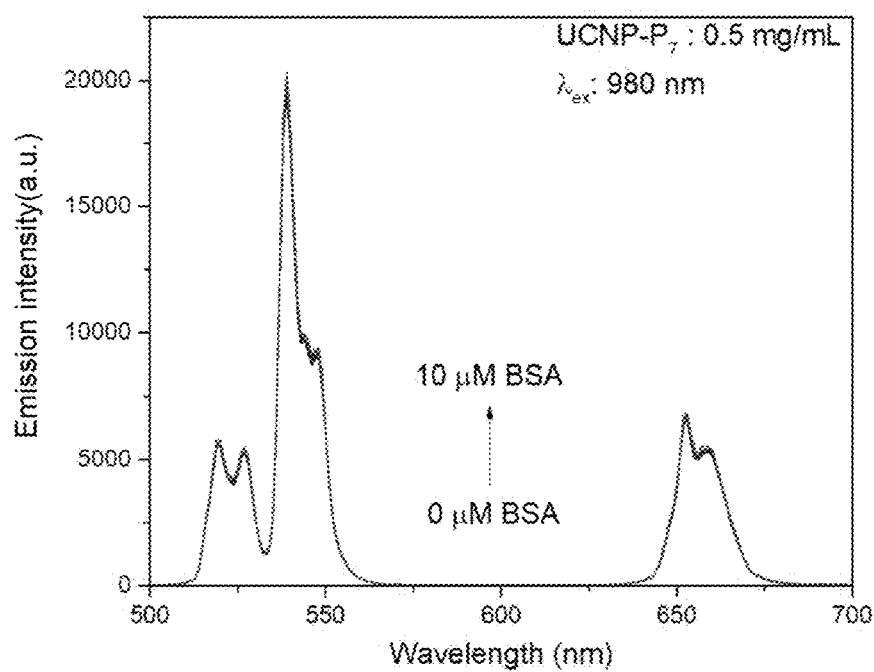
Figure 29:
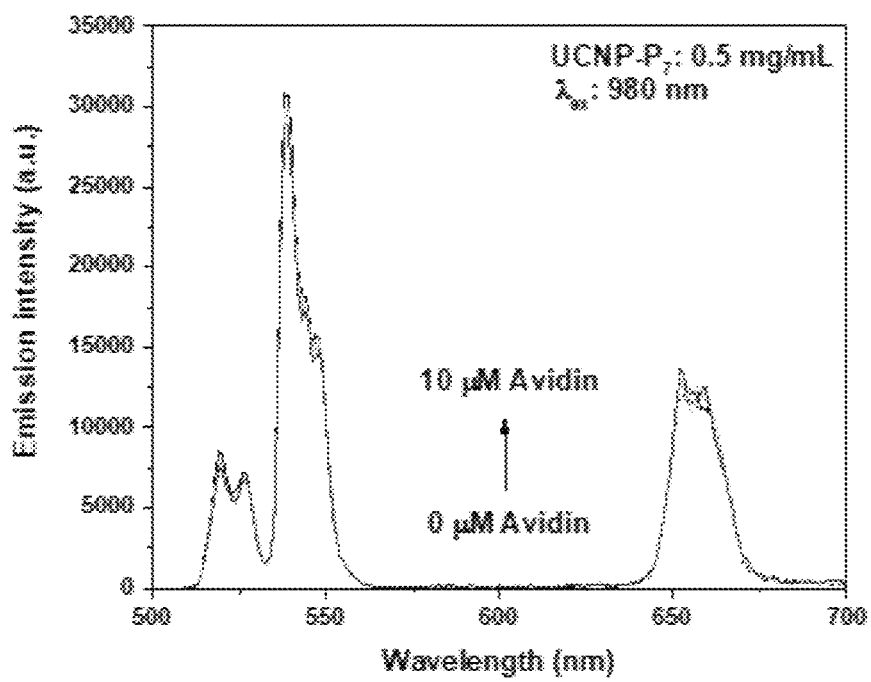
Figure 29:
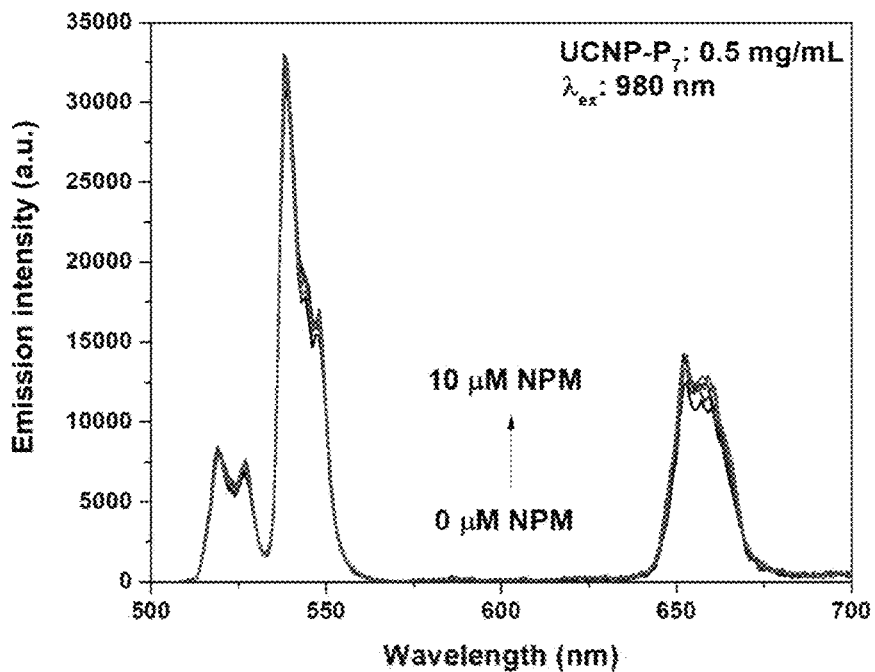
Figure 29:
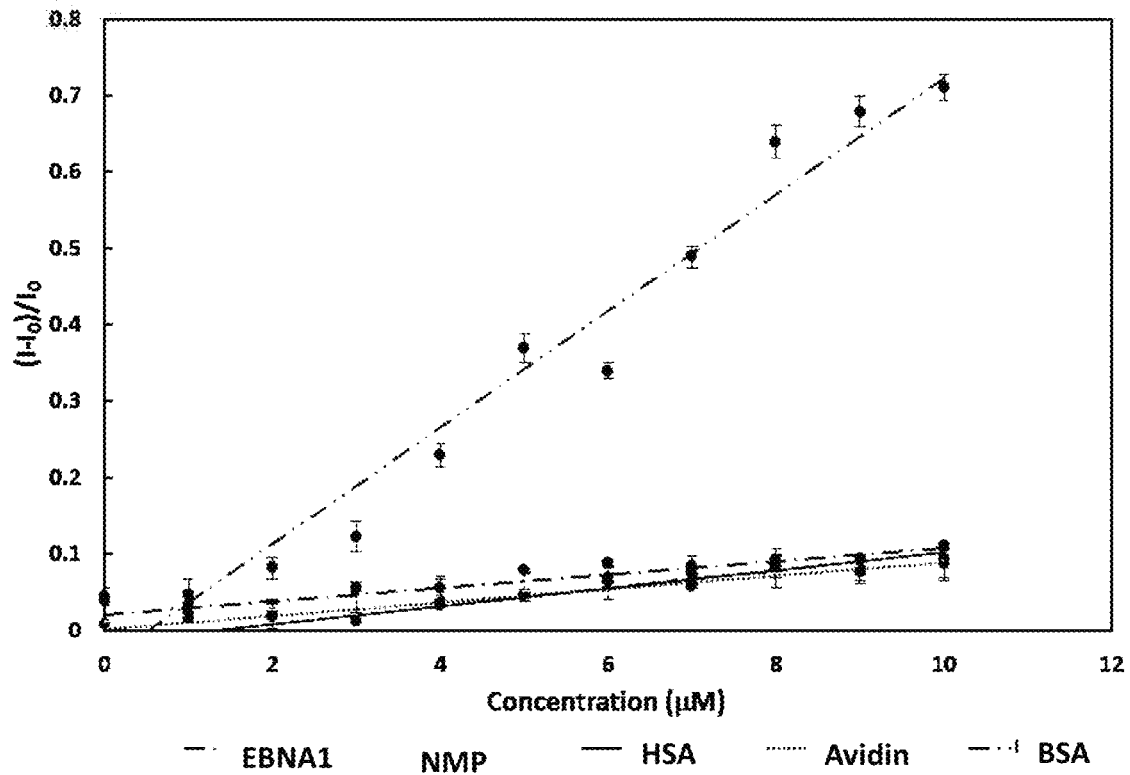

Luminescence titration assays in PBS buffer were conducted with five proteins: BSA, HSA, avidin, NPM and EBNA1 to evaluate the binding affinity of UCNP and UCNP-P$_n$ [n=5, 6 and 7 (SEQ ID NO: 5, 6, 7)]. As shown in FIG. 26, there was nearly no emission difference in UCNP upon the addition of these five proteins; the same was observed for UCNP-P$_n$ [n=5, 6 and 7 (SEQ ID NO: 5, 6, 7)] with the addition of NPM, avidin, HSA and BSA (FIG. 27, FIG. 28 and FIG. 29, respectively). A two-fold enhancement in emission intensity was observed for UCNP-P$_n$ [n=5, 6 and 7 (SEQ ID NO: 5, 6, 7)] upon addition of 10 mM EBNA1 when compared with the emission of UCNP-P$_n$ [n=5, 6 and 7 (SEQ ID NO: 5, 6, 7)] without any additives (FIG. 2C and FIG. 29A). Additionally, the changes in emission intensity of UCNP and UCNP-P$_n$ [n=5, 6 and 7 (SEQ ID NO: 5, 6, 7)] towards EBNA1, BSA, HSA, avidin and NPM are plotted in FIG. 26F, FIG. 2D, FIG. 27F and FIG. 29F, respectively. The results implied that the YFMVF motif (for targeting EBNA1) of the newly designed peptides on the UCNP surface could bind with EBNA1 and induce aggregation between the nanoprobes and EBNA1, hence leading to the emission enhancement. It also indicated that UCNP-P$_n$ [n=5, 6 and 7 (SEQ ID NO: 5, 6, 7)] is highly selective to EBNA1 over NPM, avidin, BSA and HSA, which is consistent with our previous work on UCNP-P$_4$. The results were also supported by molecular dynamics (MD) simulations, which showed that stable RMSD values were obtained for all three peptides binding to the dimerization surface (FIG. 23 and FIG. 24).

EBNA1 dimerization/oligomerization inhibition assays were performed to reveal the ability of interrupting EBNA1 dimerization/oligomerization in the presence of the previous nanoprobe UCNP-P$_4$ and the nanoplatforms in situ. As shown in FIG. 2E, UCNP-P$_4$ and UCNP-P$_n$ [n=5, 6 and 7 (SEQ ID NO: 5, 6, 7)] could hinder EBNA1 dimerization/oligomerization at a low concentration of 0.3 mg/mL, UCNP-P$_4$, UCNP-P$_5$ and UCNP-P$_6$ are able to eradicate all 90 mg EBNA1 dimers and oligomers, showing the strongest inhibitory capacity among all the samples.

The density of EBNA1 dimers was maintained at the same high level after incubation with PBS buffer and UCNP. These results are consistent with the data from luminescence titration assay.

Figure 3:
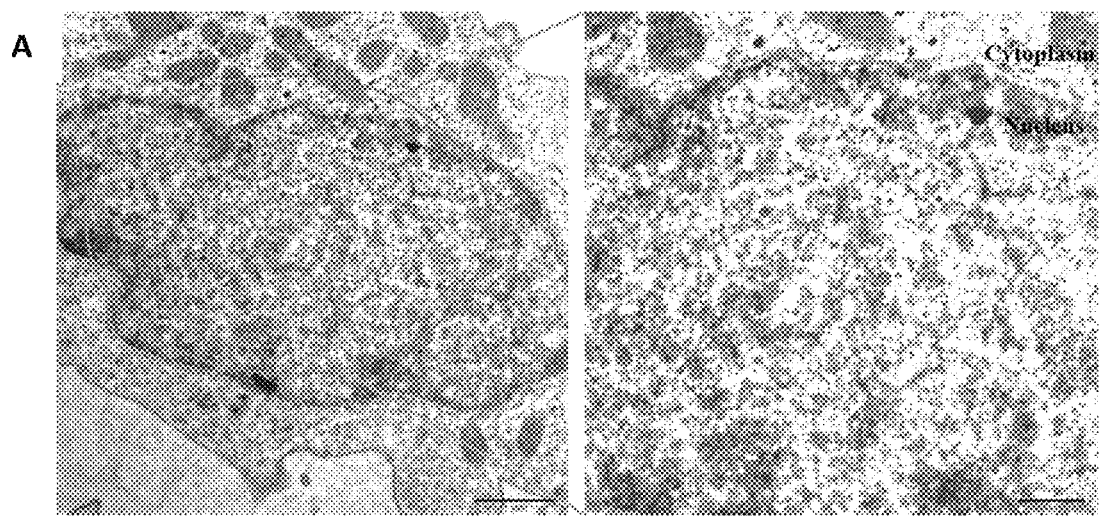
FIG. 3 depicts Bio-TEM images of the localization of (A) UCNP-P$_5$ and (B) UCNP in EBV-infected C666 cells after 24 h treatment.
Figure 3:
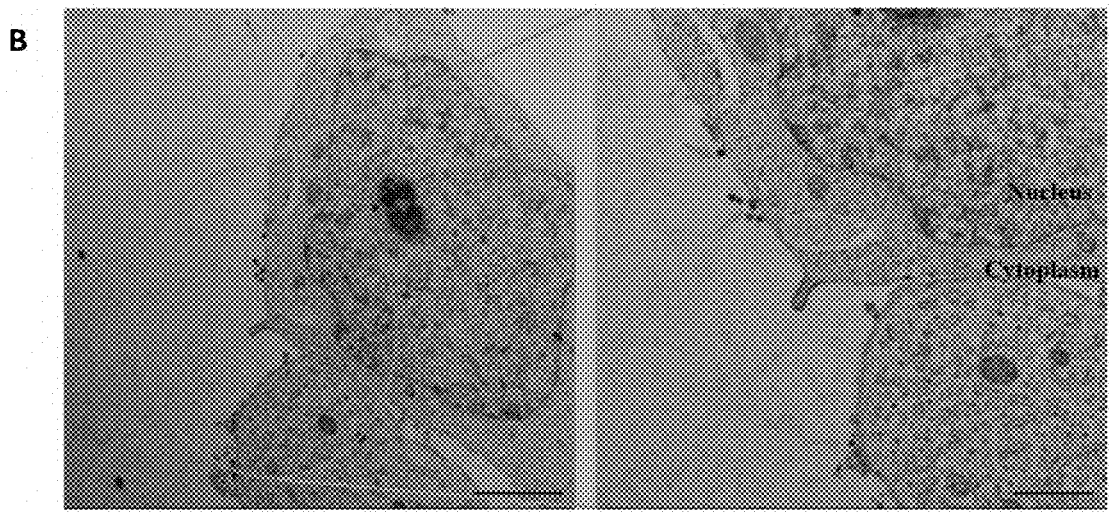

To further evaluate the cellular distribution of the nanoplatforms, bio-TEM analysis was carried out in EBV-infected C666 cells. The cells were harvested, fixed and sectioned for bio-TEM after co-incubation with UCNP and UCNP-P$_5$ for 24 h. UCNP-P$_5$ was mainly located in nucleus, but some was in the cytoplasm, as shown in FIG. 3A. The dual-targeting peptide P$_5$ may endow the initial UCNP with the ability of entering EBV-infected C666 cell nucleus due to its RrRK motif. In sharp contrast, as shown in FIG. 3B, UCNP was located in the cell membrane and cytoplasm, even the majority of them was adjacent to cell membrane and none of them arrived at the nucleus.

Figure 4:
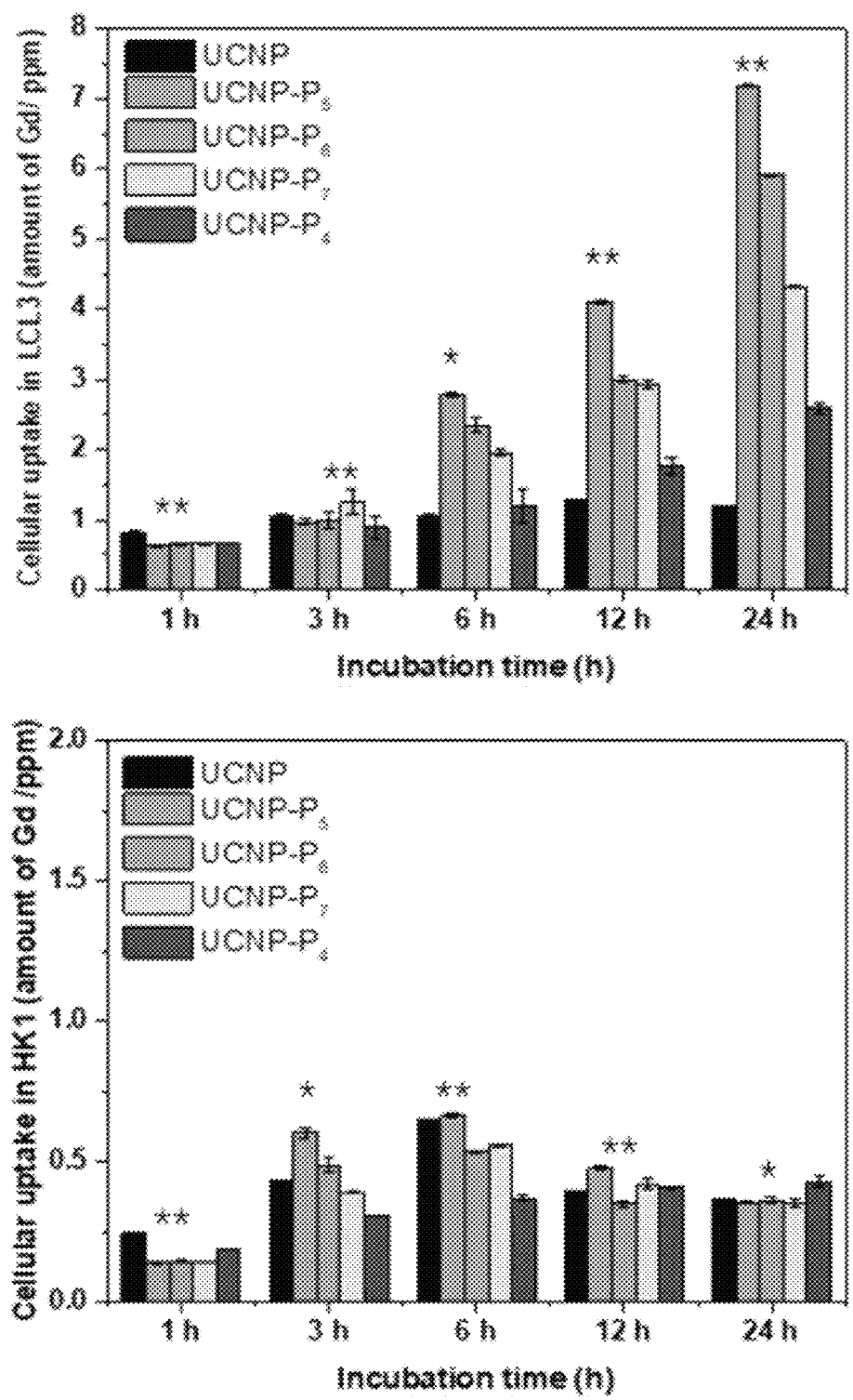
FIG. 4 depicts the cellular uptake profile of UCNP, UCNP-P$_n$ [n=5, 6 and 7 (SEQ ID NO: 5, 6, 7)] and UCNP-P$_4$ by ICP-MS in LCL3, HK1-LMP1, HK1, and C666. Data are presented as mean±standard deviation (SD), n=3, statistically significant differences between various treatments are calculated by Student's t-test (*P<0.05, **P<0.01).
Figure 4:
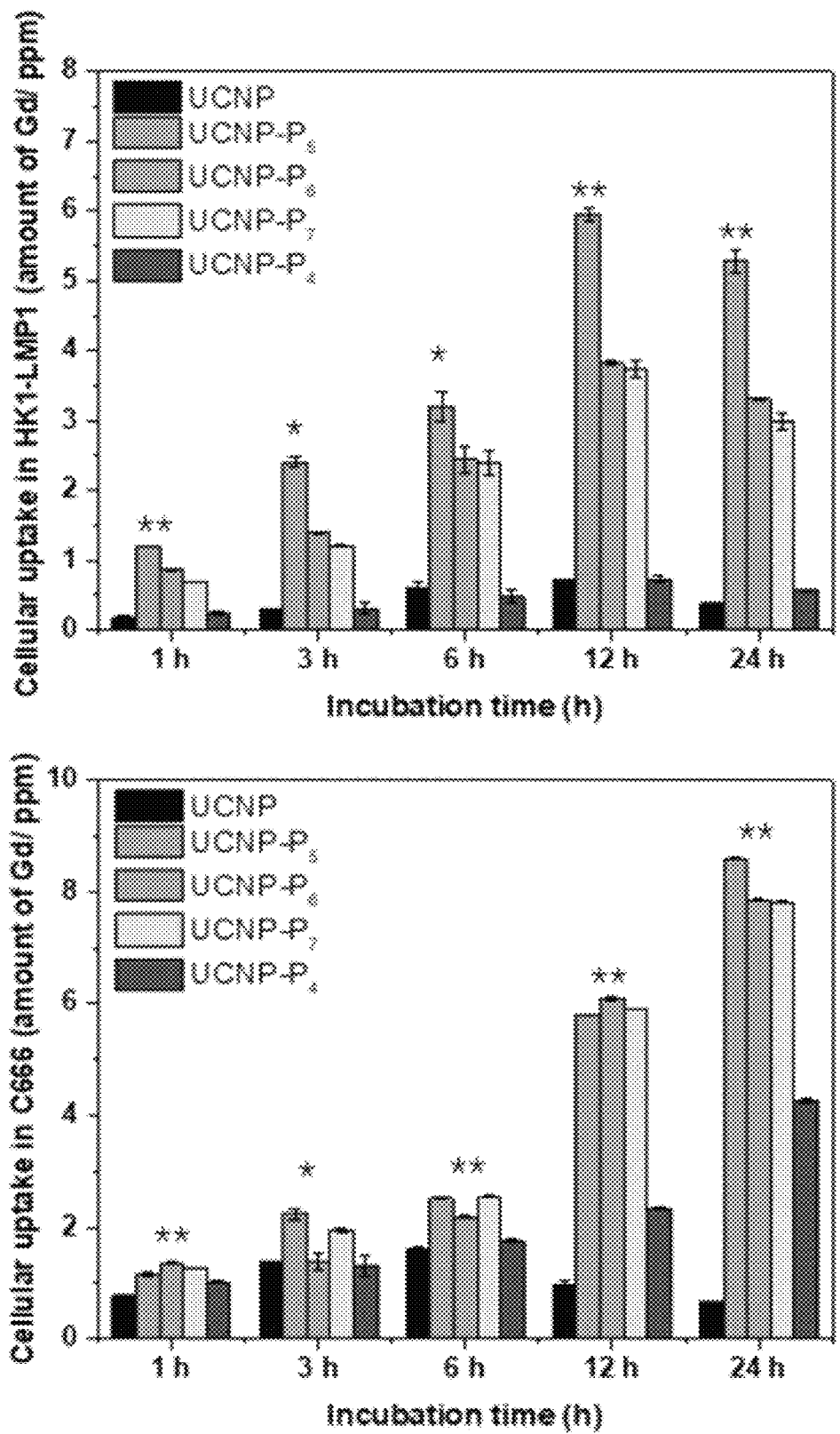

Bio-TEM results demonstrated that nanoplatforms were capable of entering the nuclei of EBV-associated tumor cells. Subsequently, the quantitative distribution and uptake efficiency of nanoprobes in vitro in C666, HK1, HK1-LMP1 and LCL3 cells lines were monitored and investigated by evaluating the lanthanide content originating from the nanoprobes using inductively coupled plasma mass spectrometry (ICP-MS). As shown in FIG. 4, UCNP-P$_5$ exhibited the largest amount of cellular uptake in LCL3, HK-LMP1 and C666 cells. UCNP-P$_6$ and UCNP-P$_7$ showed similar uptake rate among these cell lines due to enhanced cell permeability with hydrophilic peptides and effective peptide-protein binding, indicating interaction between the specific peptides and LMP1 and EBNA1. In addition, the Gd amounts of UCNP-P$_5$ is over twice the amount of old nanoprobes UCNP-P$_4$ in LCL3 and C666 cell lines after 24 h incubation time, which demonstrated that the new generation of nanoprobes exhibited the extraordinary high cellular uptake and accumulation inside EBNA1-positive cells and LMP1-positive cells compared with UCNP-P$_4$, contributed by the dual-EBNA1/LMP1-targeting ability. For the uptake analysis using the HK1 and HK1-LMP1 cell pair, the uptake of UCNP-P$_5$ was ~ two-fold higher than UCNP-P$_6$ and UCNP-P$_7$, while negligible low signals were observed for all nano-compounds in HK1 cells. This indicated that the location of the C-terminal FWLY motif is critical for the uptake of UCNP-P$_5$, and its uptake is LMP1-dependent. The Gd uptake amount in UCNP among all the cell lines is much lower than other nanoprobes because there are no specific peptides coated on the UCNP, hence, UCNP cannot attach to and accumulate in EBV-positive or LMP1-positive cells selectively.

Figure 32:
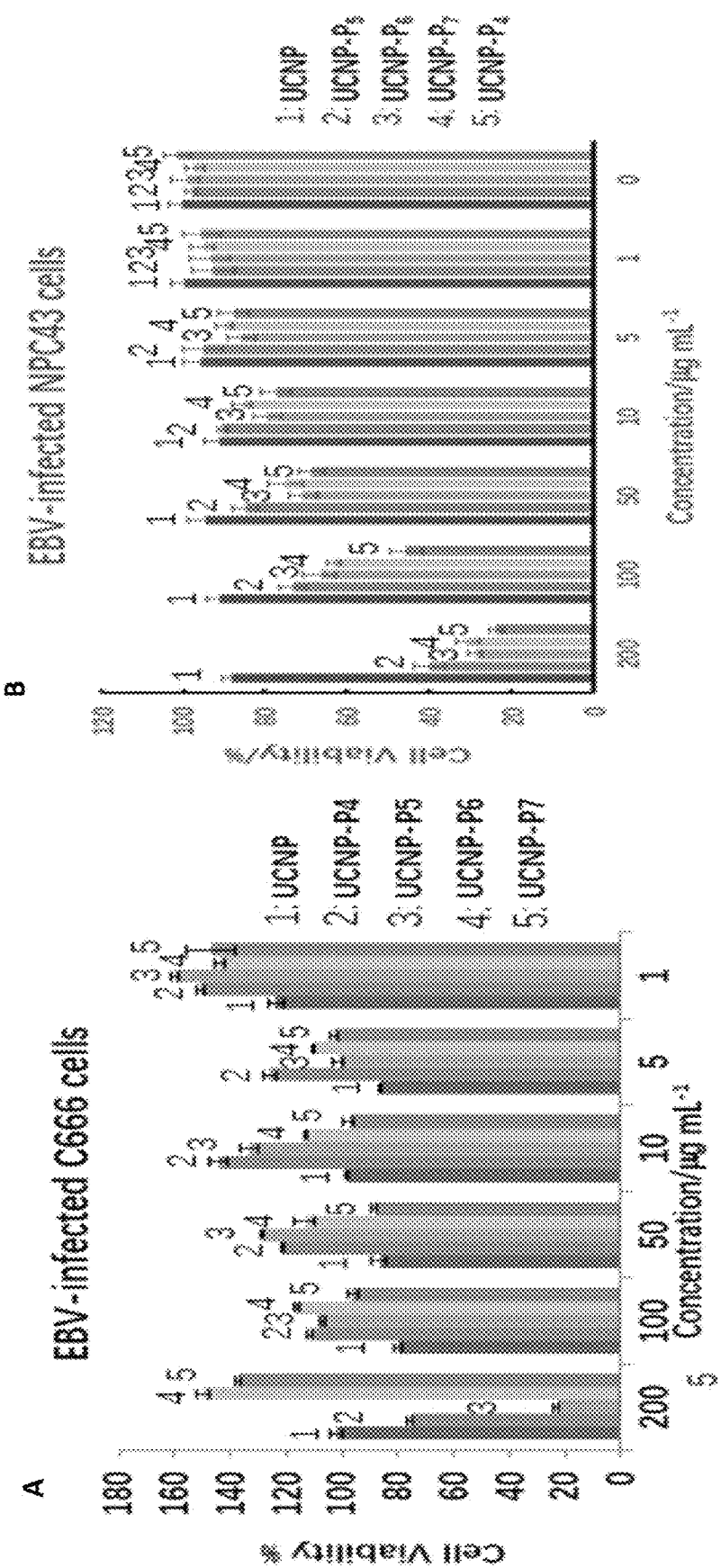
FIG. 32 depicts cytotoxicity assay of UCNP, UCNP-$P_n$ [n=5, 6 and 7 (SEQ ID NO: 5, 6, 7)], UCNP-$P_4$ on (A) EBV-infected C666 cells, (B) EBV-infected NPC43 cells, (C) LMP1 positive Raji cells and (D) LMP1 positive LCL3 cells were assayed (incubation time: 24 hours). (E) EBV-infected C666 cells (incubation time: 5 days).
Figure 32:
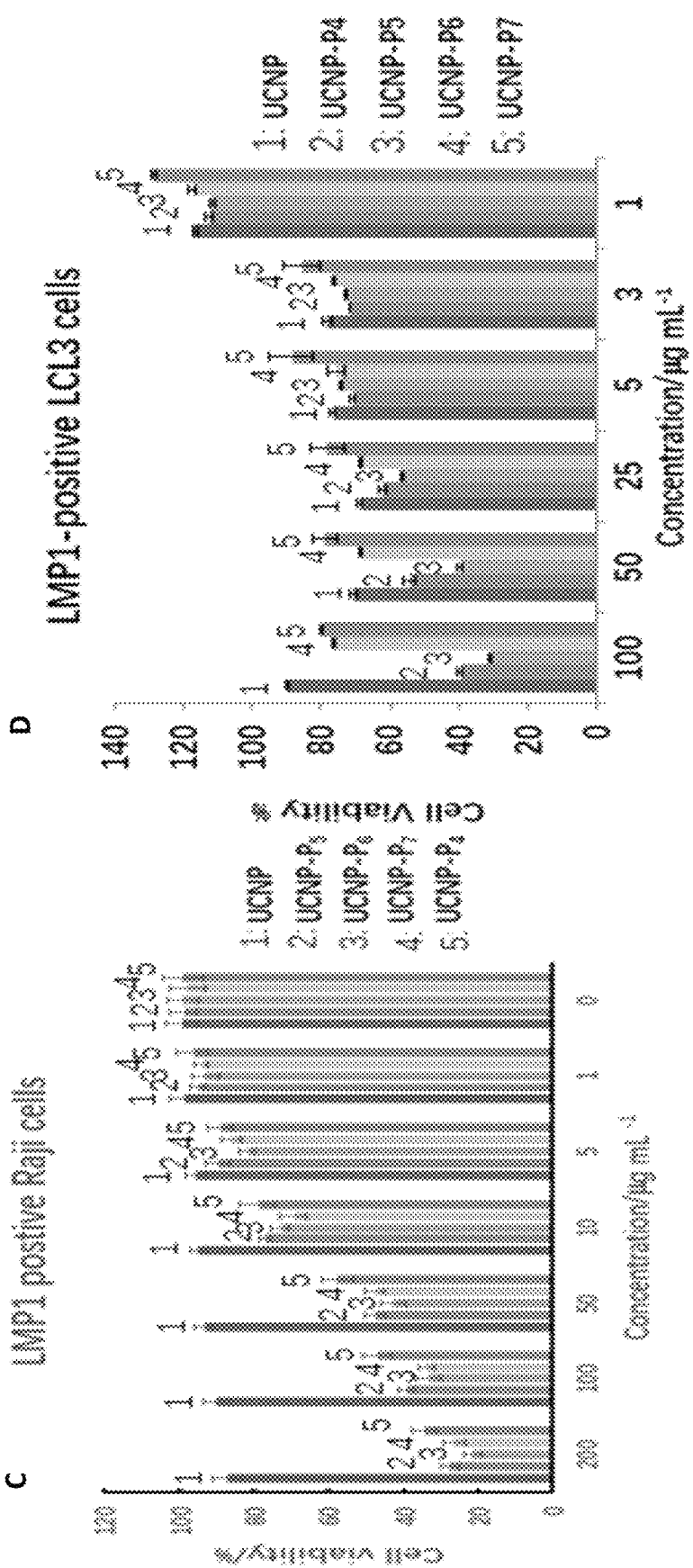
Figure 32:
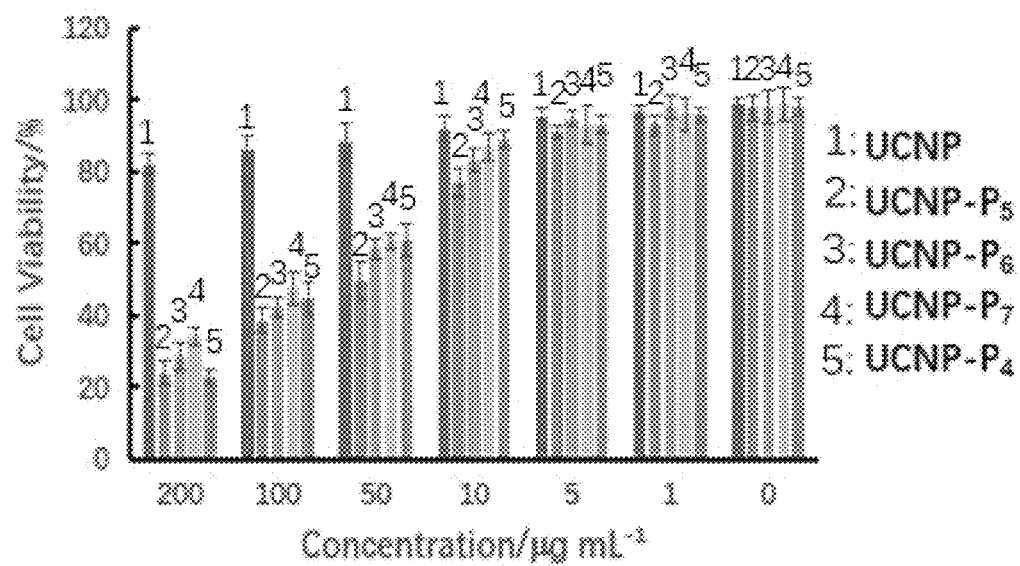
Figure 33:
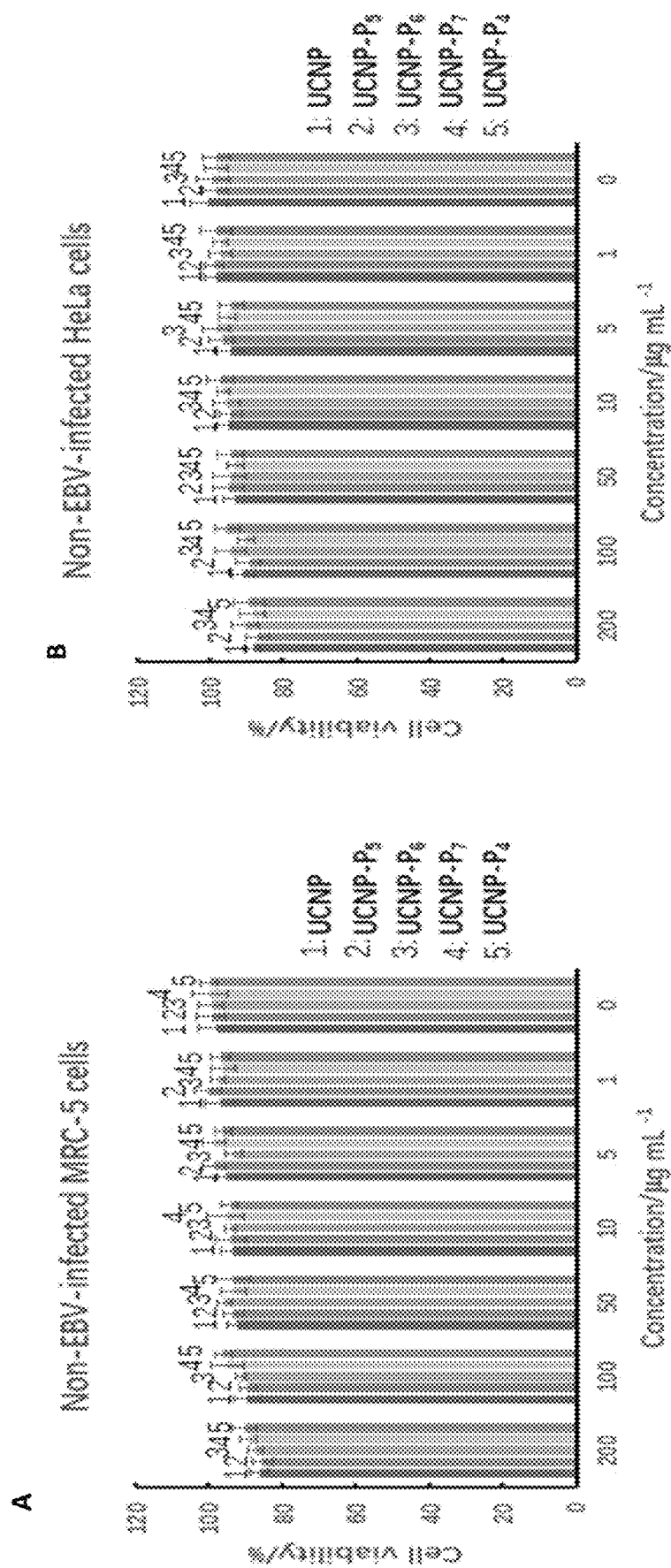
FIG. 33 depicts cytotoxicity assay of UCNP, UCNP-$P_n$ [n=5, 6 and 7 (SEQ ID NO: 5, 6, 7)], UCNP-$P_4$ on (A) EBV-negative MRC-5 cells, (B) EBV-negative HeLa cells, (C) LMP1 negative HK1 cells and (D) LMP1 positive HK1-LMP1 cells were assayed (incubation time: 24 hours).
Figure 33:
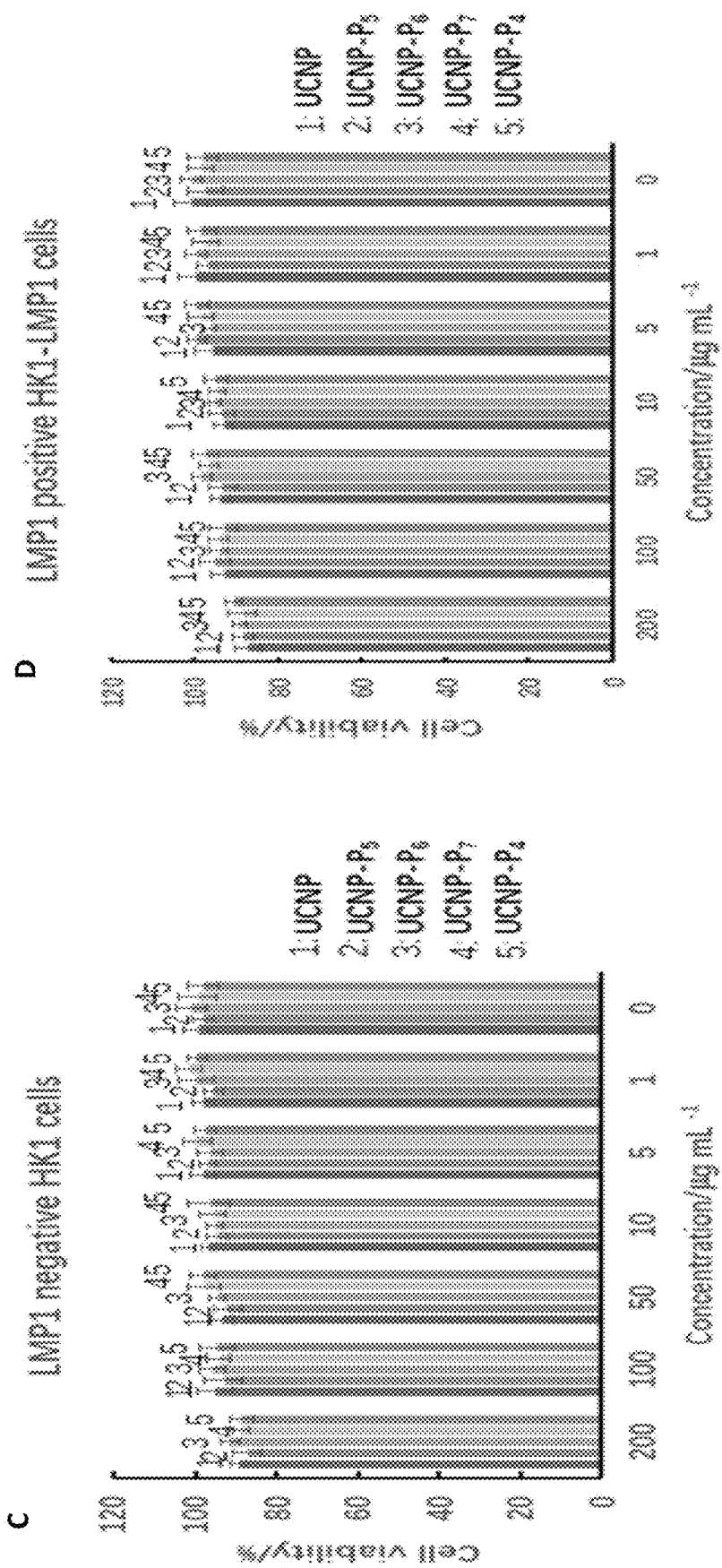

The inhibitory effects of the novel nanoprobes on both EBV-infected cancer cells and non-EBV-infected cancer cells were investigated by MTT assays to test the cell viability. The cytotoxic assays were performed in EBV-positive C666 and NPC43 cells, LMP1-positive LCL3 and Raji cells, and the LMP1-positive and -negative HK1 cell pair. HK1, MRC-5 and HeLa cell lines are EBV-negative and they serve as negative controls. All the cell lines applied in this study are listed in Table 3. The MTT cell viability assays of P$_n$ [n=5, 6 and 7 (SEQ ID NO: 5, 6, 7)] were firstly performed, as shown in FIG. 30 and FIG. 31. The results revealed high cytotoxicity among EBV-positive cells (C666, and NPC43) and LMP1-positive cells (LCL3) when compared with EBV-negative cell lines (MRC-5, HeLa, HK1). In addition, UCNP-P$_4$, EBNA1-specific peptide coated UCNPs was included as control group, so the ability of inhibiting EBV-related cancer cells can be directly compared with UCNP-P$_n$ [n=5, 6 and 7 (SEQ ID NO: 5, 6, 7)]. As shown in FIG. 32 and FIG. 33, UCNP-P$_6$ exhibits the strongest inhibitory effect in all EBV-positive cells and LMP1-positive cells after 24 h incubation except the HK1-LMP1 cell line. This might be due to the fact that the recipient HK1 cells are not dependent on the LMP1-induced NF-kB signal for cell growth, a property selected as its EBV genome was previously lost during long-term culture. P$_n$ [n=5, 6 and 7 (SEQ ID NO: 5, 6, 7)] did not cause any significant cytotoxicity in the EBV-negative cell lines (HK1, MRC-5 and HeLa) even at a high dosage of 200 mg/mL. In addition, the IC$_{50}$ values of UCNP-P$_5$ in EBV-positive cell lines C666 and NPC43 (C666, $IC_{50}$=37 mg/mL; NPC43, $IC_{50}$=38 mg/mL), LMP1-positive LCL3 ($IC_{50}$=19 mg/mL) are much lower than those in EBV- and LMP1-negative HK1 cells ($IC_{50}$=1027 mg/mL), EBV-negative HeLa ($IC_{50}$=1086 mg/mL) and MRC-5 ($IC_{50}$=1280 mg/mL) cells. Similar results were observed with UCNP-$P_5$ and UCNP-$P_7$, demonstrating the selectivity of the newly designed dual-targeting protein-specific peptides on UCNP-$P_n$ [n=5, 6 and 7 (SEQ ID NO: 5, 6, 7)] and pH-responsive linkers which facilitate the delivery of the peptides towards EBV-associated cancer cell lines, thereby verifying that UCNP-$P_n$ [n=5, 6 and 7 (SEQ ID NO: 5, 6, 7)] can selectively kill EBV-infected carcinoma cells but remain relatively nontoxic to non-EBV-infected tumor cells.

TABLE 3

Summary of all cell lines used.

|  | EBNA1(+) | LMP1(+) | Cell lines |
|---|---|---|---|
| EBV(+) cells | √[a] | √ √ | LCL3, Raji |
|  | √ √[b] | √ | C666, NPC43 |
| EBV(−) cells | x[c] | √ √ | HK1-LMP1 |
|  | x | x | HK1, HeLa, MRC-5 |

[a](Positive);
[b](Highly positive);
[c](Negative)

The $IC_{50}$ (half inhibitory concentration) values of EBNA1-positive and LMP1-positive cells are summarized for each sample in Table 4. Notably, these results are consistent with our previously reported probes $L_2P_4$, UCNP-$P_4$ and $ZRL_5P_4$, which showed significant inhibitory effect on EBV-infected cell lines. More importantly, the results from molecular dynamics (MD) simulations suggested that the binding affinity of $P_6$ with EBNA1 is higher than $P_5$. However, better uptake in vitro of UCNP-$P_5$ is observed (FIG. 4). Therefore, it is possible that UCNP-$P_6$ exhibits a stronger inhibitory effect than UCNP-$P_5$ in the short term (24 h). During a longer experimental period, UCNP-$P_5$ exceeded UCNP-$P_6$ in a 5-day cytotoxicity test and exhibited the best inhibitory performance among EBNA1-positive and LMP1-positive cells (FIG. 32E), which demonstrated that UCNP-$P_5$ would be efficiently taken up and accumulated by EBV-related cancer cells. It is worth noting that UCNP-$P_n$ [n=5, 6 and 7 (SEQ ID NO: 5, 6, 7)] is more selective towards EBV-infected carcinoma cells compared with the previous bioprobes due to the conjugation of the dual-EBNA1/LMP1-targeting peptides on the surface of UCNP. In addition, the cytotoxicity of UCNP-$P_5$ was much higher than UCNP-$P_4$ and exhibited lower $IC_{50}$ values as shown in Table 4, especially in LMP1-positive cells, which indicated that UCNP-$P_5$ is likely to be more able to eradicate EBV-infected tumor cell progression compared with old generation nanoprobe UCNP-$P_4$. The transmembrane protein LMP1 in EBV-infected cancer cells is first targeted by the FWLY membrane-targeting motif, then the EBNA1-inhibiting YFMVF motif and nucleus-permeable RrRK motif are prone to cause inhibitory effect on the nucleus, where EBNA1 is initially located. Therefore, the dimerization process of EBNA1 can be hindered efficiently and EBV-infected tumor cells were significantly inhibited. UCNP-$P_5$ shows promising potential for being an anti-tumor candidate of multi-targeted therapy and monitoring with pH-responsive property.

TABLE 4

Summary on $IC_{50}$ (half inhibitory concentration) values of UCNP, UCNP-$P_n$ [n = 5, 6 and 7 (SEQ ID NO: 5, 6, 7)] and UCNP-$P_4$ in C666, LCL3, NPC43 and Raji cells for 24 h incubation time and 5-day incubation time respectively.

|  | $IC_{50}$ C666 | | $IC_{50}$ LCL3 | | $IC_{50}$ NPC43 | | $IC_{50}$ Raji | |
|---|---|---|---|---|---|---|---|---|
| UCNP | 947[a] | 626[b] | 1024 | 585 | 879 | 462 | 963 | 441 |
| UCNP-$P_5$ | 69 | 38 | 36 | 22 | 52 | 36 | 58 | 28 |
| UCNP-$P_6$ | 37 | 41 | 19 | 21 | 38 | 34 | 27 | 29 |
| UCNP-$P_7$ | 49 | 54 | 28 | 29 | 61 | 49 | 55 | 39 |
| UCNP-$P_4$ | 58 | 51 | 443 | 361 | 73 | 47 | 61 | 52 |

[a]($IC_{50}$ values for 24 h incubation time in black);
[b]($IC_{50}$ values for 5-day incubation time in bold).

Figure 5:
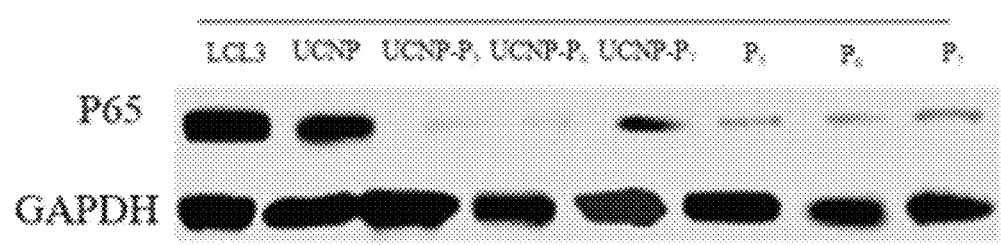
FIG. 5 depicts (A) western blotting of UCNP and UCNP-P$_n$ (n=5, 6 and 7) in cytosolic and nuclear fraction in LCL3 cells; (B) Quantitative analysis of p65 protein expression level in cytosolic and nuclear fraction in LCL3 cells after various treatments. *P<0.05, **P<0.01.
Figure 5:
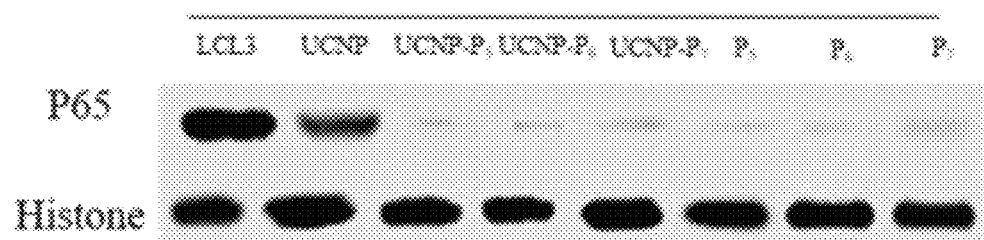
Figure 5:
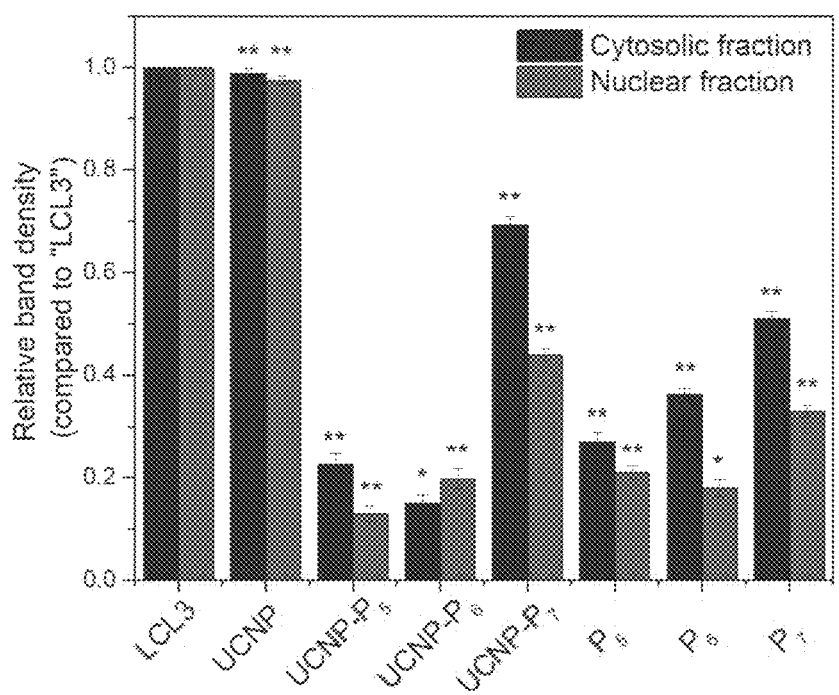
Figure 34:
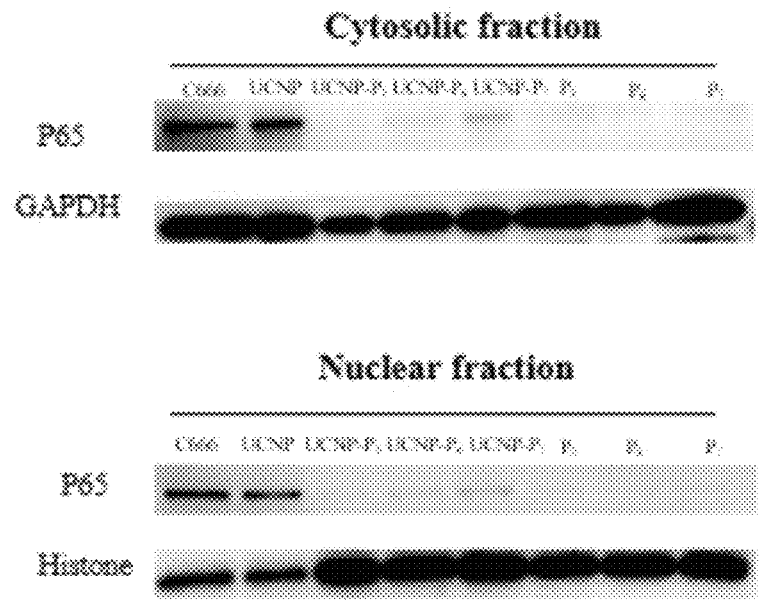
FIG. 34 depicts (A) western blotting of UCNP and UCNP-$P_n$ [n=5, 6 and 7 (SEQ ID NO: 5, 6, 7)] in cytosolic and nuclear fraction in C666 cells; (B) Quantitative analysis of p65 protein expression level in cytosolic and nuclear fraction in C666 cells after various treatments. *P<0.05, **P<0.01.
Figure 34:
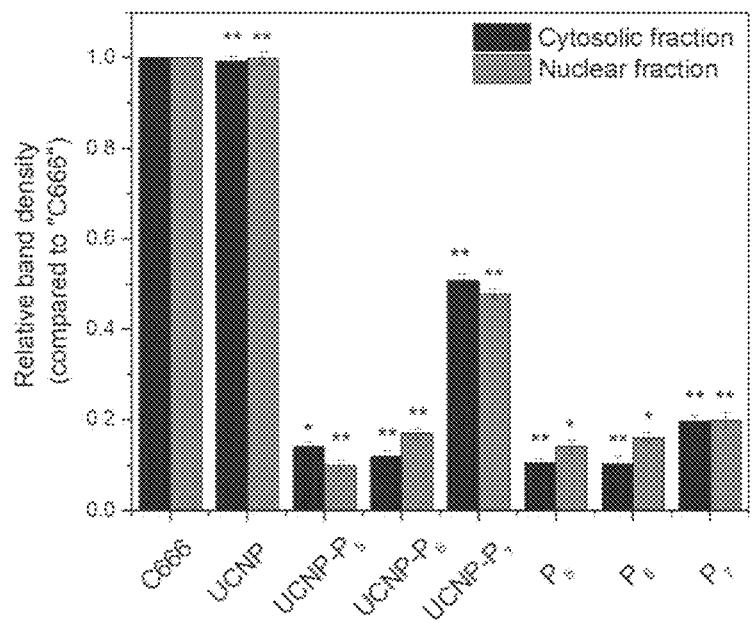
Figure 35:
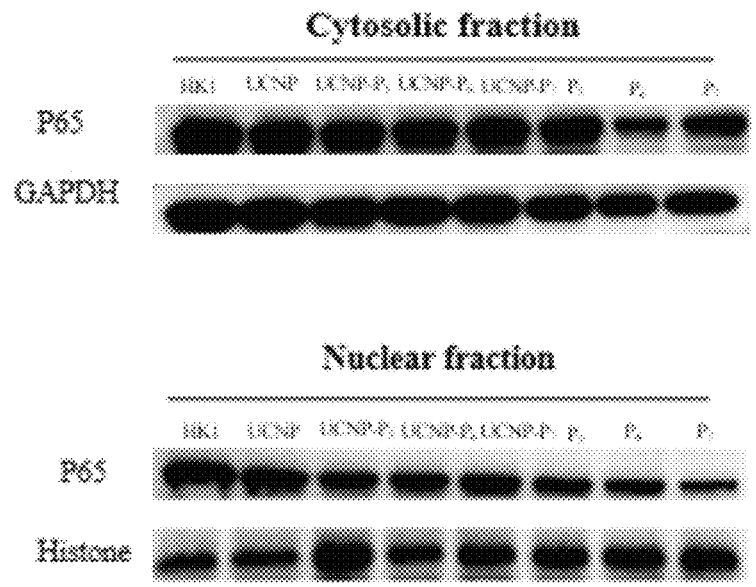
FIG. 35 depicts (A) western blotting of UCNP and UCNP-$P_n$ [n=5, 6 and 7 (SEQ ID NO: 5, 6, 7)] in cytosolic and nuclear fraction in HK1 cells; (B) Quantitative analysis of p65 protein expression level in cytosolic and nuclear fraction in HK1 cells after various treatments. *P<0.05, **P<0.01.
Figure 35:
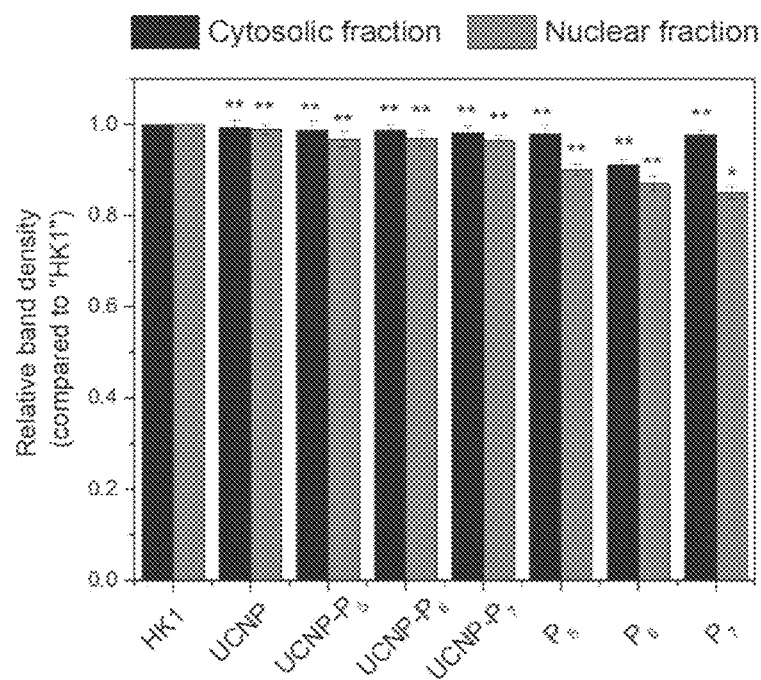

NF-κB signaling pathway is critical for the survival of EBV-infected tumor cells. Here we investigated if our nanoprobes could affect this oncogenic pathway. EBV-positive LCL3 and C666 cells were used as models, EBV-negative HK1 cells were used as control and Western blot was used to analyze the protein expression of p65, a major transcription factor in the NF-κB family. As shown in FIG. 5A and FIG. 34A, UCNP-$P_6$ showed the lowest protein expression level of p65 as a whole, indicating the down-regulation effect on specific LCL3 and C666 cells, respectively. GAPDH and Histone are regarded as internal standards in cytosolic and nuclear fractions, respectively. In the cytosolic fraction, UCNP-$P_6$ showed the most significant inhibitory effect on p65 (85% and 87% of reduced p65 expression level in LCL3 and C666 cells respectively) whereas in the nuclear fraction, $P_5$ and UCNP-$P_5$ displayed the strongest binding affinity toward p65 with 86% and 89% decreased expression in LCL3 and C666 cells respectively (FIG. 5B and FIG. 34B). This is consistent with the cellular uptake results. The negligible differences of p65 expression level in HK1 cells were quantified after various treatments in FIG. 35.

After the study of cellular uptake, fluorescent confocal microscopy was used to study the sub-cellular localization with the same set of EBV-/LMP1-positive and -negative cell lines. All these cell lines were treated with as-prepared samples for different time intervals of 1 h, 3 h, 6 h, 12 h and 24 h. Fluorescence signals in the cells were imaged under 980 nm excitation.

Figure 6:
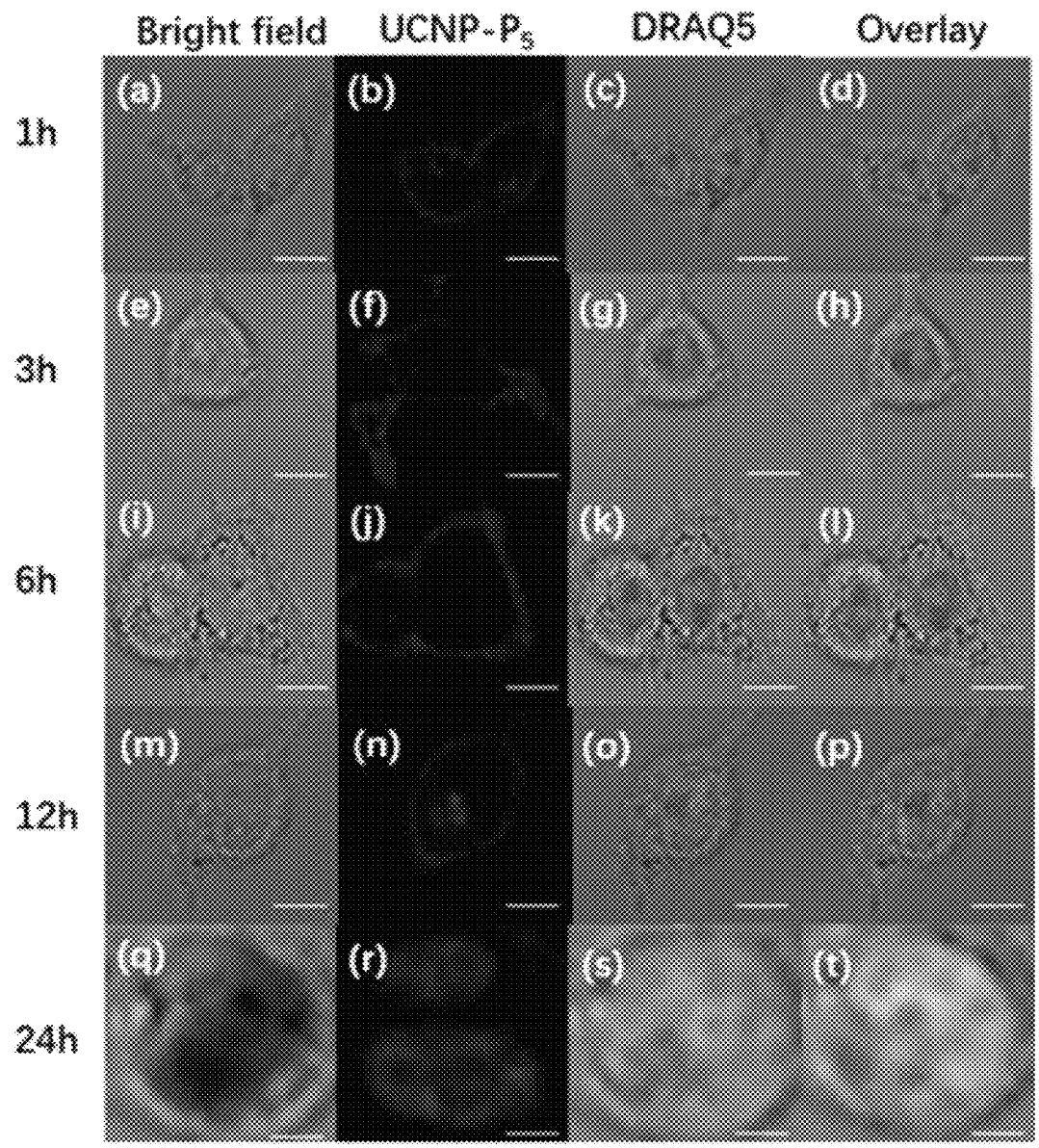
FIG. 6 depicts two-photon confocal images of UCNP-P$_5$ in EBV-positive C666 cells ($l_{ex}$=980 nm, $l_{em}$=500-700 nm); (A-D): bright field, UCNP-P$_5$ treated with C666 cells for 1 h, DRAQ5 fluorescence and overlay image respectively; (E-H): bright field, UCNP-P$_5$ treated with C666 cells for 3 h, DRAQ5 fluorescence and overlay image respectively; (I-L): bright field, UCNP-P$_5$ treated with C666 cells for 6 h, DRAQ5 fluorescence and overlay image respectively; (M-P): bright field, UCNP-P$_5$ treated with C666 cells for 12 h, DRAQ5 fluorescence and overlay image respectively; (Q-T): bright field, UCNP-P$_5$ treated with C666 cells for 24 h, DRAQ5 fluorescence and overlay image respectively; (U) Lambda scan of UCNP-P$_5$ in EBV-positive C666 cells in different time intervals of 1 h, 3 h, 6 h, 12 h and 24 h.
Figure 6:
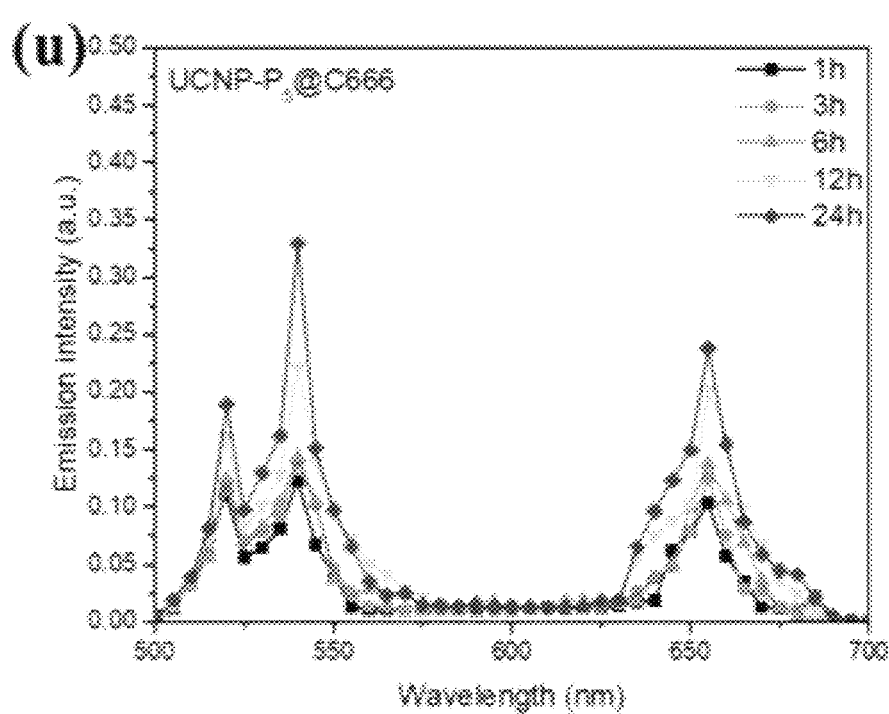
Figure 36:
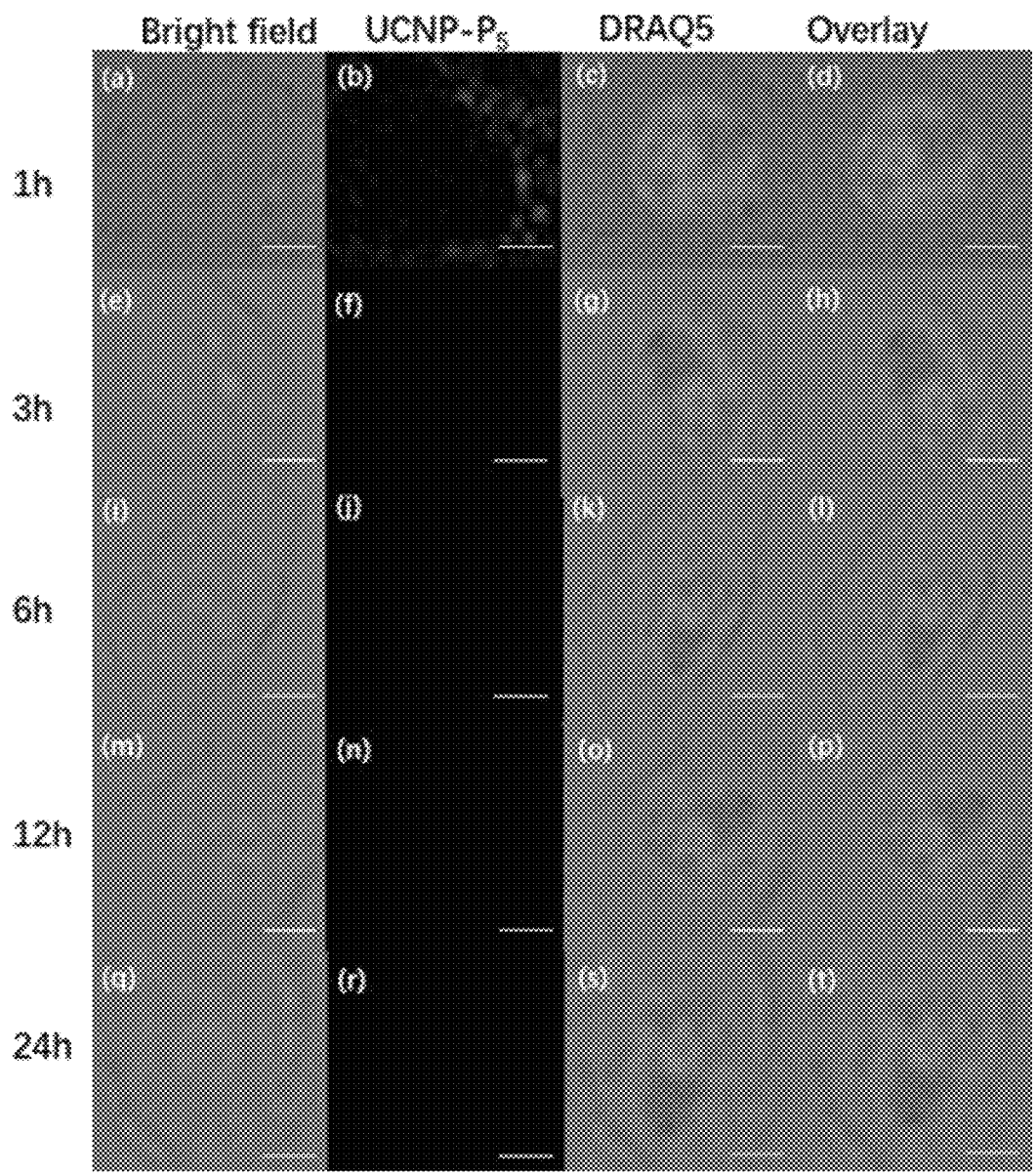
FIG. 36 depicts two-photon confocal images of UCNP-$P_5$ in EBV-negative HK1 cells ($l_{ex}$=980 nm, $l_{em}$=500-700 nm); (A-D): bright field, UCNP-$P_5$ treated with HK1 cells for 1 h, DRAQ5 fluorescence and overlay image respectively; (E-H): bright field, UCNP-$P_5$ treated with HK1 cells for 3 h, DRAQ5 fluorescence and overlay image respectively; (I-L): bright field, UCNP-$P_5$ treated with HK1 cells for 6 h, DRAQ5 fluorescence and overlay image respectively; (M-P): bright field, UCNP-$P_5$ treated with HK1 cells for 12 h, DRAQ5 fluorescence and overlay image respectively; (Q-T): bright field, UCNP-$P_5$ treated with HK1 cells for 24 h, DRAQ5 fluorescence and overlay image respectively; (U) Lambda scan of UCNP-$P_5$ in EBV-negative HK1 cells in different time intervals of 1 h, 3 h, 6 h, 12 h and 24 h.
Figure 36:
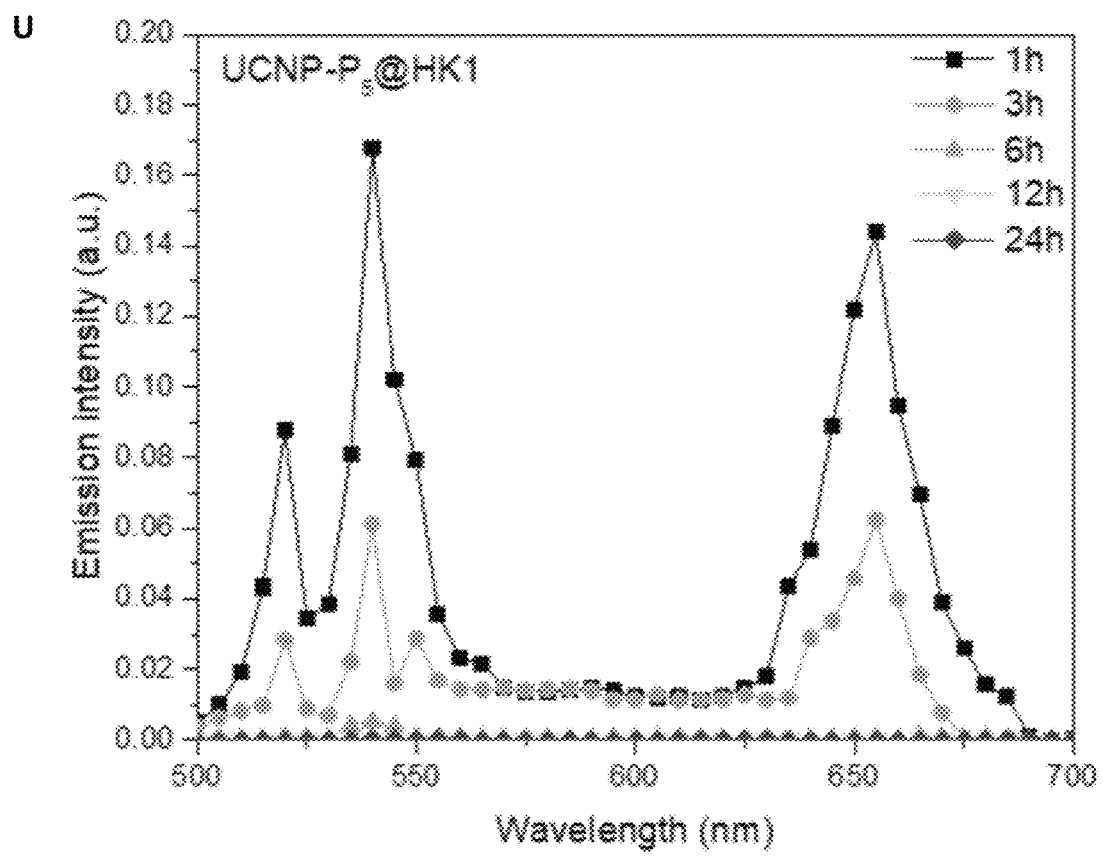
Figure 37:
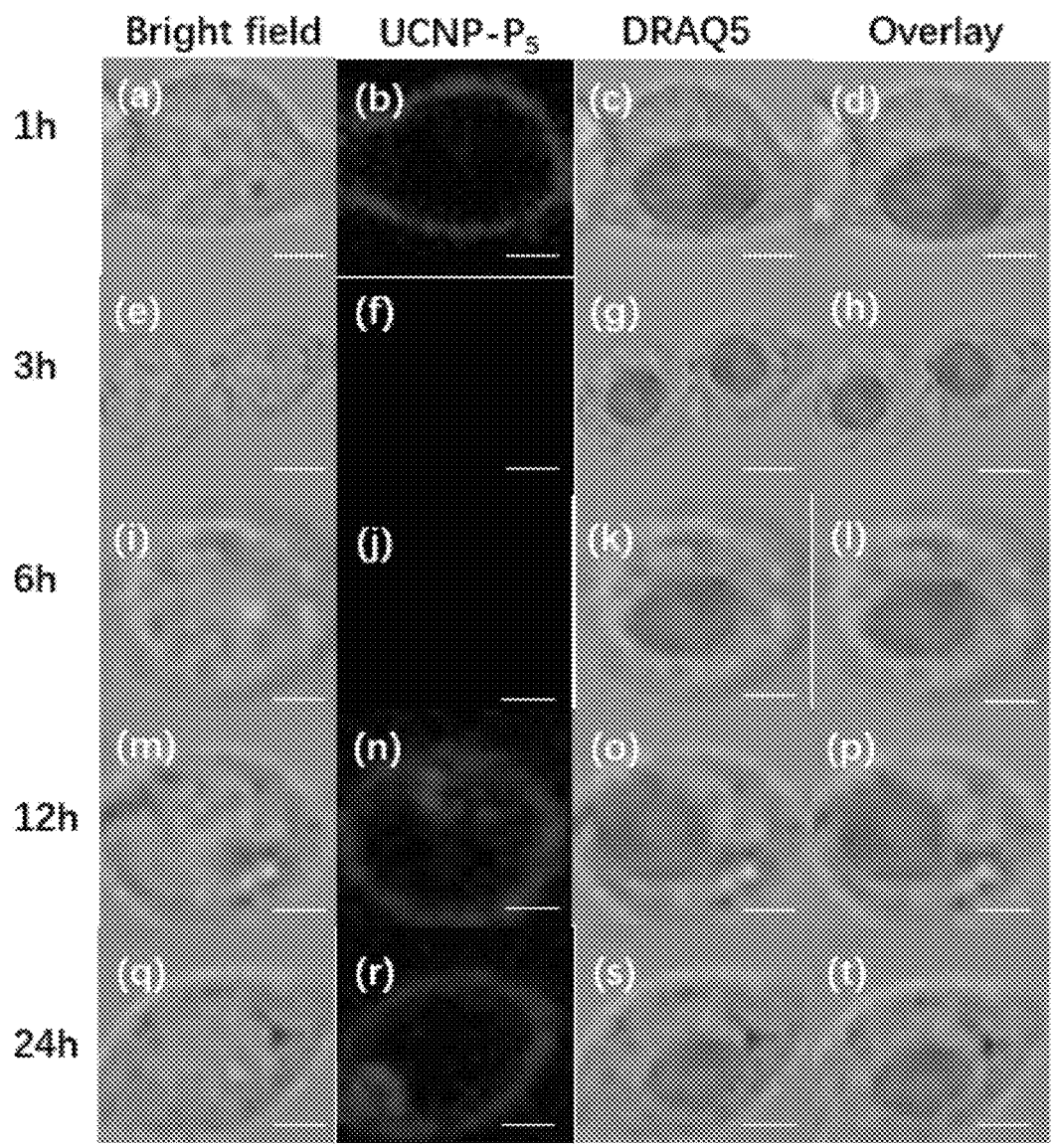
FIG. 37 depicts two-photon confocal images of UCNP-$P_5$ in EBV-negative HK1-LMP1 cells ($l_{ex}$=980 nm, $l_{em}$=500-700 nm); (A-D): bright field, UCNP-$P_5$ treated with HK1-LMP1 cells for 1 h, DRAQ5 fluorescence and overlay image respectively; (E-H): bright field, UCNP-$P_5$ treated with HK1-LMP1 cells for 3 h, DRAQ5 fluorescence and overlay image respectively; (I-L): bright field, UCNP-$P_5$ treated with HK1-LMP1 cells for 6 h, DRAQ5 fluorescence and overlay image respectively; (M-P): bright field, UCNP-$P_5$ treated with HK1-LMP1 cells for 12 h, DRAQ5 fluorescence and overlay image respectively; (Q-T): bright field, UCNP-$P_5$ treated with HK1-LMP1 cells for 24 h, DRAQ5 fluorescence and overlay image respectively; (U) Lambda scan of UCNP-$P_5$ in EBV-negative HK1-LMP1 cells in different time intervals of 1 h, 3 h, 6 h, 12 h and 24 h.
Figure 37:
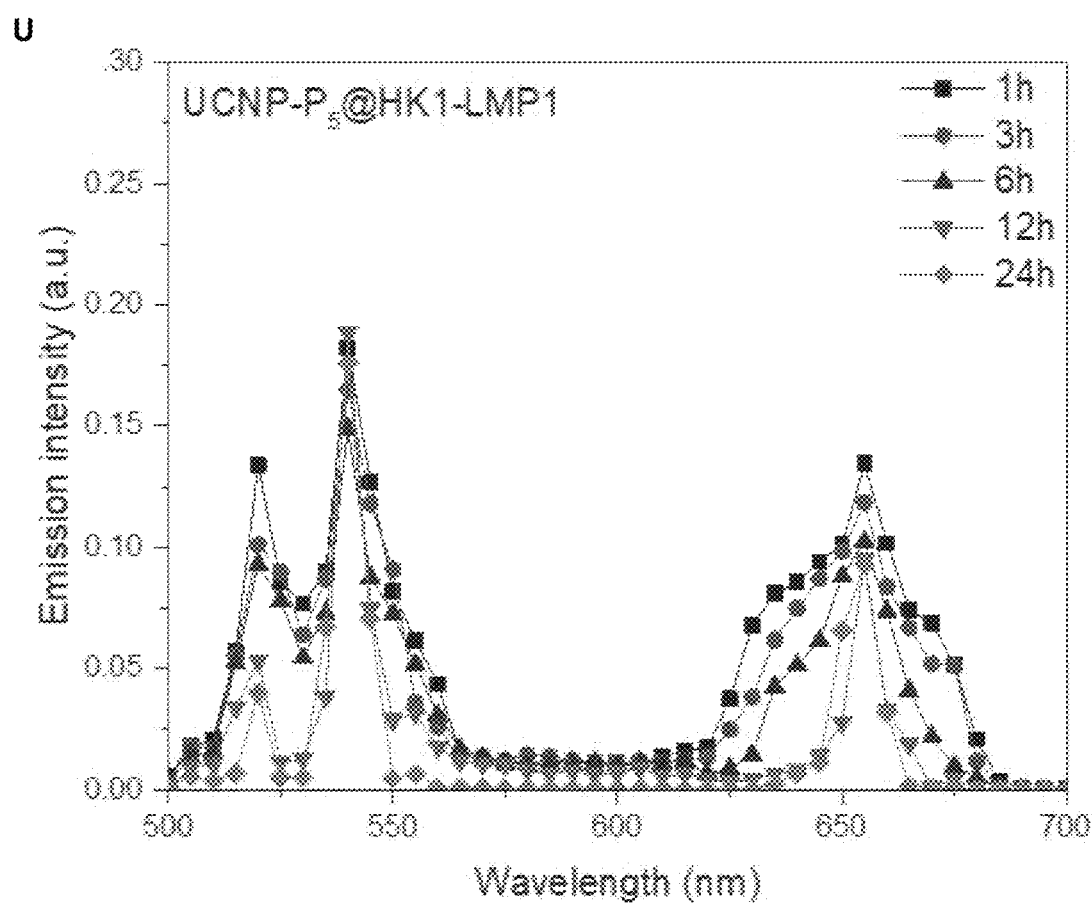
Figure 38:
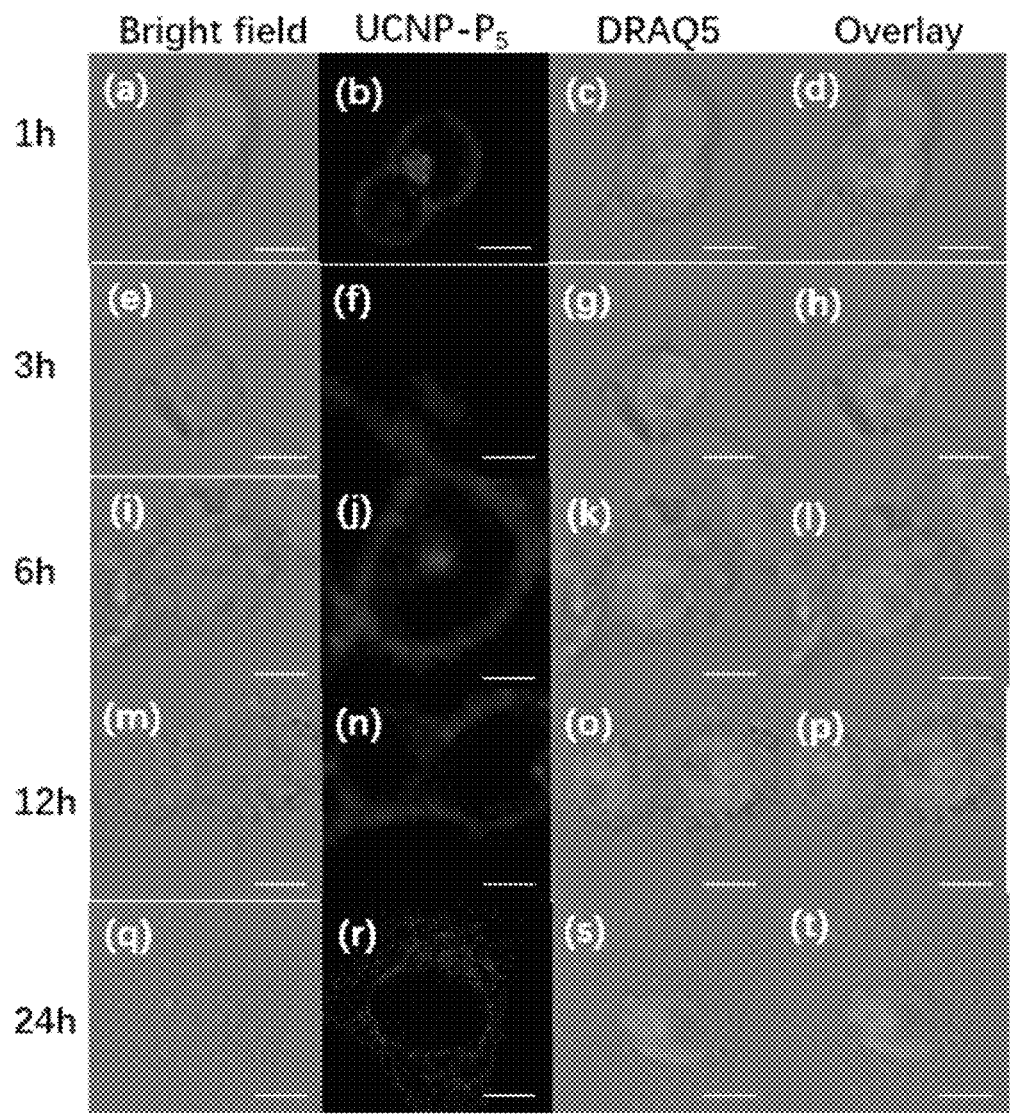
FIG. 38 depicts two-photon confocal images of UCNP-$P_5$ in EBV-negative HK1 cells ($l_{ex}$980 nm, $l_{em}$=500-700 nm); (A-D): bright field, UCNP-$P_5$ treated with HK1 cells for 1 h, DRAQ5 fluorescence and overlay image respectively; (E-H): bright field, UCNP-$P_5$ treated with HK1 cells for 3 h, DRAQ5 fluorescence and overlay image respectively; (I-L): bright field, UCNP-$P_5$ treated with HK1 cells for 6 h, DRAQ5 fluorescence and overlay image respectively; (M-P): bright field, UCNP-$P_5$ treated with HK1 cells for 12 h, DRAQ5 fluorescence and overlay image respectively; (Q-T): bright field, UCNP-$P_5$ treated with HK1 cells for 24 h, DRAQ5 fluorescence and overlay image respectively; (U) Lambda scan of UCNP-$P_5$ in EBV-negative HK1 cells in different time intervals of 1 h, 3 h, 6 h, 12 h and 24 h.
Figure 38:
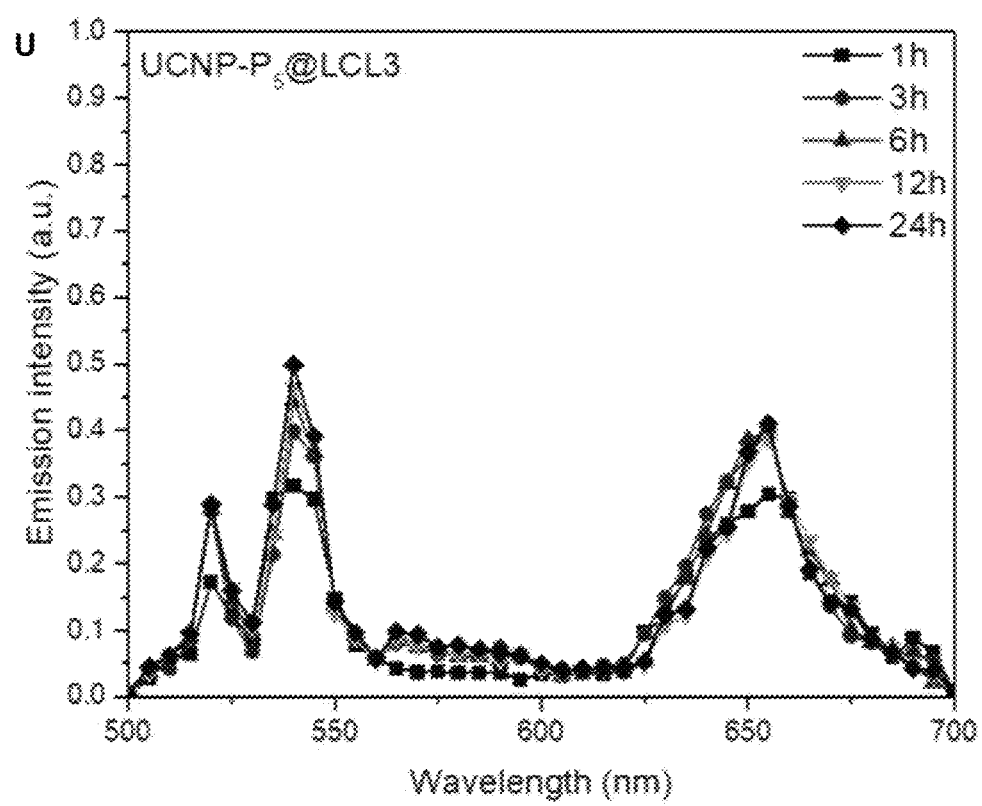
Figure 39:
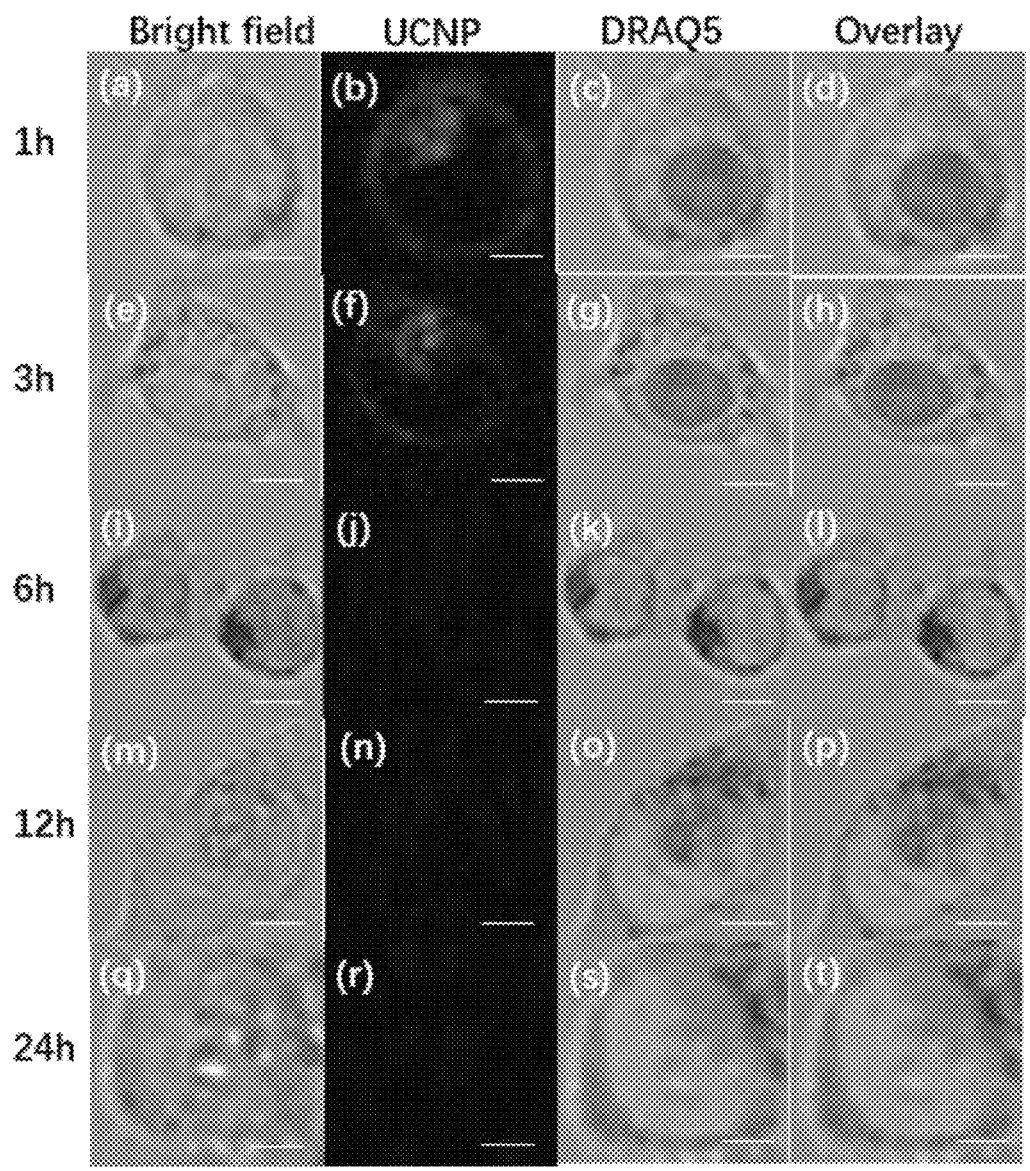
FIG. 39 depicts two-photon confocal images of UCNP in EBV-positive C666 cells ($l_{ex}$=980 nm, $l_{em}$=500-700 nm); (A-D): bright field, UCNP treated with C666 cells for 1 h, DRAQ5 fluorescence and overlay image respectively; (E-H): bright field, UCNP treated with C666 cells for 3 h, DRAQ5 fluorescence and overlay image respectively; (I-L): bright field, UCNP treated with C666 cells for 6 h, DRAQ5 fluorescence and overlay image respectively; (M-P): bright field, UCNP treated with C666 cells for 12 h, DRAQ5 fluorescence and overlay image respectively; (Q-T): bright field, UCNP treated with C666 cells for 24 h, DRAQ5 fluorescence and overlay image respectively; (U) Lambda scan of UCNP in EBV-positive C666 cells in different time intervals of 1 h, 3 h, 6 h, 12 h and 24 h.
Figure 39:
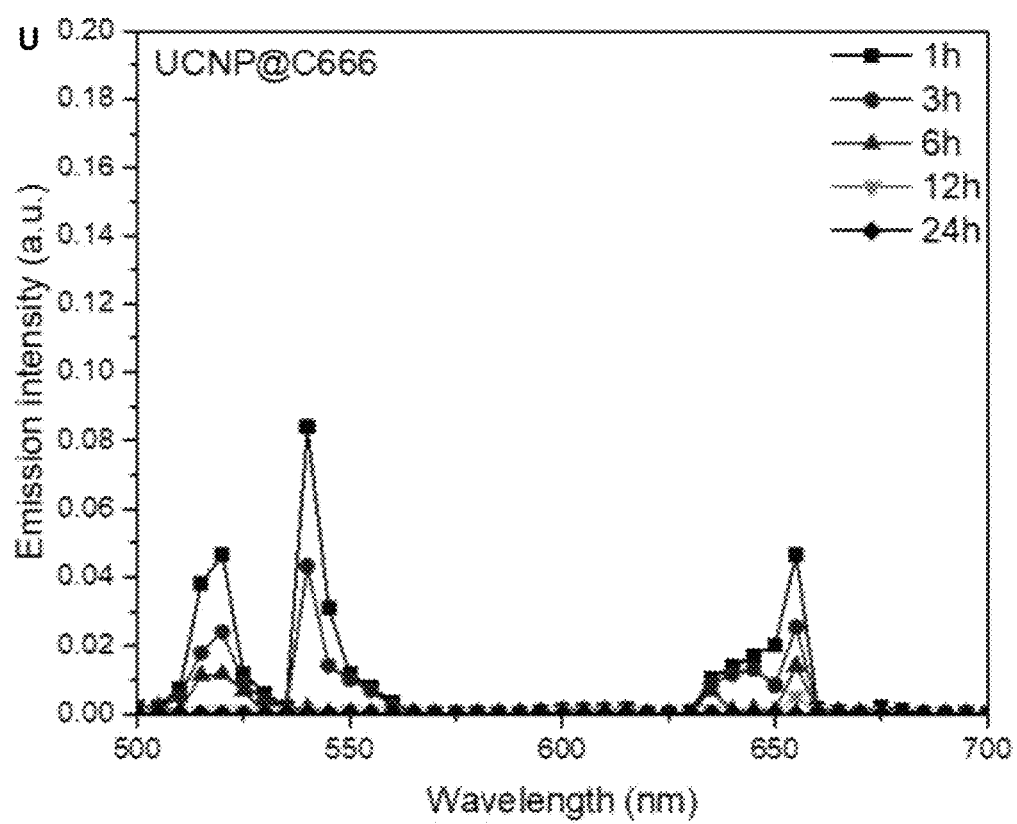
Figure 40:
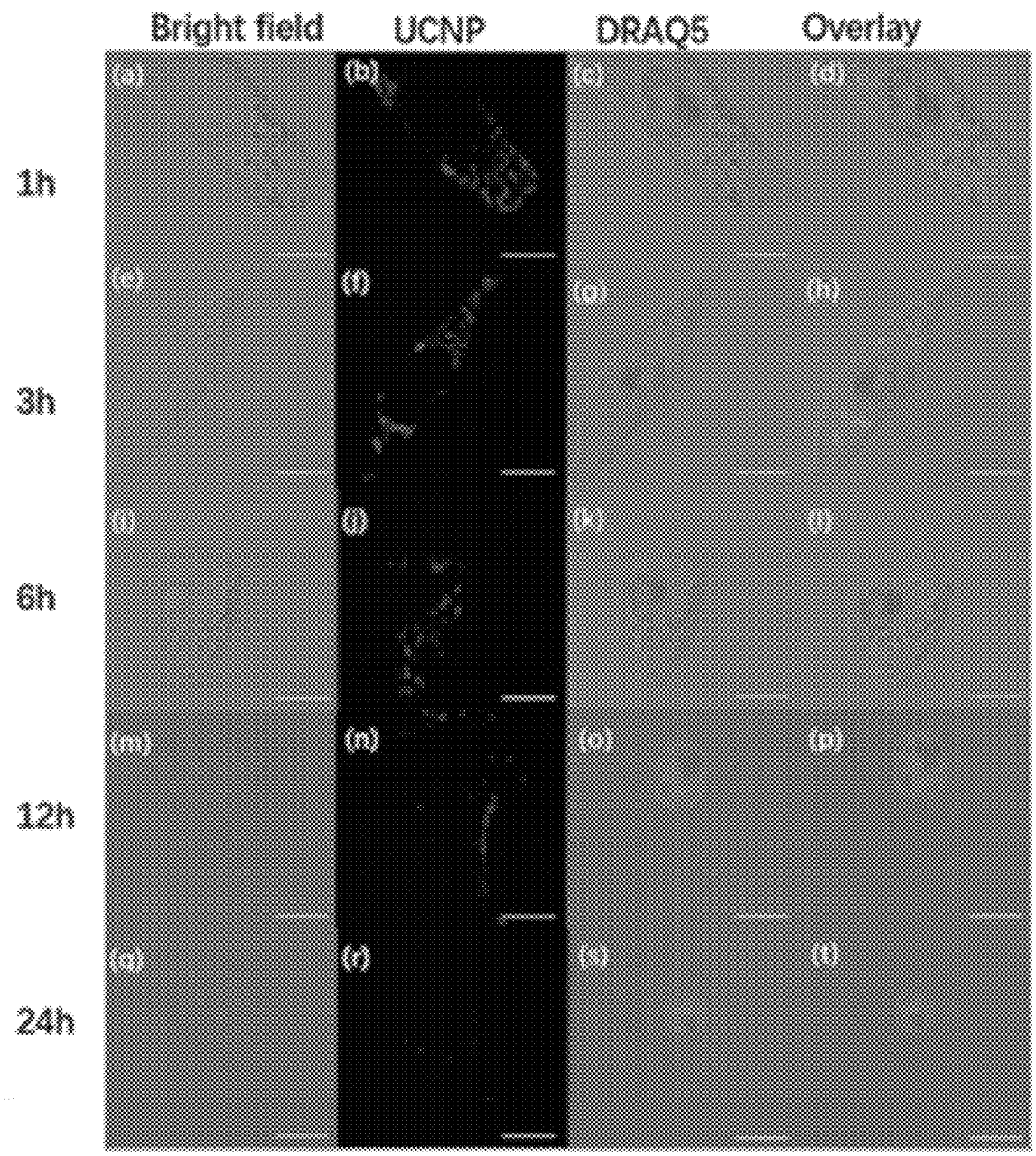
FIG. 40 depicts two-photon confocal images of UCNP in EBV-negative HK1 cells ($l_{ex}$=980 nm, $l_{em}$=500-700 nm); (A-D): bright field, UCNP treated with HK1 cells for 1 h, DRAQ5 fluorescence and overlay image respectively; (E-H): bright field, UCNP treated with HK1 cells for 3 h, DRAQ5 fluorescence and overlay image respectively; (I-L): bright field, UCNP treated with HK1 cells for 6 h, DRAQ5 fluorescence and overlay image respectively; (M-P): bright field, UCNP treated with HK1 cells for 12 h, DRAQ5 fluorescence and overlay image respectively; (Q-T): bright field, UCNP treated with HK1 cells for 24 h, DRAQ5 fluorescence and overlay image respectively; (U) Lambda scan of UCNP in EBV-negative HK1 cells in different time intervals of 1 h, 3 h, 6 h, 12 h and 24 h.
Figure 40:
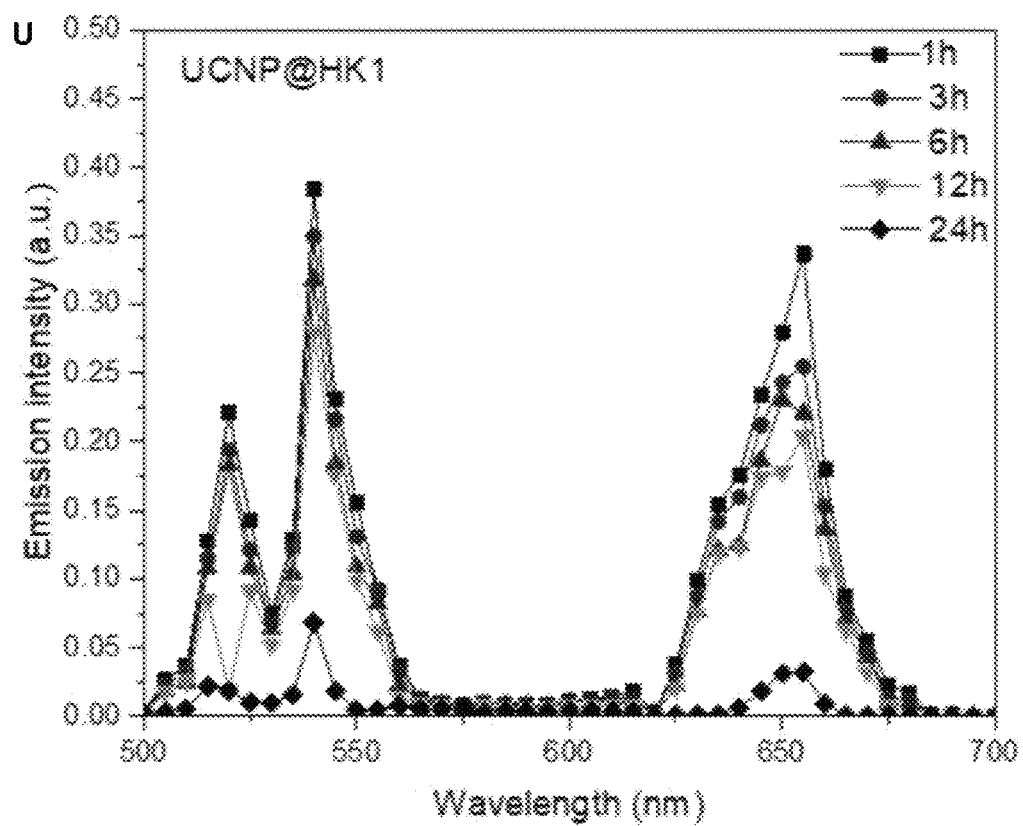
Figure 41:
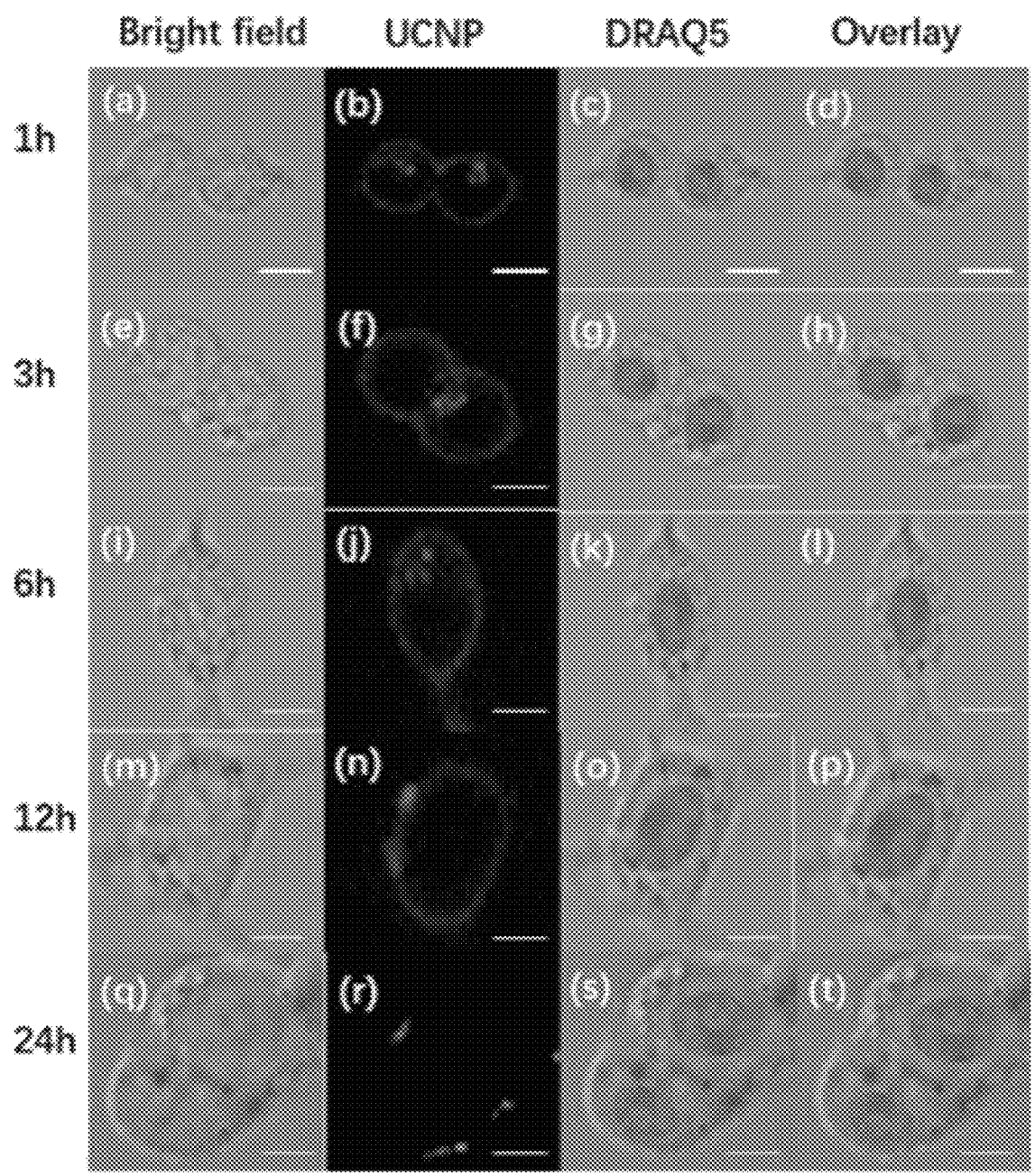
FIG. 41 depicts two-photon confocal images of UCNP in EBV-negative HK1-LMP1 cells ($l_{ex}$=980 nm, $l_{em}$=500-700 nm); (A-D): bright field, UCNP treated with HK1-LMP1 cells for 1 h, DRAQ5 fluorescence and overlay image respectively; (E-H): bright field, UCNP treated with HK1-LMP1 cells for 3 h, DRAQ5 fluorescence and overlay image respectively; (I-L): bright field, UCNP treated with HK1-LMP1 cells for 6 h, DRAQ5 fluorescence and overlay image respectively; (M-P): bright field, UCNP treated with HK1-LMP1 cells for 12 h, DRAQ5 fluorescence and overlay image respectively; (Q-T): bright field, UCNP treated with HK1-LMP1 cells for 24 h, DRAQ5 fluorescence and overlay image respectively; (U) Lambda scan of UCNP in EBV-negative HK1-LMP1 cells in different time intervals of 1 h, 3 h, 6 h, 12 h and 24 h.
Figure 41:
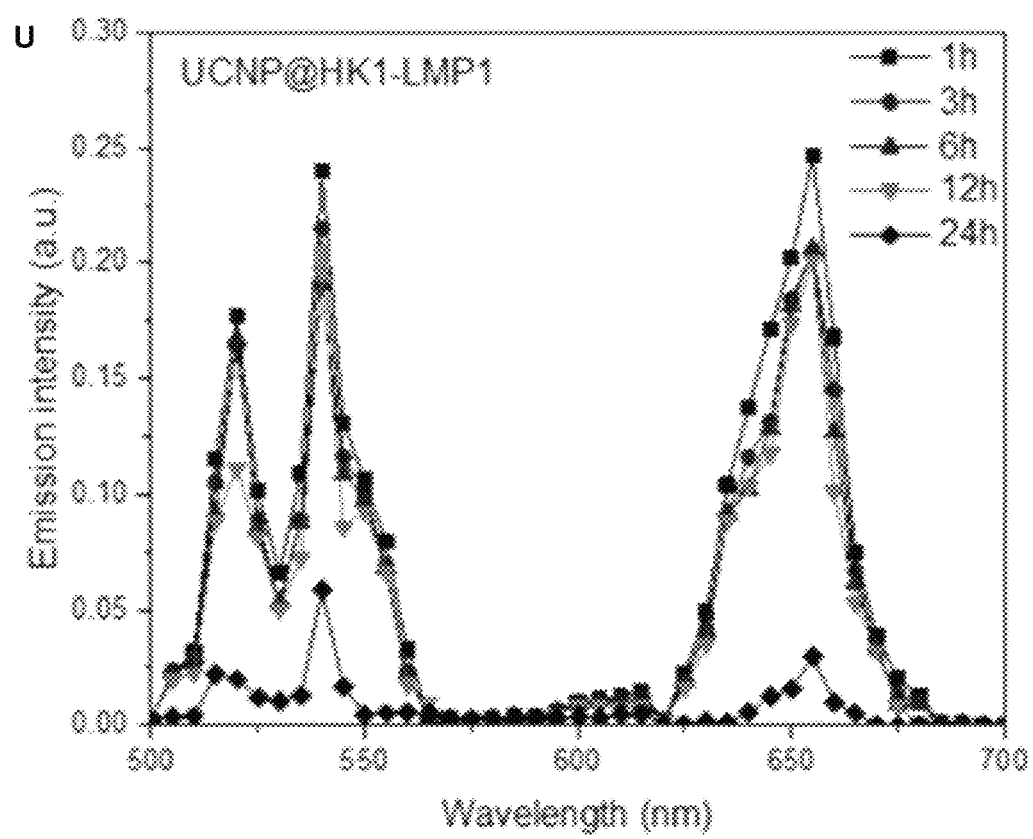
Figure 42:
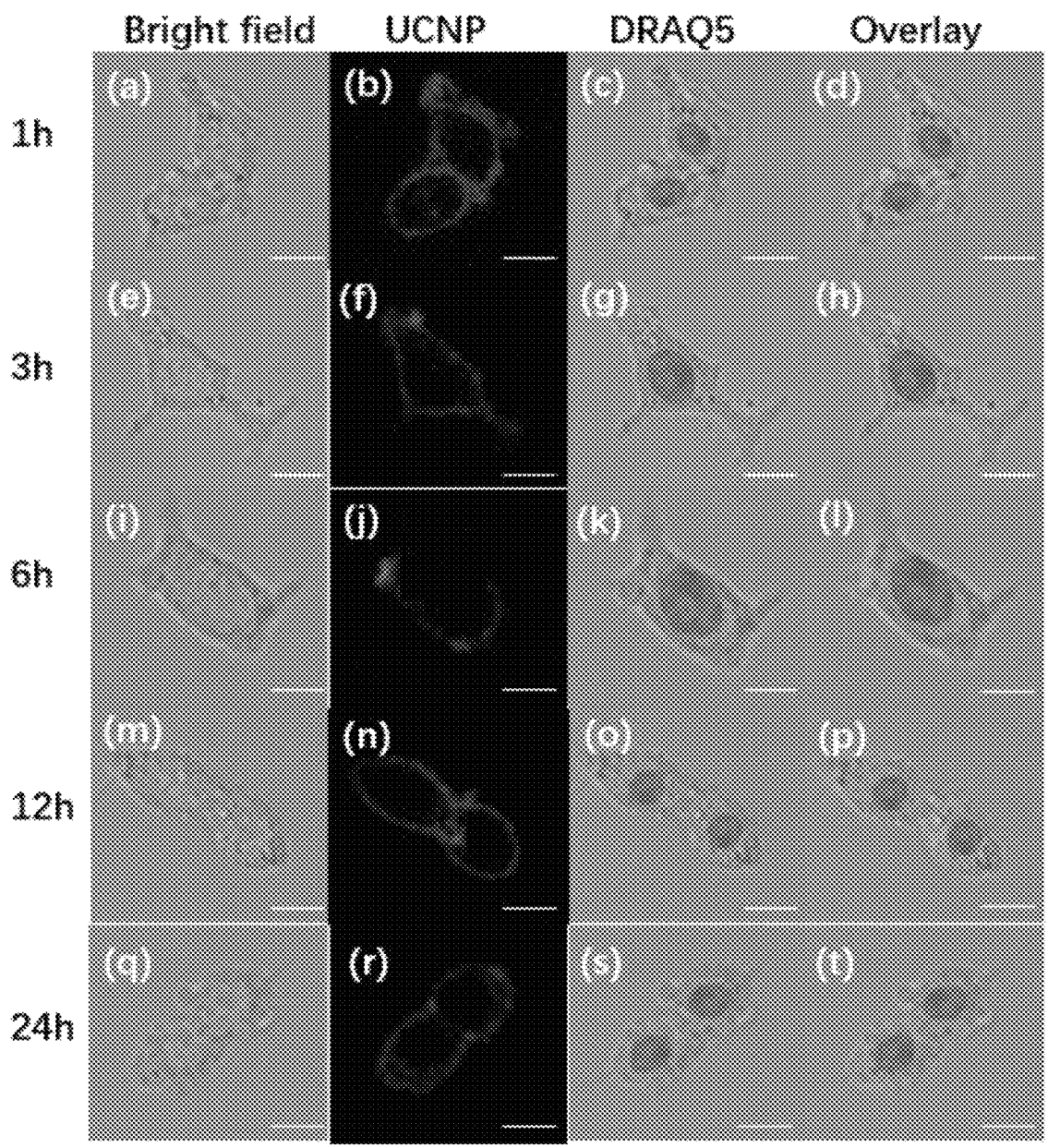
FIG. 42 depicts two-photon confocal images of UCNP in EBV-positive LCL3 cells ($l_{ex}$=980 nm, $l_{em}$=500-700 nm); (A-D): bright field, UCNP treated with LCL3 cells for 1 h, DRAQ5 fluorescence and overlay image respectively; (E-H): bright field, UCNP treated with LCL3 cells for 3 h, DRAQ5 fluorescence and overlay image respectively; (I-L): bright field, UCNP treated with LCL3 cells for 6 h, DRAQ5 fluorescence and overlay image respectively; (M-P): bright field, UCNP treated with LCL3 cells for 12 h, DRAQ5 fluorescence and overlay image respectively; (Q-T): bright field, UCNP treated with LCL3 cells for 24 h, DRAQ5 fluorescence and overlay image respectively; (U) Lambda scan of UCNP in EBV-positive LCL3 cells in different time intervals of 1 h, 3 h, 6 h, 12 h and 24 h.
Figure 42:
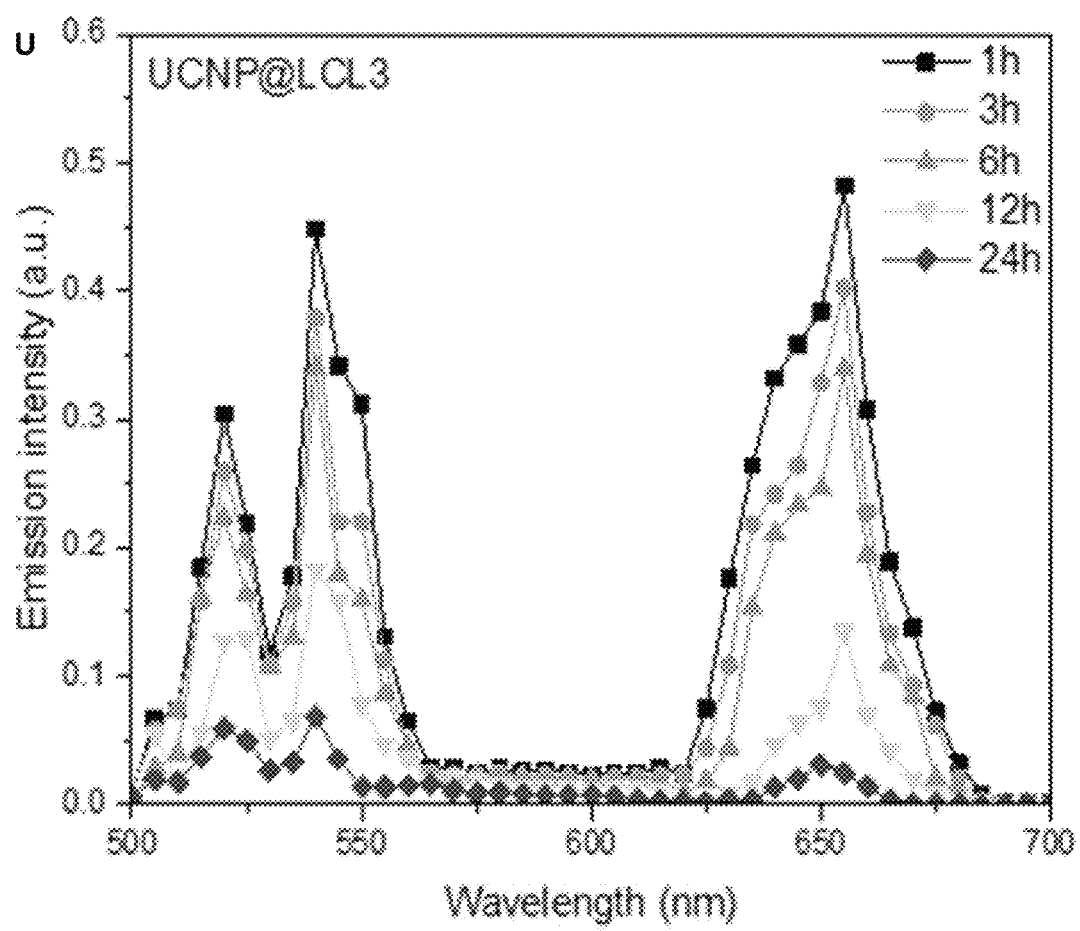
Figure 43:
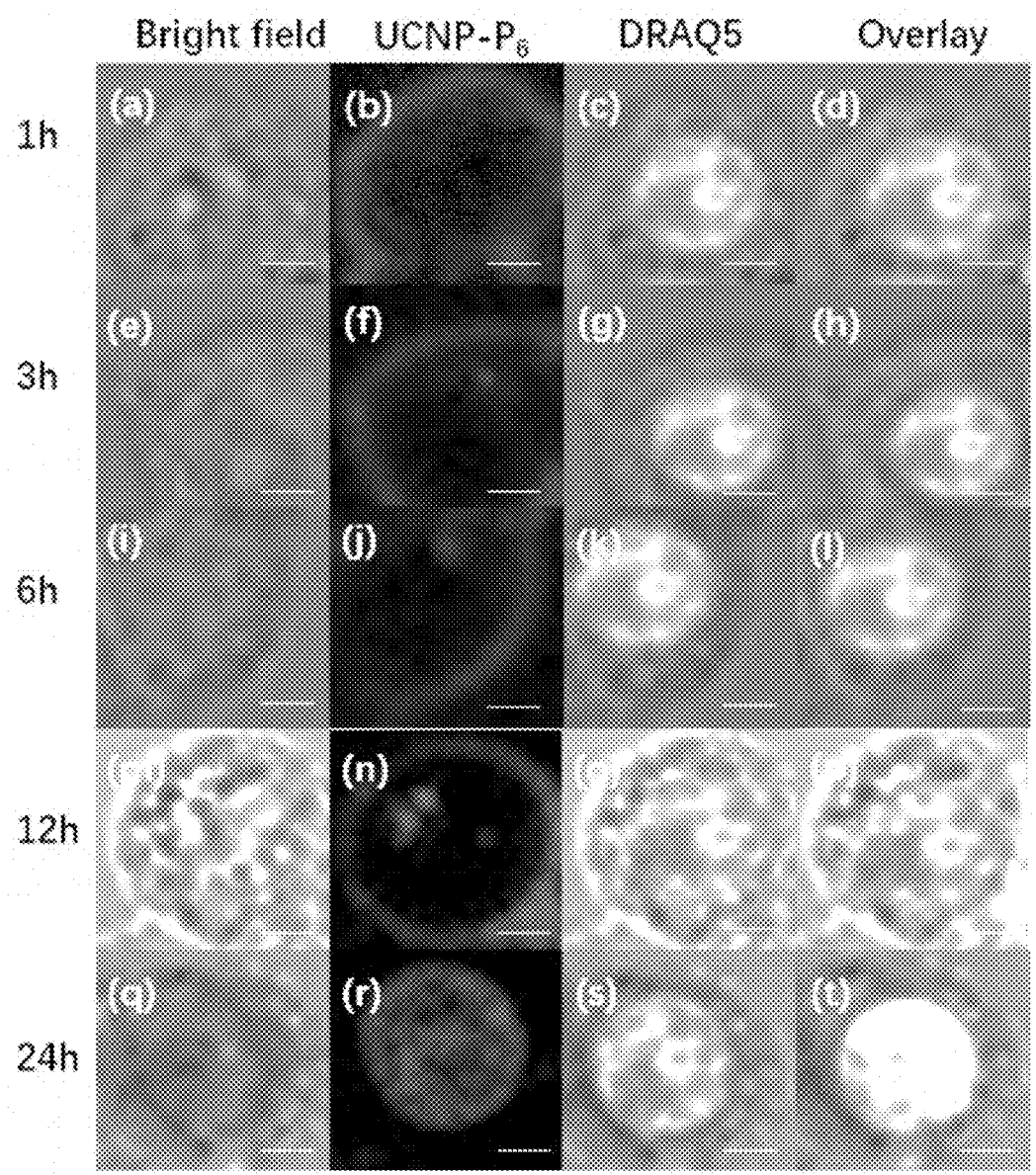
FIG. 43 depicts two-photon confocal images of UCNP-$P_6$ in EBV-positive C666 cells ($\lambda_{ex}$=980 nm, $\lambda_{em}$=500-700 nm); (A-D): bright field, UCNP-$P_6$ treated with C666 cells for 1 h, DRAQ5 fluorescence and overlay image respectively; (E-H): bright field, UCNP-$P_6$ treated with C666 cells for 3 h, DRAQ5 fluorescence and overlay image respectively; (I-L): bright field, UCNP-$P_6$ treated with C666 cells for 6 h, DRAQ5 fluorescence and overlay image respectively; (M-P): bright field, UCNP-$P_6$ treated with C666 cells for 12 h, DRAQ5 fluorescence and overlay image respectively; (Q-T): bright field, UCNP-$P_6$ treated with C666 cells for 24 h, DRAQ5 fluorescence and overlay image respectively; (U) Lambda scan of UCNP-$P_6$ in EBV-positive C666 cells in different time intervals of 1 h, 3 h, 6 h, 12 h and 24 h.
Figure 43:
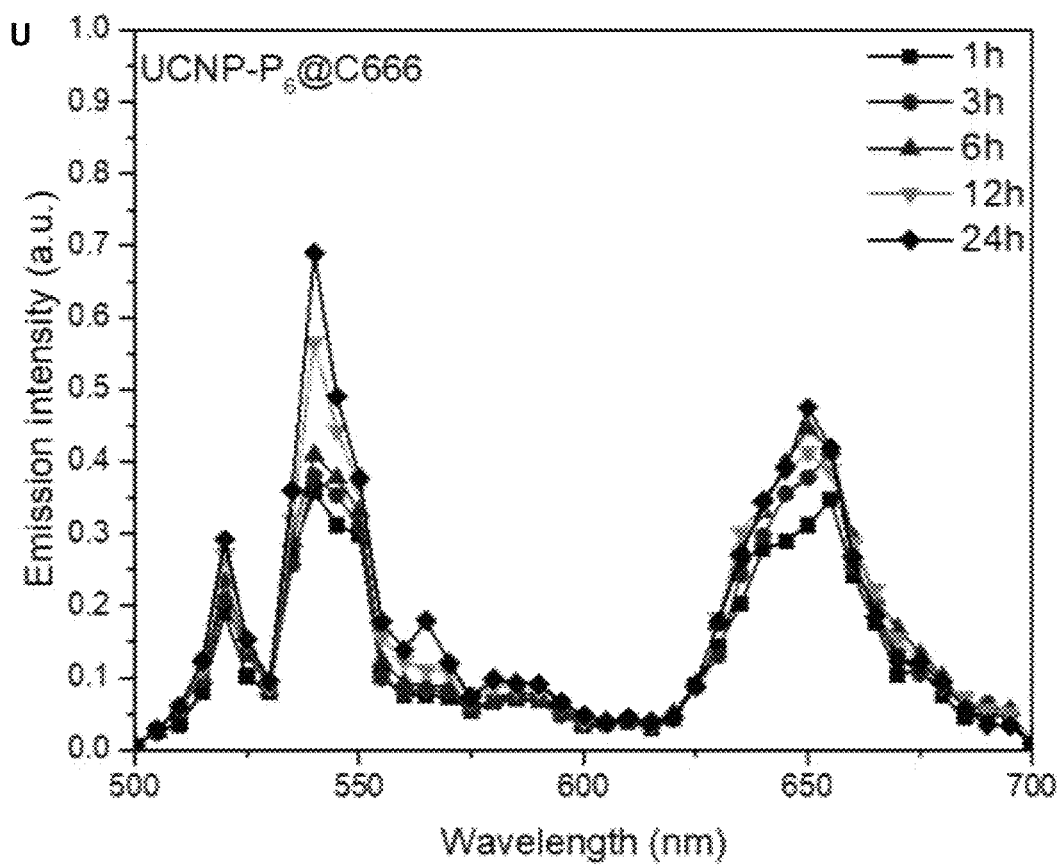
Figure 44:
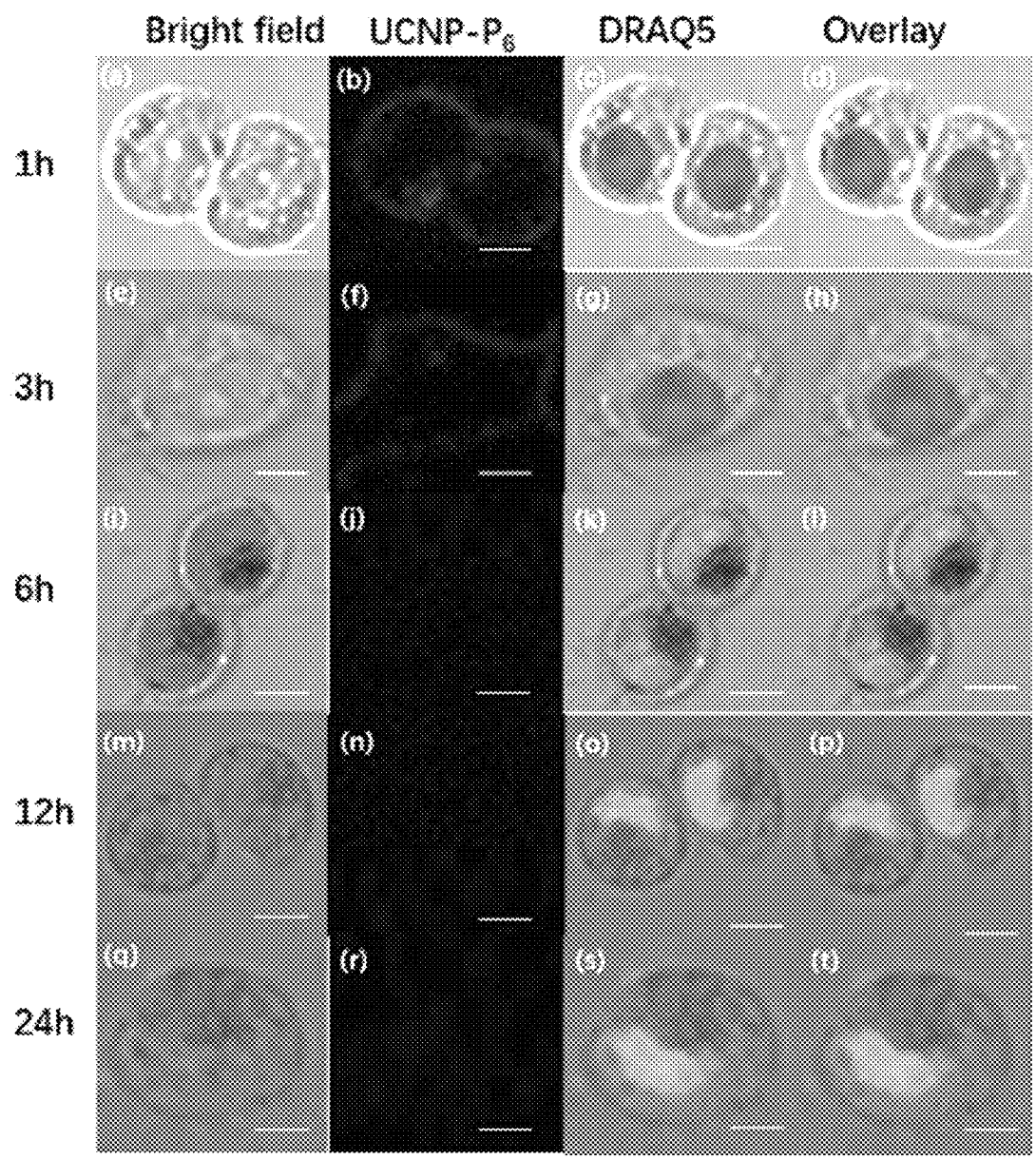
FIG. 44 depicts two-photon confocal images of UCNP-$P_6$ in EBV-negative HK1 cells ($l_{ex}$=980 nm, $l_{em}$=500-700 nm); (A-D): bright field, UCNP-$P_6$ treated with HK1 cells for 1 h, DRAQ5 fluorescence and overlay image respectively; (E-H): bright field, UCNP-$P_6$ treated with HK1 cells for 3 h, DRAQ5 fluorescence and overlay image respectively; (I-L): bright field, UCNP-$P_6$ treated with HeLa cells for 6 h, DRAQ5 fluorescence and overlay image respectively; (M-P): bright field, UCNP-$P_6$ treated with HK1 cells for 12 h, DRAQ5 fluorescence and overlay image respectively; (Q-T): bright field, UCNP-$P_6$ treated with HK1 cells for 24 h, DRAQ5 fluorescence and overlay image respectively; (U) Lambda scan of UCNP-$P_6$ in EBV-negative HK1 cells in different time intervals of 1 h, 3 h, 6 h, 12 h and 24 h.
Figure 44:
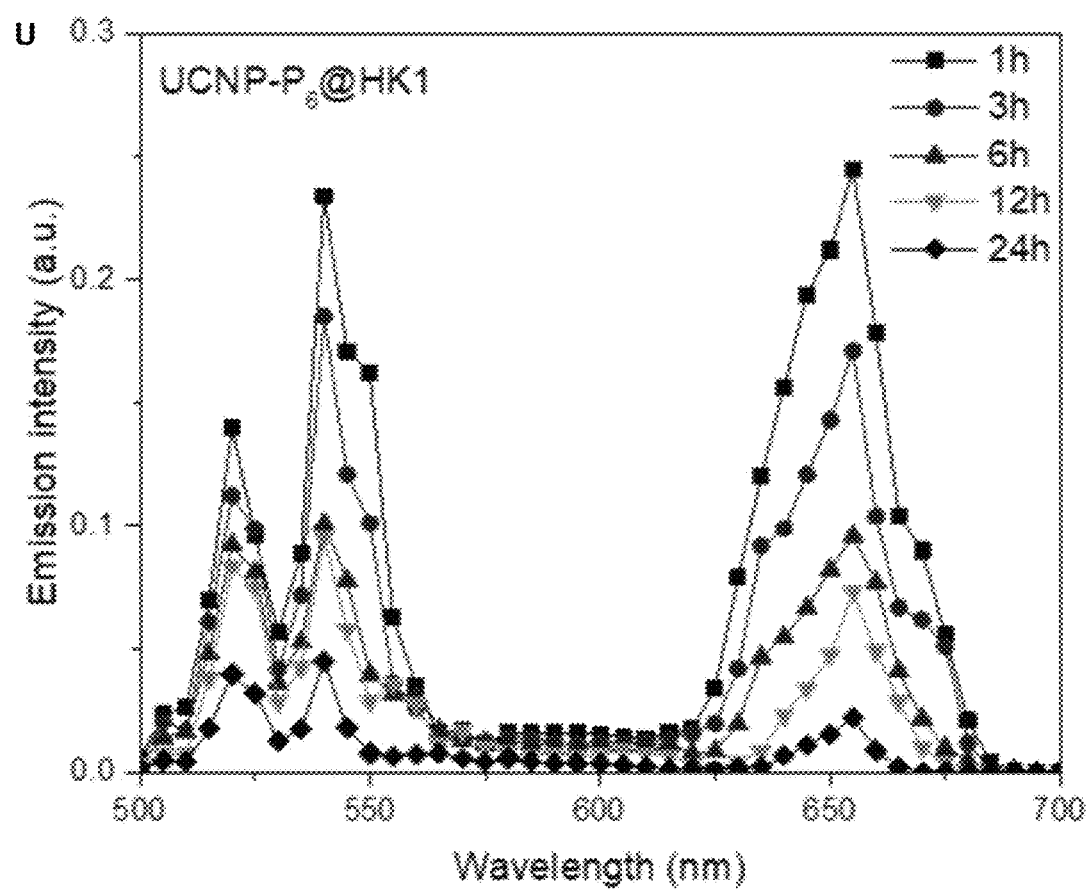
Figure 45:
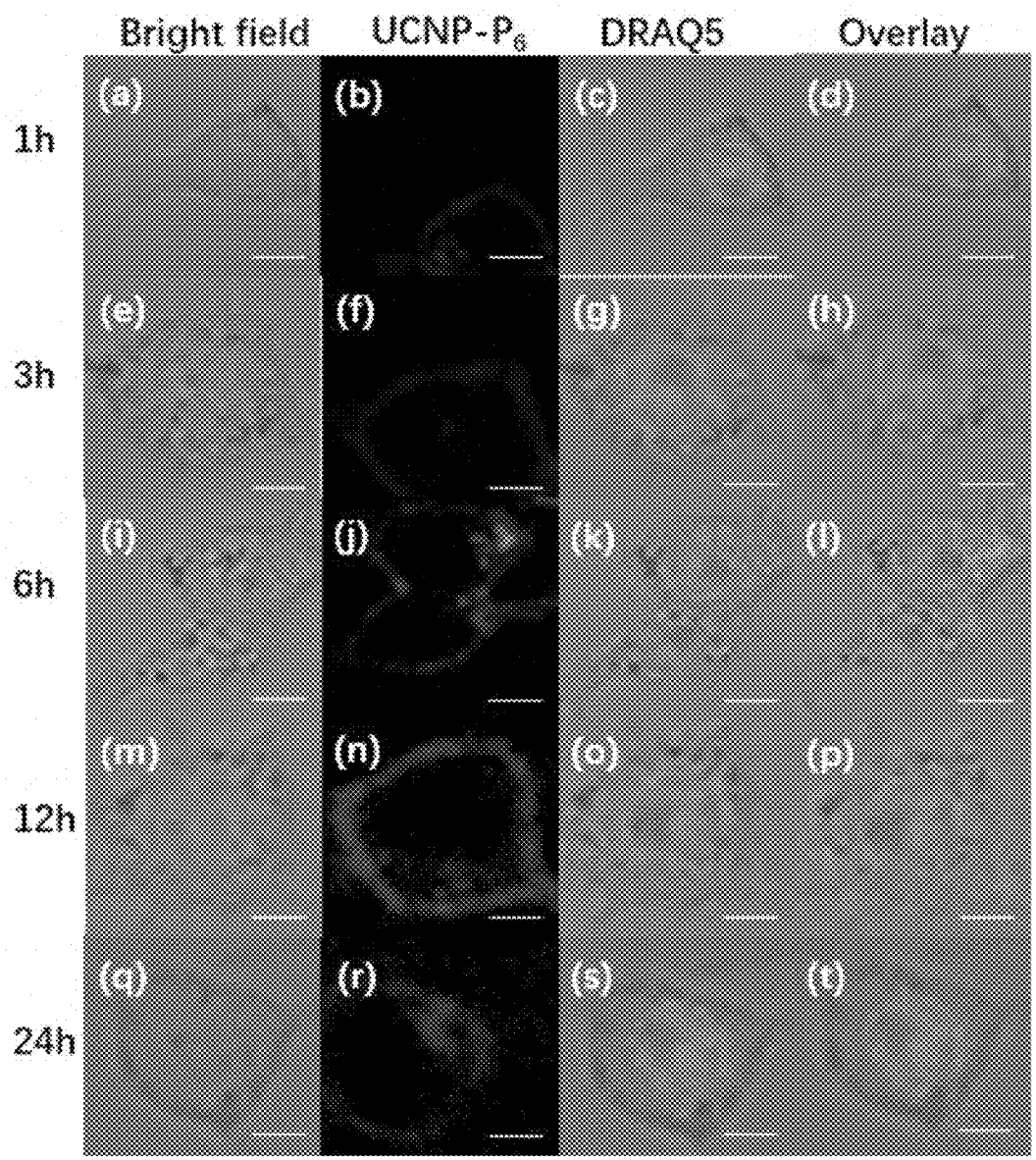
FIG. 45 depicts two-photon confocal images of UCNP-$P_6$ in EBV-negative HK1-LMP1 cells ($\lambda_{ex}$=980 nm, $\lambda_{em}$=500-700 nm); (A-D): bright field, UCNP-$P_6$ treated with HK1-LMP1 cells for 1 h, DRAQ5 fluorescence and overlay image respectively; (E-H): bright field, UCNP-$P_6$ treated with HK1-LMP1 cells for 3 h, DRAQ5 fluorescence and overlay image respectively; (I-L): bright field, UCNP-$P_6$ treated with HK1-LMP1 cells for 6 h, DRAQ5 fluorescence and overlay image respectively; (M-P): bright field, UCNP-$P_6$ treated with HK1-LMP1 cells for 12 h, DRAQ5 fluorescence and overlay image respectively; (Q-T): bright field, UCNP-$P_6$ treated with HK1-LMP1 cells for 24 h, DRAQ5 fluorescence and overlay image respectively; (U) Lambda scan of UCNP-$P_6$ in EBV-negative HK1-LMP1 cells in different time intervals of 1 h, 3 h, 6 h, 12 h and 24 h.
Figure 45:
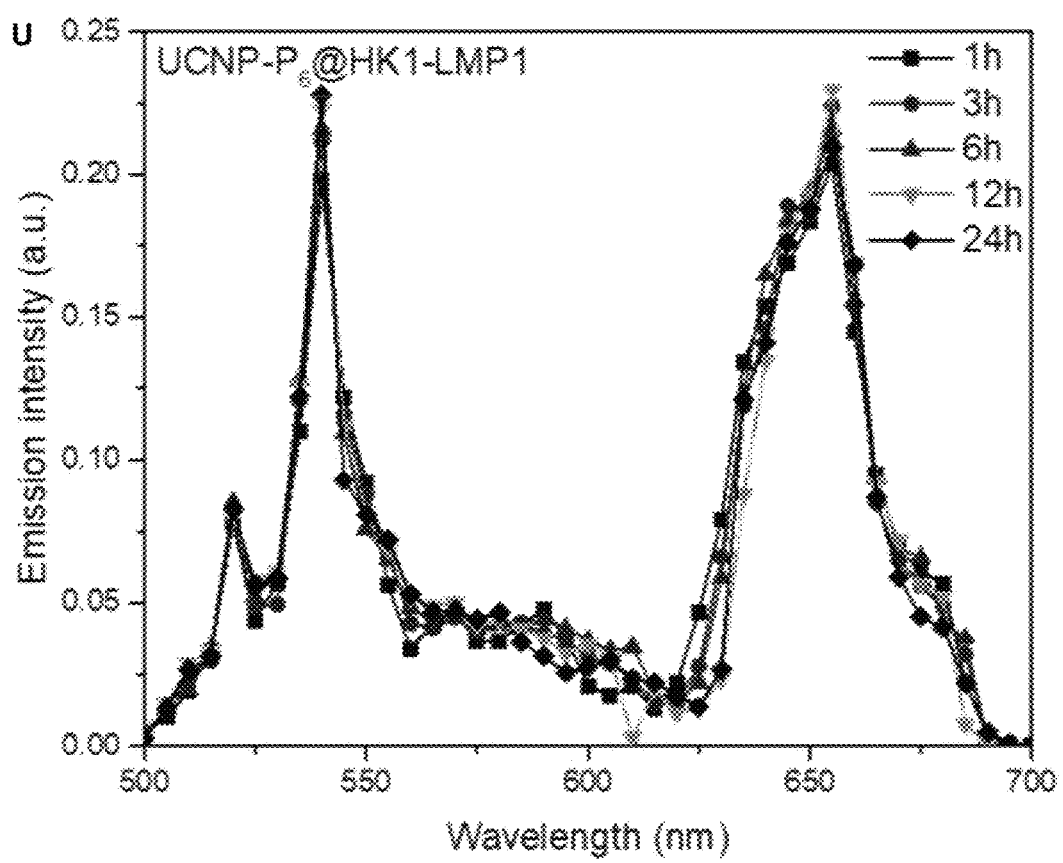
Figure 46:
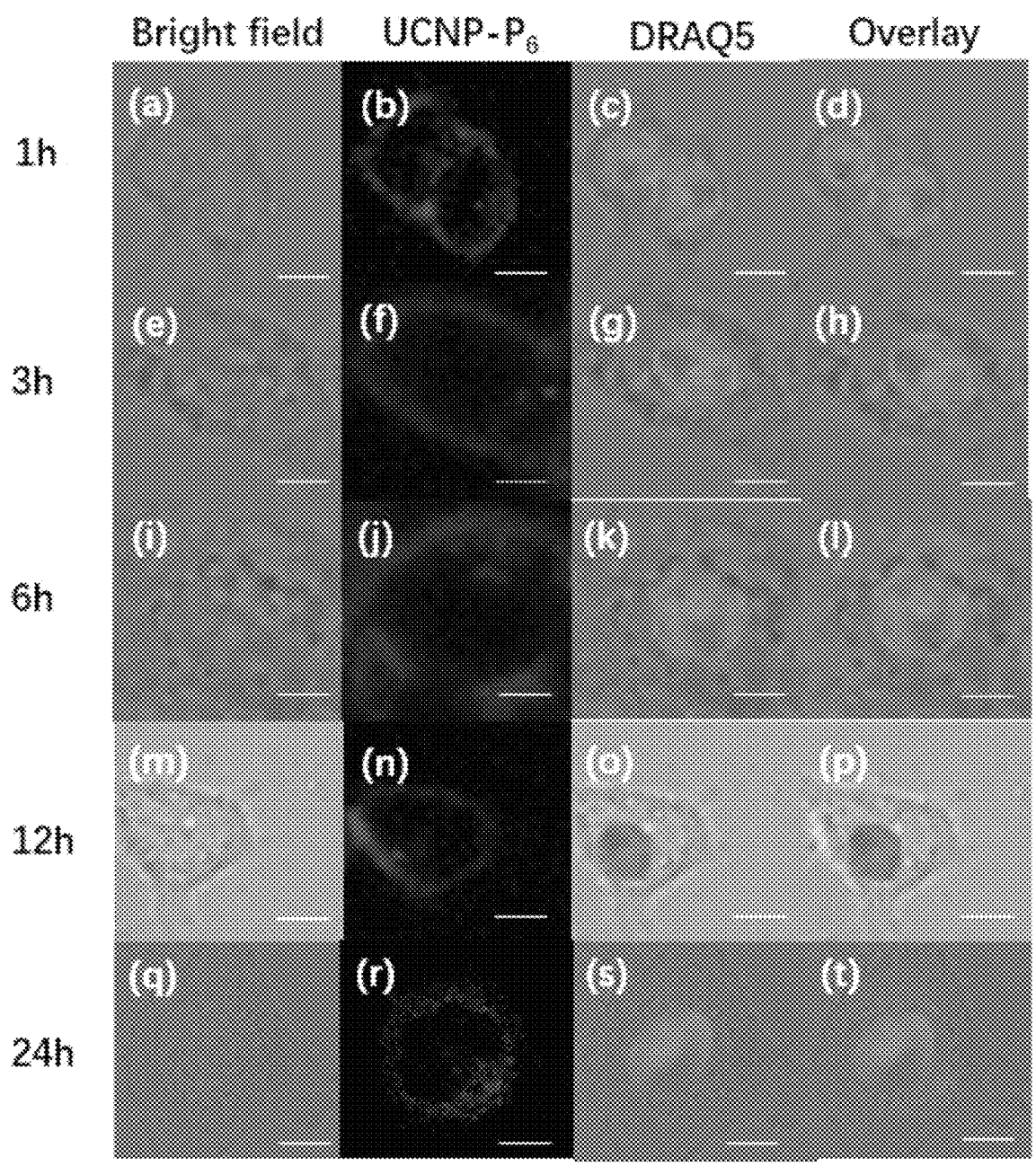
FIG. 46 depicts two-photon confocal images of UCNP-$P_6$ in EBV-positive LCL3 cells ($\lambda_{ex}$=980 nm, $\lambda_{em}$=500-700 nm); (A-D): bright field, UCNP-$P_6$ treated with LCL3 cells for 1 h, DRAQ5 fluorescence and overlay image respectively; (E-H): bright field, UCNP-$P_6$ treated with LCL3 cells for 3 h, DRAQ5 fluorescence and overlay image respectively; (I-L): bright field, UCNP-$P_6$ treated with LCL3 cells for 6 h, DRAQ5 fluorescence and overlay image respectively; (M-P): bright field, UCNP-$P_6$ treated with LCL3 cells for 12 h, DRAQ5 fluorescence and overlay image respectively; (Q-T): bright field, UCNP-$P_6$ treated with LCL3 cells for 24 h, DRAQ5 fluorescence and overlay image respectively; (U) Lambda scan of UCNP-$P_6$ in EBV-positive LCL3 cells in different time intervals of 1 h, 3 h, 6 h, 12 h and 24 h.
Figure 46:
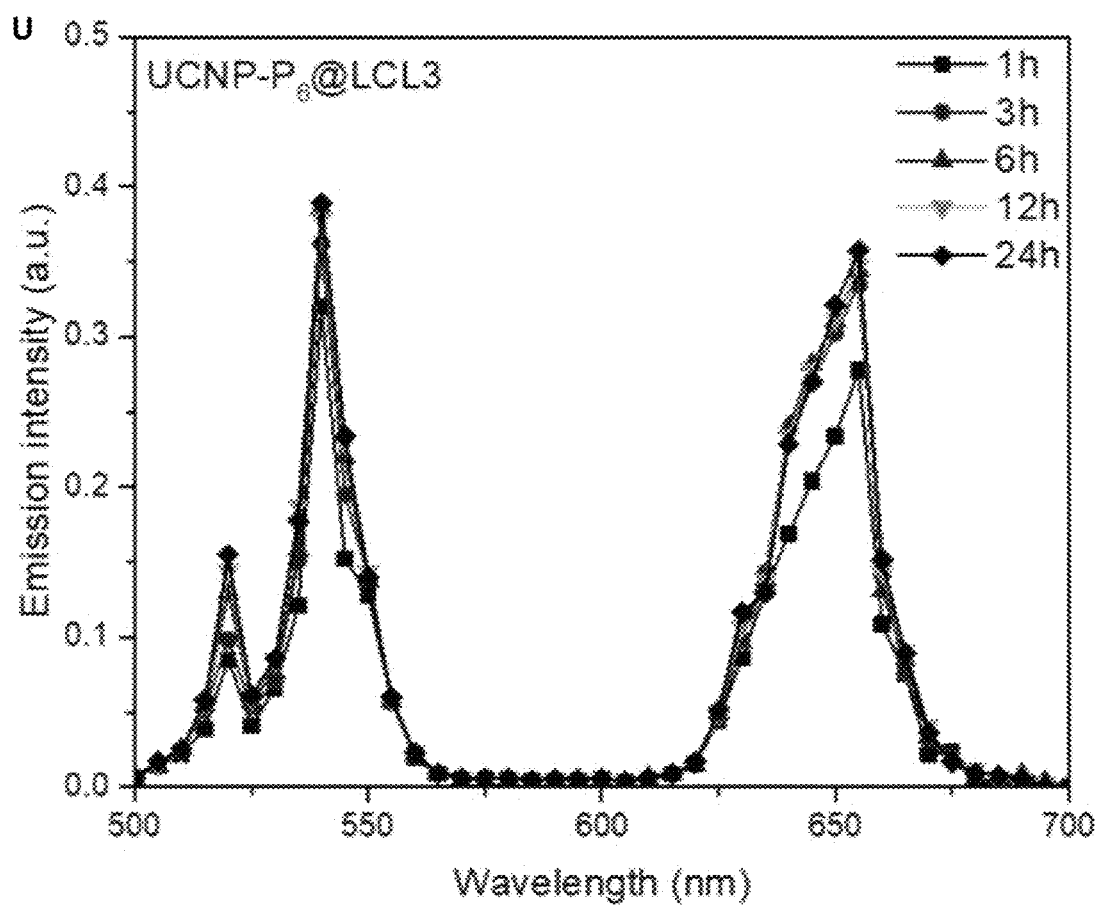
Figure 47:
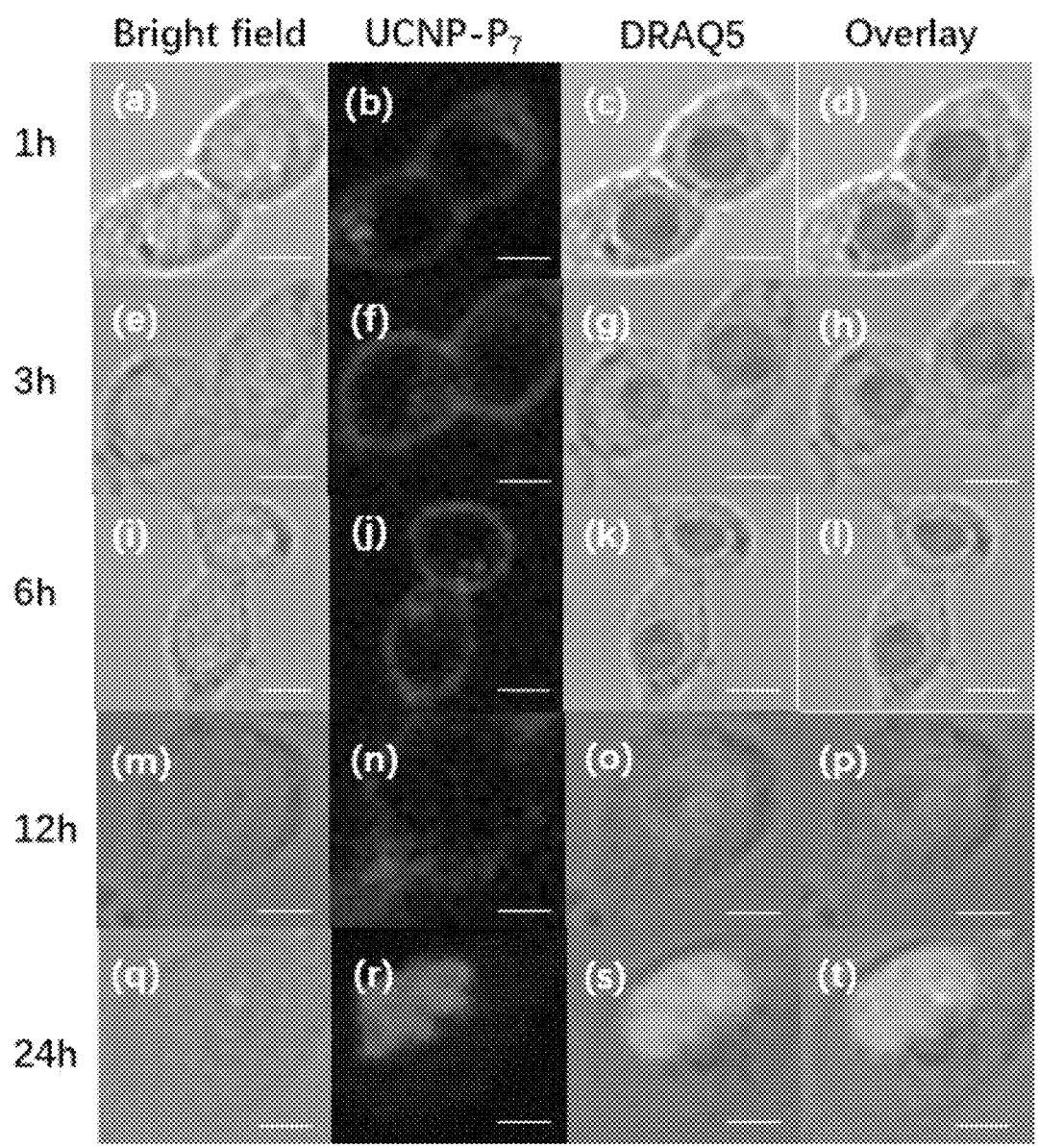
FIG. 47 depicts two-photon confocal images of UCNP-$P_7$ in EBV-positive C666 cells ($\lambda_{ex}$=980 nm, $\lambda_{em}$=500-700 nm); (A-D): bright field, UCNP-$P_7$ treated with C666 cells for 1 h, DRAQ5 fluorescence and overlay image respectively; (E-H): bright field, UCNP-$P_7$ treated with C666 cells for 3 h, DRAQ5 fluorescence and overlay image respectively; (I-L): bright field, UCNP-$P_7$ treated with C666 cells for 6 h, DRAQ5 fluorescence and overlay image respectively; (M-P): bright field, UCNP-$P_7$ treated with C666 cells for 12 h, DRAQ5 fluorescence and overlay image respectively; (Q-T): bright field, UCNP-$P_7$ treated with C666 cells for 24 h, DRAQ5 fluorescence and overlay image respectively; (U) Lambda scan of UCNP-$P_7$ in EBV-positive C666 cells in different time intervals of 1 h, 3 h, 6 h, 12 h and 24 h.
Figure 47:
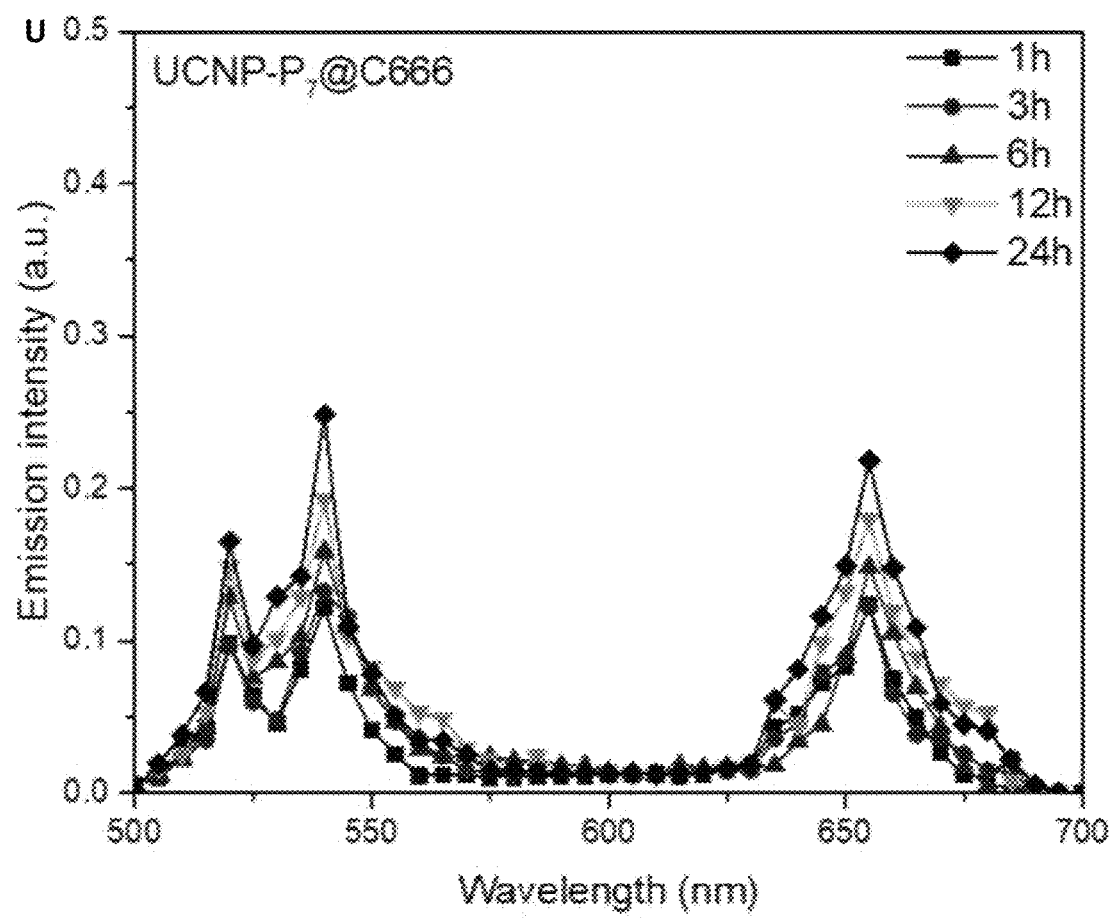
Figure 48:
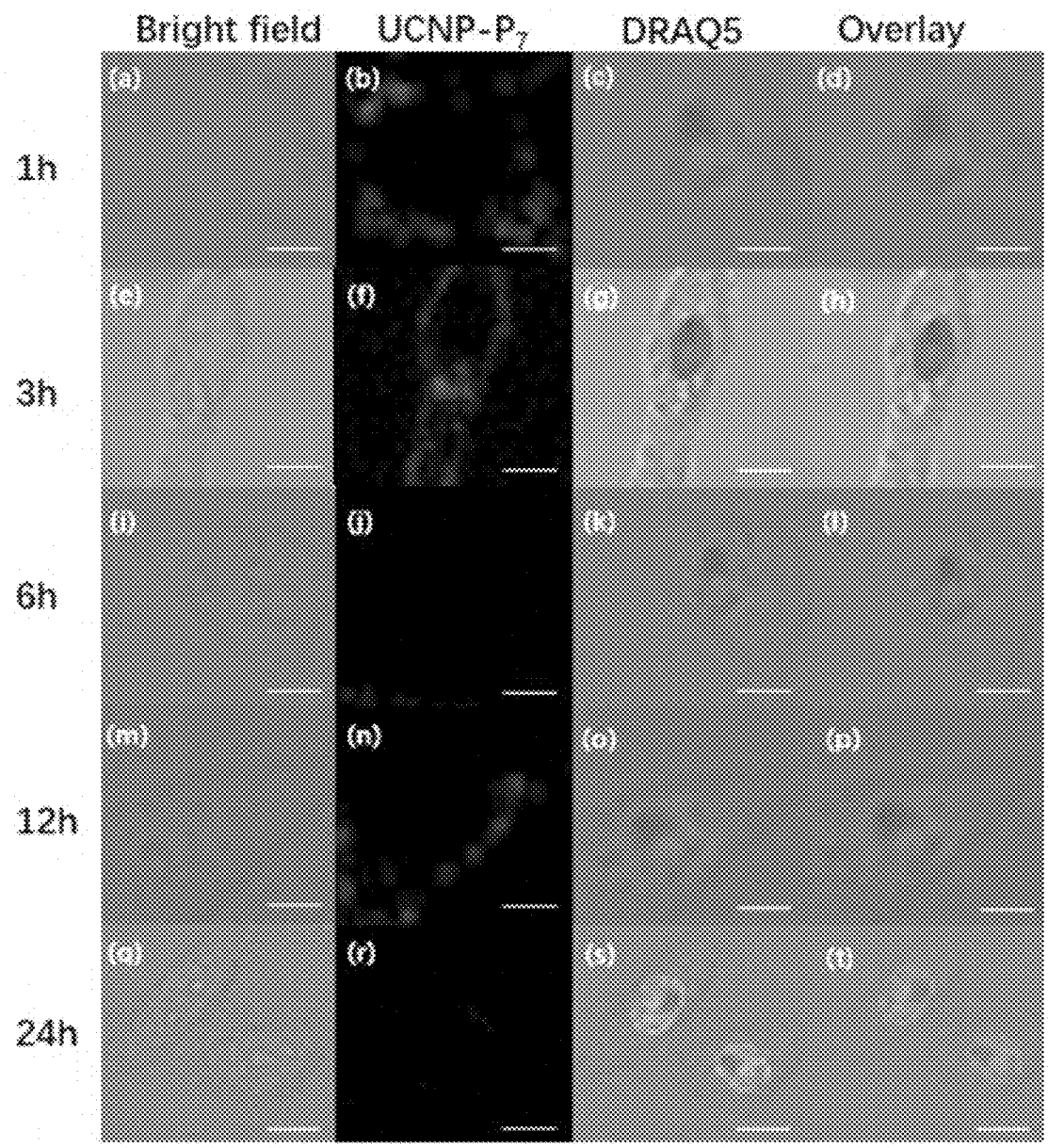
FIG. 48 depicts two-photon confocal images of UCNP-$P_7$ in EBV-negative HK1 cells ($\lambda_{ex}$=980 nm, $\lambda_{em}$=500-700 nm); (A-D): bright field, UCNP-$P_7$ treated with HK1 cells for 1 h, DRAQ5 fluorescence and overlay image respectively; (E-H): bright field, UCNP-$P_7$ treated with HK1 cells for 3 h, DRAQ5 fluorescence and overlay image respectively; (I-L): bright field, UCNP-$P_7$ treated with HK1 cells for 6 h, DRAQ5 fluorescence and overlay image respectively; (M-P): bright field, UCNP-$P_7$ treated with HK1 cells for 12 h, DRAQ5 fluorescence and overlay image respectively; (Q-T): bright field, UCNP-$P_7$ treated with HK1 cells for 24 h, DRAQ5 fluorescence and overlay image respectively; (U) Lambda scan of UCNP-$P_7$ in EBV-negative HK1 cells in different time intervals of 1 h, 3 h, 6 h, 12 h and 24 h.
Figure 48:
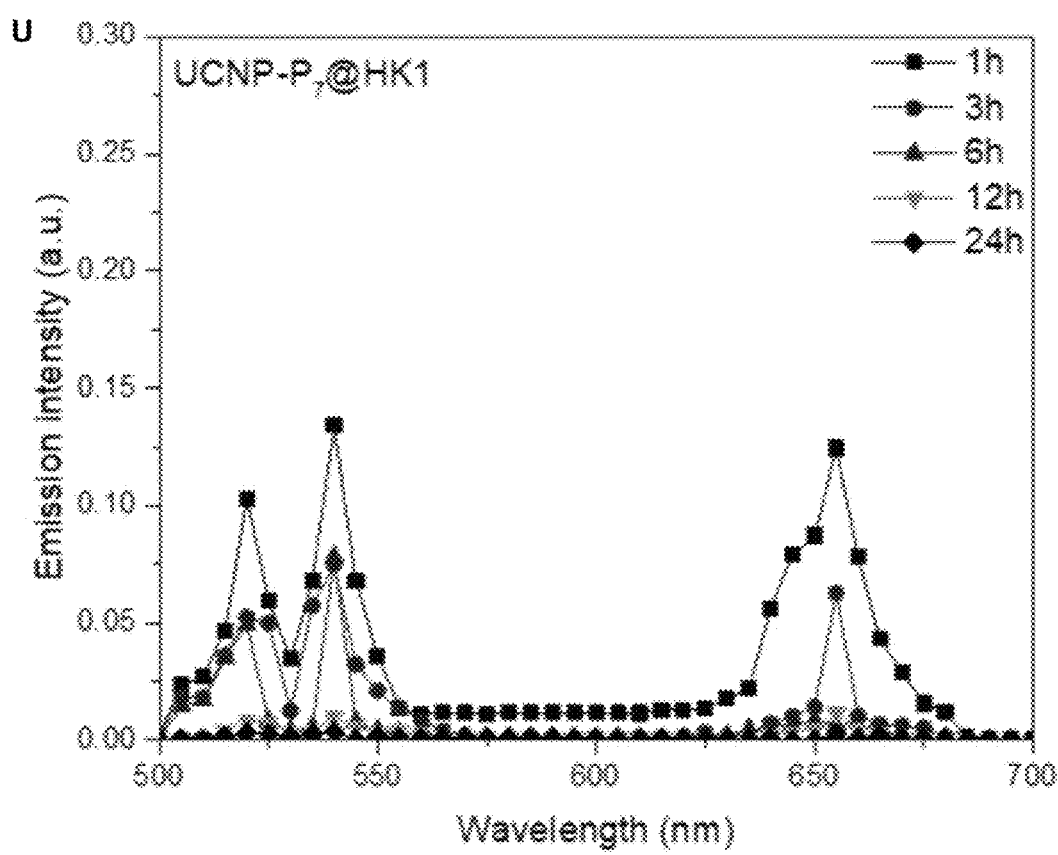
Figure 49:
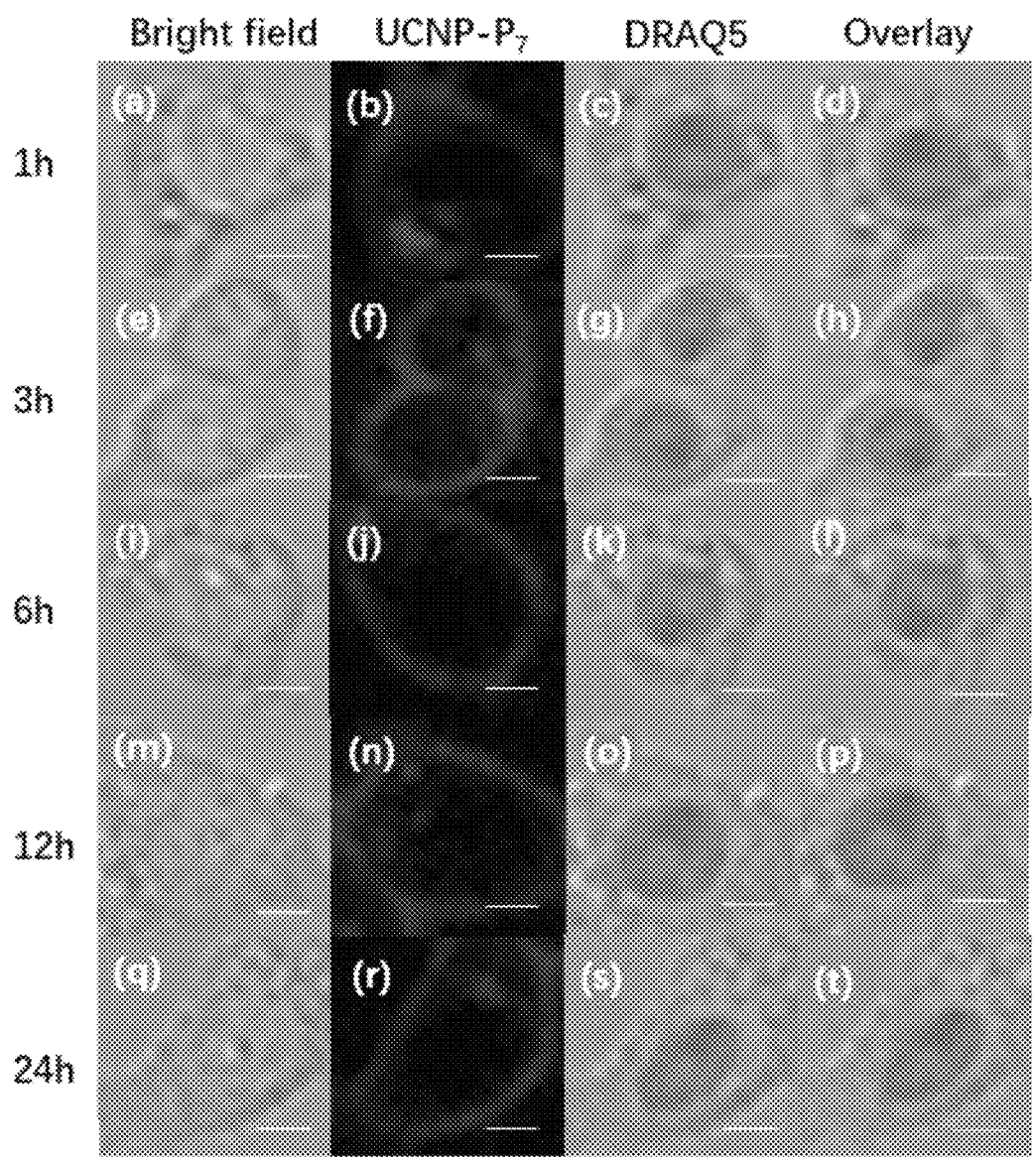
FIG. 49 depicts two-photon confocal images of UCNP-$P_7$ in EBV-negative HK1-LMP1 cells ($\lambda_{ex}$=980 nm, $\lambda_{em}$=500-700 nm); (A-D): bright field, UCNP-$P_7$ treated with HK1-LMP1 cells for 1 h, DRAQ5 fluorescence and overlay image respectively; (E-H): bright field, UCNP-$P_7$ treated with HK1-LMP1 cells for 3 h, DRAQ5 fluorescence and overlay image respectively; (I-L): bright field, UCNP-$P_7$ treated with HK1-LMP1 cells for 6 h, DRAQ5 fluorescence and overlay image respectively; (M-P): bright field, UCNP-$P_7$ treated with HK1-LMP1 cells for 12 h, DRAQ5 fluorescence and overlay image respectively; (Q-T): bright field, UCNP-$P_7$ treated with HK1-LMP1 cells for 24 h, DRAQ5 fluorescence and overlay image respectively; (U) Lambda scan of UCNP-$P_7$ in EBV-negative HK1-LMP1 cells in different time intervals of 1 h, 3 h, 6 h, 12 h and 24 h.
Figure 49:
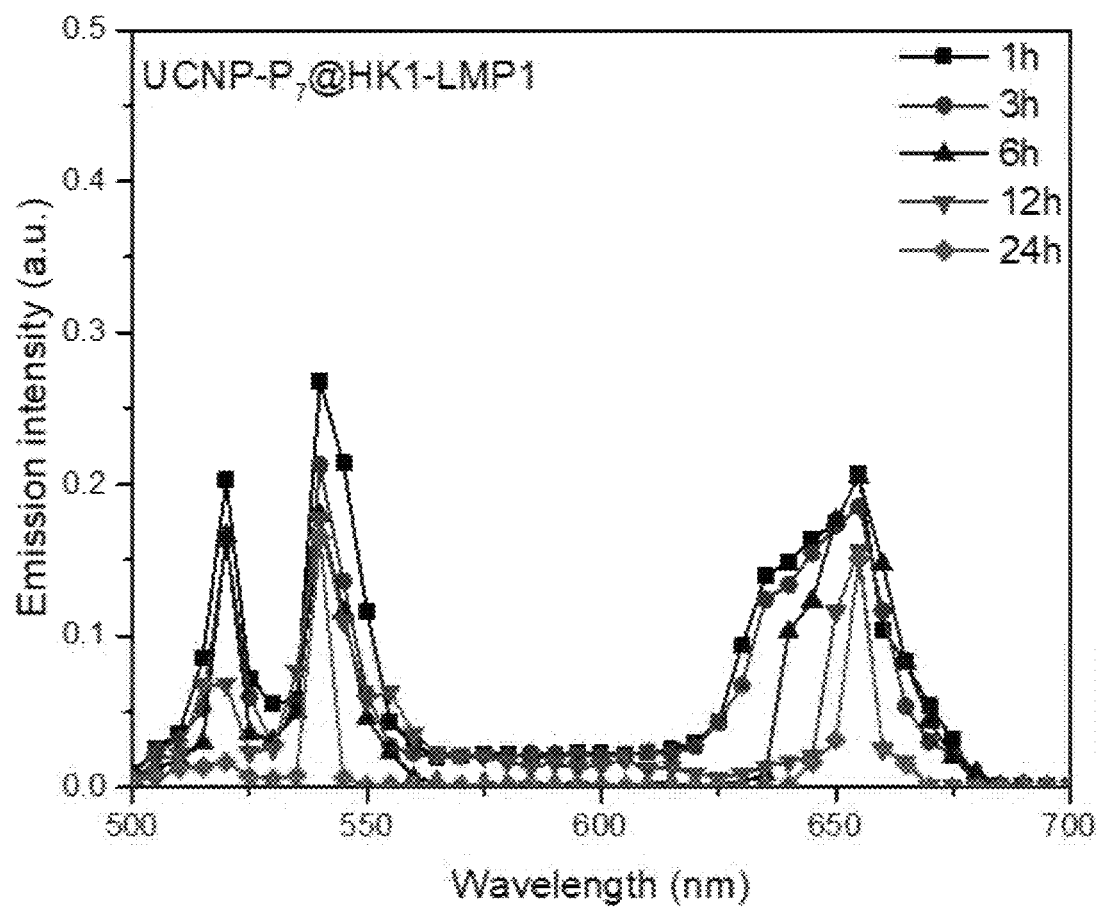
Figure 50:
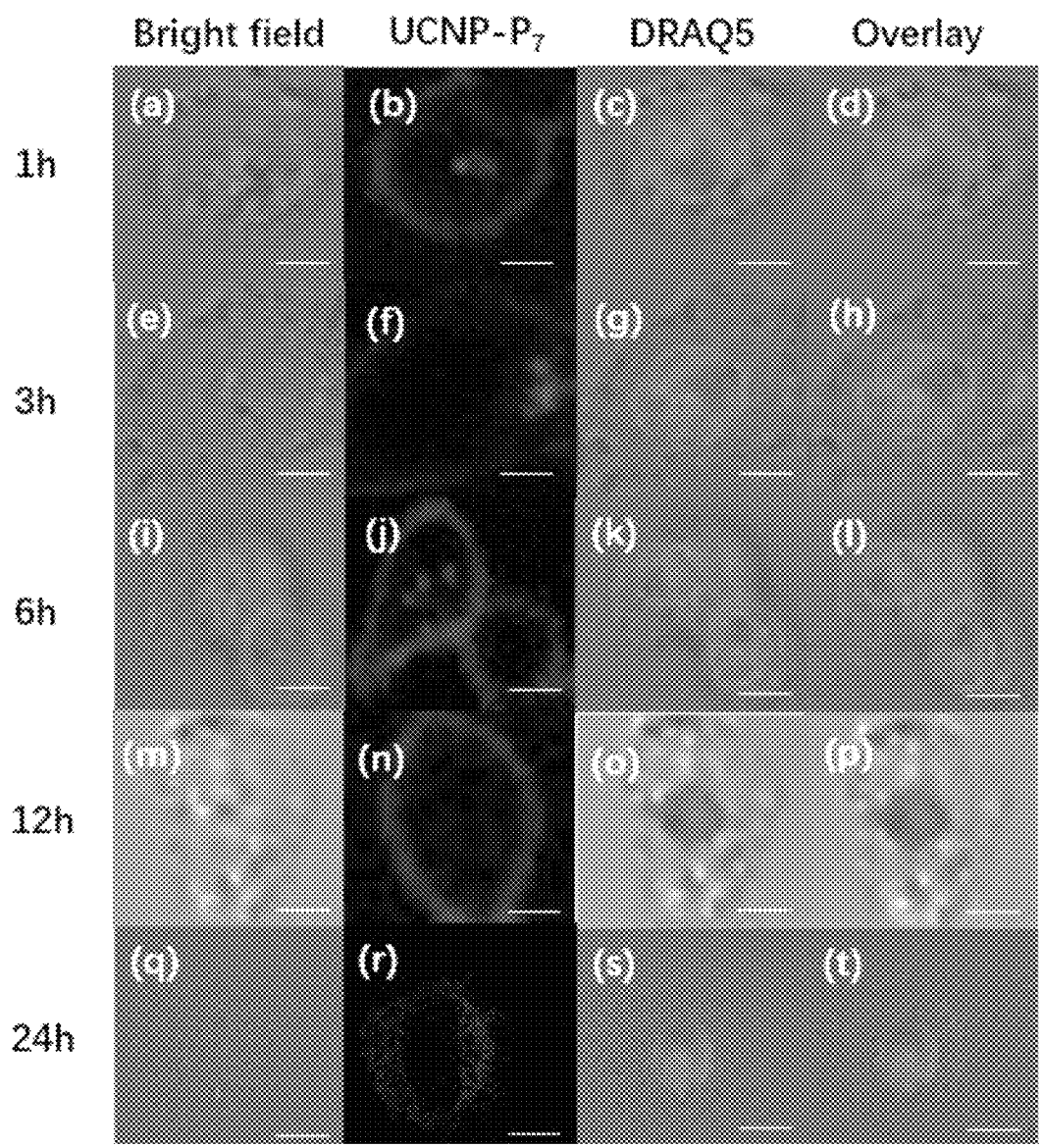
FIG. 50 depicts two-photon confocal images of UCNP-$P_7$ in EBV-positive LCL3 cells ($\lambda_{ex}$=980 nm, $\lambda_{em}$=500-700 nm); (A-D): bright field, UCNP-$P_7$ treated with LCL3 cells for 1 h, DRAQ5 fluorescence and overlay image respectively; (E-H): bright field, UCNP-P₇ treated with LCL3 cells for 3 h, DRAQ5 fluorescence and overlay image respectively; (I-L): bright field, UCNP-P₇ treated with LCL3 cells for 6 h, DRAQ5 fluorescence and overlay image respectively; (M-P): bright field, UCNP-P₇ treated with LCL3 cells for 12 h, DRAQ5 fluorescence and overlay image respectively; (Q-T): bright field, UCNP-P₇ treated with LCL3 cells for 24 h, DRAQ5 fluorescence and overlay image respectively; (U) Lambda scan of UCNP-P₇ in EBV-positive LCL3 cells in different time intervals of 1 h, 3 h, 6 h, 12 h and 24 h.
Figure 50:
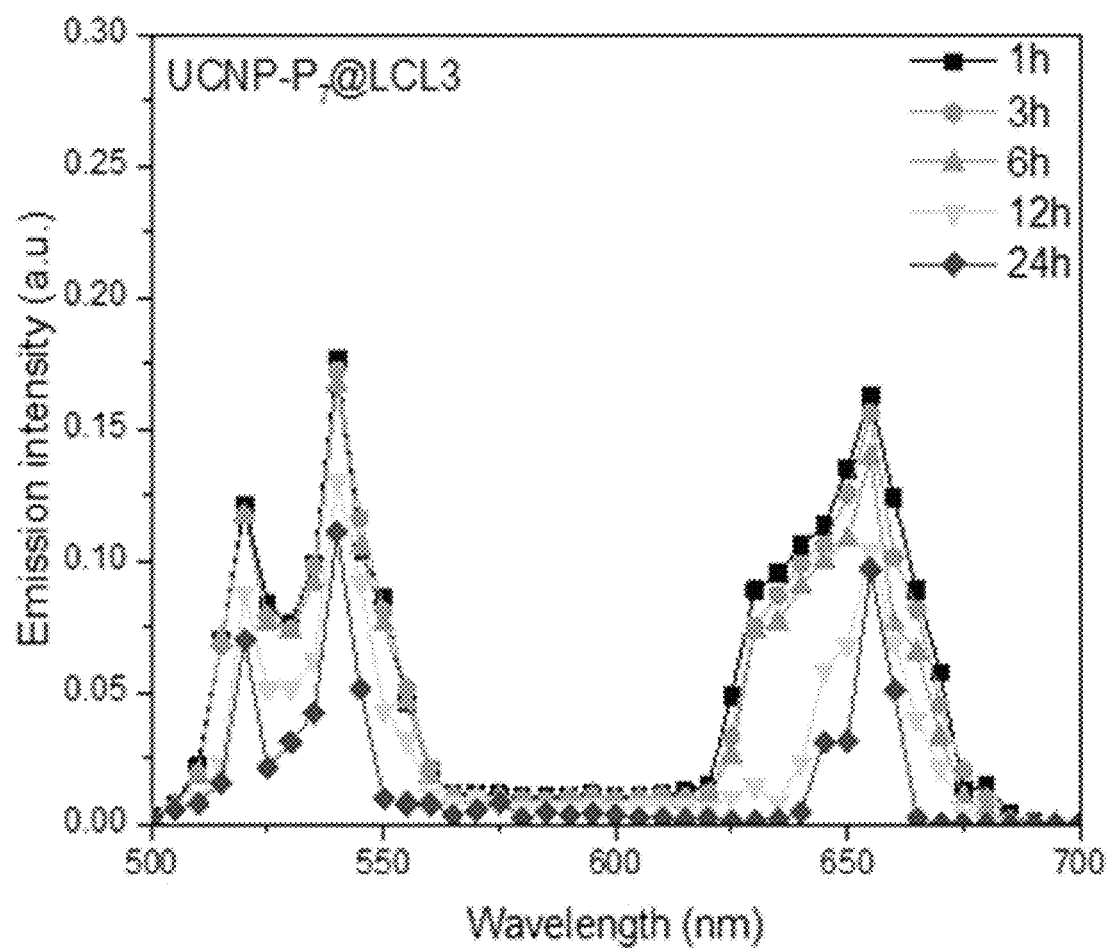

As shown in FIG. 6, the UCNP-$P_5$ nanoprobe was mainly localized in the cell membrane and weak signals were observed in the cytoplasm in C666 cells from 1 to 3 hours. From 6 hours onwards, disperse nuclear signal was observed, and only strong signals in the nuclei were observed 24 hours. For EBV- and LMP1-negative HK1 cells, as shown in FIG. 36, very weak signals were detected at the cell membrane from 1 to 6 hours, but from 12 hours onwards, barely detectable signals were observed, as both targeted proteins, LMP1 and EBNA1, are absent in this cell line. For HK1-LMP1 cells, weak signals were observed in cell membrane and cytoplasm from 1 to 3 hours, increased fluorescent signals with similar patterns were observed from 6 to 24 hours (FIG. 37). For LCL3 cells, from 1 to 6 hours fluorescent signals were mainly observed in cell membrane, cytoplasmic signals were detected at 12 hours, and weak nuclear signals were observed at 24 hours (FIG. 38).

It is likely that the FWLY motif in UCNP-$P_5$ can enhance the cellular uptake with LMP1 located on the plasma membrane and endoplasmic reticulum, as reflected by the HK1-LMP1 and HK1 cell pair. For C666 and LCL3 cells, the nanoplatforms are likely to be attracted onto the transmembrane, probably via endocytosis to enter the cytoplasm, and eventually arrive at the nuclei with assistance of the RrRK nuclear location signal sequence, eventually binding with the EBNA1 protein by the YFMVF motif. Lambda scans were run on all the cells and the in vitro emission spectra were recorded at each time interval to detect erbium transitions, since its emission intensity can be regarded as direct evidence of the presence of nanoplatforms. More importantly, a two-fold responsive UC emission enhancement was observed after 24 h incubation in EBV-positive cells, which is consistent with luminescence titration results. Furthermore, the emission was detected mainly from the nucleus, which can be confirmed by fluorescence of DRAQ5 nuclear dye.

Figure 51:
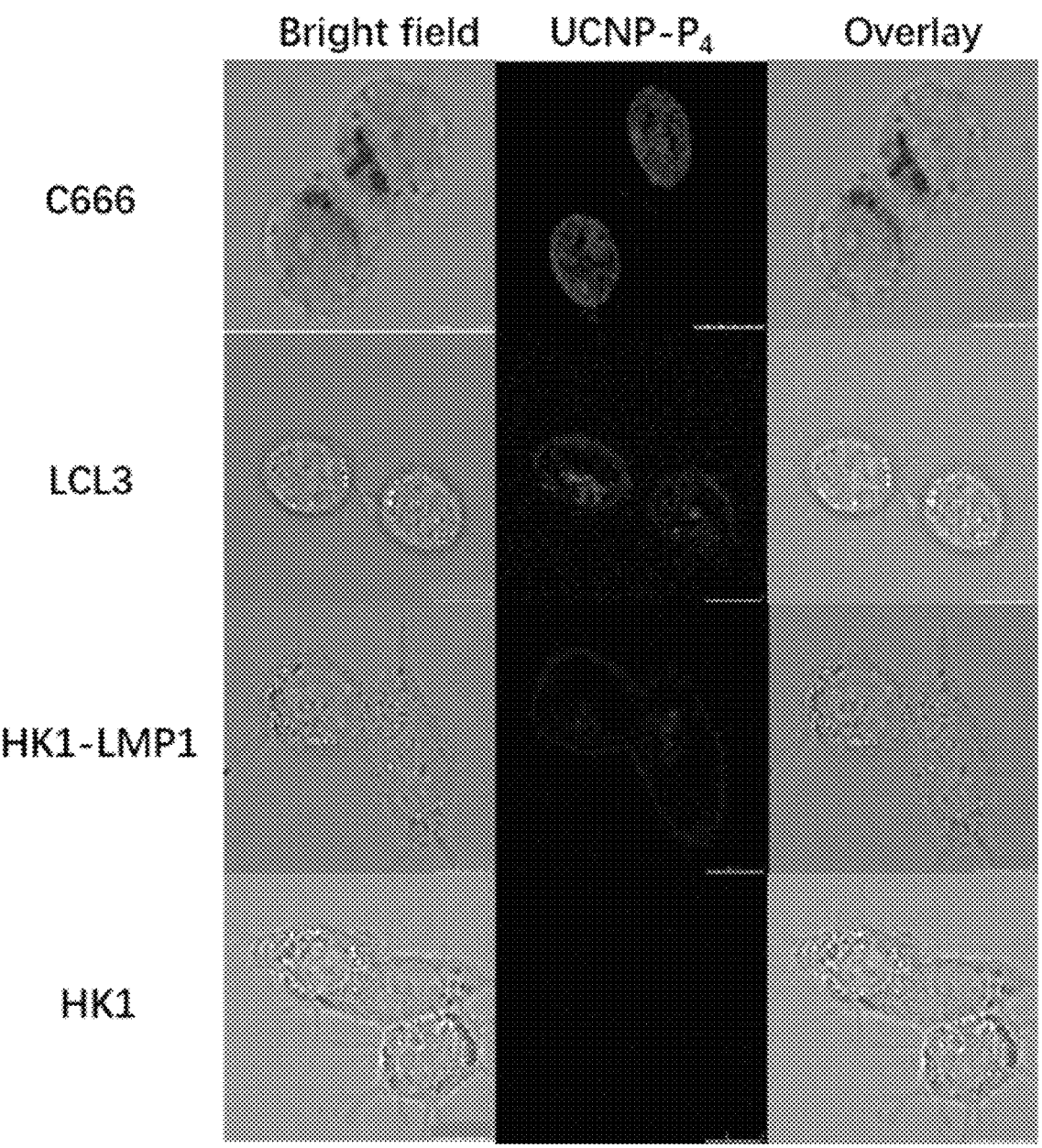
FIG. 51 Two-photon confocal images of UCNP-P₄ in EBV-positive C666 cells, LMP1-positive LCL3 and HK1-LMP1 cells, EBV-negative HK1 cells. ($l_{ex}$=980 nm, incubation time: 24 h)

The UCNP control was rapidly excreted out of the cells, therefore, UCNP not only had no inhibitory effect on any cells, but also exhibited weak or absent emission signals after 24 h, as shown in FIG. 39, FIG. 40, FIG. 41 and FIG. 42. Moreover, similar to UCNP-$P_5$, UCNP-$P_6$ and UCNP-$P_7$ exhibited two-fold responsive emission enhancement mainly from the nuclei in C666 cells as well, while in HK1 cells the intensity declined dramatically, and no signals could be detected. Notably, the emission intensity from cellular transmembrane was maintained even after 24 h incubation in HK1-LMP1 and LCL3 cells, as shown in FIG. 43, FIG. 44, FIG. 45 and FIG. 46, and FIG. 47, FIG. 48, FIG. 49 and FIG. 50, respectively. In addition, UCNP-$P_4$ only exhibited strong emission in the nucleus of EBNA1-positive C666 cells after 24 h incubation, as shown in FIG. 51.

As we had demonstrated previously, the hydroxyl and amine groups with high vibrational energies from the peptide coating would quench the excited state of lanthanide ions. Strong interactions of the YFMVF and RrRK motifs with EBNA1 can disturb the surface quenching process and, as a result, the nanoprobes exhibited a recovery in emission signal. Once the nanoplatforms are taken up into a tumor cell, their pH-responsive linkers are presumably cleaved in the weakly acidic tumor microenvironment in the cancer cell, and more peptides will be released into, hence enhancing the inhibitory activity.

Figure 7:
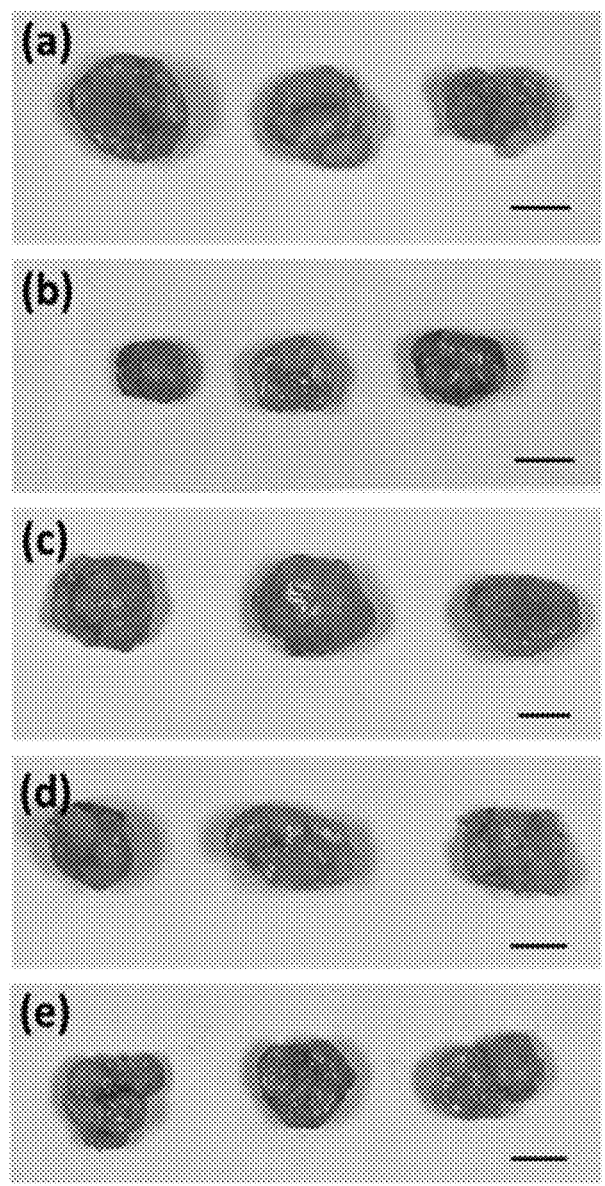
FIG. 7 depicts Digital photographs of tumor after treatment of (A) PBS (B) UCNP-P$_5$ (C) UCNP-P$_6$ (D) UCNP-P$_7$ (E) UCNP. Scale bar: 10 mm; (F) Tumor volume after treatment of UCNP, UCNP-P$_5$, UCNP-P$_6$, UCNP-P$_7$ and PBS during 33-day experimental period; (G) Tumor weight after treatment of UCNP, UCNP-P$_5$, UCNP-P$_6$, UCNP-P$_7$ and PBS during 33-day experimental period; (H) Body weight in UCNP, UCNP-P$_5$, UCNP-P$_6$, UCNP-P$_7$ and PBS group after experimental period of 33 days (I) Weights of vital organs, i.e. heart, lung, liver, spleen, skin, kidney and brain in UCNP, UCNP-P$_5$, UCNP-P$_6$, UCNP-P$_7$ and PBS group after experimental period of 33 days; (J) ICP-MS results in different organs and tumor by detecting Gd ions after treatment of UCNP and UCNP-P$_n$ [n=5, 6 and 7 (SEQ ID NO: 5, 6, 7)]; (K) H&E-stained sections of C666 and HeLa derived tumors after different treatments including PBS, UCNP, UCNP-P$_5$, UCNP-P$_6$ and UCNP-P$_7$. The black star-like labels indicate cell necrosis in the tumors. Scale bar=100 µm.
Figure 7:
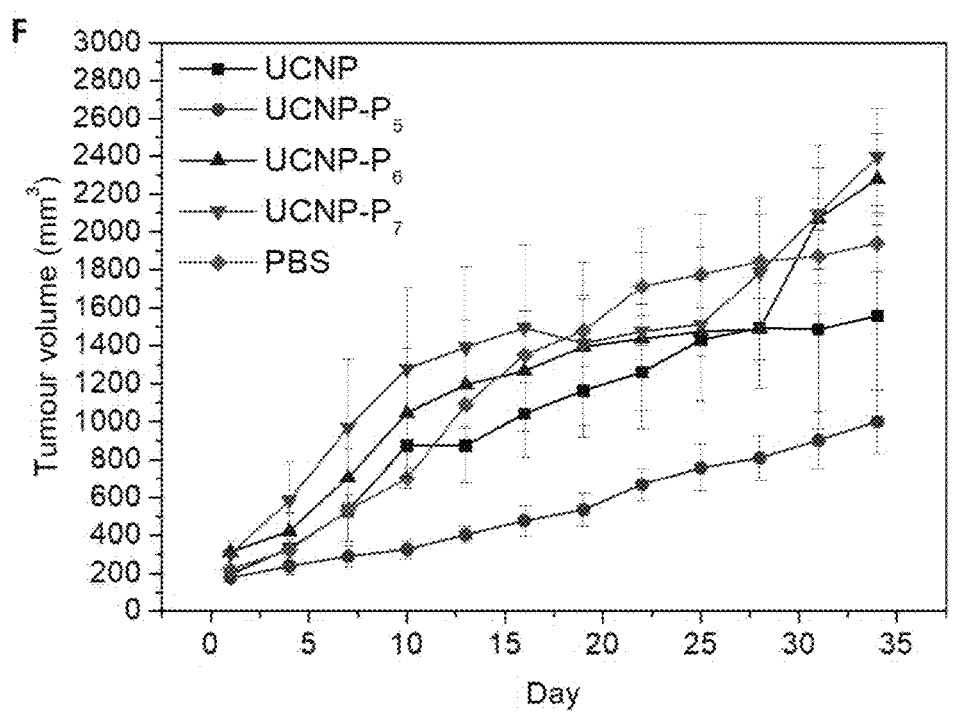
Figure 7:
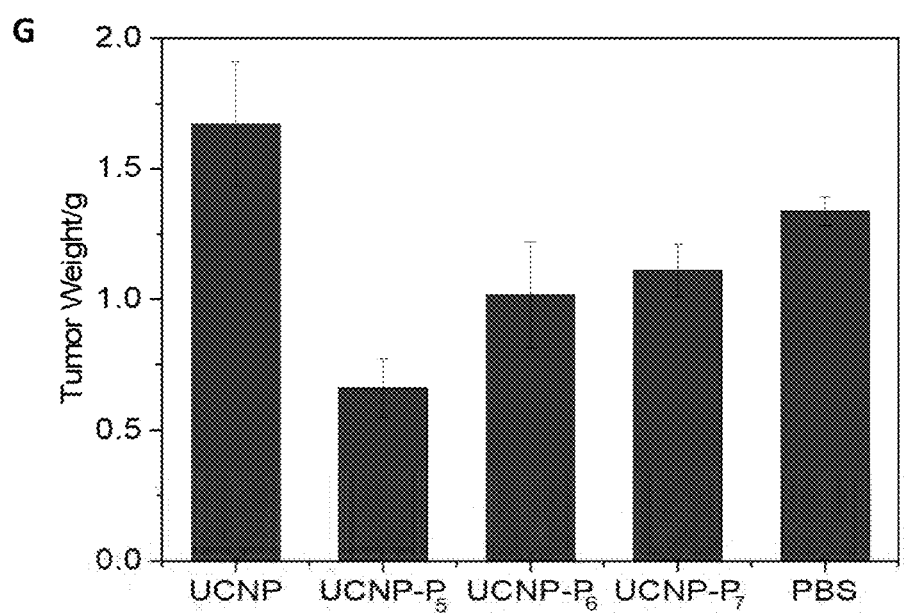
Figure 7:
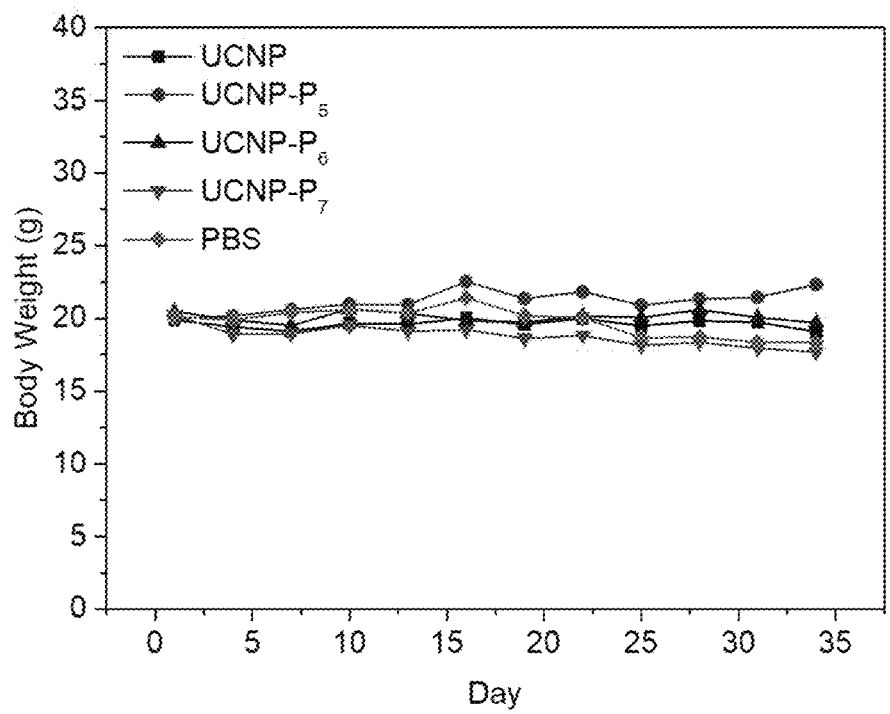
Figure 7:
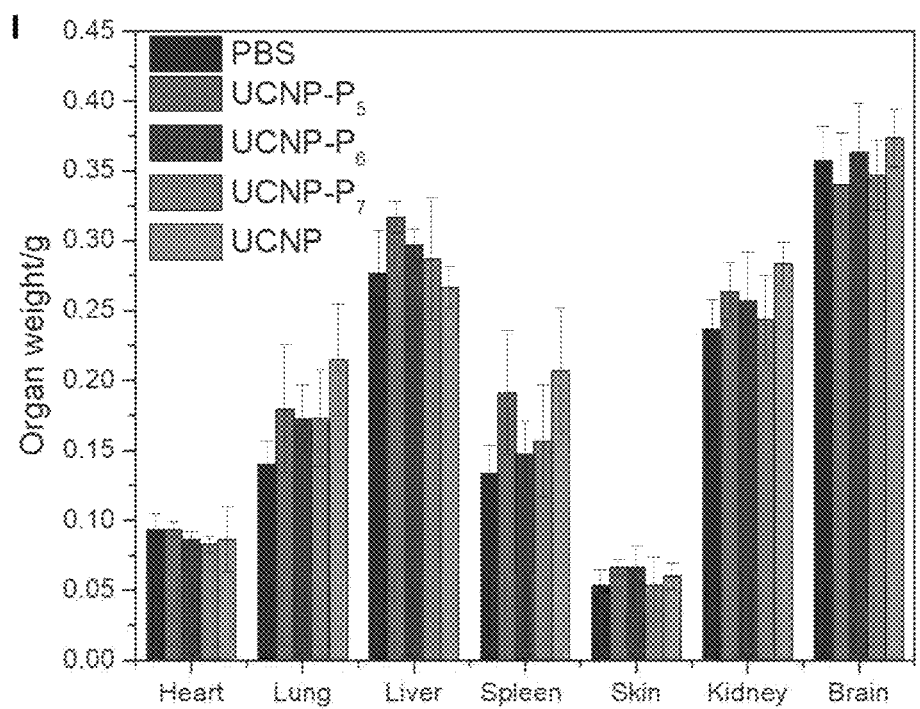
Figure 7:
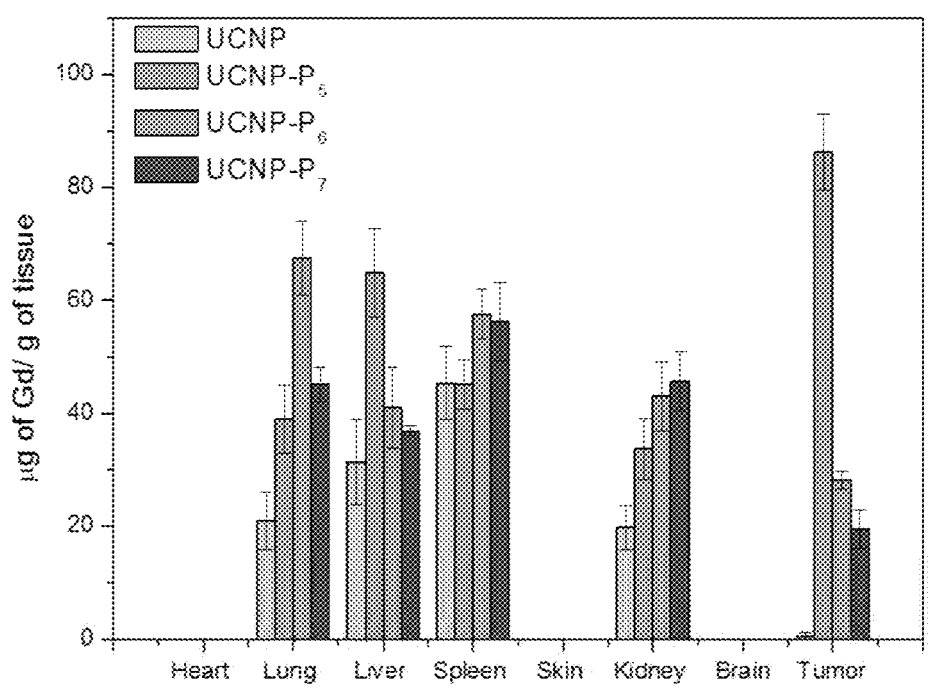
Figure 7:
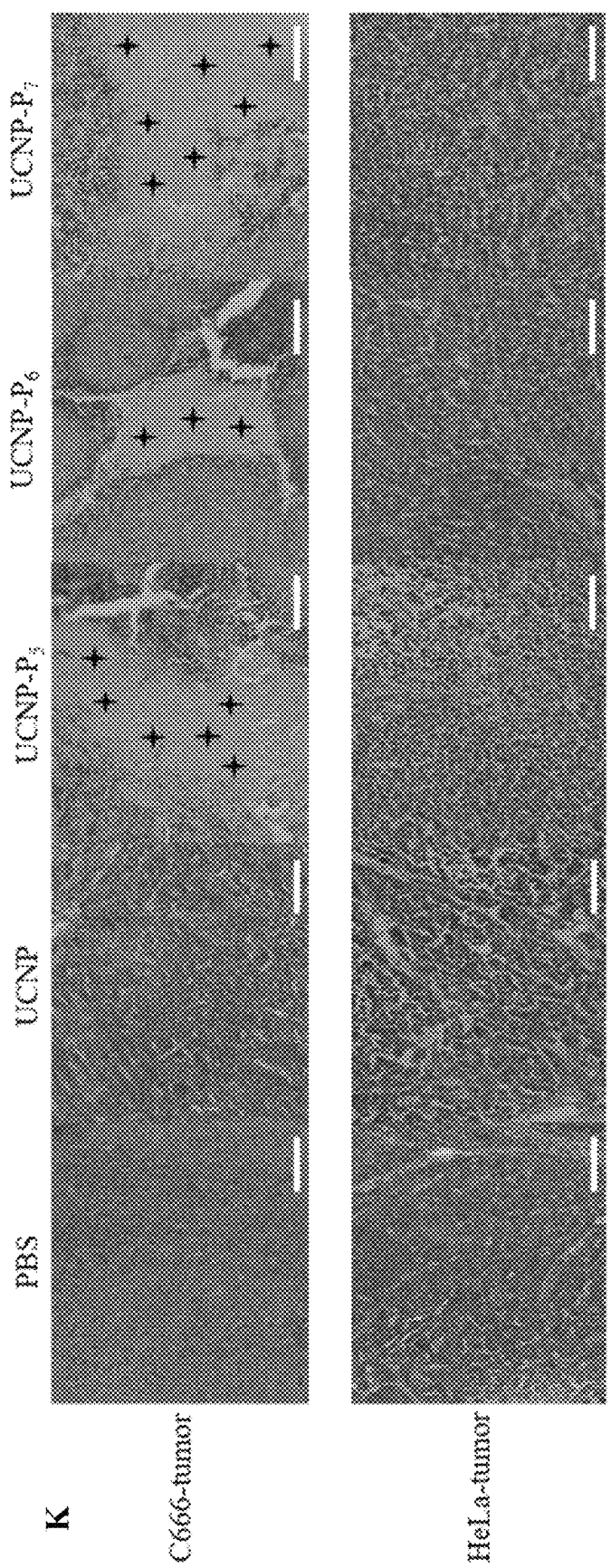
Figure 52:
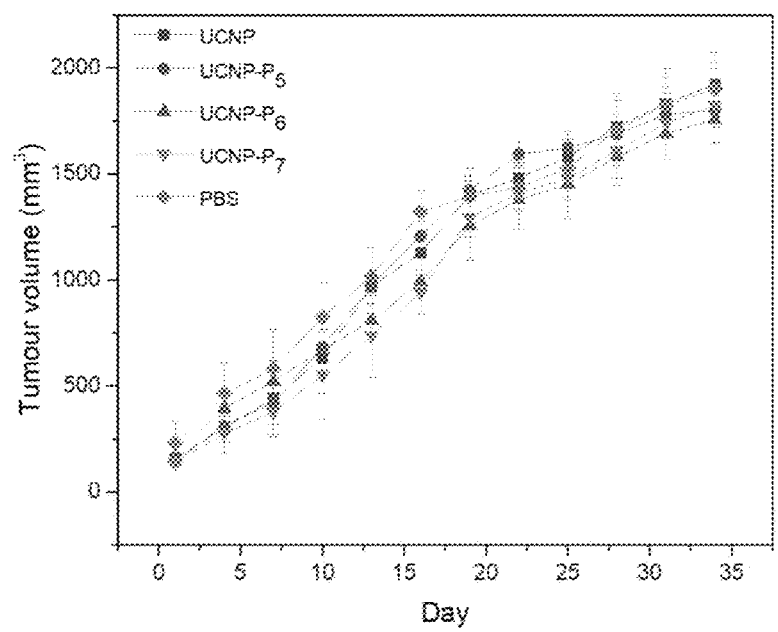
FIG. 52 depicts (A) tumor volume of HeLa cell xenograft after treatment of UCNP, UCNP-P₅, UCNP-P₆, UCNP-P₇ and PBS during 33-day experimental period; (B) Body weight after treatment of UCNP, UCNP-P₅, UCNP-P₆, UCNP-P₇ and PBS.
Figure 52:
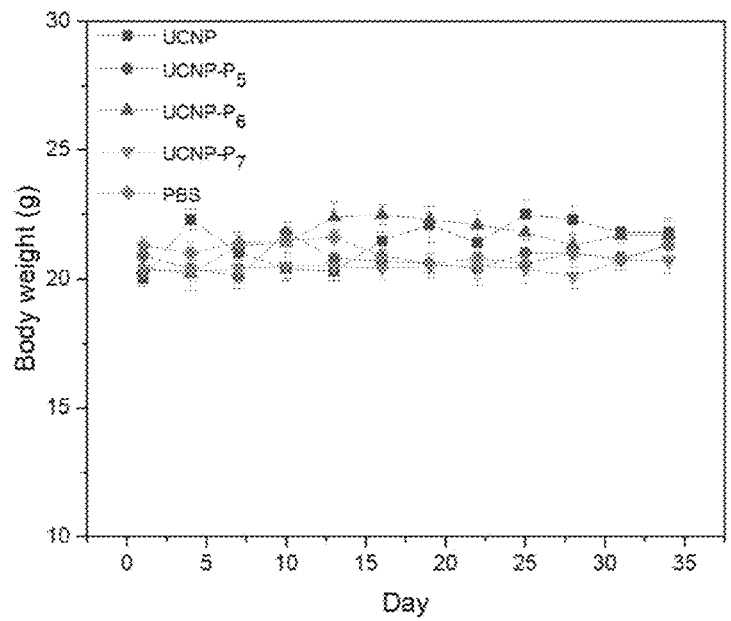

To determine the antitumor efficacy of the new nanoprobes in vivo, their therapeutic effects were investigated in C666 and HeLa derived xenografts in BALB/c nude mice. The mice were randomly divided into five groups: (1) control (PBS), (2) UCNP, (3) UCNP-$P_5$, (4) UCNP-$P_6$, (5) UCNP-$P_7$. In order to recapitulate the clinical setting of drug delivery, intravenous injection (via a tail vein) was used to deliver these agents to the immunocompromised animal. The preliminary results have shown that 12.5 mg/kg UCNP-$P_5$ could significantly reduce the average tumor size of the C666-derived tumor in nude mice (FIG. 7A-FIG. 7G). In contrast, the same amount of UCNP-$P_6$ or UCNP-$P_7$ had no obvious effect on the tumor size when compared with the solvent and the UCNP-alone (without any EBNA-LMP1 binding peptide) controls, slight reduction of body weight was observed in these animals (FIG. 7H). With the UCNP-$P_5$ treatment, the average body weight and various organ weights slightly increased during the experimental period (FIG. 7H and FIG. 7I), these data can be interpreted as an indicator for the drug efficacy and safety. On the other hand, the in vivo biodistribution detected by ICP-MS has shown that UCNP-$P_5$ was taken up by the tumor ~3-fold higher than UCNP-$P_6$, and UCNP-$P_7$, and UCNP-alone was nearly undetectable in the tumor (FIG. 7J). This can explain why UCNP-$P_5$ is the most effective UCNP-associated compound when delivered through the circulation, and also indicating that the conjugated peptide contributes to its tumor-specificity. In addition, partial accumulation of nanoprobes in the reticuloendothelial system (RES), such as liver, spleen and lung, where UCNP-$P_5$ had been taken up, but their uptake values were less than the tumors after injection which inferred that excretion occurred. None of our nanoprobes had any significant effect on the tumor growth of HeLa (FIG. 52), suggesting that UCNP-$P_5$ is a specific agent towards EBV-associated tumors via targeting EBNA1 and LMP1, with desired safety and therapeutic effectiveness.

Figure 53:
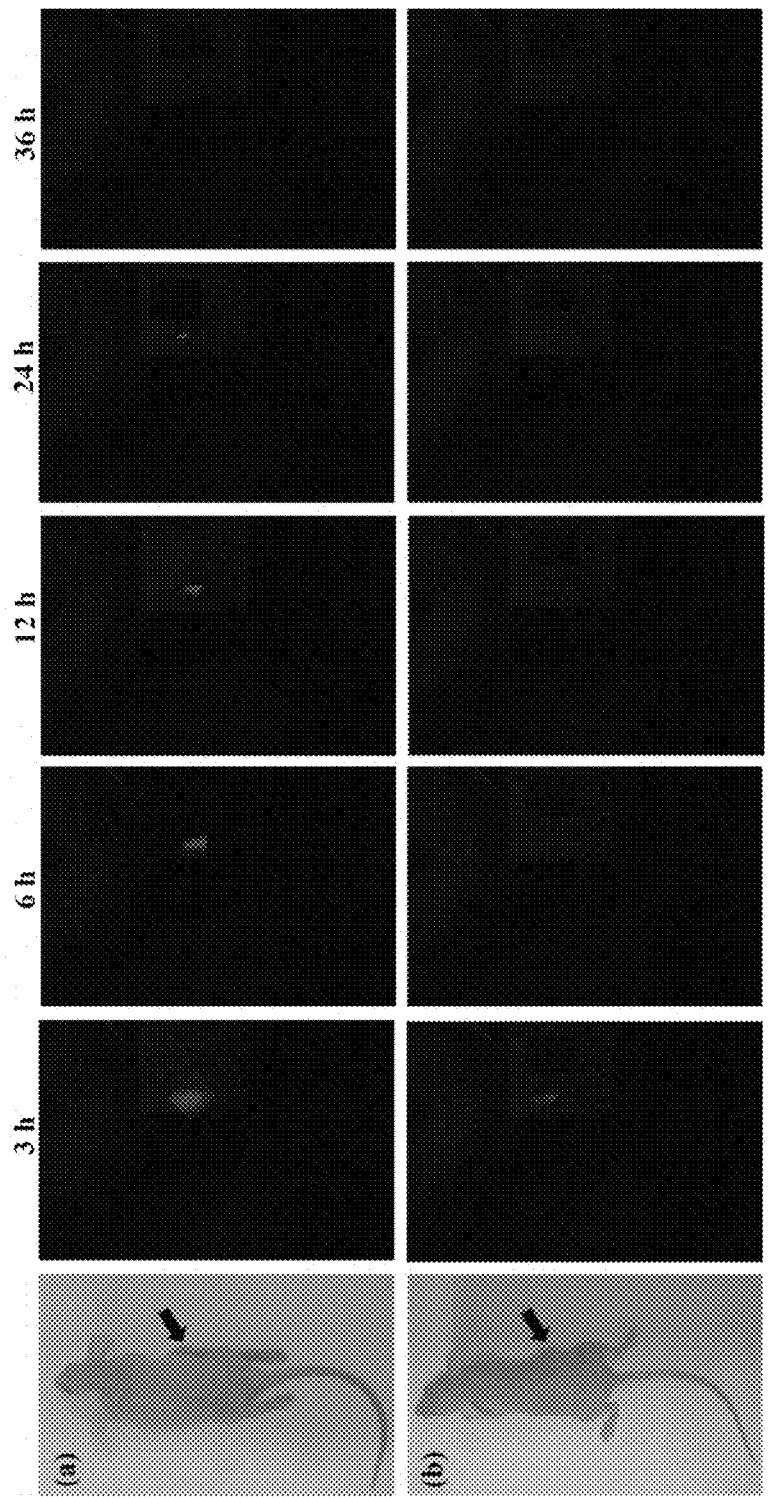
FIG. 53 depicts In vivo upconversion luminescence images of (A) C666-tumor-bearing (B) HeLa-tumor-bearing nude mice treating with UCNP-P₅ after various intravenous post injection time at 3 h, 6 h, 12 h, 24 h and 36 h under 980 nm excitation. Arrows indicate the tumor sites.

In vivo upconversion luminescence imaging was performed using UCNP-$P_5$ under 980 nm excitation (laser power: 3 W). C666-tumor-bearing and HeLa-tumor-bearing nude mice were injected with UCNP-$P_5$ through the tail vein. Upconversion luminescence images of the mice were collected at different time intervals of 3 h, 6 h, 12 h, 24 h, 36 h after the injection, and green emission signals from tumors were recorded (FIG. 53). In nude mice with a HeLa derived xenograft, the emission signal of UCNP-P$_5$ from the tumor site was only observed at 3 h after the injection, the signal declined dramatically and was absent afterwards. In sharp contrast, UCNP-P$_5$ showed a lasting upconversion luminescence signal from the tumor site, which decayed with time but persisted even 24 h after the injection in C666-tumor-bearing nude mice. This result manifested that UCNP-P$_5$ possessed specific targeting capability in EBV-positive tumor, which induced the accumulation and retention enhancement of nanoplatforms in the C666-tumor.

Figure 54:
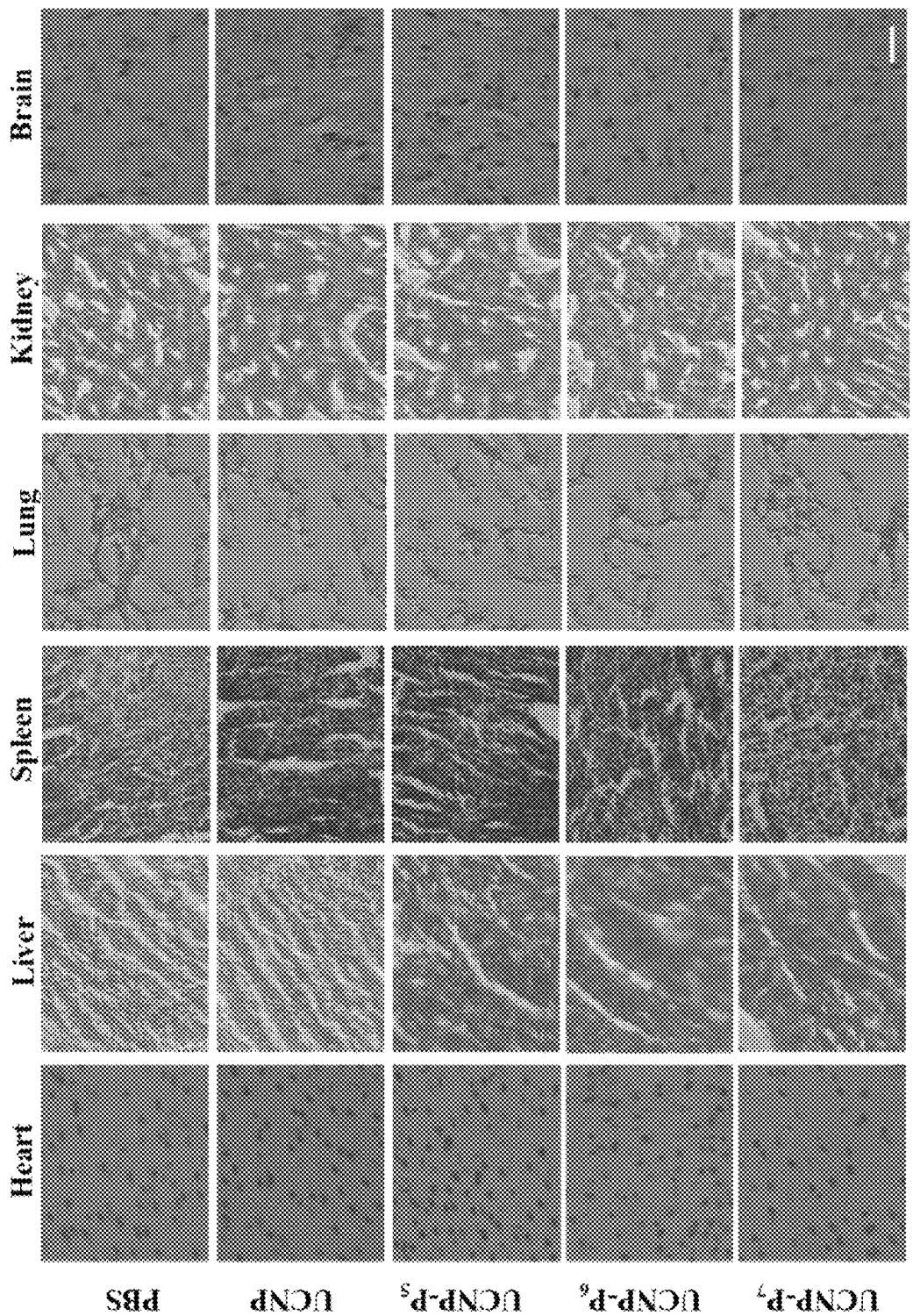
FIG. 54 depicts H&E staining of heart, liver, spleen, lung, kidney and brain from C666 tumor-bearing mice after different treatments including PBS, UCNP, UCNP-P₅, UCNP-P₆ and UCNP-P₇. Scale bar=100 μm.
Figure 55:
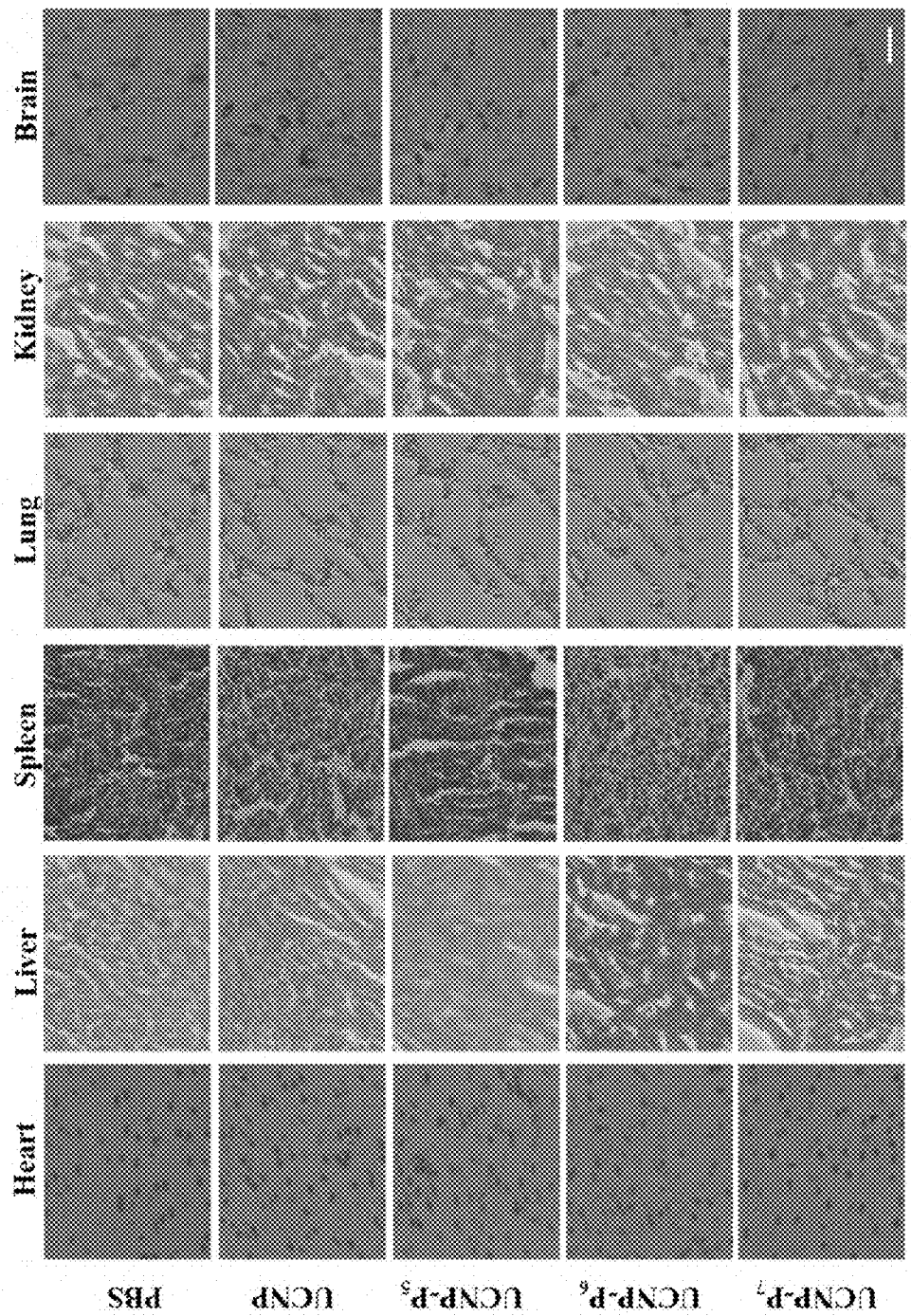
FIG. 55 depicts H&E staining of heart, liver, spleen, lung, kidney and brain from HeLa tumor-bearing mice after different treatments including PBS, UCNP, UCNP-P₅, UCNP-P₆ and UCNP-P₇. Scale bar=100 μm.
Figure 56:
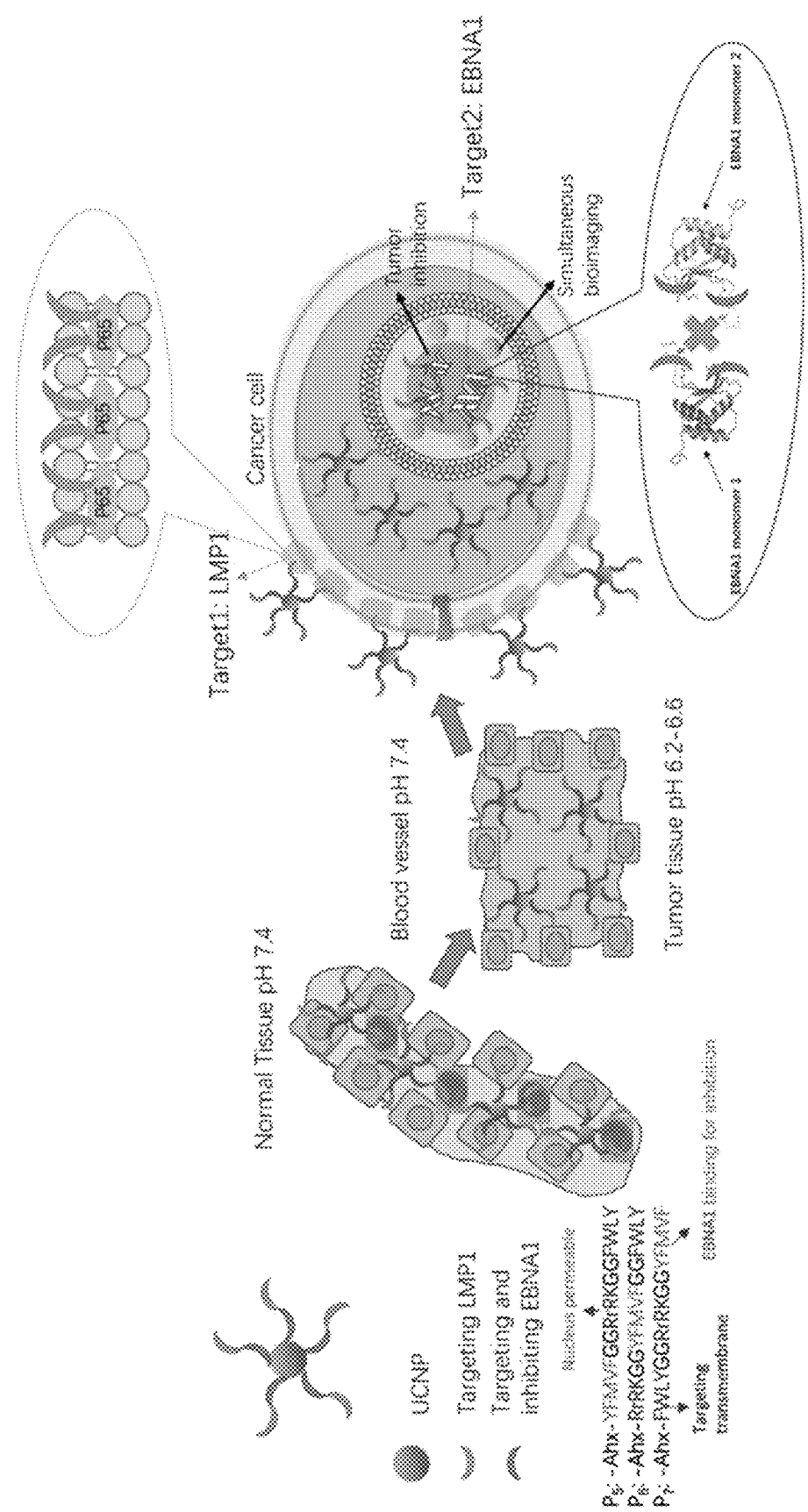
FIG. 56 depicts an exemplary illustration showing the path of entry of the nanoprobe UCNP-P$_n$, [P₅: -Ahx-YFMVFGGRrRKGGFWLY (SEQ ID NO:5)], [P₆: -Ahx-RrRKGGYFMVFGGFWLY (SEQ ID NO:6)], and [P₇: -Ahx-FWLYGGRrRKGGYFMVF (SEQ ID NO:7)] into an EBV-infected cancer cell from normal tissues through sequential and selective targeting.

Moreover, hematoxylin and eosin (H&E) staining of C666 and HeLa tumor sections showed that only C666 cancer cells and vasculature were noticeably damaged with UCNP-P$_n$[n=5, 6 and 7 (SEQ ID NO: 5, 6, 7)] treatment (FIG. 7K), which implied that cell necrosis occurred inside the tumor. Meanwhile, the PBS and UCNP groups exhibited negligible damage in C666 derived xenografts. In sharp contrast, tightly packed cancer cells were observed among all experimental groups in the HeLa derived tumors. In addition, the H&E histological analysis of major organs in C666-tumor-bearing and HeLa-tumor-bearing nude mice indicated that UCNP-P$_n$ [n=5, 6 and 7 (SEQ ID NO: 5, 6, 7)] did not cause any side effects and pathological abnormalities (FIG. 54 and FIG. 55), indicating the satisfactory safety and biocompatibility of the novel nanoplatforms.

Experimental

Chemicals and reagents: Gadolinium(III) acetate hydrate, ytterbium (III) acetate hydrate and erbium(III) acetate hydrate (99.9% trace metals basis), human serum albumin (HSA), avidin, bovine serum albumin (BSA), nucleophosmin (NPM), ammonium fluoride (NH$_4$F), cyclohexane, dimethyl sulfoxide (DMSO), ethanol, hydrochloric acid (HCl), methanol, oleic acid (OA), 1-octadecene (ODE), sodium hydroxide (NaOH) and triethylamine (TEA) and were purchased from Sigma-Aldrich and used without purification. SH-PEG$_{2k}$-CHO was purchased from Shanghai Yuanyang Biotech Co., Ltd. Metal salt solutions were prepared in deionized water; NH$_4$F and NaOH solutions were prepared in methanol.

Synthesis of NaGdF$_4$: Yb$^{3+}$, Er$^{3+}$ core upconversion nanoparticles: Core NaGdF$_4$:Yb$^{3+}$, Er$^{3+}$ was fabricated through the co-precipitation method which followed the reported synthetic steps. More particularly, 4 mL OA, 6 mL ODE and gadolinium(III) acetate hydrate (0.312 mM), ytterbium (III) acetate hydrate (0.08 mM) and erbium(III) acetate hydrate (0.008 mM) were mixed and stirred at 150° C. for 40 min, followed by the addition of methanolic solutions of 1.6 mM NH$_4$F and 1 mM NaOH. The mixture was then stirred at 50° C. for 30 min and subsequently put under vacuum at 100° C. for 10 min. Then, the reaction flask put under a nitrogen atmosphere and heated at 290° C. for 90 min. The reaction mixture was then cooled to room temperature, washed with cyclohexane and ethanol (twice) and the product was collected via centrifugation.

Synthesis of NaGdF$_4$: Yb$^{3+}$, Er$^{3+}$@NaGdF$_4$ core-shell upconversion nanoparticles: First, 2 mL of gadolinium(III) acetate hydrate (0.2 M), 4 mL OA and 6 mL ODE were mixed in a 50 mL flask and then maintained at 150° C. for 40 min to yield the shell precursors. The core nanoparticles, 5 mL NaOH (1 mM) and NH$_4$F (1.6 mM) were injected after cooling down to 50° C. and the reaction mixture was stirred at 50° C. for 30 min, then vacuuming at 100° C. for 10 min. Upon restoration of a nitrogen atmosphere, the reaction mixture was heated at 280° C. for 1 h and then cooled to room temperature. Ethanol was added to precipitate the resultant nanoparticles and they were collected and washed with ethanol through centrifugation at 6000 rpm for 3 min.

Synthesis of hydrophilic aldehyde-functionalized core-shell upconversion nanoparticles: The UCNP-CHO with good biocompatibility were synthesized by strong thiol-metal interactions between the Gd$^{3+}$ ion and thiol group. 0.1 M HCl was added to the nanoparticles and were sonicated at 50° C. for 1 h to get rid of the oleic ligand on surface. The ligand-free nanoparticles were gathered after centrifugation at 14000 rpm for 30 min and then redispersed in deionized water. 10 mL of SH-PEG$_{2k}$-CHO (200 mg) was added to the nanoparticles and the mixture was stirred slowly at room temperature for 24 h. Centrifugation at 14000 rpm for 30 min was performed again to remove excess SH-PEG$_{2k}$-CHO and the UCNP-CHO was obtained.

Coating of dual-EBNA1/LMP1-targeting specific peptide on the UCNP: Automated solid-phase peptide synthesis is prepared on a CEM Liberty 1 single-channel microwave (MW) peptide synthesizer equipped with a Discovery microwave unit. Amino acid side chain functionality is protected, and reactions are carried out using the default 10 minutes MW coupling cycle at 75° C. with the power of 25 W. Filling with nitrogen gas is used to ensure efficient agitation of the reaction mixture during each step. The UCNP-P$_n$ [n=5, 6 and 7 (SEQ ID NO: 5, 6, 7)] were synthesized through a Schiff base reaction. Briefly, UCNP-CHO (100 mg), dual-targeting protein specific peptide P$_n$ [n=5, 6 and 7 (SEQ ID NO: 5, 6, 7)] (80 mg) and 21 µL of triethylamine (TEA) were co-dissolved in DMSO (2 mL). The mixed solution was maintained for 24 h at 40° C. under magnetic stirring at 300 rpm. The mixture was rinsed with methanol to remove extra peptide and UCNP-P$_n$ (n=5, 6 and 7) was obtained after freeze drying.

Characterization: The as-prepared UCNP and UCNP-P$_n$ [n=5, 6 and 7 (SEQ ID NO: 5, 6, 7)] were characterized with Transmission Electron Microscope (TEM), X-ray diffraction (XRD), Fourier transform infrared spectra (FTIR), dynamic light scattering (DLS) and zeta-potential measurements. Visible emission spectra of UCNP and UCNP-P$_n$ [n=5, 6 and 7 (SEQ ID NO: 5, 6, 7)] were measured using a Spectro-Fluorometer System (Horiba/Fluoromax-4) equipped with a 980 nm laser as the excitation source. UV-vis absorbance measurements were recorded by Agilent Technologies Cary 8454 UV-Vis machine.

Cell culture: HK1-LMP1 was generated by stably expressing the EBV oncoprotein, latent membrane protein1 (LMP1) variant (B95.8) into the parental HK1 cell line by transfection. This cell line was established and cultured as previously described. Other cell lines were obtained from the same affiliations in the previous work.

LMP1-positive HK1-LMP1 cells and LMP1-negative HK1 cells were grown in Dulbecco's Modified Eagle Medium (DMEM); LMP1-positive LCL3, Raji cells were maintained in RPMI 1640 medium. The media used in cell culture of NPC43, HeLa, C666 and MRC-5 cells were consistent with reported cell cultures. 10% fetal bovine serum (FBS), 1% penicillin and streptomycin were all used to supplement the media used.

In vitro confocal imaging and nuclear localization imaging: The cells were cultured in 35 mm cell culture dishes for 24 h prior to incubation in dark with 30 mg/mL of UCNP and UCNP-P$_n$ [n=5, 6 and 7 (SEQ ID NO: 5, 6, 7)] for different time intervals (1 h, 3 h, 6 h, 12 h and 24 h). The cells were then co-stained with 0.05 mM nuclear dye DRAQ5 for 0.5 h for confocal imaging with a Leica SP8 confocal microscope equipped with a coherent femtosecond laser (690-

1050 nm), argon laser (432 nm, 457 nm and 488 nm), He—Ne laser (632 nm), UV lamp. A stage-top cell culture chamber was also used to maintain the atmospheric conditions of 2-7% $CO_2$ and a temperature of 37° C.

Western blotting: EBV-positive C666, LCL3 and EBV-negative HK1 cell pellets were treated with phosphatase and protease inhibitors at 0-4° C. for 30 min. The total protein concentrations were calculated by protein absorbance. The protein was resolved by sodium dodecyl sulfate-polyacrylamide gel electrophoresis (SDS-PAGE) and transferred to cellulose filter membranes. The membranes were blocked with 3% BSA in Tris-buffered saline in 0.1% Tween 20 (TBST) for 1 h with gentle shaking and subsequently incubated with primary antibodies (1:1000) in 3% BSA in TBST at 4° C. for overnight. After rinsing with TBST buffer three times, the blots were then incubated with corresponding secondary anti-rabbit antibody (1:6000) for 1 h. After that, the blots were rinsed again with 3% BSA in TBST for 1 h shaking at room temperature. Lastly, the density of bands was determined by image analysis system after washing with TBST buffer three times.

Cellular uptake of nanoprobes by ICP-MS: To examine the intracellular concentration of nanoprobes in different cell lines, namely C666, HK1, HK1-LMP1, LCL3 cells, $1 \times 10^5$ cells were plated in each well in six-well plates and incubated with UCNP, UCNP-$P_n$ [n=5, 6 and 7 (SEQ ID NO: 5, 6, 7)] and the old nanoprobe UCNP-$P_4$ at 50 µg/mL for different time intervals of 1 h, 3 h, 6 h, 12 h, and 24 h. After co-incubation, the cell culture medium containing the nanoprobes was removed, and the exposed cells were further rinsed with 1 mL PBS three times. After that, the cells were trypsinized and re-dispersed in 1 mL cell medium. The cells were collected by centrifugation at 1500 rpm, and the cell pellet was digested in 100 µL concentrated $HNO_3$ (69%) at room temperature for 3 h. Then, each cell pellet in centrifuge tube was filled up to 10 mL with 1% $HNO_3$. The cellular uptake of all the nanoprobes was recorded via an Agilent 7500 series ICP-MS instrument. All ICP experiments were performed three times, and the values of Gd concentration (ppm) obtained were calculated and averaged.

In vitro cytotoxic assays: The cytotoxicity of our nanoprobes was determined by MTT reduction assay. The cells ($3 \times 10^3$ per well) were seeded onto 96-well plates and incubated overnight, followed by treatment with $P_n$ [n=5, 6 and 7 (SEQ ID NO: 5, 6, 7)], UCNP, UCNP-$P_n$ [n=5, 6 and 7 (SEQ ID NO: 5, 6, 7)] and UCNP-$P_4$ individually at 37° C., 5% $CO_2$ for 24 h in dark. The cell monolayers were rinsed with PBS and 50 µL of MTT, 3-(4,5-dimethylthiazol-2-yl)-2,5-diphenyltetrazolium bromide solution (0.5 mg $mL^{-1}$) was added per well and the cells were further incubated for 3 h at 37° C. The solution was subsequently discarded, and the formazan crystals were dissolved in 100 µL of DMSO per well under shaking. The absorptions of the formazan crystal solutions at 540 nm and 690 nm were measured using a dual-wavelength Labsystem Multiskan microplate reader (Merck Eurolab).

Dimerization inhibition assay: 90 mg of the EBNA1 (DNA-binding domain fragment of a.a.468-607) was first incubated with UCNP and UCNP-$P_n$ [n=5, 6 and 7 (SEQ ID NO: 5, 6, 7)] (conc.: 0.3 mg/mL) at 4° C. overnight. Then, 2 mM disuccinimidyl suberate (DSS) was added to allow the samples to undergo crosslinking reaction at room temperature for 30 min. The samples were run and separated on an SDS-denaturing gel and proteins were detected using Coomassie Blue staining. PBS buffer was used as control group.

Modelling and simulation of peptides: The designed peptides were docked into the dimerization interface of a putative EBNA1 monomer reported in previous study (obtained from Protein database ID: 1B3T) using HADDOCK version 2.2. The parameters reported for non-standard residue (Ahx) was used in this simulation. The system was described using ff14SB variant force field. After solvation with 10 Å explicit TIP3P water box, the system was minimized and proceed to unbiased MD simulation using GPU version of PMEMD engine in Amber 16 Software Package. All systems were heated from 100K to 300K in 1 ns. The system was further equilibrated for 1 ns with constant pressure and temperature before proceeding to the 200 ns NPT production stage. SHAKE-enabled setting to constrict hydrogen bonds were used for all equilibration and production stages. Langevin thermostat was used to control the temperature throughout the simulations.

Post-simulation analysis: The conformational clusters of EBNA1-complex were obtained using default settings with distance defined by $C_\alpha$ atoms Root Mean Square Deviation (RMSD) by using cpptraj. The most abundant cluster for all complexes were used for interaction analysis. The binding free energies between protein and peptides were calculated using molecular mechanics Poisson-Boltzmann surface area (MMPBSA) method. The whole production trajectory for all systems were used. The salt concentration was set to 0.1 M in GB calculation.

In vivo suppression assays: EBV-positive C666 and EBV-negative HeLa cells were suspended in 200 µL of serum-free RMPI 1640 and DMEM respectively. Female BALB/c nude mice (6-8 weeks) which obtained from HKU were then injected with the cells in the right flank. Intravenous injections were performed when the average tumor volumes reached ~200 $mm^3$. 0.25 mg/tumor dose of UCNP and UCNP-$P_n$ [n=5, 6 and 7 (SEQ ID NO: 5, 6, 7)] in 100 mL PBS buffer were injected through tail vein of mice using a 24-gauge syringe. Mice injected with the same volume of PBS buffer served as control. The body weight and tumor volumes of the mice were measured three times per week; in which the latter is calculated by $(L \times W^2)/2$, where L and W are the longer and shorter tumor dimensions respectively. Intravenous injection at the tail vein were performed twice a week and the mice were sacrificed after 33-day experimental period; the tumors were extracted and weighed. The treatment groups are unknown to the investigators for the experimental and data analysis processes. The animal experiments conducted were approved by the Department of Health of the HKSAR Government. All animal procedures are within the Guidelines for Care and Use of Laboratory Animals of HKBU and approved by the Animal Ethics Committee of HKBU.

In vivo upconversion luminescence imaging: C666 and HeLa cells ($10^6$ cells) were inoculated subcutaneously in BALB/c female nude mice (6 weeks). When the tumors reached 0.2-0.3 cm in diameter, the C666-tumor-bearing and HeLa-tumor-bearing mice were anesthetized and injected intravenously with UCNP-$P_5$ (150 µl, 12.5 mg/kg per mouse). The in vivo upconversion luminescence images were recorded at different time points (3 h, 6 h, 12 h, 24 h, 36 h).

Hematoxylin and eosin (H&E) staining: In general, the transplanted C666 and HeLa derived tumor tissues were collected and fixed with formalin, followed by embedding in paraffin. The histologic sections were then stained with hematoxylin and eosin. Other major organ tissues (heart, liver, spleen, lung, kidney, brain) were conducted in the same procedures.

Analytical HPLC: Analytical HPLC was performed on an Agilent 1100 series HPLC system (Agilent Technologies, Stockport, UK) equipped with a diode-array detection (DAD) detector and Agilent C18 column (250 mm×4.6 mm) for corresponding peptides ($P_5$, $P_6$, $P_7$) at the following gradient:

| Time | A % ($H_2O$ + 0.1% TFA) | B % (MeCN + 0.1% TFA) | Flow |
|---|---|---|---|
| 0 | 80 | 20 | 0.5 |
| 40 | 20 | 80 | 0.5 |
| 41 | 0 | 100 | 0.5 |
| 50 | 0 | 100 | 0.5 |

Statistical analyses: All experiments were conducted in triplicate. All experimental data were based on independent experiments and presented as the mean±standard deviation (SD) (n=3). Student's t-test was employed for statistical analysis by using Origin 2016. Difference with P<0.05 (*) or P<0.01(**) was considered statistically significant.

In conclusion, we have designed and synthesized dual-EBV-oncoproteins-targeting and pH-responsive luminescent nanoprobes with responsive upconversion emission for precision targeting, monitoring and inhibition of EBV-associated cancer. A pH-responsive linker prepared by Schiff base reaction was introduced to link the UCNP and dual-EBNA1/LMP1-targeting peptide. Such a rational design not only empowered the nanoprobes to be released once entering the tumor cell after attachment by the LMP1-specific motif, but could also reduce the undesired side effects on normal tissues. Furthermore, our nanoprobe UCNP-$P_5$ was also able to display specific and sensitive emission enhancement responses toward EBV-positive cell lines. Notably, selective cytotoxicity towards EBV-infected cancer cells was achieved by the EBNA1-specific motif, and was further enhanced by targeting LMP1. More importantly, the therapeutic efficacy of UCNP-$P_5$ was clearly demonstrated by the in vivo inhibition of EBV-positive tumors and the enhanced specific uptake. This study has opened a new avenue for precision biomedical application using a dual-functional peptide. In addition, the nanoplatform can function as an imaging agent due to its responsive photophysical properties. Results of this study have demonstrated the successful use of EBV proteins as drug targets, and we envisage our dual-targeting peptide-guided approach could be conveniently translated and applied to other cancers.

Synthesis

Figure 8:
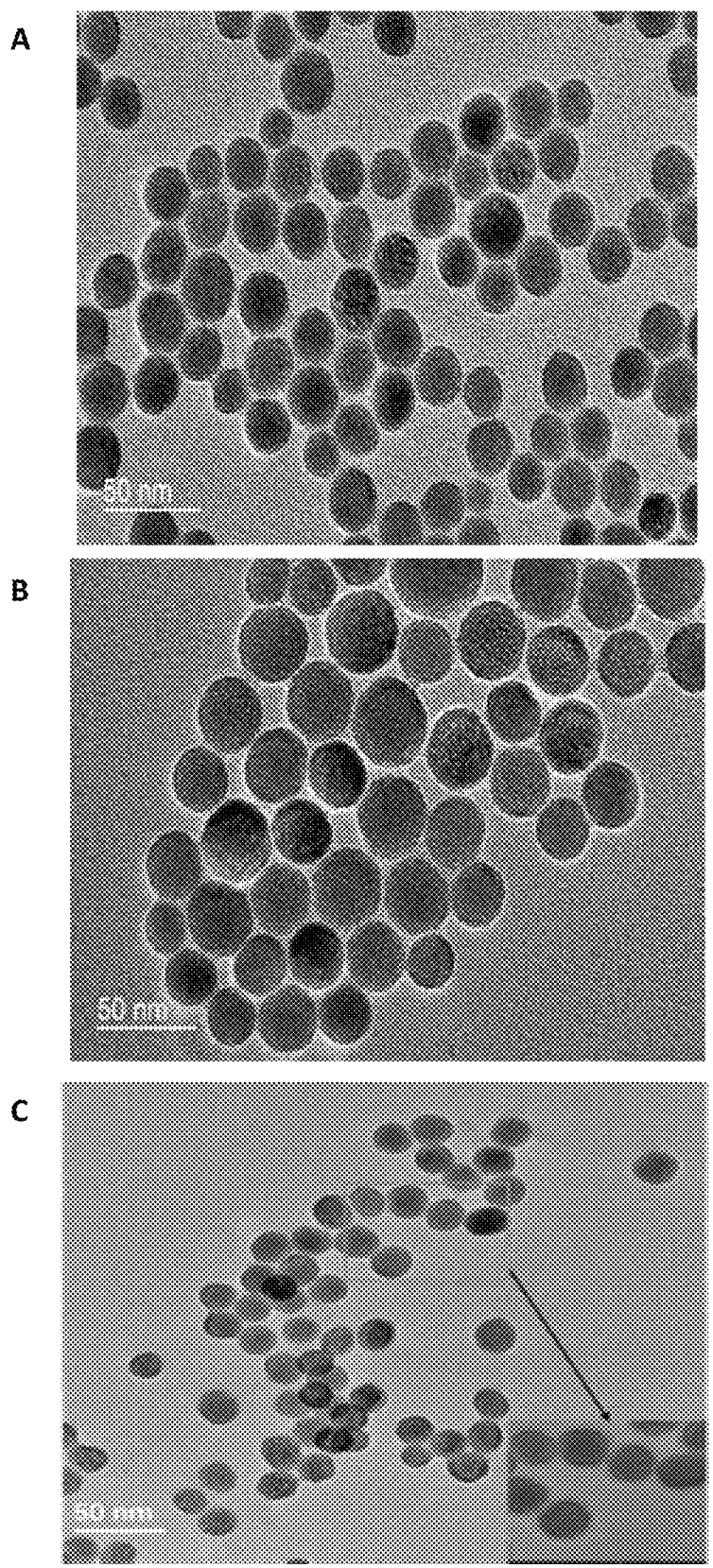
FIG. 8 depicts TEM images of (A) core upconversion nanoparticles NaGdF$_4$: Yb$^{3+}$, Er$^{3+}$, (B) NaGdF$_4$: Yb$^{3+}$, Er$^{3+}$@NaGdF$_4$ (UCNP), (C) UCNP coated with dual-targeting protein specific peptide P$_5$ (UCNP-P$_5$) (Scale bar: 50 nm)
Figure 9:
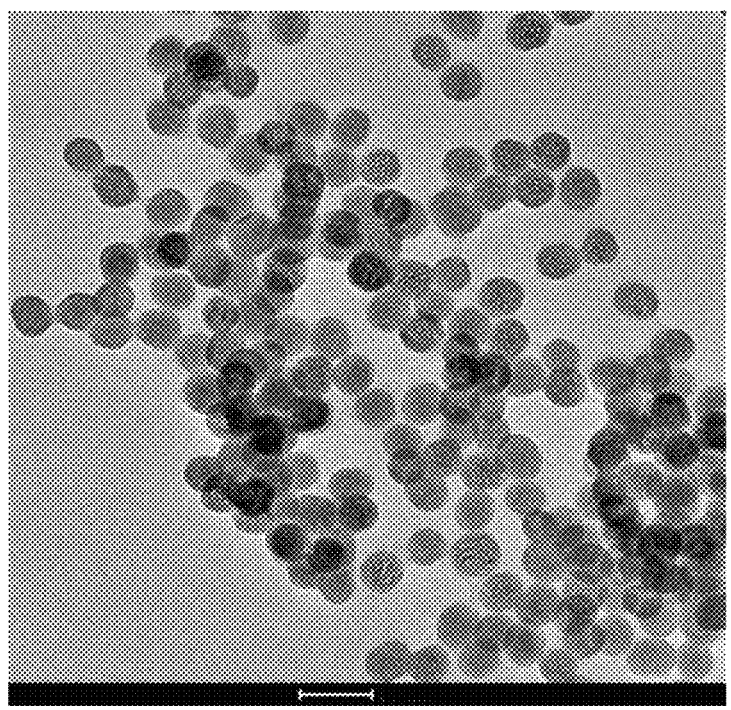
FIG. 9 depicts TEM image of UCNP coated with dual-targeting protein specific peptide (A) P$_6$ (UCNP-P$_6$) (Scale bar: 50 nm) and (B) magnified resolution TEM image (Scale bar: 20 nm)
Figure 9:
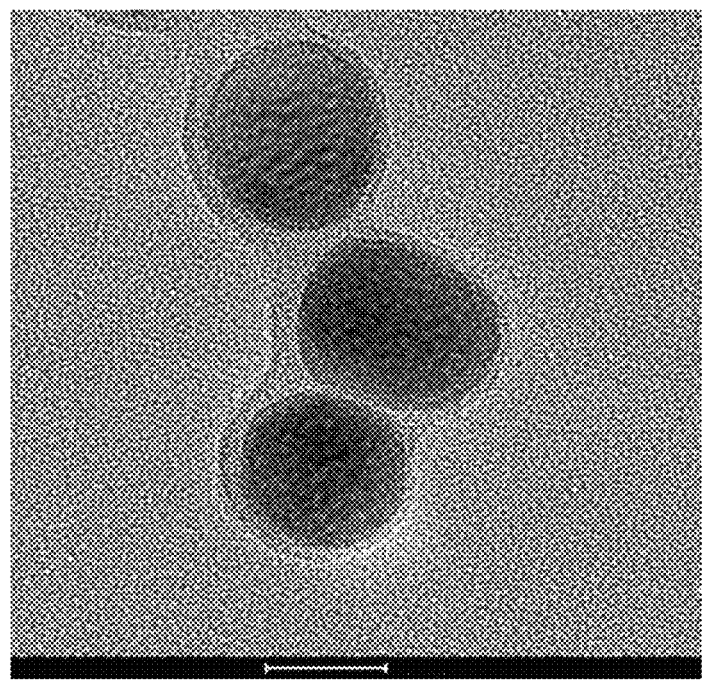
Figure 10:
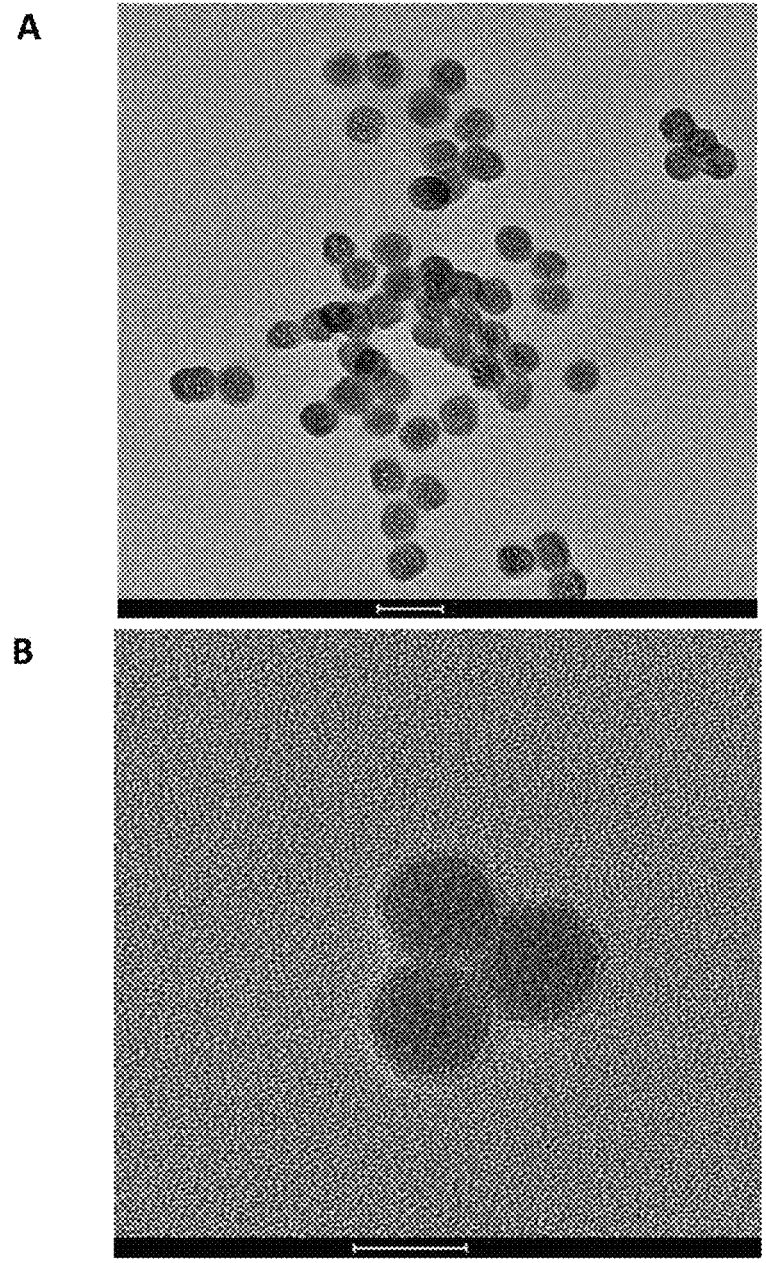
FIG. 10 depicts (A) TEM image of UCNP coated with dual-targeting protein specific peptide P$_7$ (UCNP-P$_7$) (Scale bar: 50 nm) and (B) magnified resolution TEM image (Scale bar: 20 nm)
Figure 11:
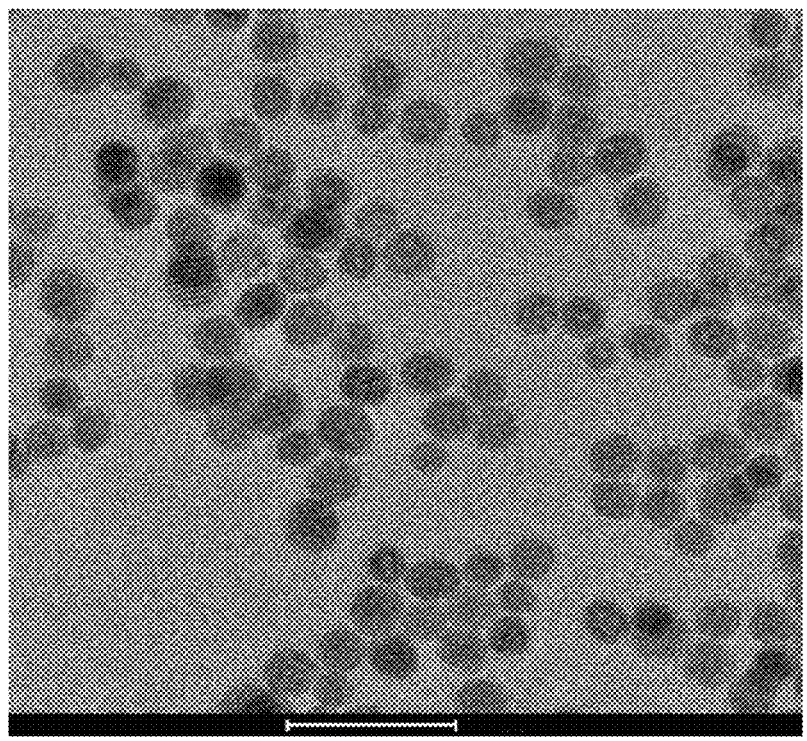
FIG. 11 depicts TEM image of UCNP coated with EBNA1 specific peptide P$_4$ (UCNP-P$_4$) (Scale bar: 50 nm)

The transmission electron microscopy (TEM) images of $NaGdF_4$: $Yb^{3+}$, $Er^{3+}$ (size: ~25 nm), $NaGdF_4$: $Yb^{3+}$, $Er^{3+}$@$NaGdF_4$ (size: ~30 nm) and UCNP-$P_5$ (size: ~33 nm) are shown in FIG. 8A, FIG. 8B and FIG. 8C, respectively. As seen in FIG. 8C, a thin layer on the surface of UCNP can be observed in the inset. Similar TEM images of UCNP-$P_6$ and UCNP-$P_7$ are shown in FIG. 9 and FIG. 10. A size increase of around 3 nm in UCNP-$P_n$[n=5, 6 and 7 (SEQ ID NO: 5, 6, 7)] compared to UCNP was observed, implying successful bioconjugation of UCNP with $P_n$ [n=5, 6 and 7 (SEQ ID NO: 5, 6, 7)]. Likewise, the old nanoprobe UCNP-$P_4$, which targets EBNA1, was also synthesized with uniform morphology, as shown in FIG. 11. UCNP-$P_4$ was included as a control compound.

Figure 12:
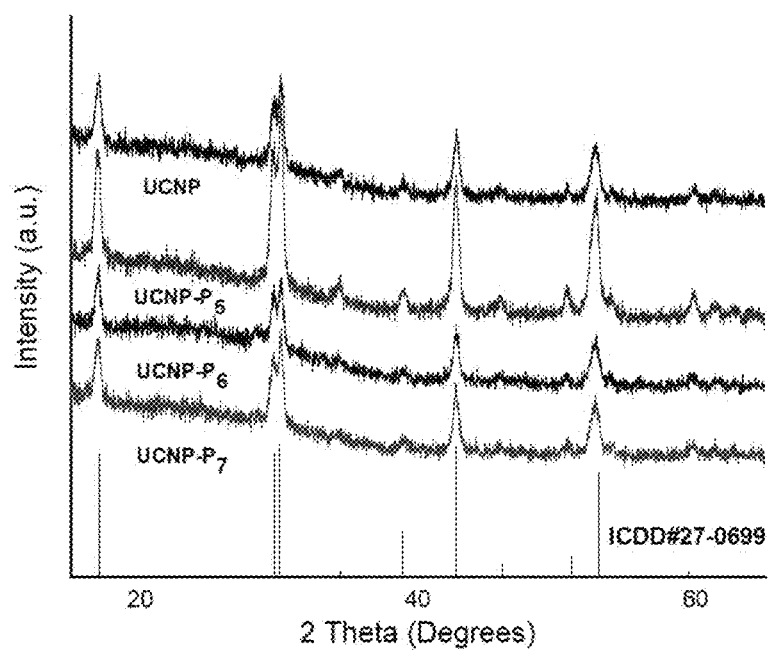
FIG. 12 depicts x-ray diffraction (XRD) patterns of initial nanoparticles (UCNP) and the peptide capped nanoparticles UCNP-P$_n$ [n=5, 6 and 7 (SEQ ID NO: 5, 6, 7)] indexed with a standard hexagonal-phase NaGdF$_4$ (ICDD #27-0699).

To further investigate the crystal phase of UCNP and UCNP-$P_n$ [n=5, 6 and 7 (SEQ ID NO: 5, 6, 7)], the X-ray diffraction (XRD) patterns of the as-prepared samples were obtained. As shown in FIG. 12, the XRD patterns of UCNP-$P_n$ [n=5, 6 and 7 (SEQ ID NO: 5, 6, 7)] were consistent with UCNP in terms of the diffraction angles the patterns of UCNP and UCNP-$P_n$ [n=5, 6 and 7 (SEQ ID NO: 5, 6, 7)] and matched well with the standard hexagonal phase structure of $NaGdF_4$ (ICDD #27-0699), which indicates that there is no impure phase introduced during the process of surface modification. All the samples formed the pure hexagonal phase structure.

Figure 13:
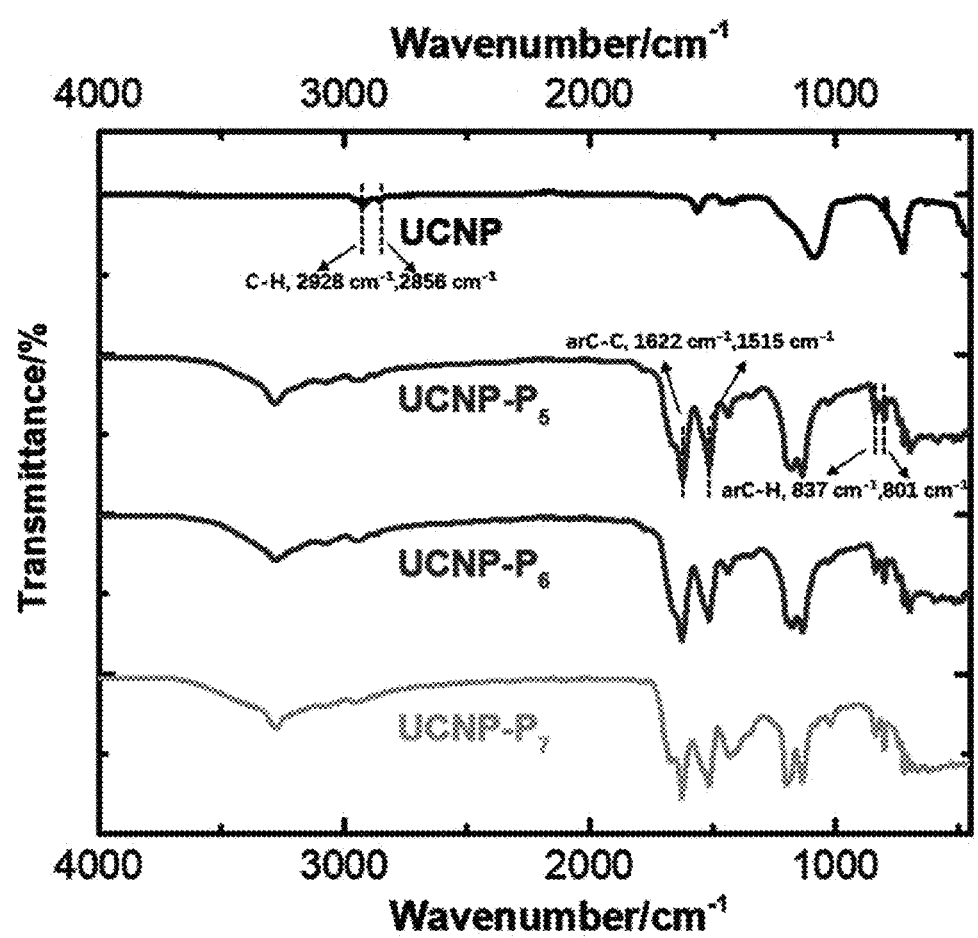
FIG. 13 Fourier transform infrared (FTIR) spectroscopy transmission spectrum of UCNP, dual-targeting protein specific peptides coated UCNP-P$_5$, UCNP-P$_6$ and UCNP-P$_7$.
Figure 14:
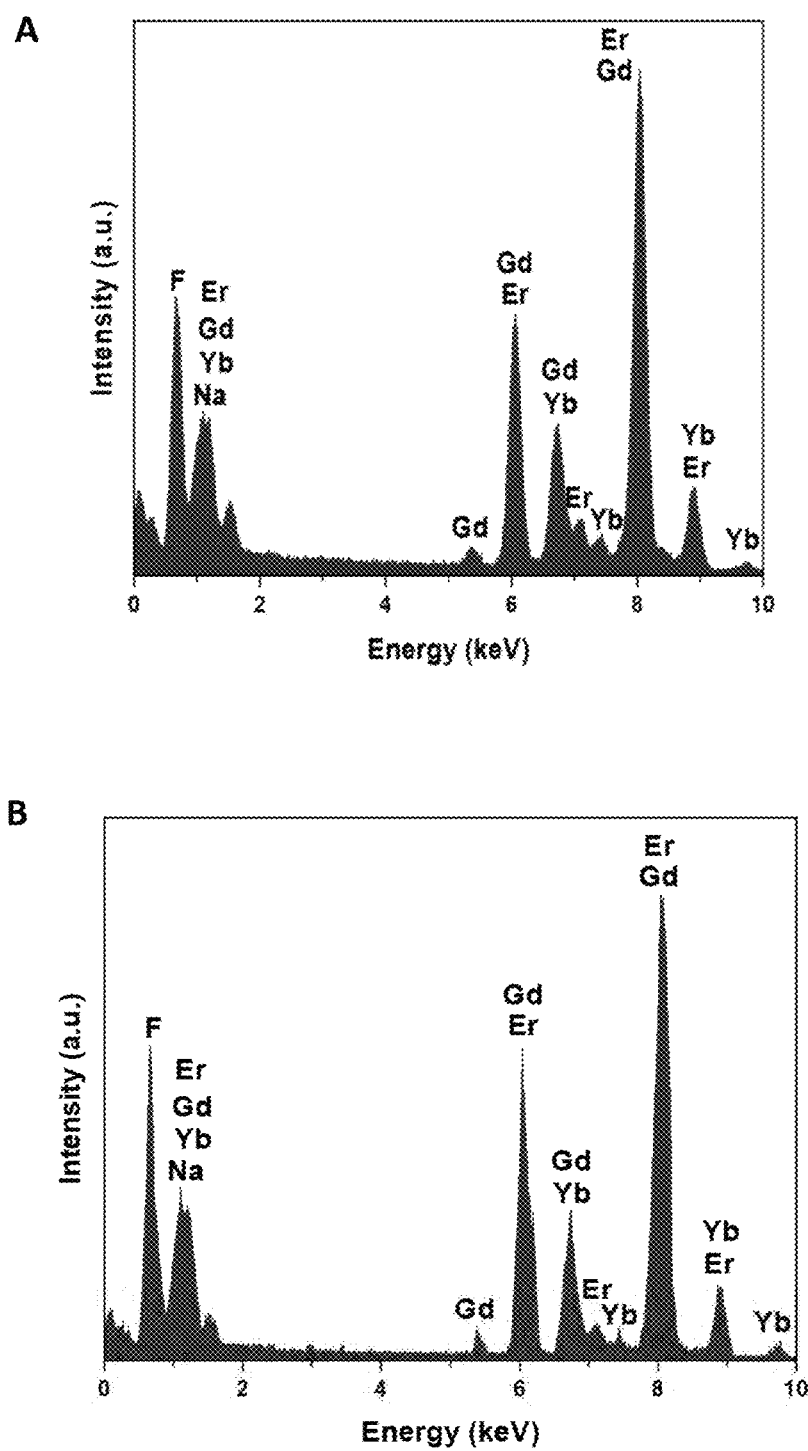
FIG. 14 depicts energy-dispersive X-ray (EDS) spectra of (A) UCNP (B) UCNP-P$_5$ (C) UCNP-P$_6$ (D) UCNP-P$_7$.
Figure 14:
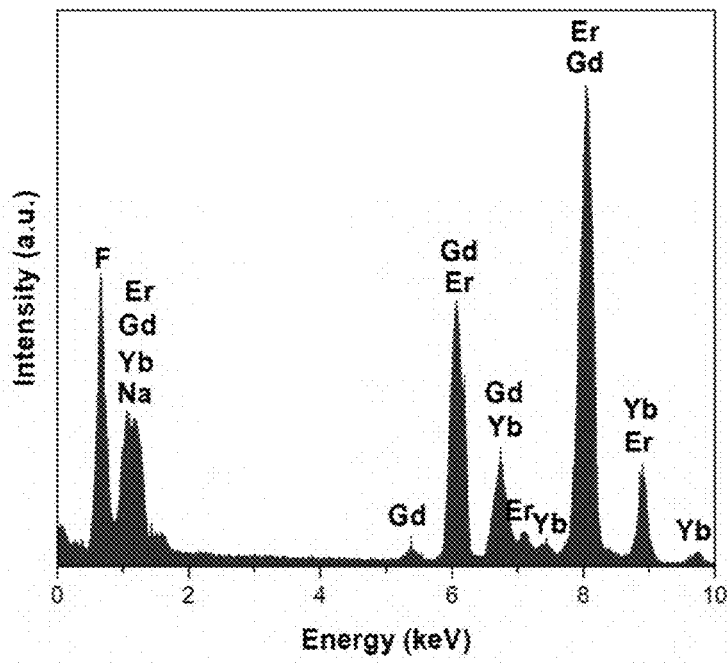
Figure 14:
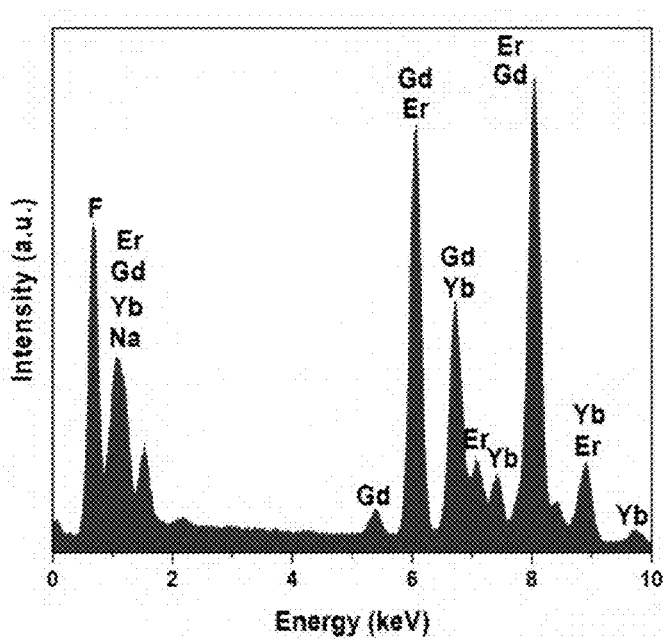

The corresponding Fourier-transform infrared (FTIR) transmission spectrum was obtained to study the process of peptide conjugation with UCNP. As shown in FIG. 13, the stretching vibration of the C—H bond showed absorption peaks at 2928 and 2856 $cm^{-1}$. After the coating of dual-targeting protein-specific peptides, the stretching vibration of the aromatic C—C bond (1622, 1515 $cm^{-1}$) and C—H bond (837, 801 $cm^{-1}$) is observed as doublet absorption peaks because of the existence of benzene ring in the FWLY motif. Therefore, the surface modification was evidenced and confirmed by the corresponding FTIR transmission spectrum. Additionally, the energy-dispersive spectroscopy (EDS) spectra of UCNP and UCNP-$P_n$ [n=5, 6 and 7 (SEQ ID NO: 5, 6, 7)] in FIG. 14 further manifested the elemental composition of nanoprobes.

Figure 15:
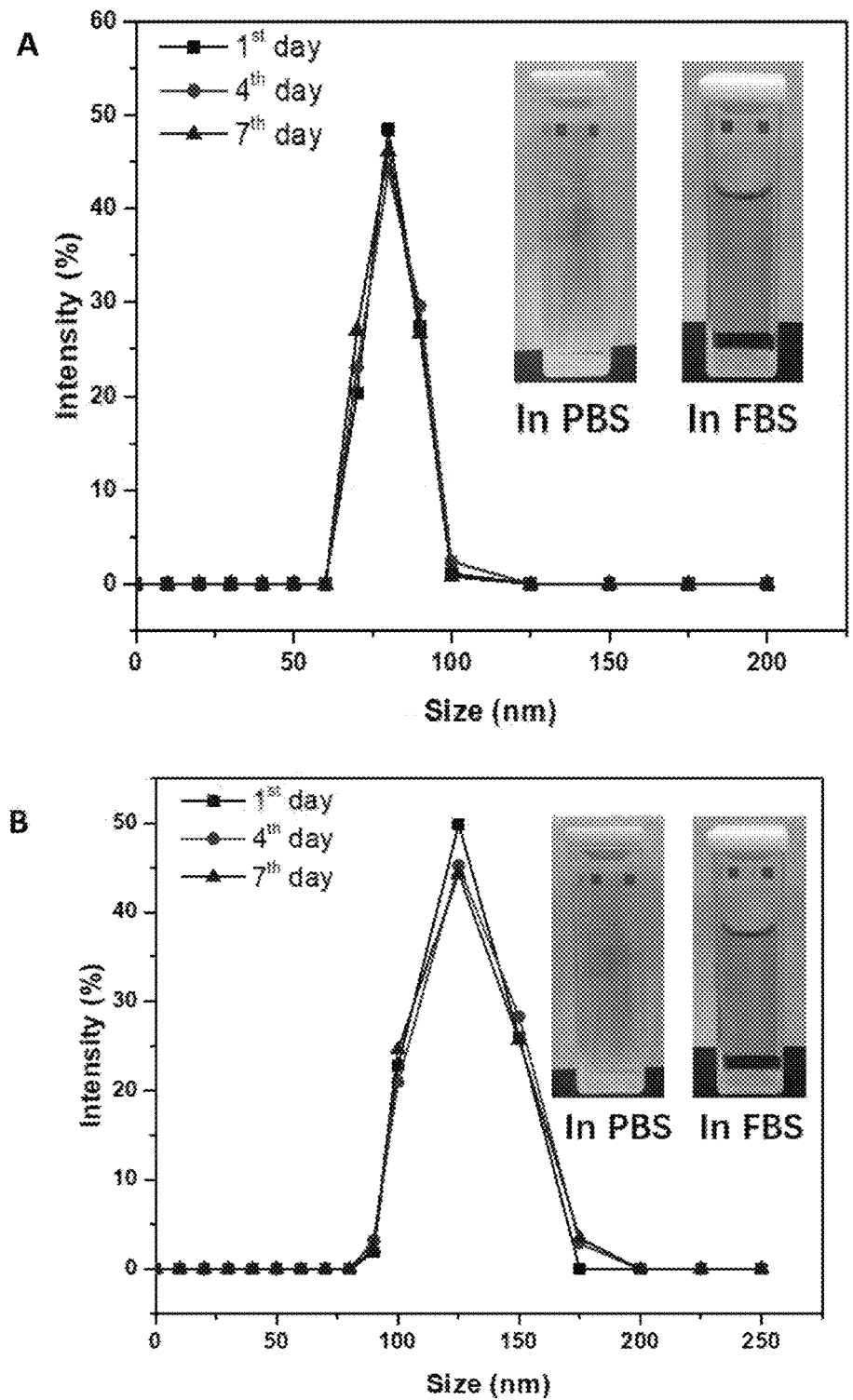
FIG. 15 depicts dynamic light scattering (DLS) measurements and stability studies of (A) UCNP (B) UCNP-P$_5$ (C) UCNP-P$_6$ (D) UCNP-P$_7$ in PBS and FBS solution. The insets in (A), (B), (C) and (D) demonstrate the corresponding digital photograph of PBS and FBS solution containing UCNP, UCNP-P$_5$, UCNP-P$_6$, and UCNP-P$_7$, respectively.
Figure 15:
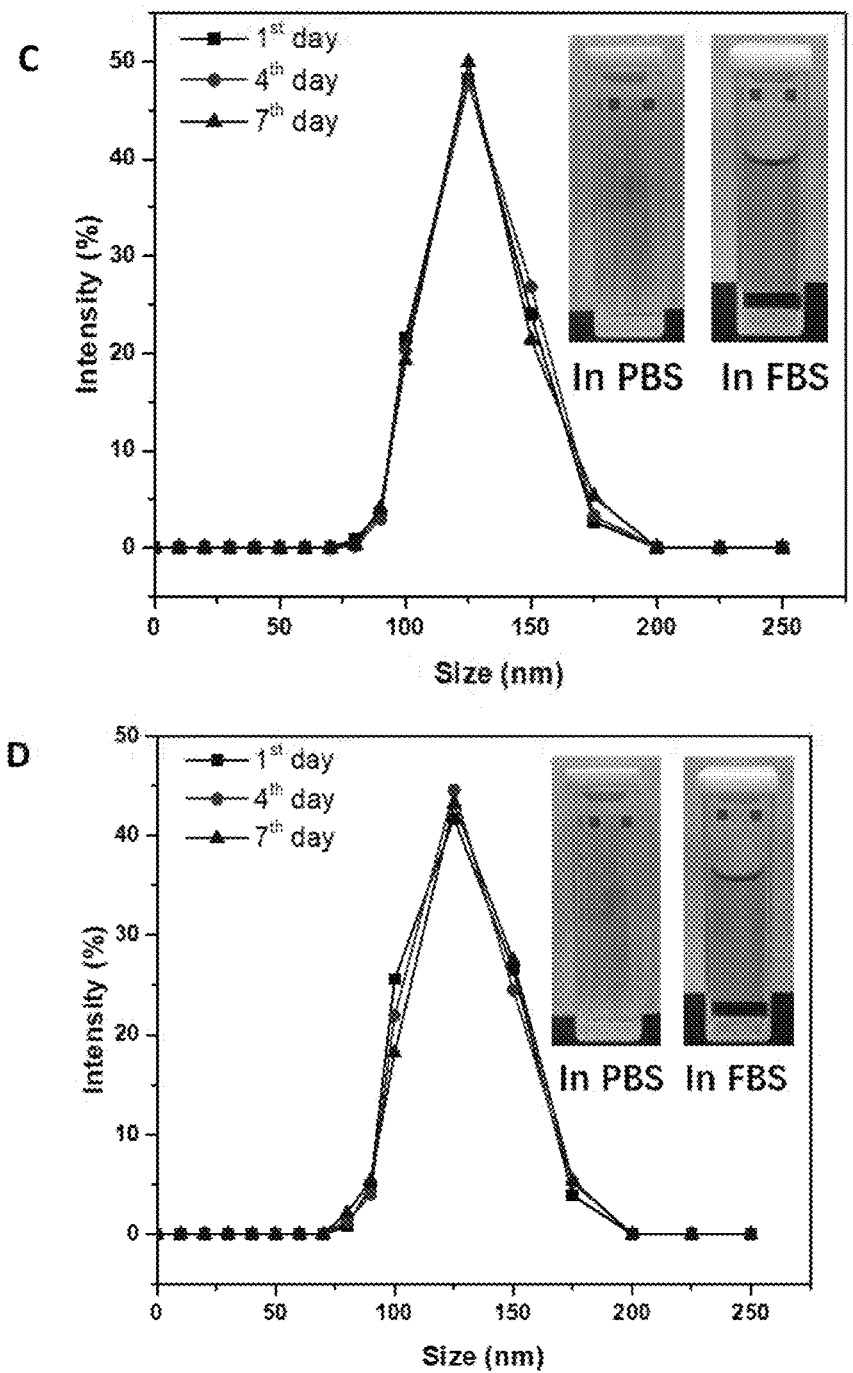

To further evaluate the aggregation degree of the as-prepared samples, dynamic light scattering (DLS) measurements and stability studies were carried out (FIG. 15). The solutions of UCNP and UCNP-$P_n$ [n=5, 6 and 7 (SEQ ID NO: 5, 6, 7)] displayed negligible aggregation in phosphate buffer solution (PBS) and fetal bovine serum (FBS) after 1, 4 and 7 days, revealing desirable stability, low aggregation tendency and uniform size distribution, which are highly consistent with TEM results.

Figure 16:
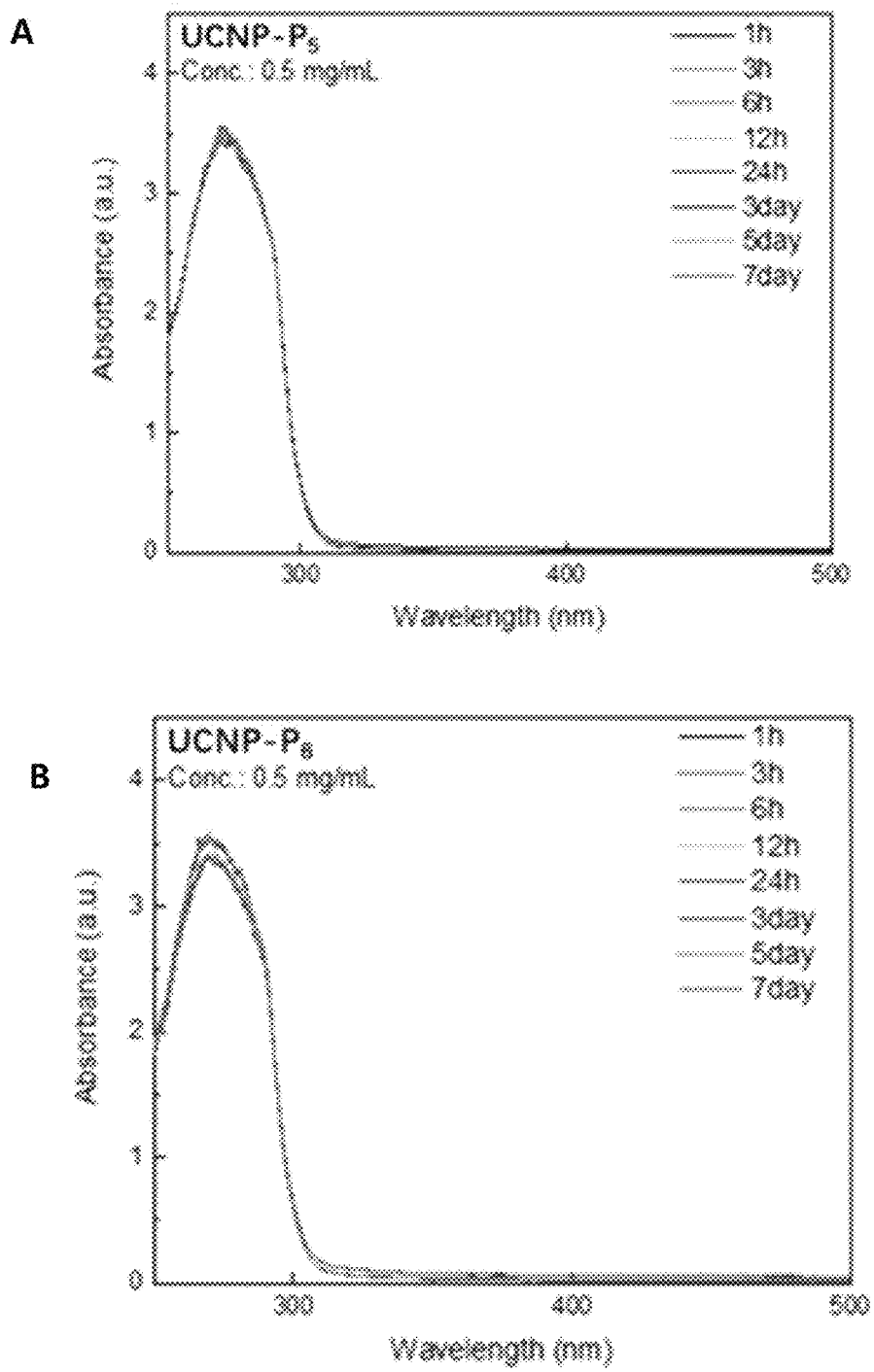
FIG. 16 depicts UV-vis absorbance spectra of (A) UCNP-P$_5$ (B) UCNP-P$_6$ (C) UCNP-P$_7$ (D) UCNP-P$_4$ under different time intervals. (Conc.: 0.5 mg/mL)
Figure 16:
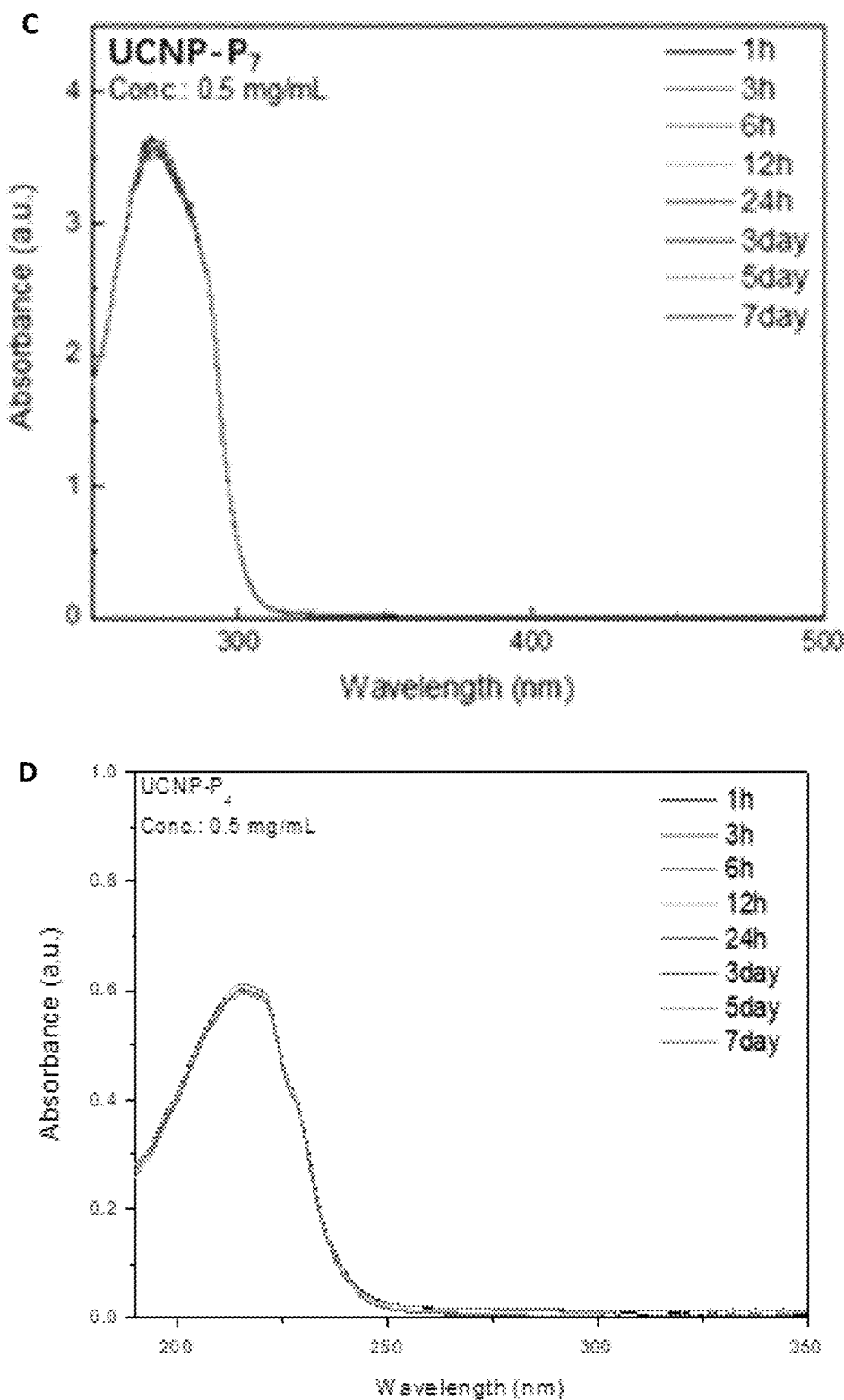
Figure 17:
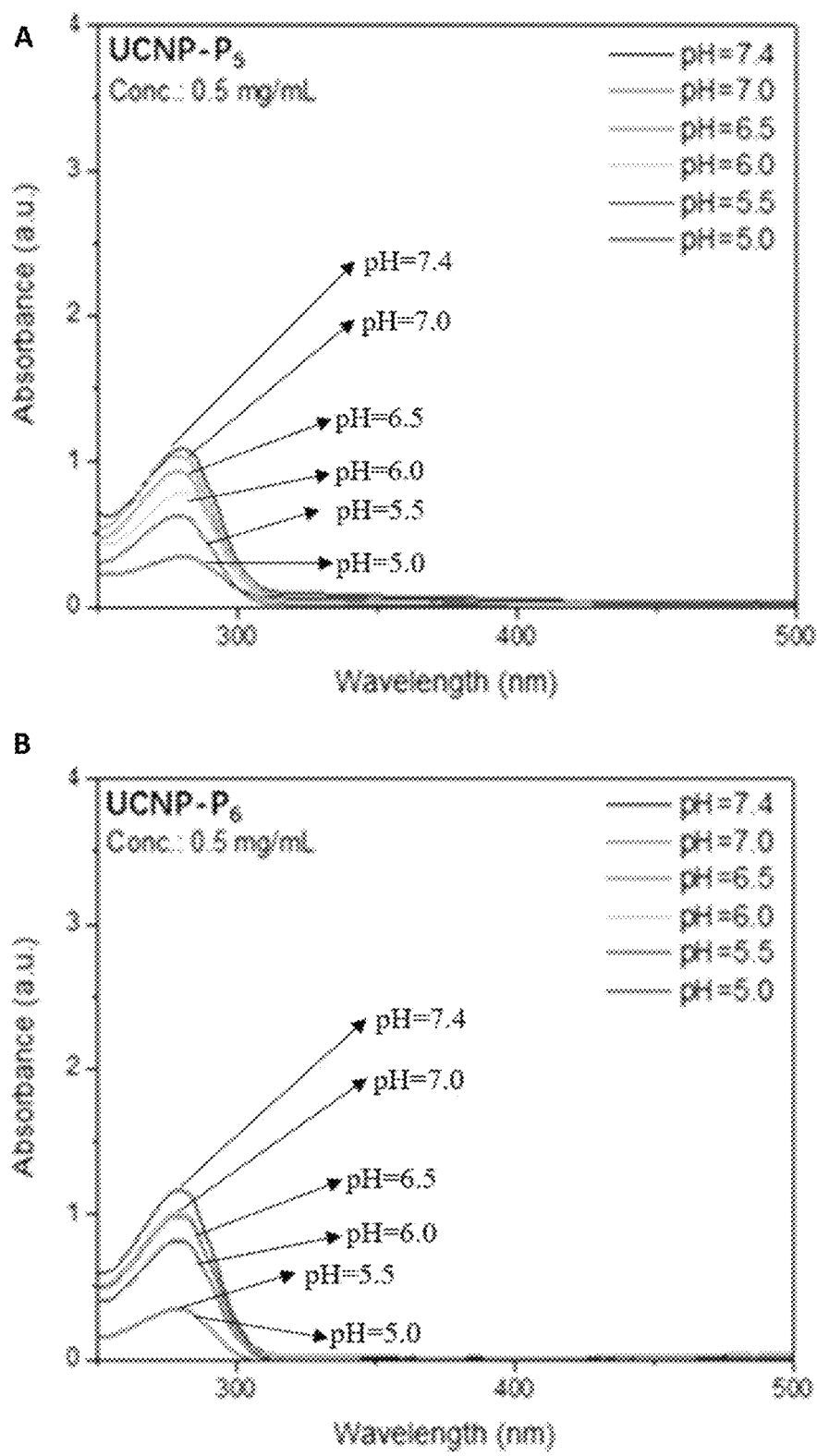
FIG. 17 depicts UV-vis absorbance spectra of (A) UCNP-P$_5$ (B) UCNP-P$_6$ (C) UCNP-P$_7$ (D) UCNP-P$_4$ under different pH buffer. (Conc.: 0.5 mg/mL). Nanoprobes were incubated in various pH buffers 24 h before measurement.
Figure 17:
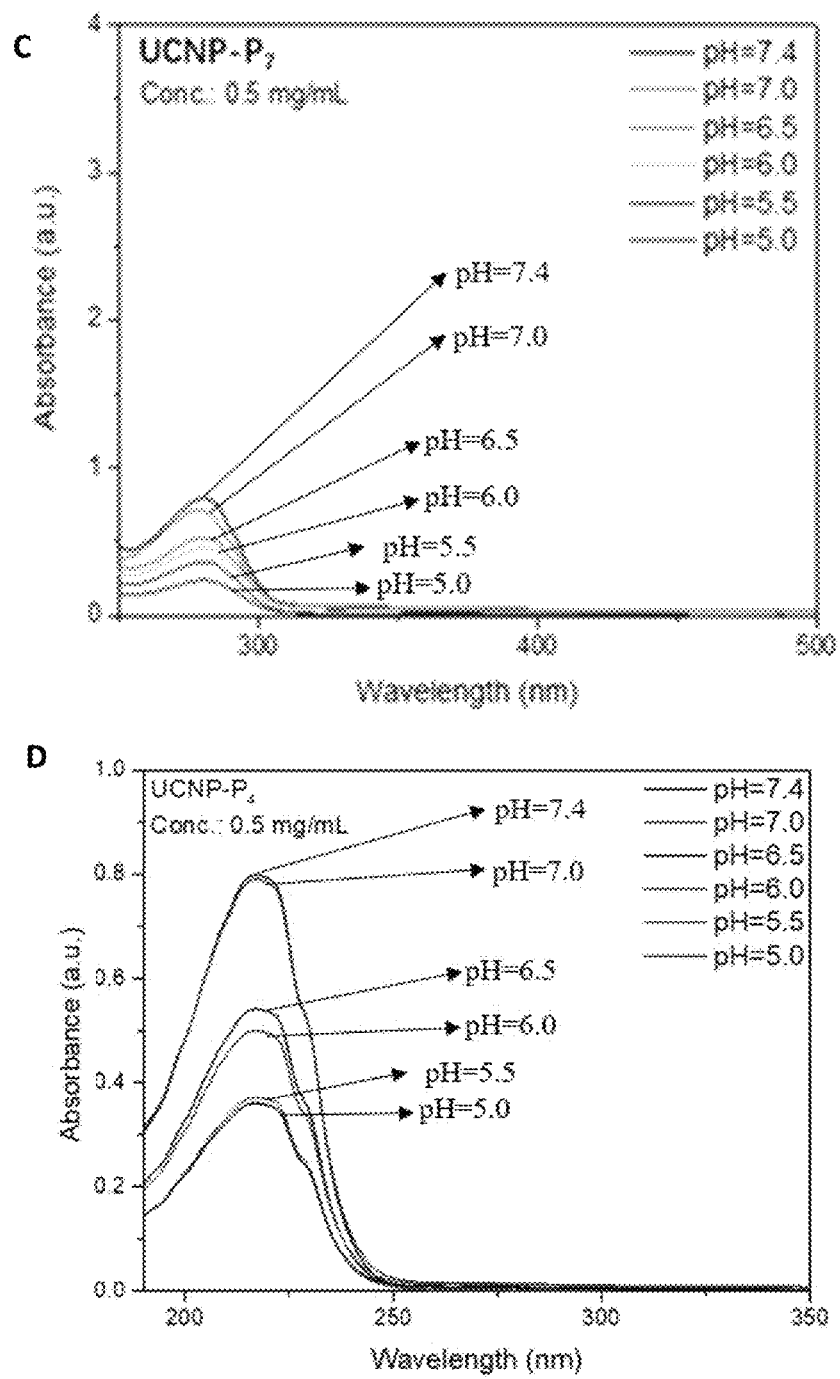

The stability and capability of cleavage of the pH linker were also studied. The UV-vis absorption spectra of UCNP-$P_4$ and UCNP-$P_n$ [n=5, 6 and 7 (SEQ ID NO: 5, 6, 7)] under different time intervals (Conc.: 0.5 mg/mL) were recorded as shown in FIG. 16. The characteristic peak of the aromatic group was observed in the range of 260-280 nm and tiny differences of absorbance peak intensity were observed among all nanoprobes during the experimental period of 7 days, which were quantified and summarized in Table 1 for each time interval. These indicated that the peptide layer on the nanoprobes also had excellent stability as the nanoprobes provided solid support for the peptide coating layer. More importantly, TEM images of UCNP-$P_5$ at different pH buffers were observed and investigated in FIG. 1, providing direct evidence on pH-responsive peptide release from UCNP. Moreover, remarkable differences in absorbance intensity were observed in the range of pH 7.4 to pH 5.0 buffers, as shown in FIG. 17.

TABLE 1

Quantitative analysis of peptide release behaviors of nanoprobes under various time intervals. The peptide release rate for each nanoprobe at different time intervals is calculated using the following equation:

$$\text{release rate \%} = \frac{(I_A - I_B)}{I_A} \times 100\%,$$

where $I_A$ is relative absorbance intensity at 1 h and $I_B$ is relative absorbance intensity at other various time intervals correspondingly.

| Sample | \multicolumn{8}{c}{Peptide release rates under different time intervals} |
|---|---|---|---|---|---|---|---|---|
|  | 1 h | 3 h | 6 h | 12 h | 24 h | 3 day | 5 day | 7 day |
| UCNP-P$_5$ | 0% | 0% | 0.1% | 0.5% | 0.7% | 0.8% | 1.1% | 1.9% |
| UCNP-P$_6$ | 0% | 0% | 0.3% | 0.8% | 1.4% | 1.9% | 2.9% | 5.9% |
| UCNP-P$_7$ | 0% | 0% | 0.2% | 0.7% | 1.0% | 1.6% | 2.0% | 2.6% |
| UCNP-P$_4$ | 0% | 0% | 0.3% | 0.8% | 1.3% | 2.1% | 3.4% | 5.6% |

Figure 18:
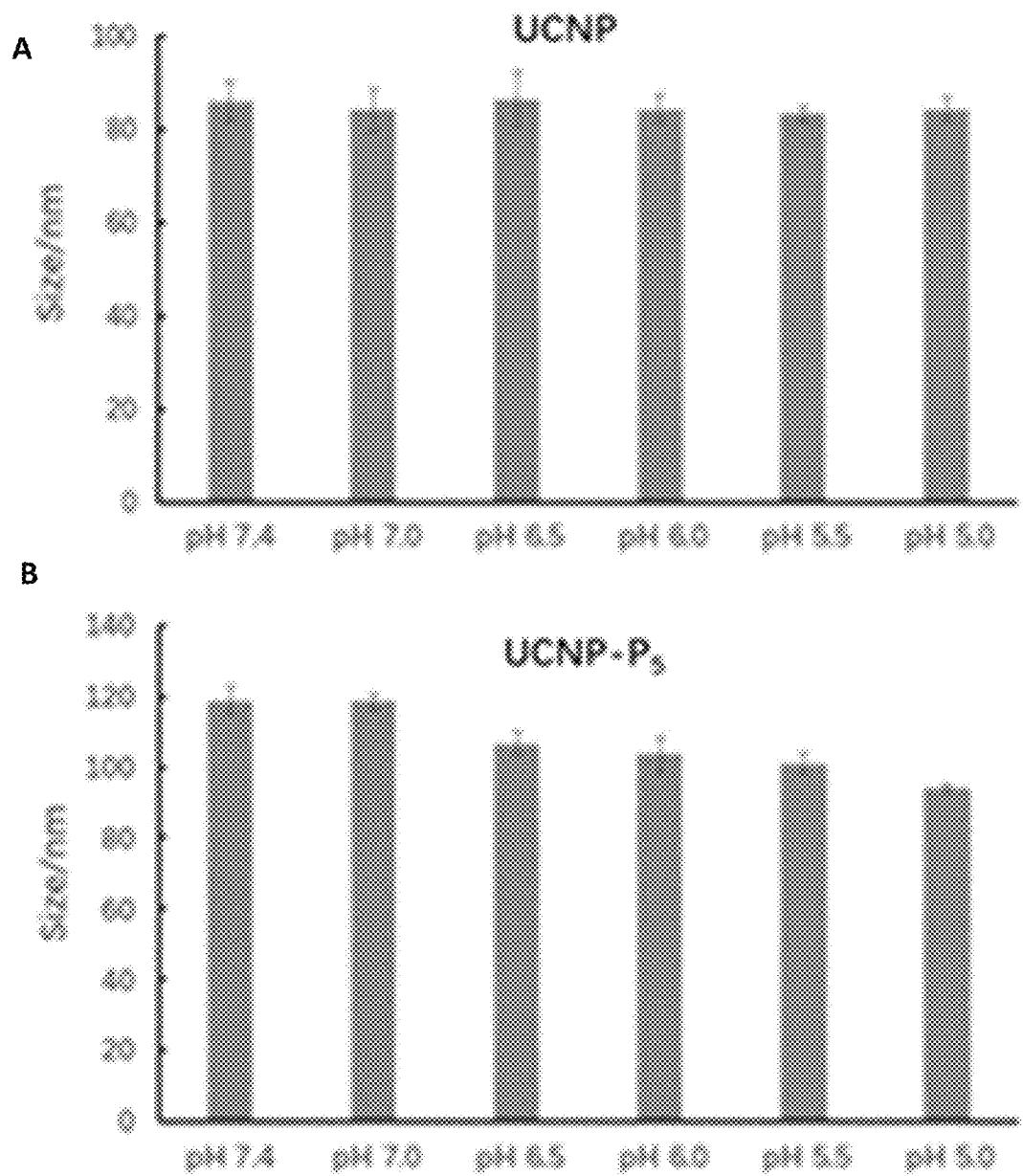
FIG. 18 depicts (A-D) size variation of nanoprobes in pH range from pH 7.4 to 5.0.
Figure 18:
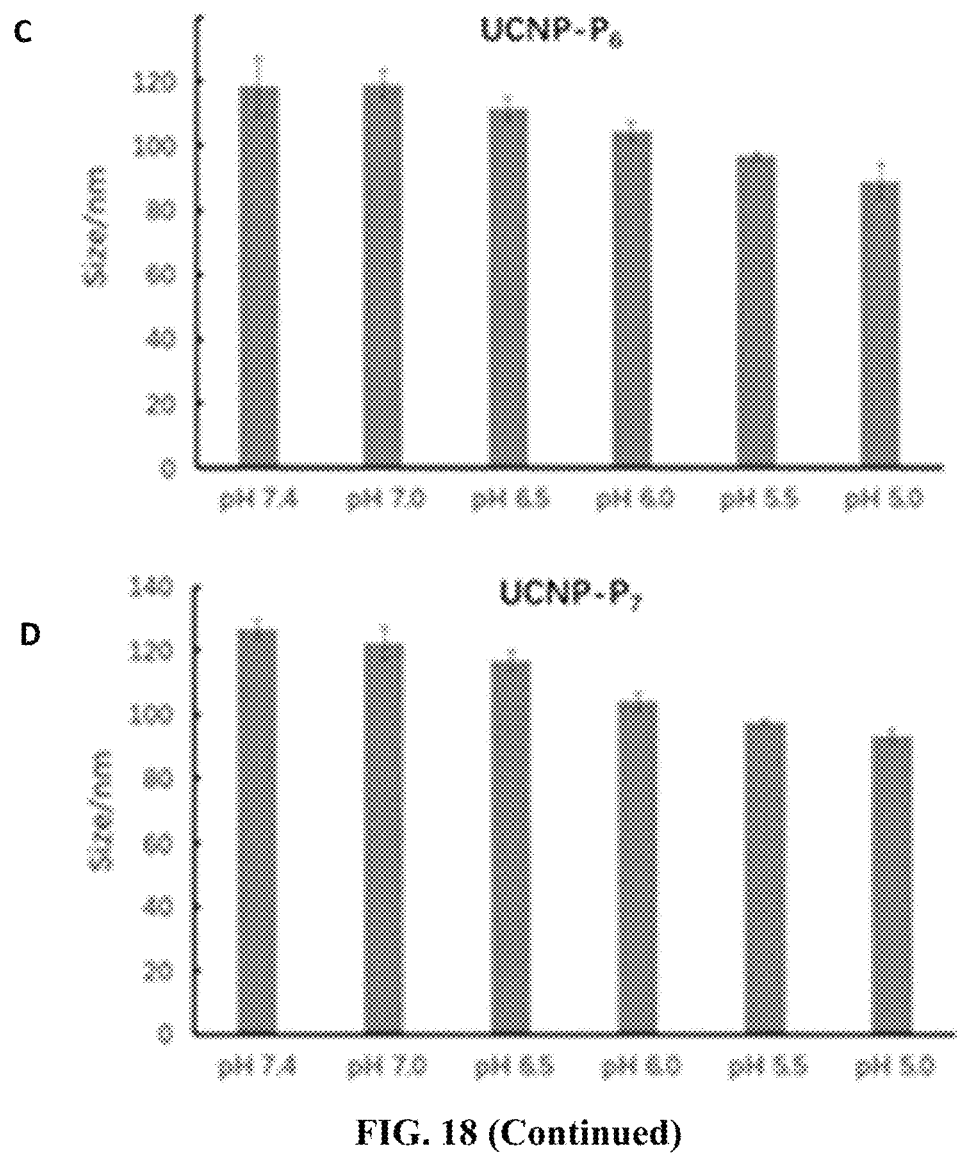
Figure 19:
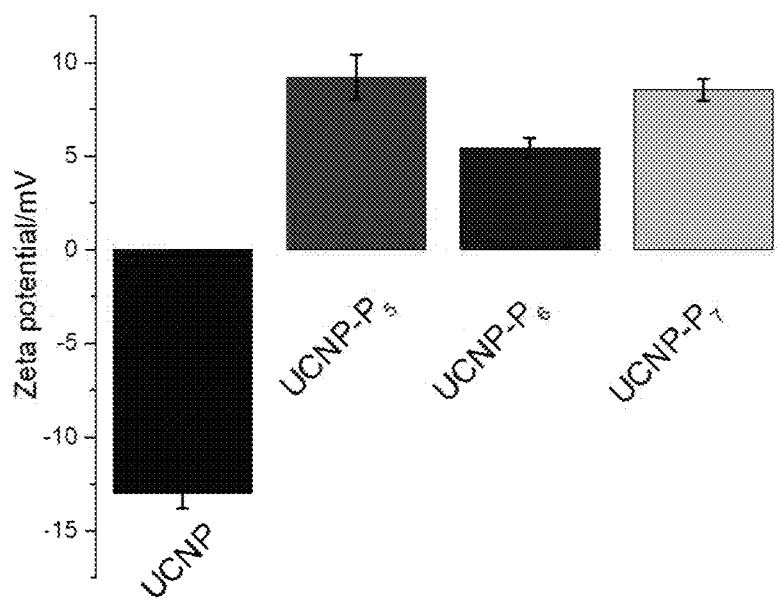
FIG. 19 depicts zeta potential of UCNP, UCNP-P$_5$, UCNP-P$_6$ and UCNP-P$_7$.

Additionally, quantitative analysis of peptide release behaviors of UCNP-P$_n$ [n=5, 6 and 7 (SEQ ID NO: 5, 6, 7)] showed that over 80% of specific peptides (P$_5$, P$_6$ and P$_7$) were released from the initial nanoprobes as the pH decreased, as displayed in FIG. 17 and Table 2. It is worth noting that the sizes of nanoprobes UCNP-P$_n$ [n=5, 6 and 7 (SEQ ID NO: 5, 6, 7)] when measured with DLS decreased significantly in buffers of pH 7.4 to pH 5.0 whereas the size of UCNP remains nearly the same in different pH buffers, as shown in FIG. 18. This suggests the pH-cleavable linker, introduced in the nanoprobes by a Schiff base reaction, has an excellent sensitivity towards an acidic environment. The nanoprobes could be separated into two parts, UCNP and P$_n$ [n=5, 6 and 7 (SEQ ID NO: 5, 6, 7)] upon inducing the cleavage of the pH imine linker in a weakly acidic environment (mimicking tumor microenvironment). Hence, it is likely that the nanoprobes are pH-responsive, which is consistent with our expectation. The surface charge of the samples was also recorded by zeta-potential measurements in FIG. 19. The results showed that the initially negatively charged surface of UCNP became positive due to the positively charged amino group from the three candidate peptides, indicating the successful conjugation of dual-targeting peptides.

TABLE 2

Quantitative analysis of peptide release behaviors of nanoprobes under various pH buffers. The peptide release rate for each nanoprobe in various pH solutions is calculated using the following equation:

$$\text{Release rate \%} = \frac{(I_0 - I_1)}{I_0} \times 100\%,$$

where $I_0$ is relative absorbance intensity in pH 7.4 solution and $I_1$ is relative absorbance intensity in other different pH buffers correspondingly.

| Sample names | \multicolumn{6}{c}{Peptide release rates under various pH buffer} |
|---|---|---|---|---|---|---|
|  | pH 7.4 | pH 7.0 | pH 6.5 | pH 6.0 | pH 5.5 | pH 5.0 |
| UCNP-P$_5$ | 0% | 6.1% | 20.9% | 34.8% | 56.1% | 84.6% |
| UCNP-P$_6$ | 0% | 4.6% | 21.5% | 32.2% | 34.1% | 83.3% |
| UCNP-P$_7$ | 0% | 7.4% | 36.1% | 48.2% | 58.5% | 81.2% |
| UCNP-P$_4$ | 0% | 1.1% | 26.4% | 36.5% | 53.6% | 57.8% |

Figure 20:
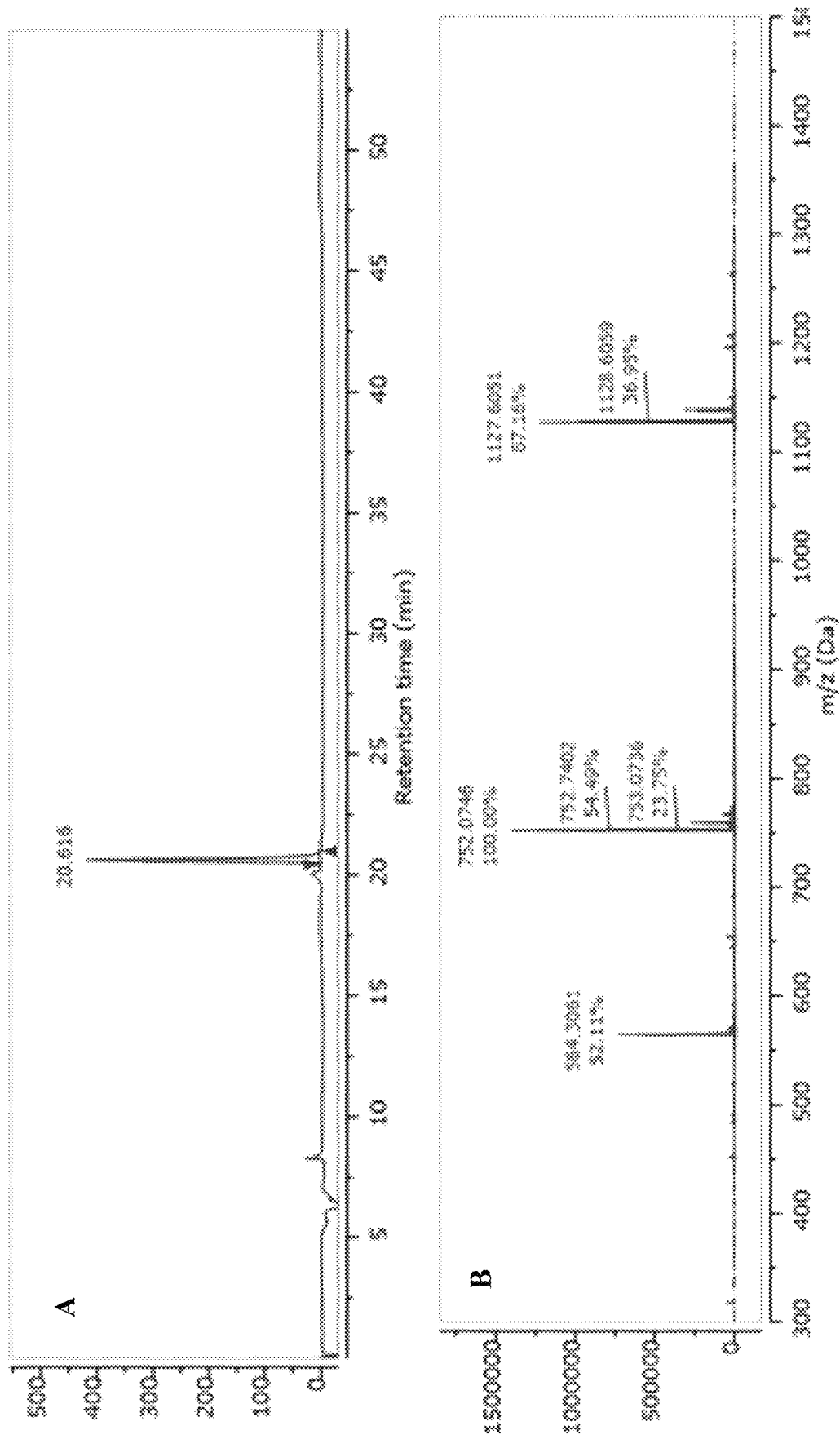
FIG. 20 depicts analytic high performance liquid chromatography (HPLC) and electrospray ionization-mass spectrometry (ESI-MS) for pre-conjugated (A-B) and post-released (C-D) P$_5$ sample. The retention times ($T_R$) are 20.616 min and 20.594 min, respectively. Molecular formula of P$_5$: $C_{110}H_{157}N_{29}O_{21}S$. ESI-MS: calc. for [M+2H]$^{2+}$1127.0988, found 1127.1019; calc. for [M+3H]$^{3+}$ 751.7349, found (E-G) 751.7385; calc. for [M+4H]$^{4+}$564.0530, found 564.0545.
Figure 20:
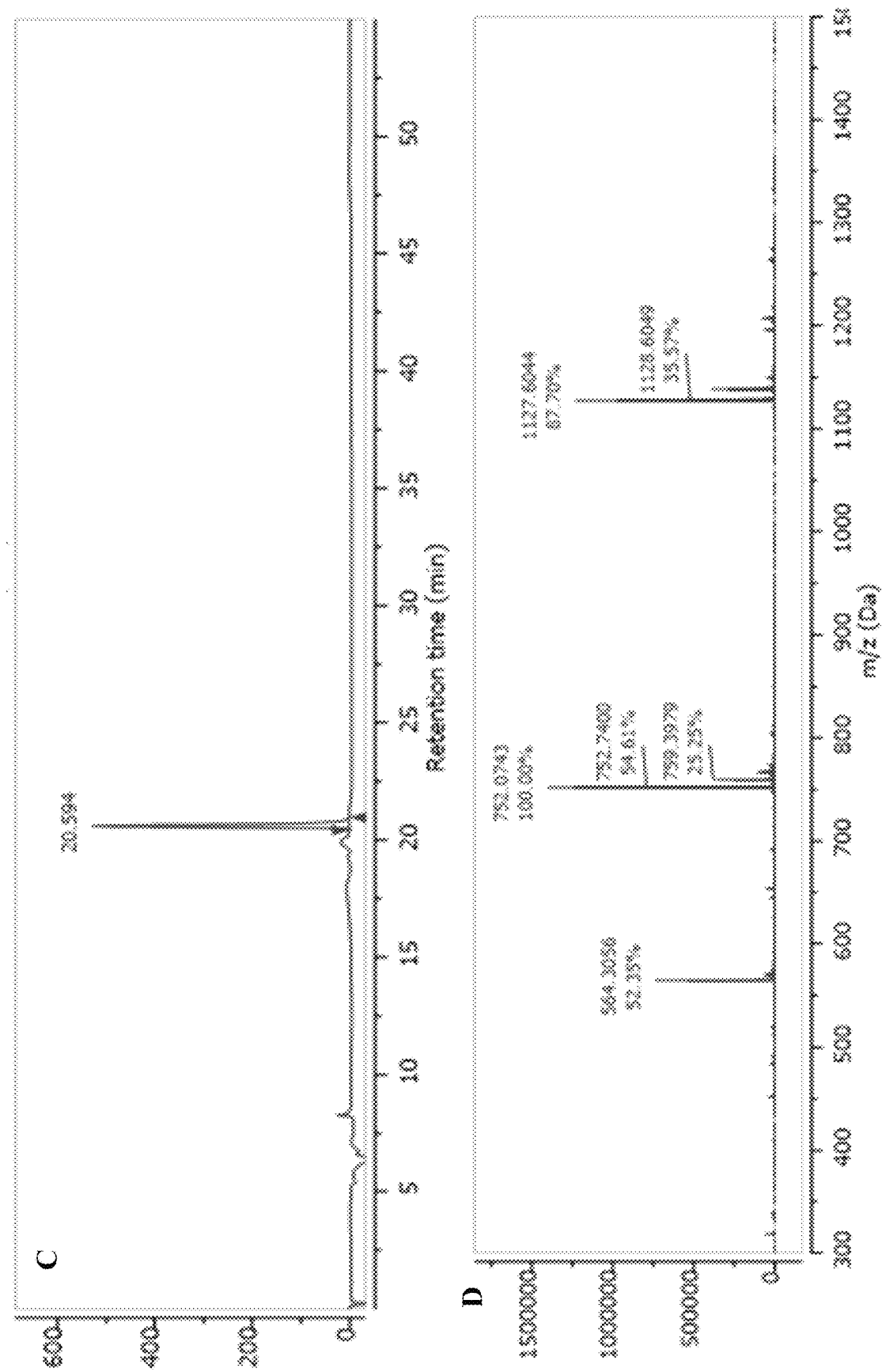
Figure 20:
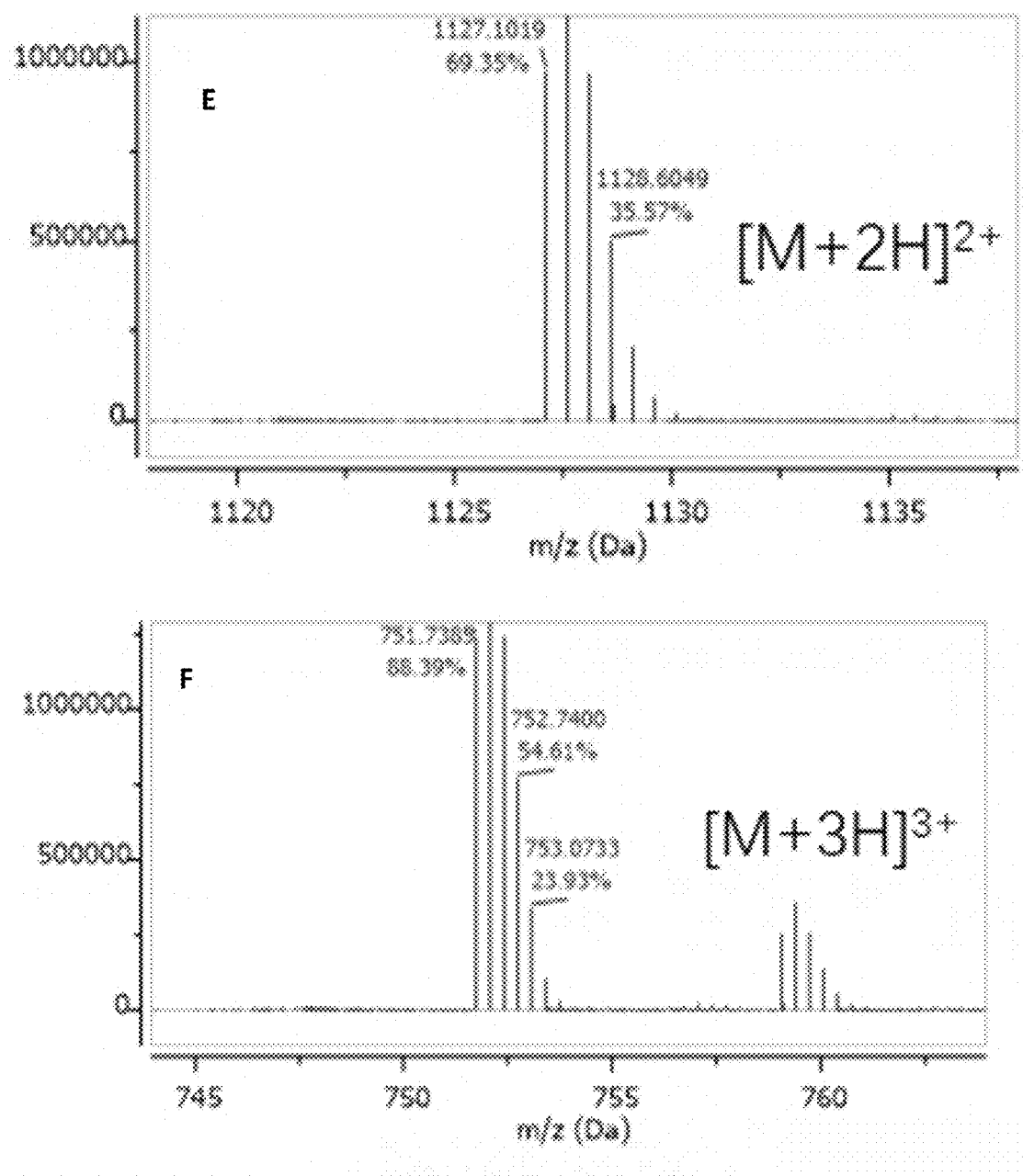
Figure 20:
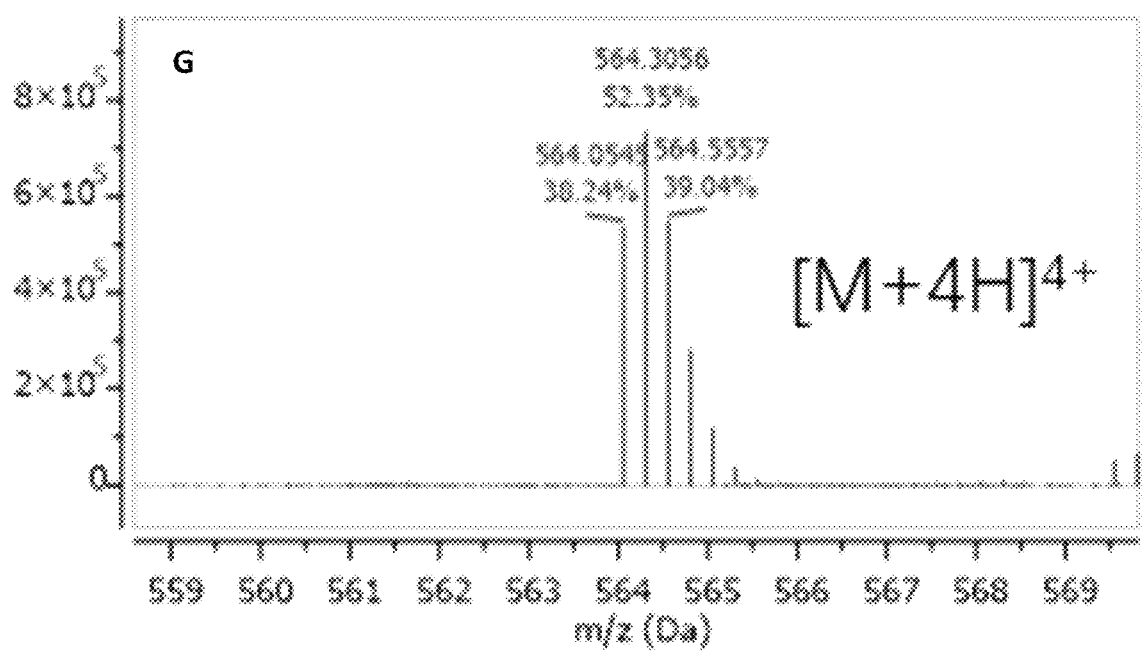
Figure 21:
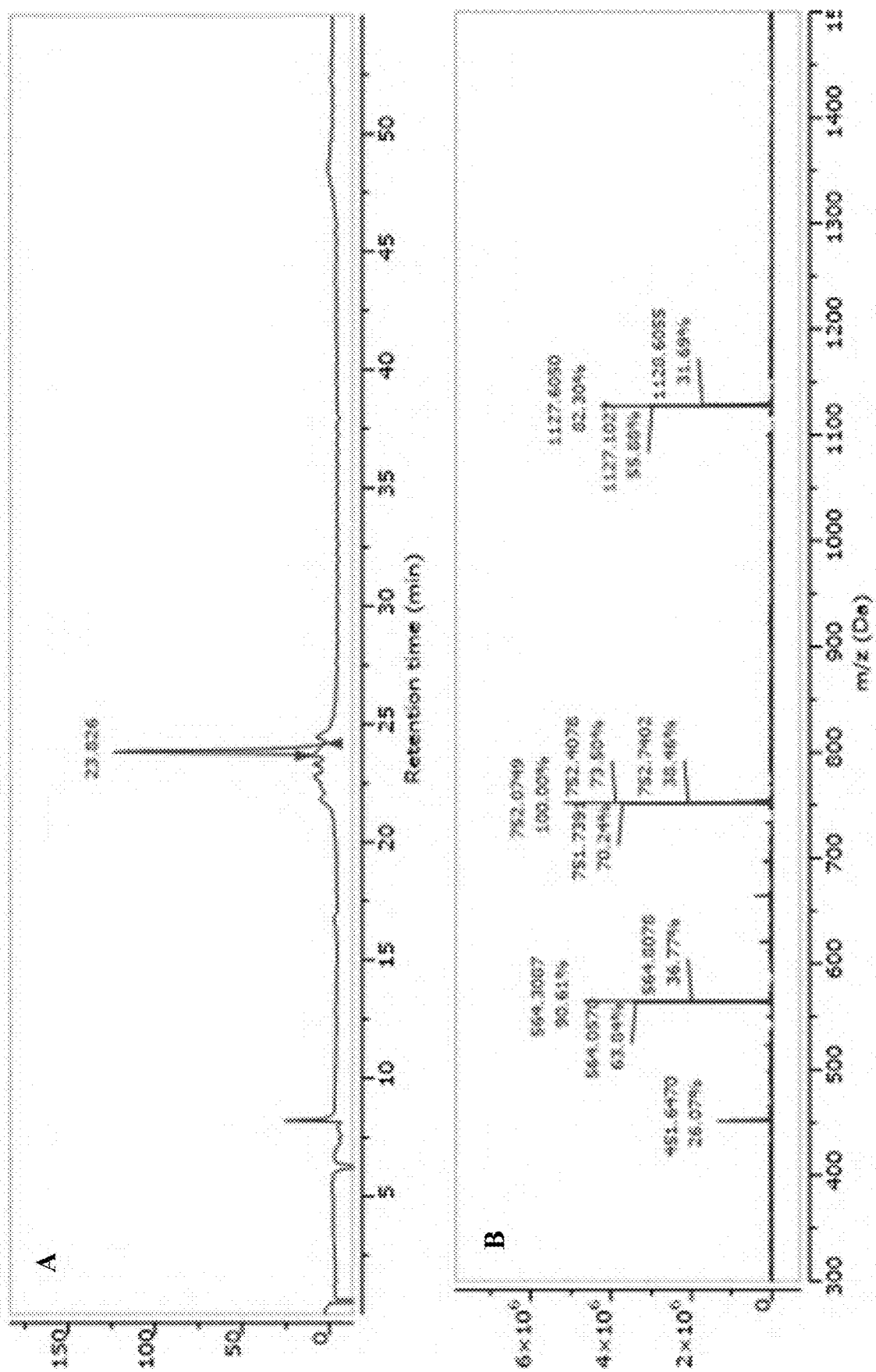
FIG. 21 depicts analytic HPLC and ESI-MS for pre-conjugated (A-B) and post-released (C-D) P$_6$ sample. The retention times ($T_R$) are 23.826 min and 23.557 min, respectively. Molecular formula of P$_6$: $C_{110}H_{157}N_{29}O_{21}S$. ESI-MS: calc. for [M+2H]$^{2+}$1127.0988, found 1127.1012; calc. for [M+3H]$^{3+}$ 751.7349, found (E-G) 751.7382; calc. for [M+4H]$^{4+}$ 564.0530, found 564.0567.
Figure 21:
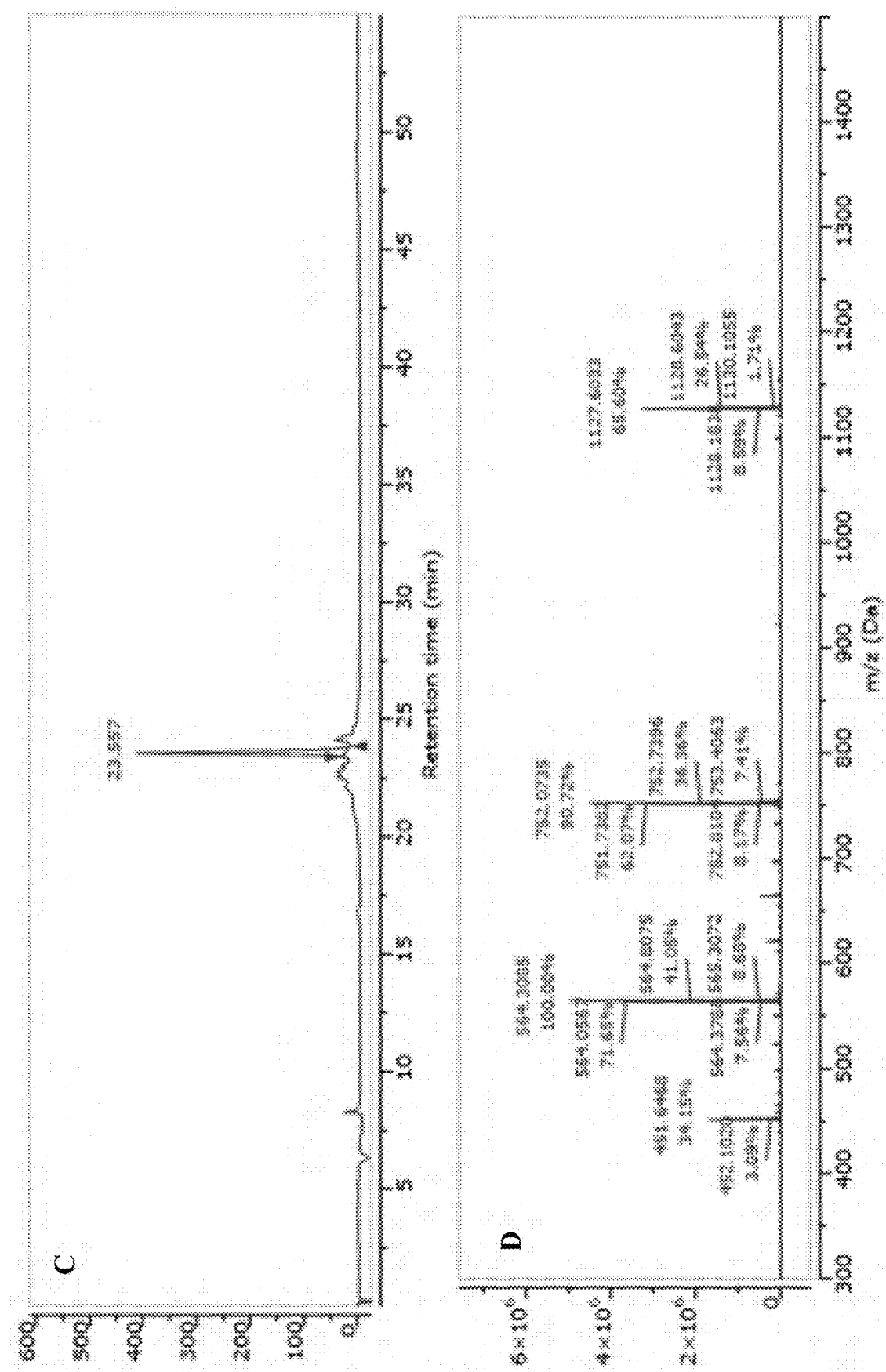
Figure 21:
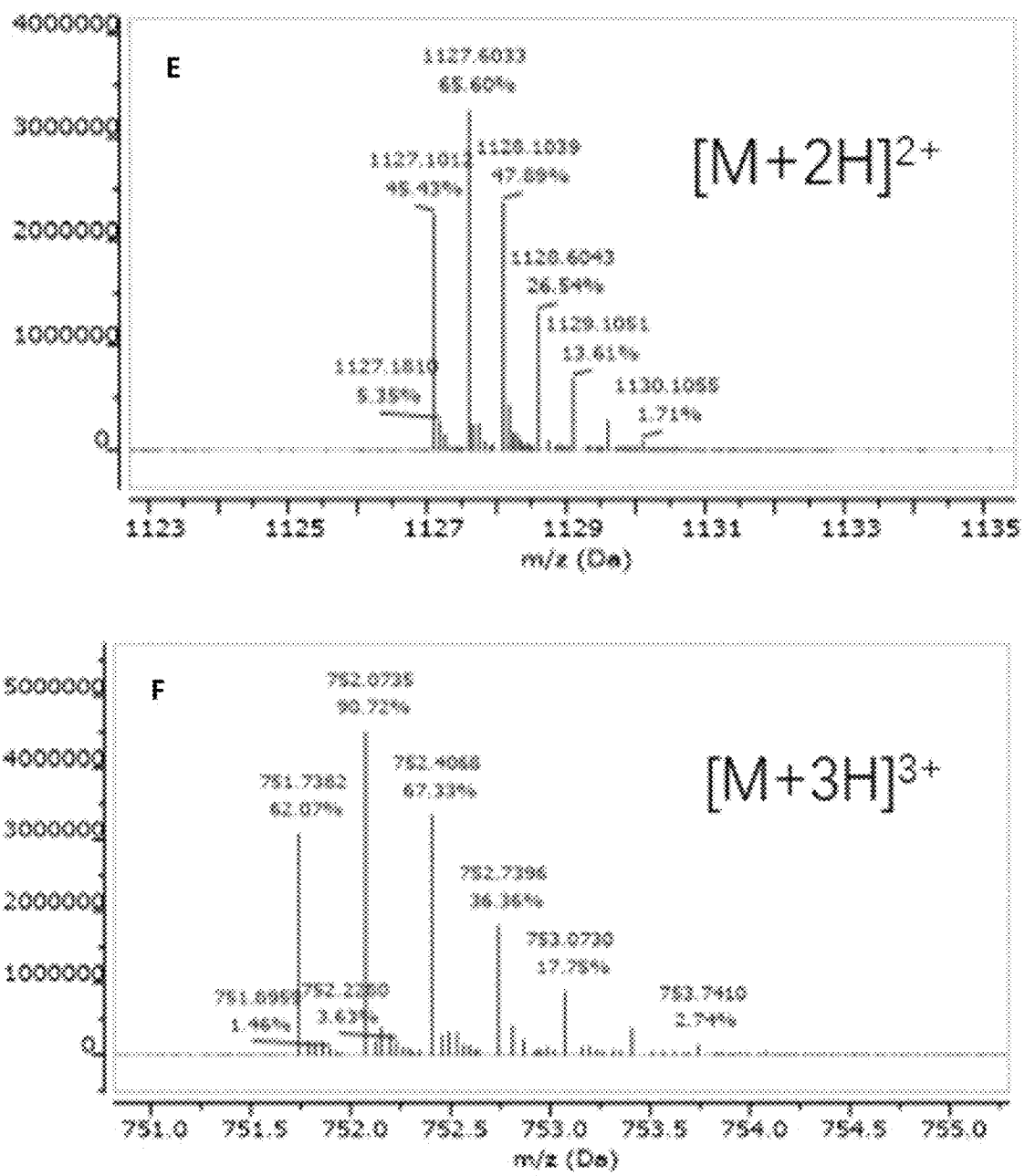
Figure 21:
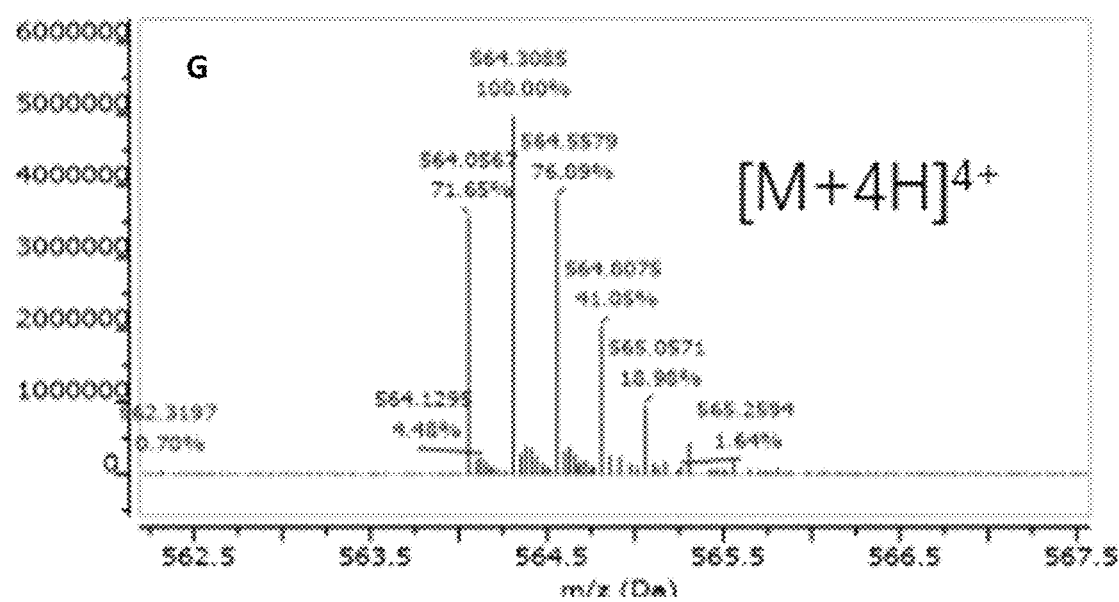
Figure 22:
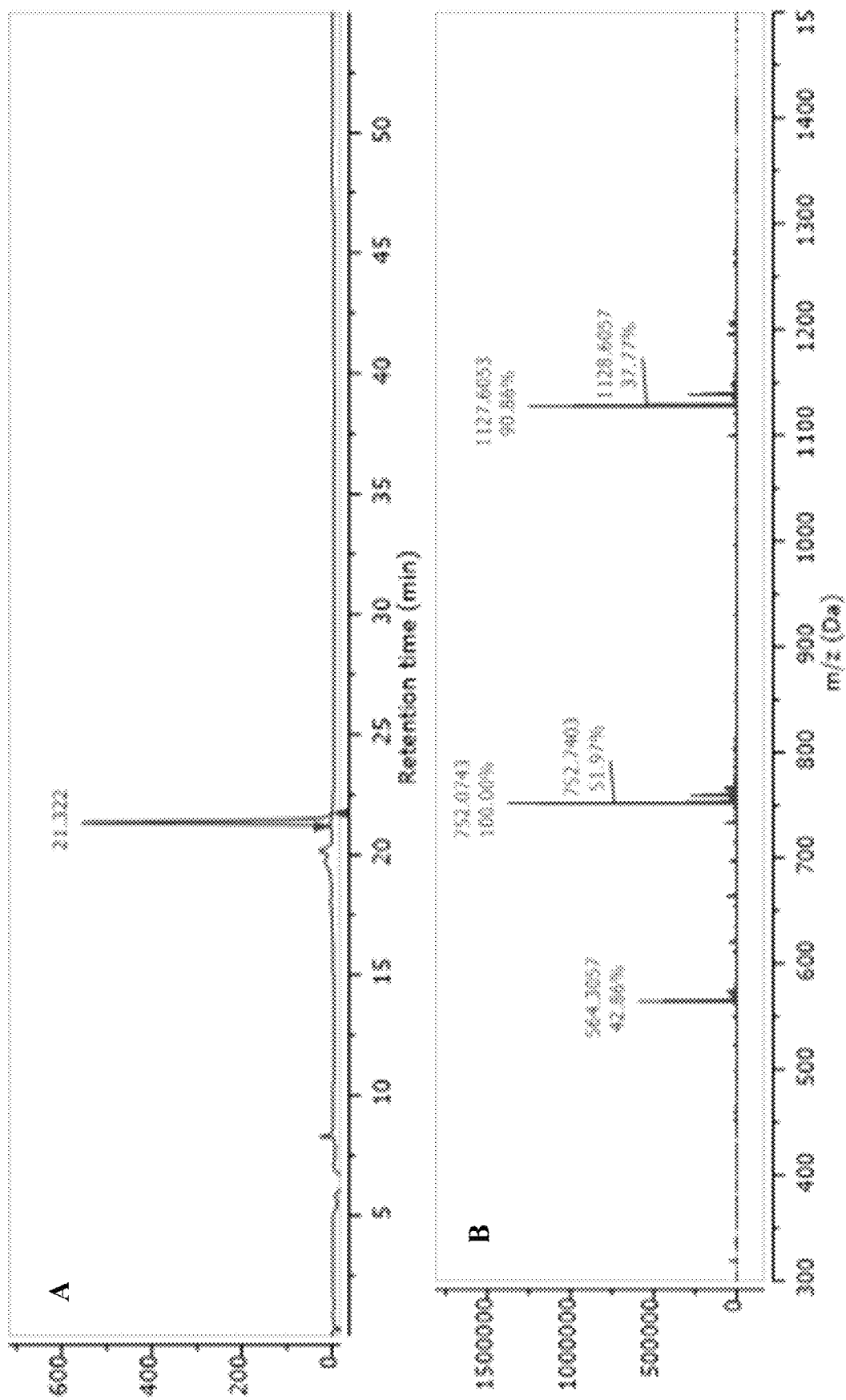
FIG. 22 depicts analytic IPLC and ESI-MS for pre-conjugated (A-B) and post-released (C-D) P$_7$ sample. The retention times ($T_R$) are 21.322 min and 21.301 min, respectively. Molecular formula of P$_7$: $C_{110}H_{157}N_{29}O_{21}S$. ESI-MS: calc. for [M+2H]$^{2+}$1127.0988, found 1127.1076; calc. for [M+3H]$^{3+}$ 751.7349, found (E-G) 751.7419; calc. for [M+4H]$^{4+}$ 564.0530, found 564.0572.
Figure 22:
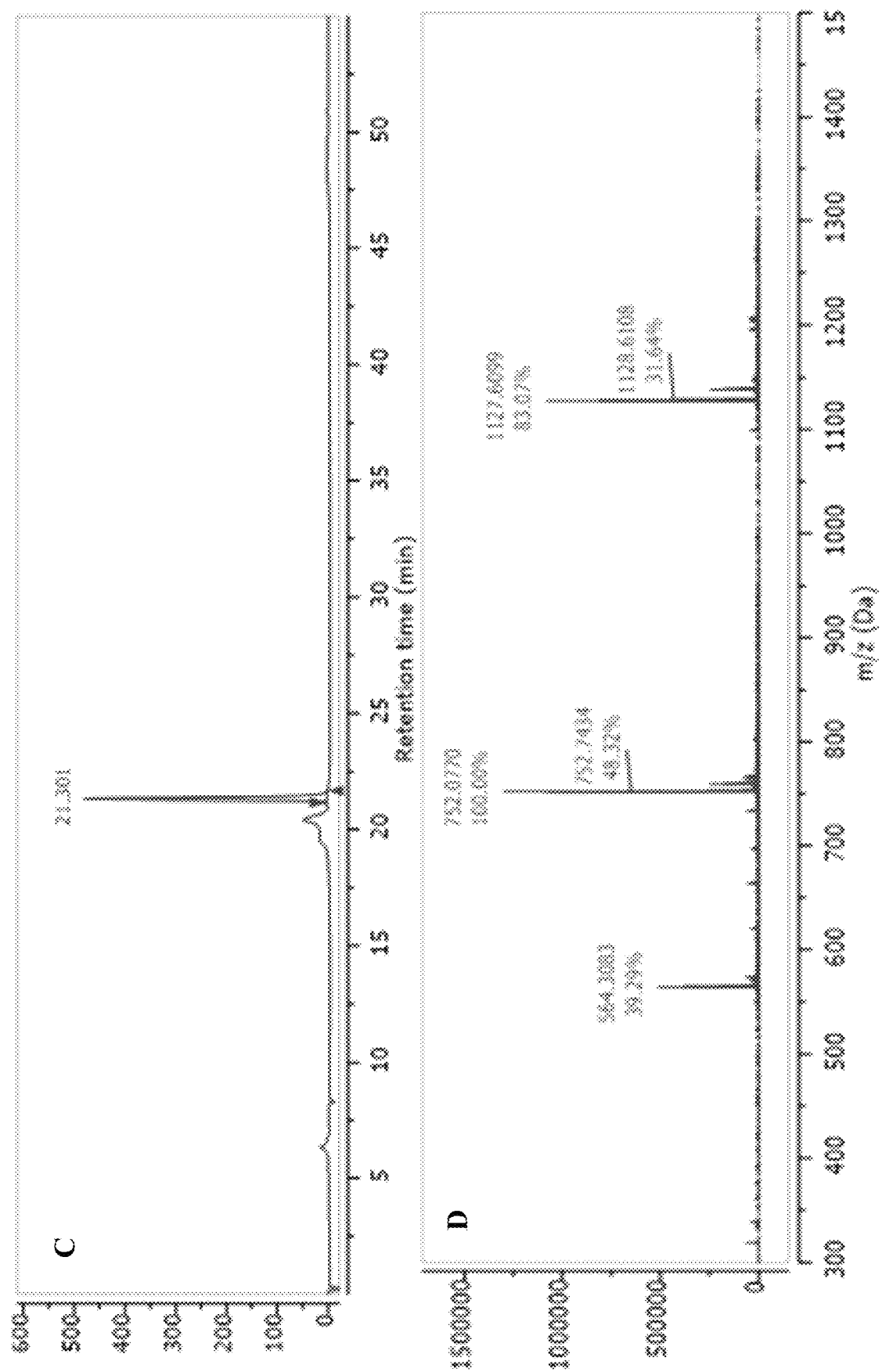
Figure 22:
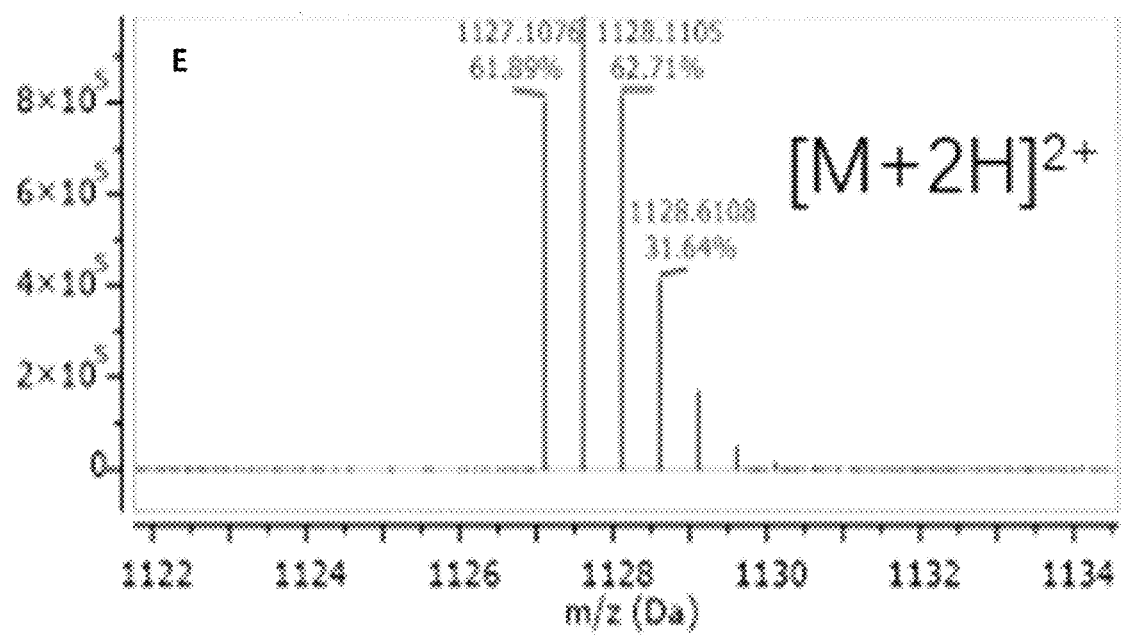
Figure 22:
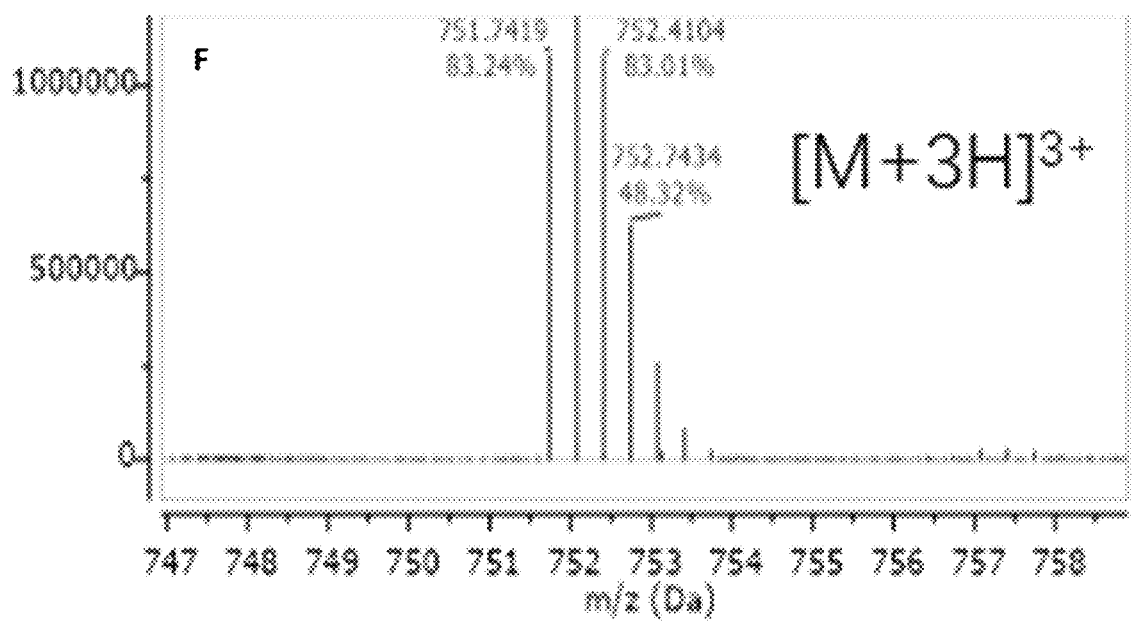
Figure 22:
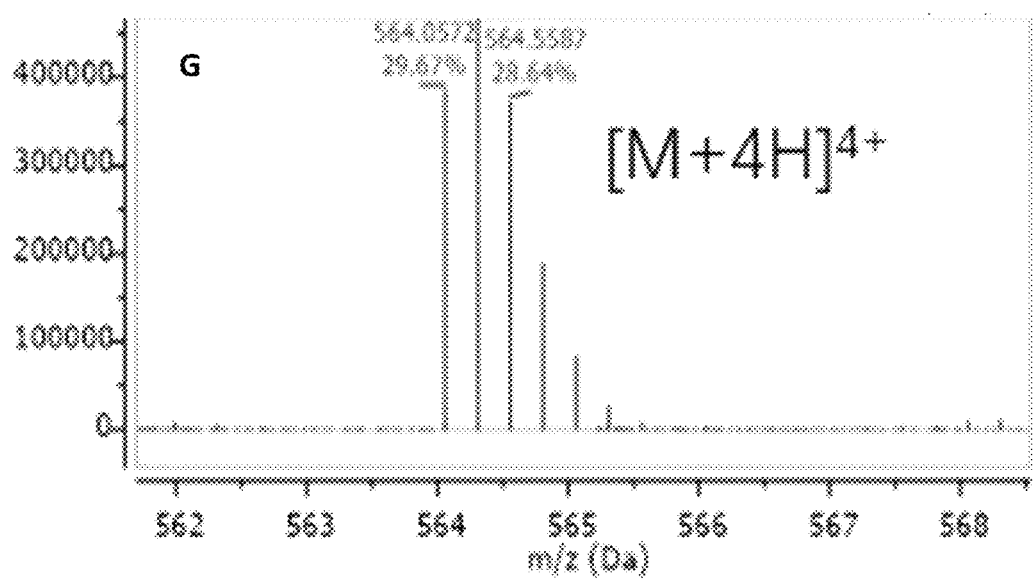

To further confirm that the peptides were intact upon their pH-induced release from UCNP, both analytical HPLC and ESI-MS were conducted. HPLC showed no difference in the retention times between original peptides and the solution released from corresponding nanoprobes. ESI-MS also confirmed both pre-conjugated and post-release samples are the desired peptides (FIG. 20, FIG. 21 and FIG. 22). Therefore, these results indicate that the peptides can be released intact from the nanoprobes under acidic conditions.

---

What is claimed is:

1. A polypeptide comprising three peptide sequences or a pharmaceutically acceptable salt or zwitterion thereof; wherein the three peptide sequences are SEQ ID NO: 1, SEQ ID NO: 2, and SEQ ID N: 3 and the polypeptide comprises in order from N-terminus to C-terminus: SEQ ID NO: 2, SEQ ID NO: 3, and SEQ ID NO: 1 or SEQ ID NO: 3, SEQ ID NO: 2, and SEQ SEQ ID NO: 1.

2. The polypeptide of claim 1 further comprising two linkers, wherein the each of the two linkers is covalently bonded between two of the three peptide sequences.

3. The polypeptide of claim 2, wherein each of the two linkers is independently a polypeptide linker consisting of 1-4 amino acid residues.

4. The polypeptide of claim 1, wherein the polypeptide consists of 15-21 amino acid residues and a linker covalently bonded to the N-terminal of the polypeptide.

5. The polypeptide of claim 1, wherein the polypeptide comprises the structure: $L^1$-A-$L^2$-B-$L^3$-C, wherein each of A, B, and C are selected from the group consisting of SEQ ID NO: 1, SEQ ID NO: 2, and SEQ ID NO: 3; $L^1$ is a linker having the formula: $NH^2(CH_2)_m(C{=}O)-$, wherein m is a whole number selected from 1-10; and each of $L^2$ and $L^3$ is independently a polypeptide linker consisting of 1-4 amino acid residues.

6. The polypeptide of claim 5, wherein each of the polypeptide linkers independently consists of 1-3 amino acid residues selected from the group consisting of alanine, asparagine, glycine; serine; and combinations thereof.

7. The polypeptide of claim 5, wherein each of $L^2$ and $L^3$ is independently a polypeptide linker consisting of 1-3 glycine residues.

8. The polypeptide of claim 5, wherein A is SEQ ID NO:2; B is SEQ ID NO:3; and C is SEQ ID NO:1 or A is SEQ ID NO:3; B is SEQ ID NO:2; and C is SEQ ID NO:1.

9. The polypeptide of claim 1, wherein the polypeptide comprises the structure: $L^1$-A-$L^2$-B-$L^3$-C, wherein A is SEQ ID NO:2: B is SEQ ID NO:3; and C is SEQ ID NO:1; A is SEQ ID NO:3; B is SEQ ID NO:2; and C is SEQ ID NO:1; $L^1$ is a linker having the formula: $NH_2(CF_2)_m(C=O)$—, wherein m is a whole number selected from 2-8; and each of $L^2$ and $L^3$ is independently a polypeptide linker consisting of 1-3 glycine residues.

10. The polypeptide of claim 1, wherein the polypeptide comprises a peptide sequence selected from the group consisting of SEQ ID NO:5 and SEQ ID NO:6.

11. An upconversion nanoparticle (UCNP) conjugate comprising a plurality of the polypeptides of claim 1 conjugated to a surface of an UCNP via a linker.

12. The UCNP conjugate of claim 11, wherein the UCNP is a lanthanide-doped nanoparticle.

13. The UCNP conjugate of claim 11, wherein the UCNP comprises $NaGdF_4$:$Yb^{3+}$, $Er^{3+}$@$NaGdF_4$.

14. The UCNP conjugate of claim 11, wherein each of the plurality of polypeptides comprise the structure: $L^4$-A-$L^2$-B-$L^3$-C, wherein each of A, B, and C are independently selected from the group consisting of SEQ ID NO: 1, SEQ ID NO: 2, and SEQ ID NO: 3; $L^4$ is a linker having the formula: *—S-A(C=N)($CH_2$)$_m$(C=O)—, wherein m is a whole number selected from 1-10; A is polyethylene glycol; and * represents the site of conjugation to the UCNP; and each of $L^2$ and $L^3$ is independently a polypeptide linker consisting of 1-4 amino acid residues and wherein the polypeptide comprises in order from N-terminus to C-terminus: SEQ ID NO: 2, SEQ ID NO: 3, and SEQ ID NO: 1 or SEQ ID NO: 3, SEQ ID NO: 2, and SEQ ID NO: 1.

15. The UCNP conjugate of claim 14, wherein A is SEQ ID NO:2; B is SEQ ID NO:3; and C is SEQ ID NO:1 or A is SEQ ID NO:3; B is SEQ ID NO:2; and C is SEQ ID NO:1; and each of $L^2$ and $L^3$ is independently a polypeptide linker consisting of 1-3 glycine residues.

16. The UCNP conjugate of claim 11, wherein each of the plurality of polypeptides comprise the structure: $L^4$-A-$L^2$-B-$L^3$-C, wherein A is SEQ. ID NO:2; B is SEQ ID NO:3; and C is SEQ ID NO:1 or A is SEQ ID NO:3; B is SEQ ID NO:2; and C is SEQ ID NO:1; $L^4$ is *—S-A(CH=N)($CH_2$)$_m$ (C=O)—, wherein m is a whole number selected from 2-8; A is polyethylene glycol; and * represents the site of conjugation to the UCNP; and each of $L^2$ and $L^3$ is a polypeptide linker consisting of 2 glycine residues.

17. The UCNP conjugate of claim 16, wherein the UCNP comprises $NaGdF_4$:$Yb^{3+}$, $Er^{3+}$@$NaGdF_4$.

18. The UCNP conjugate of claim 17, wherein A is SEQ ID NO:2; B is SEQ ID NO:3; and C is SEQ ID NO:1.

19. A pharmaceutical composition comprising an UCNP conjugate of claim 11 and at least one pharmaceutically acceptable excipient or carrier.

20. A pharmaceutical composition comprising a polypeptide of claim 1 and at least one pharmaceutically acceptable excipient or carrier.

21. A method of imaging an Epstein-Barr virus (EBV)-infected cell, the method comprising: contacting EBV-infected cell with an UCNP conjugate of claim 11; irradiating the EBV-infected cell with light; and detecting the luminescence of the conjugate.

22. A method of treating cancer in a subject in need thereof, the method comprising: administering a therapeutically effective amount of a polypeptide of claim 1 to the subject, wherein the cancer is EBV-positive.

23. A method of treating cancer in a subject in need thereof, the method comprising: administering a therapeutically effective amount of an UCNP conjugate of claim 11 to the subject, wherein the cancer is EBV-positive.

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide prepared in the lab

<400> SEQUENCE: 1

Phe Trp Leu Tyr
1

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide prepared in the lab

<400> SEQUENCE: 2

Tyr Phe Met Val Phe
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide prepared in the lab
<220> FEATURE:
<221> NAME/KEY: MISC_FEATURE
<222> LOCATION: (2)..(2)
<223> OTHER INFORMATION: Xaa at position 2 is D-arginine

<400> SEQUENCE: 3

Arg Xaa Arg Lys
1

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide prepared in the lab
<220> FEATURE:
<221> NAME/KEY: MISC_FEATURE
<222> LOCATION: (9)..(9)
<223> OTHER INFORMATION: Xaa at position 9 is D-arginine

<400> SEQUENCE: 4

Tyr Phe Met Val Phe Gly Gly Arg Xaa Arg Lys
1               5                   10

<210> SEQ ID NO 5
<211> LENGTH: 18
<212> TYPE: PRT
<213> ORGANISM: Artificial Sequence

```
<220> FEATURE:
<223> OTHER INFORMATION: Synthetic peptide prepared in the lab
<220> FEATURE:
<221> NAME/KEY: MISC_FEATURE
<222> LOCATION: (1)..(1)
<223> OTHER INFORMATION: Xaa at position 1 is 6-aminocaproic acid
<220> FEATURE:
<221> NAME/KEY: MISC_FEATURE
<222> LOCATION: (10)..(10)
<223> OTHER INFORMATION: Xaa at position 10 is D-arginine

<400> SEQUENCE: 5

Xaa Tyr Phe Met Val Phe Gly Gly Arg Xaa Arg Lys Gly Gly Phe Trp
1               5                   10                  15

Leu Tyr

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide prepared in the lab
<220> FEATURE:
<221> NAME/KEY: MISC_FEATURE
<222> LOCATION: (1)..(1)
<223> OTHER INFORMATION: Xaa at position 1 is 6-aminohexanoic acid
<220> FEATURE:
<221> NAME/KEY: MISC_FEATURE
<222> LOCATION: (3)..(3)
<223> OTHER INFORMATION: Xaa at position 3 is D-arginine

<400> SEQUENCE: 6

Xaa Arg Xaa Arg Lys Gly Gly Tyr Phe Met Val Phe Gly Gly Phe Trp
1               5                   10                  15

Leu Tyr

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide prepared in the lab
<220> FEATURE:
<221> NAME/KEY: MISC_FEATURE
<222> LOCATION: (1)..(1)
<223> OTHER INFORMATION: Xaa at position 1 is 6-aminohexanoic acid
<220> FEATURE:
<221> NAME/KEY: MISC_FEATURE
<222> LOCATION: (9)..(9)
<223> OTHER INFORMATION: Xaa at position 9 is D-arginine

<400> SEQUENCE: 7

Xaa Phe Trp Leu Tyr Gly Gly Arg Xaa Arg Lys Gly Gly Tyr Phe Met
1               5                   10                  15

Val Phe
```